US012534528B2

(12) United States Patent
Choi et al.

(10) Patent No.: US 12,534,528 B2
(45) Date of Patent: Jan. 27, 2026

(54) ANTI-LILRB1 ANTIBODY AND USES THEREOF

(71) Applicant: LG CHEM, LTD., Seoul (KR)

(72) Inventors: Yoon Aa Choi, Daejeon (KR); Jung A Kim, Daejeon (KR); Saem Jung, Daejeon (KR); Ji Hyun Lee, Daejeon (KR); Kyubong Na, Daejeon (KR); Yeonchul Kim, Daejeon (KR); Han Byul Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 889 days.

(21) Appl. No.: 17/788,493

(22) PCT Filed: Dec. 22, 2020

(86) PCT No.: PCT/KR2020/018931
§ 371 (c)(1),
(2) Date: Jun. 23, 2022

(87) PCT Pub. No.: WO2021/133036
PCT Pub. Date: Jul. 1, 2021

(65) Prior Publication Data

US 2024/0270841 A1 Aug. 15, 2024

(30) Foreign Application Priority Data

Dec. 23, 2019 (KR) ........................ 10-2019-0173414
May 22, 2020 (KR) ........................ 10-2020-0061907

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/565* (2013.01); *C07K 2317/622* (2013.01)

(58) Field of Classification Search
CPC ............ C07K 16/2803; C07K 2317/24; C07K 2317/565; C07K 2317/622; C07K 2317/33; C07K 2317/73; C07K 2317/21; C07K 2317/76; C07K 2317/92; C07K 2317/56; C07K 16/28; A61P 35/00; A61K 2039/505; A61K 39/00
See application file for complete search history.

(56) References Cited

U.S. PATENT DOCUMENTS

| | | | |
|---|---|---|---|
| 2012/0315269 | A1 | 12/2012 | Klechevsky et al. |
| 2013/0224233 | A1 | 8/2013 | Bennink et al. |
| 2013/0324593 | A1 | 12/2013 | Kim et al. |
| 2015/0174203 | A1 | 6/2015 | Chen et al. |
| 2018/0086829 | A1 | 3/2018 | Zhang et al. |
| 2018/0127502 | A1 | 5/2018 | Brentjens et al. |
| 2018/0251558 | A1 | 9/2018 | Maute et al. |
| 2018/0340014 | A1 | 11/2018 | Viney et al. |
| 2019/0241664 | A1 | 8/2019 | Maute et al. |
| 2022/0002409 | A1 | 1/2022 | Viney et al. |

FOREIGN PATENT DOCUMENTS

| | | | |
|---|---|---|---|
| CA | 2959821 | A1 | 4/2016 |
| CN | 110520436 | A | 11/2019 |
| KR | 10-2011-0011676 | A | 2/2011 |
| KR | 10-1038126 | B1 | 5/2011 |
| KR | 10-2017-0123323 | A | 11/2017 |
| KR | 10-2018-0019725 | A | 2/2018 |
| RU | 2586774 | A | 10/2014 |
| WO | 2009140361 | A1 | 11/2009 |
| WO | 2016-065329 | A1 | 4/2016 |
| WO | 2019-144052 | A1 | 7/2019 |
| WO | 2020-136147 | A1 | 7/2020 |

OTHER PUBLICATIONS

Mumberg et al., "CD4+ T Cells Eliminate MHC Class II-negative Cancer Cells in Vivo by Indirect Effects of IFN-65 ", Proceedings of the National Academy of Sciences, 1999, vol. 96, N15, pp. 8633-8638.
Kozlov et al., "Modern Problems of Immunotherapy in Oncology", 2004, pp. 13-19.
International Search Report dated Apr. 2, 2021, issued in the corresponding International Application No. PCT/KR2020/018931, 7 pages.
Kim et al., "LILRB1 Blockade Enhances Bispecific T Cell Engager Antibody-Induced Tumor Cell Killing by Effector CD8+ T Cells", The Journal of Immunology, 2019, 203: 1076-1087.
Villa-Álvarez et al., "Ig-Like Transcript 2 (ILT2) Blockade and Lenalidomide Restore NK Cell Function in Chronic Lymphocytic Leukemia", Frontiers in Immunology, 2018, vol. 9, Article 2917, 1-12.
Barkal, et al., "Engagement of MHC class I by the inhibitory receptor LILRB1 suppresses macrophages and is a target of cancer immunotherapy", Nature Immunology, 2018, vol. 19, 76-84.
Studier, F.W., Protein production by auto-induction in high-density shaking cultures, Protein Expression and Purification, (2005), 41, 207-234.
R&D Systems: "Human LILRB1/CD85j/ILT2 Antibody", Jul. 7, 2018, XP093177312 (2 pages).

*Primary Examiner* — Chun W Dahle
*Assistant Examiner* — Grace H Lunde
(74) *Attorney, Agent, or Firm* — ROTHWELL, FIGG, ERNST & MANBECK, P.C.

(57) ABSTRACT

The present invention relates to an anti-LILRB1 antibody having increased specificity for LILRB1, and to uses thereof. Specifically, provided are an anti-LILRB1 antibody or antigen-binding fragment thereof, and uses thereof in treating cancer.

14 Claims, 18 Drawing Sheets

Specification includes a Sequence Listing.

【Figure 1】
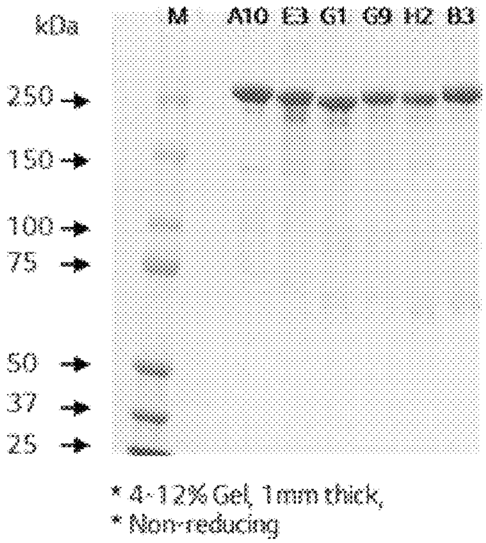
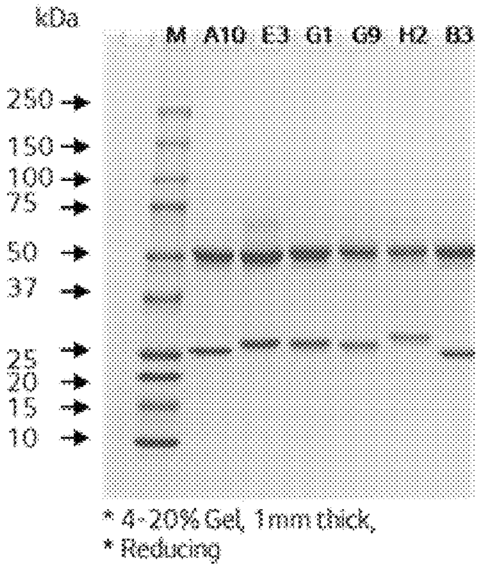

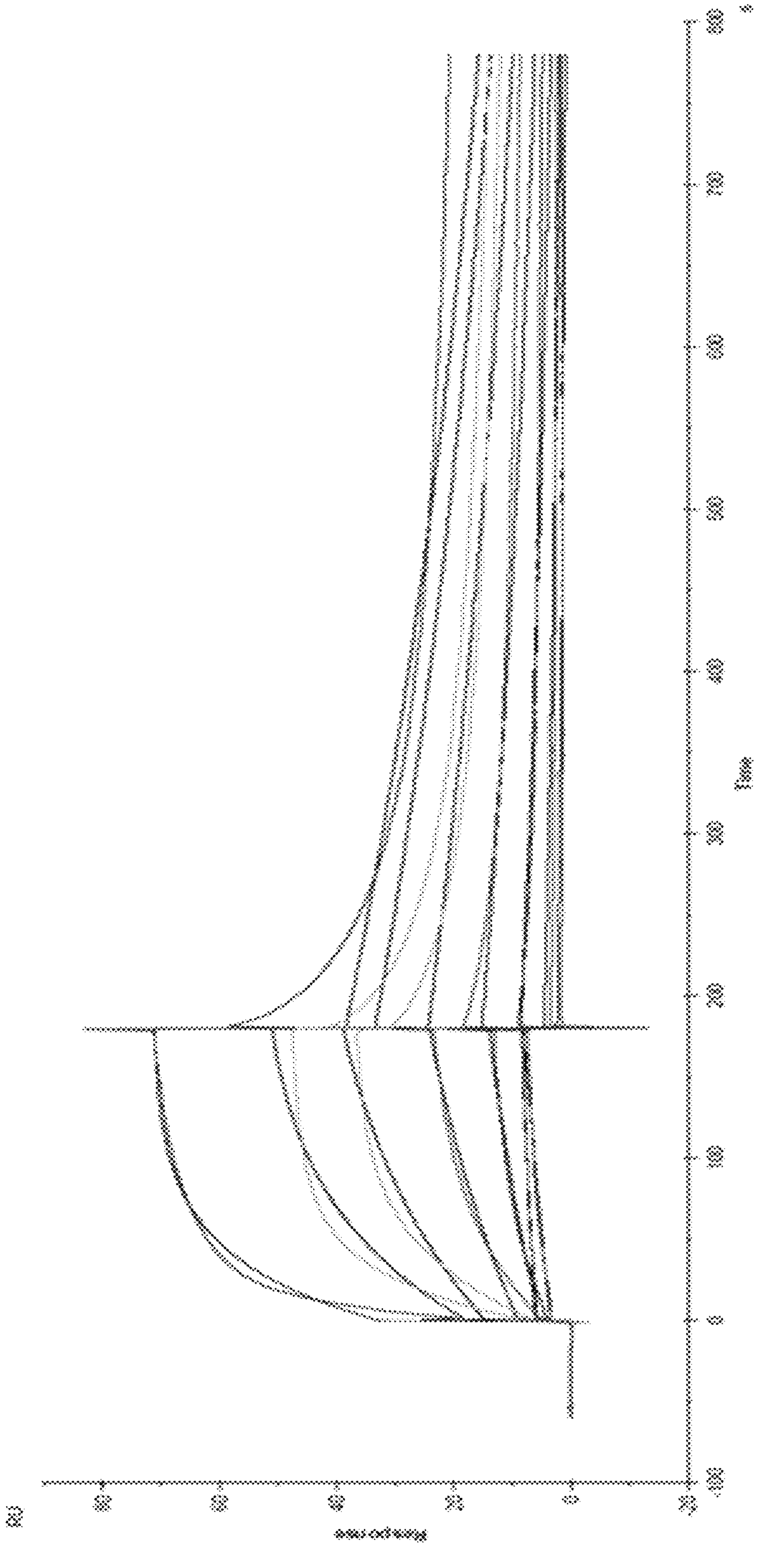
【Figure 2】

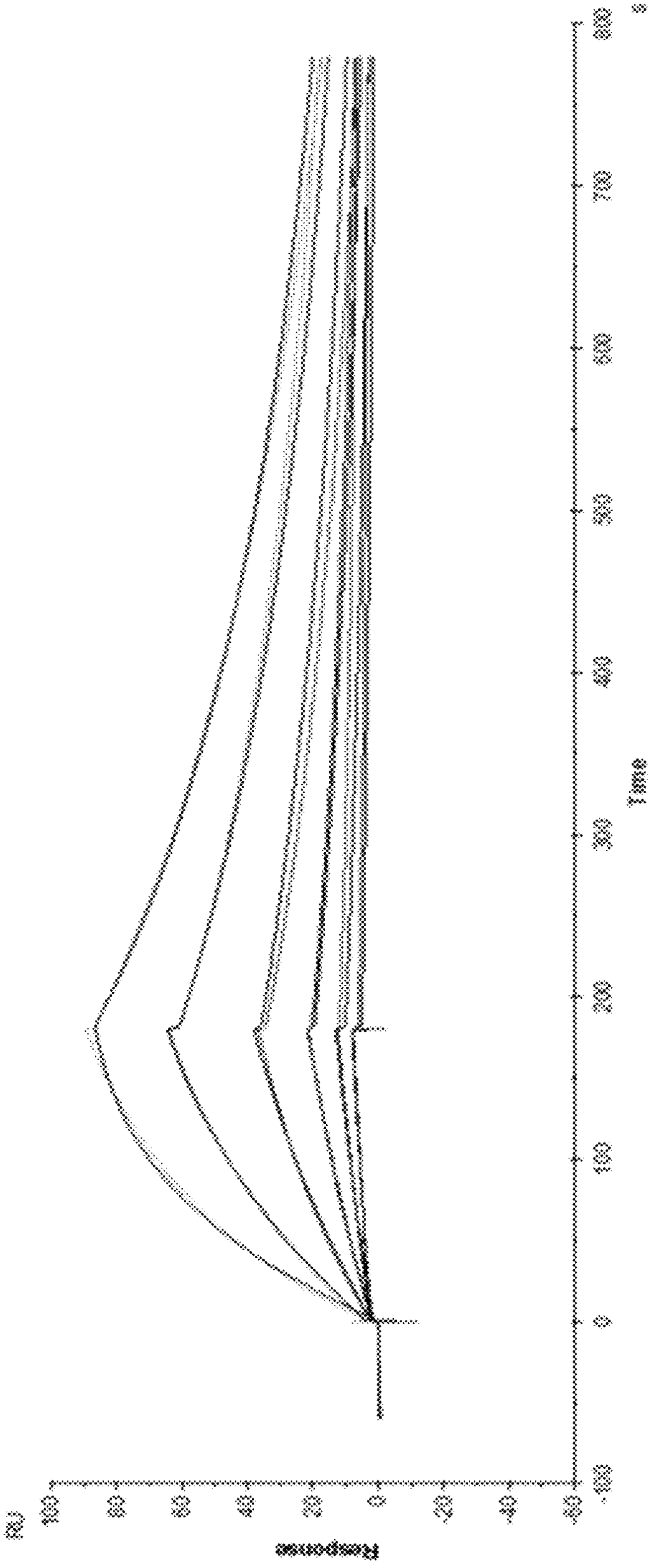
【Figure 3】

【Figure 4a】
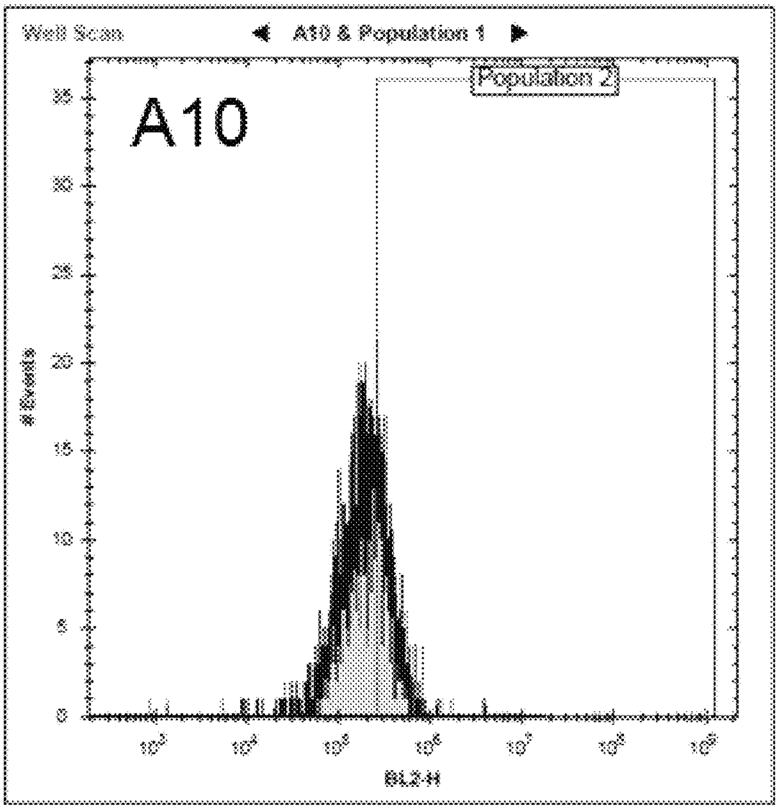

【Figure 4b】
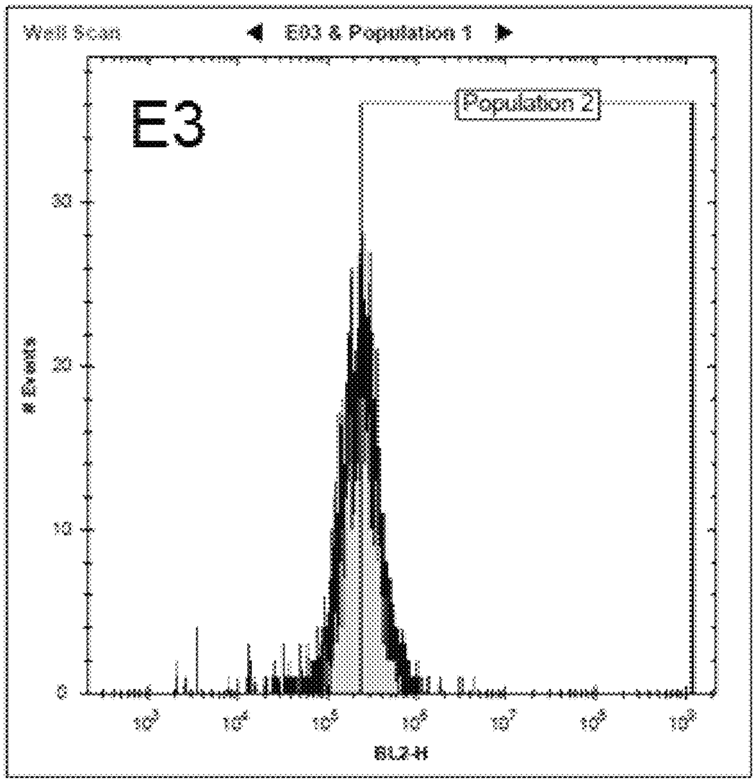

【Figure 4c】
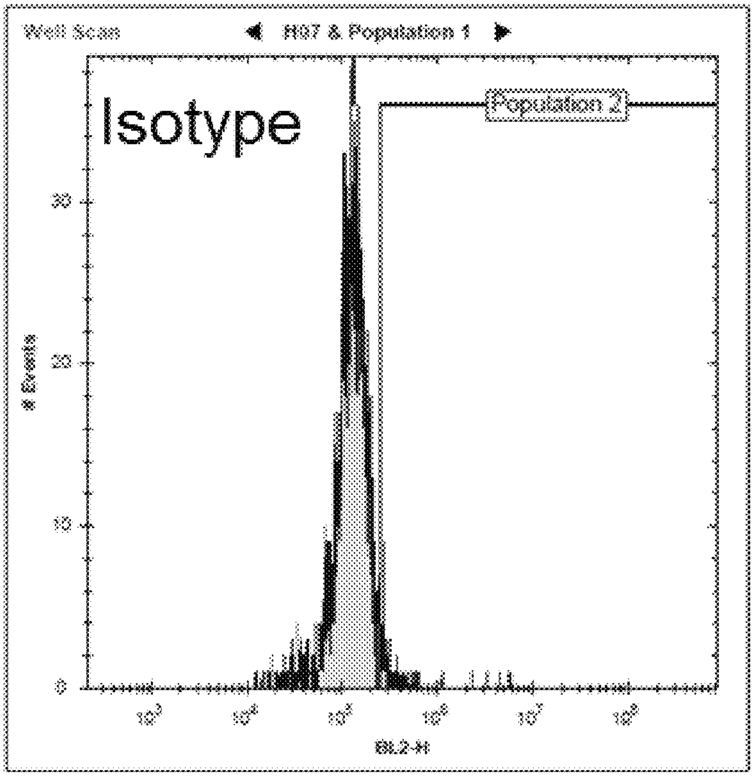
【Figure 5】
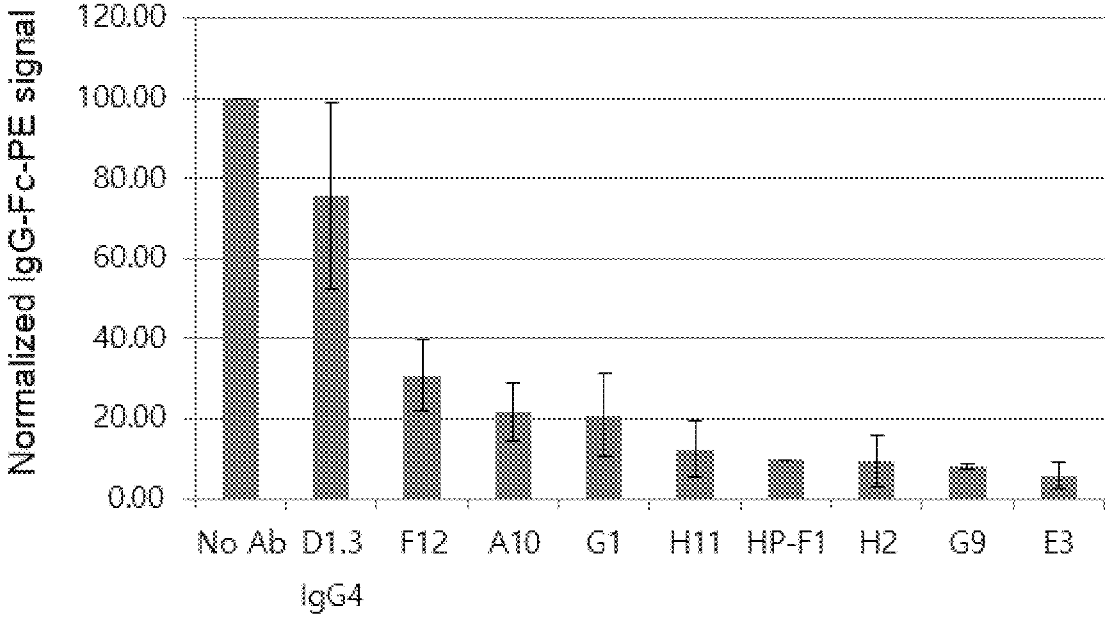

【Figure 6】
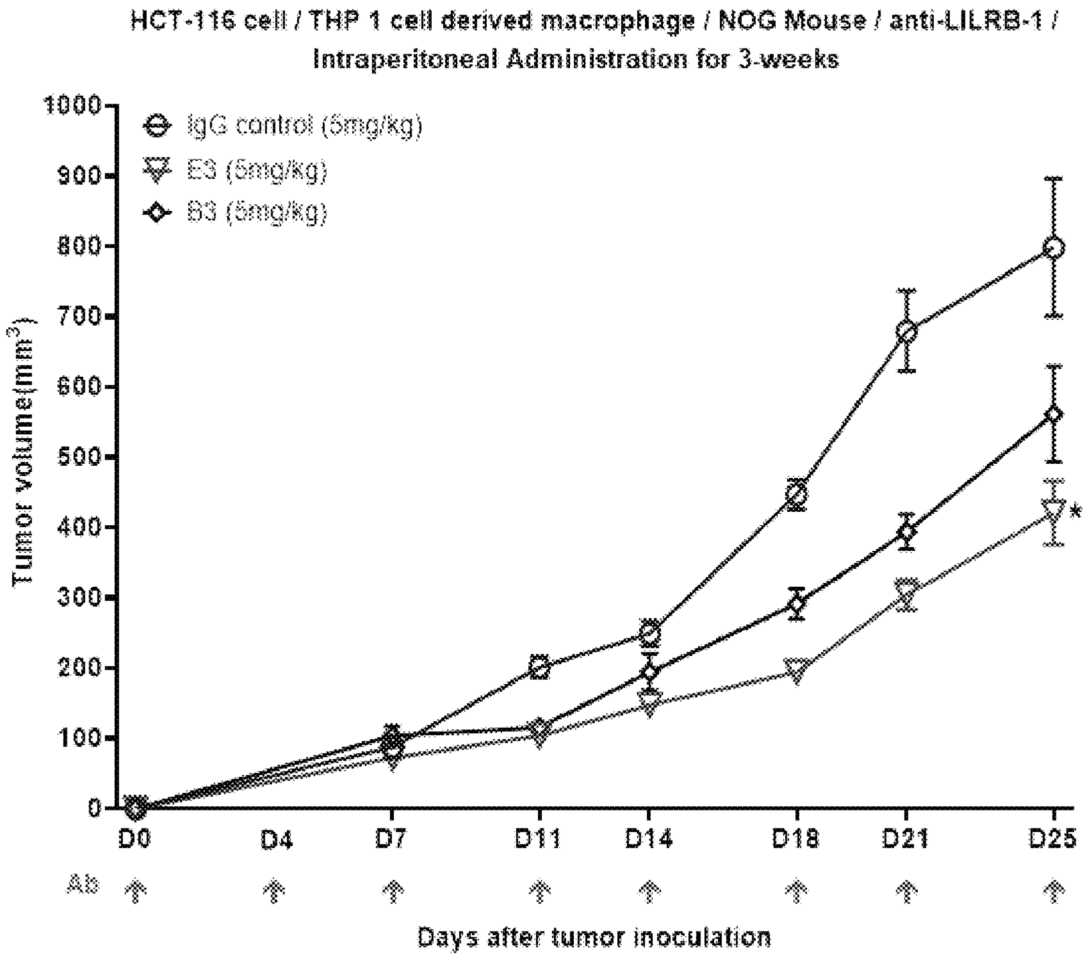
Data are presented as mean and error SEM of 6 mice per group.*P < 0.05, **P < 0.01

【Figure 7a】
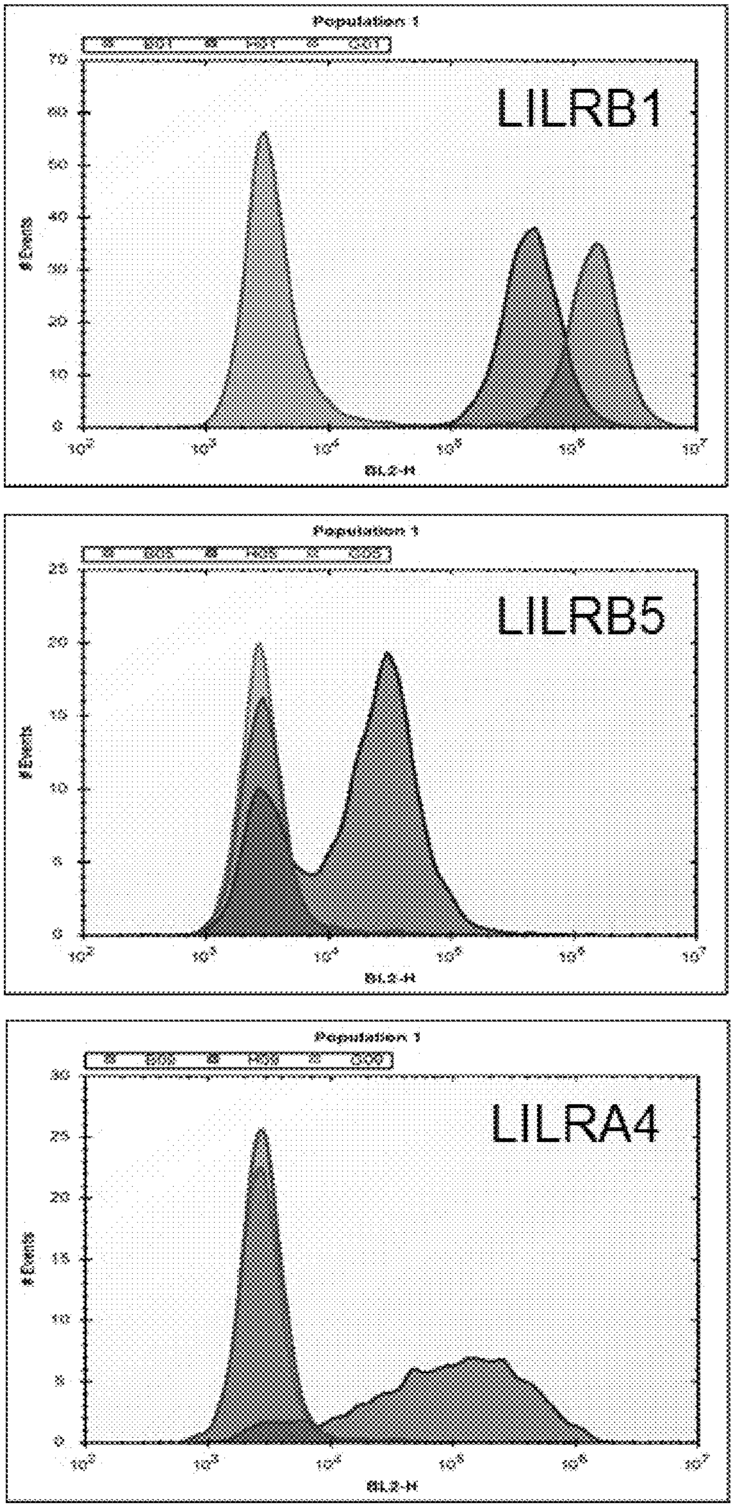

【Figure 7b】
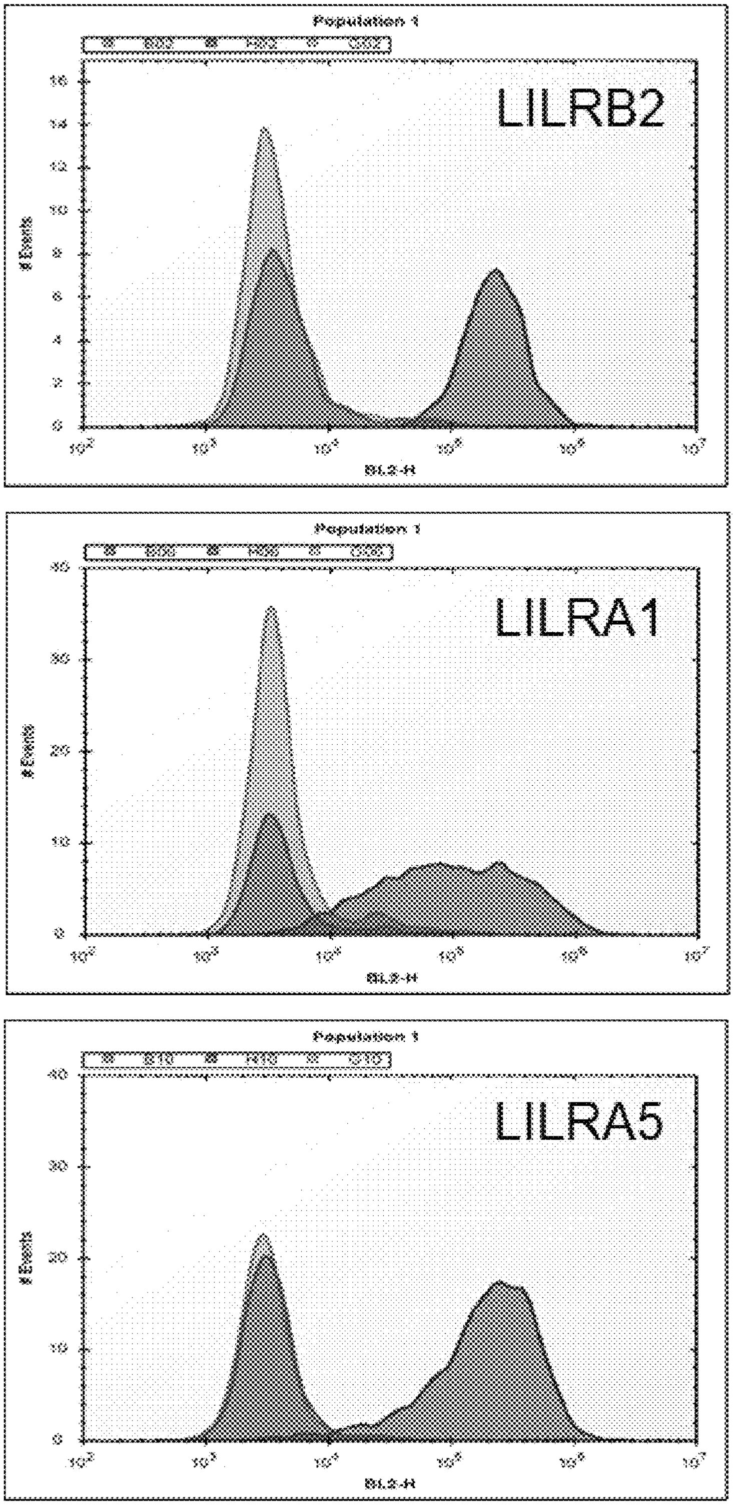

【Figure 7c】
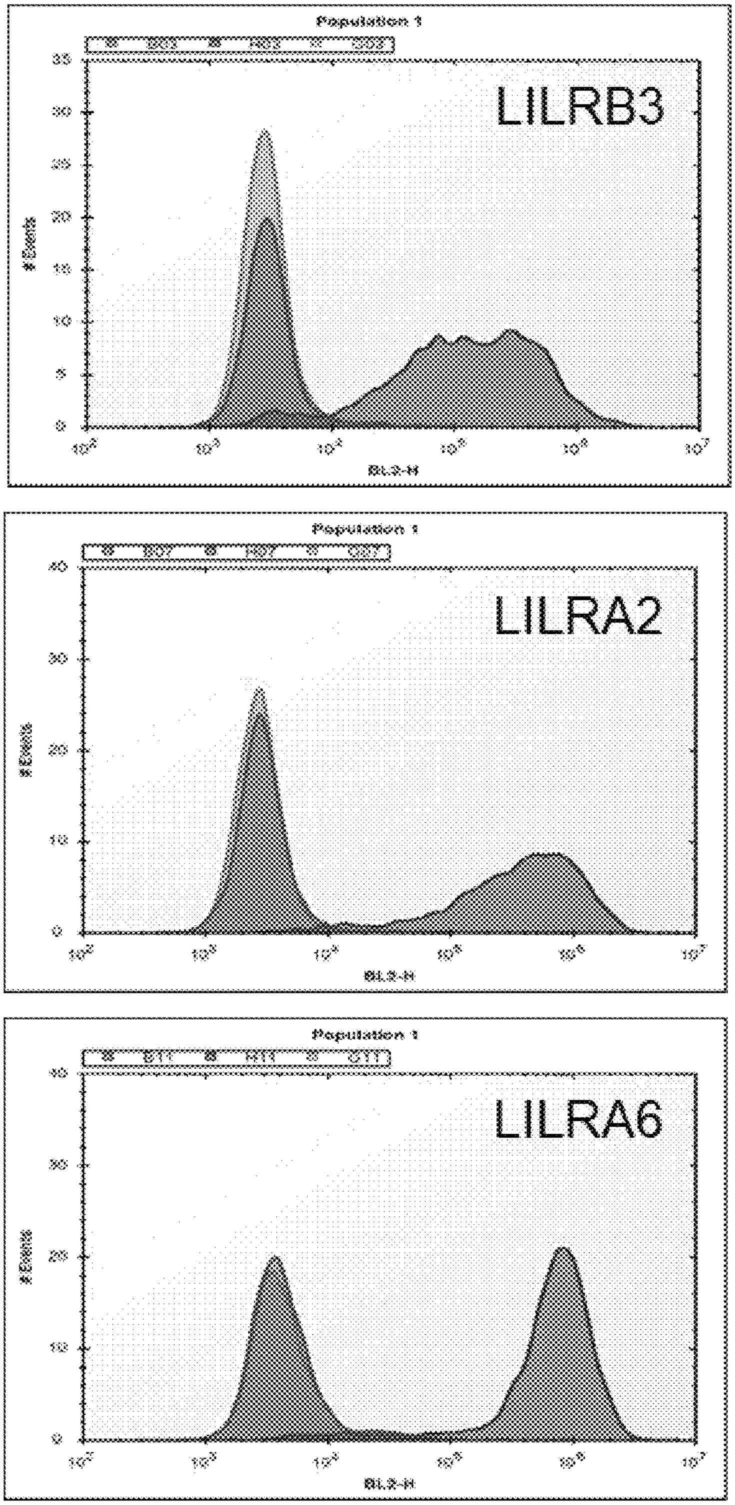

【Figure 7d】
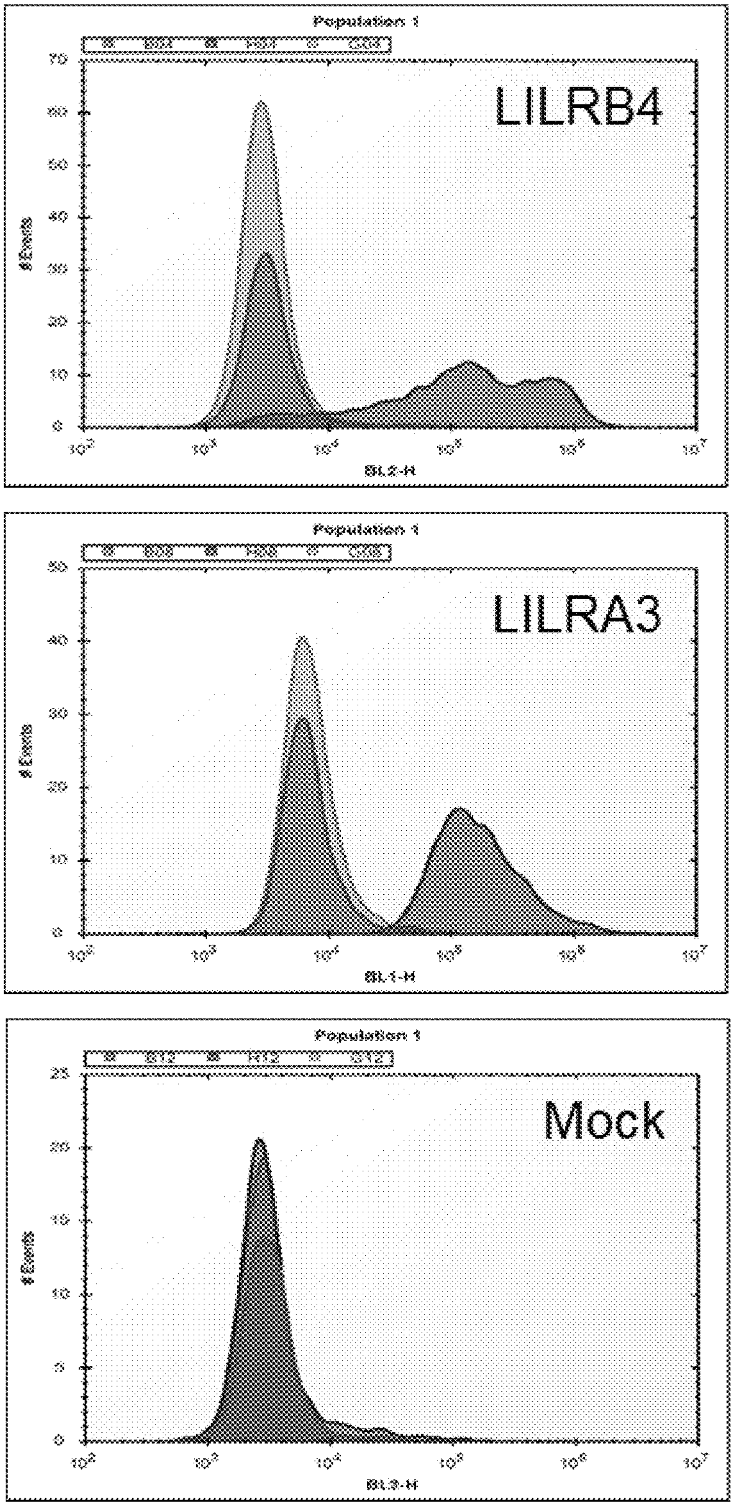

【Figure 8a】
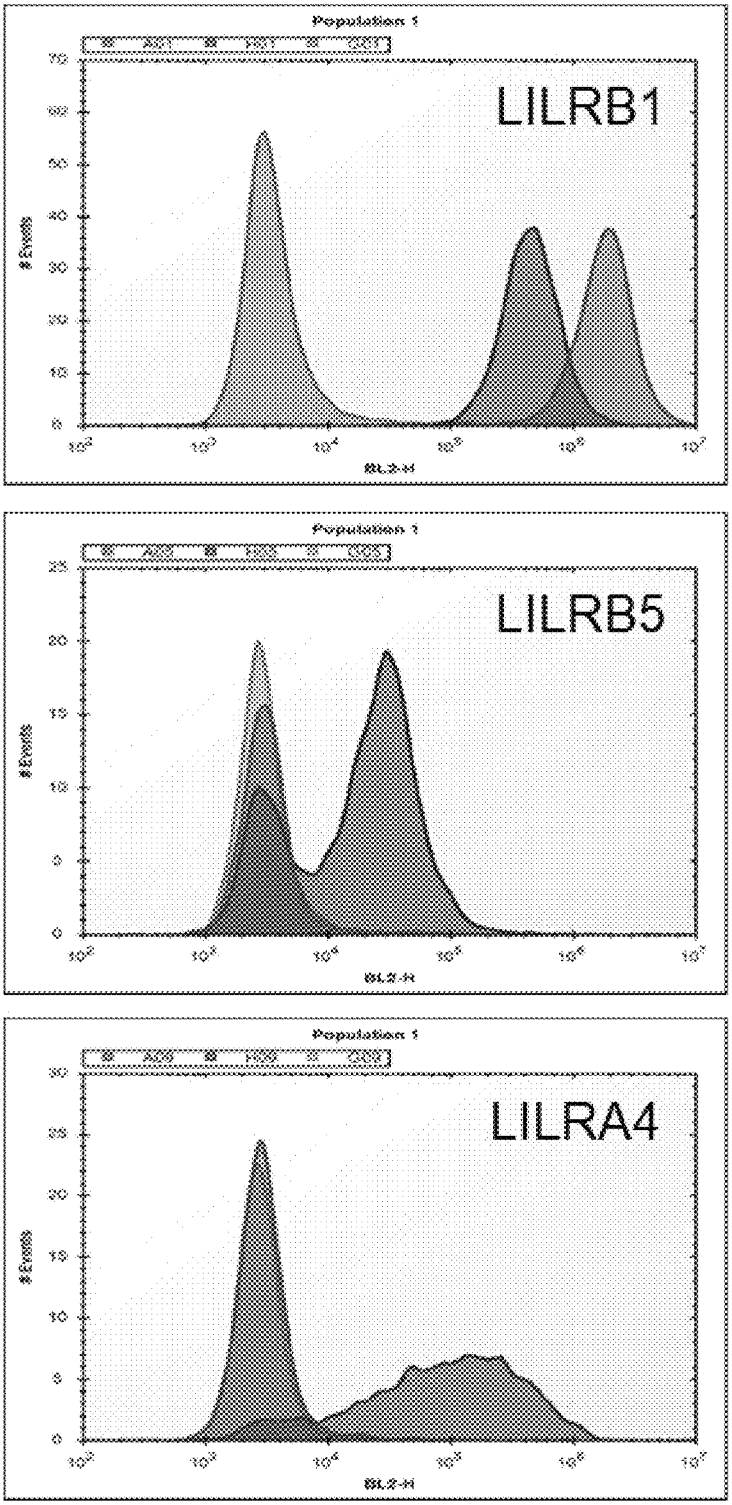

【Figure 8b】
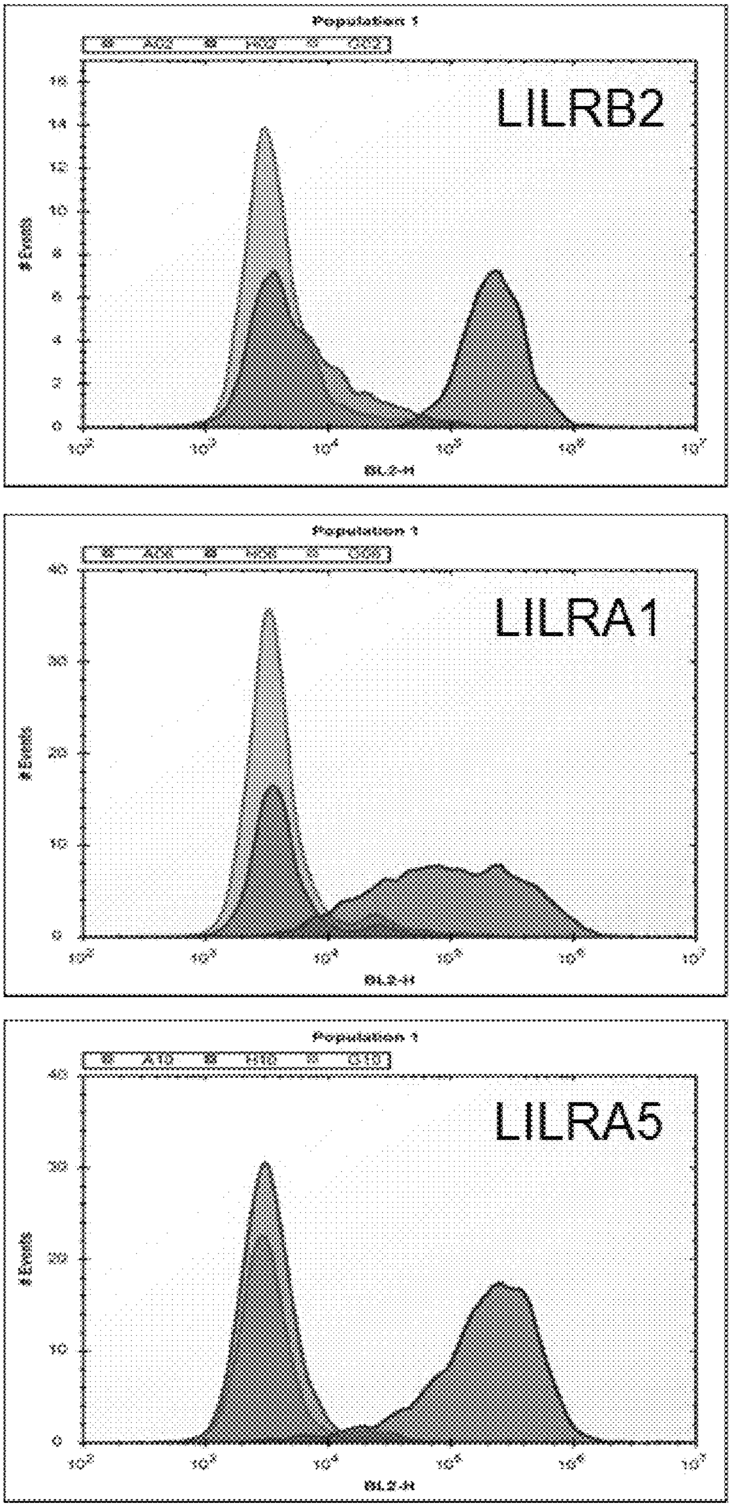

【Figure 8c】
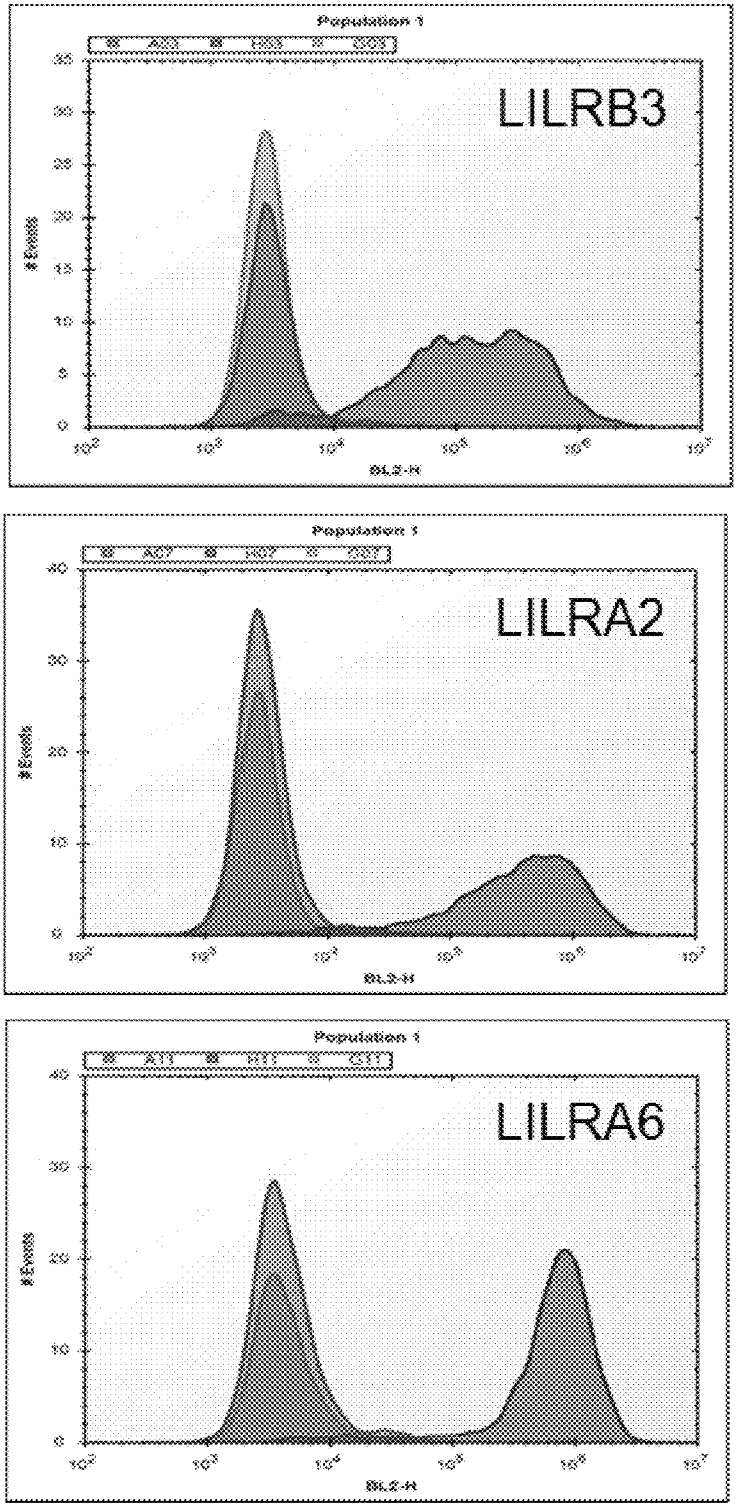

【Figure 8d】
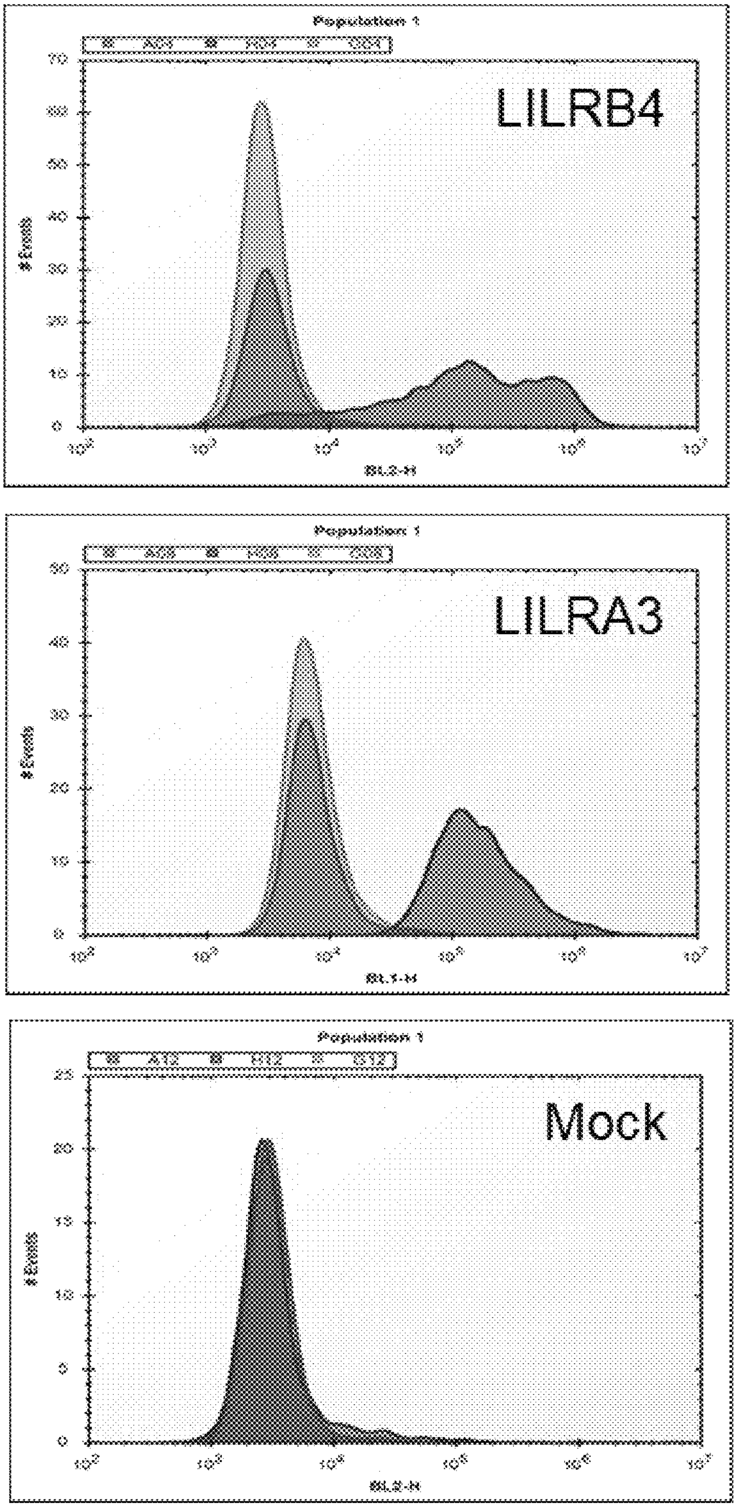

【Figure 9】
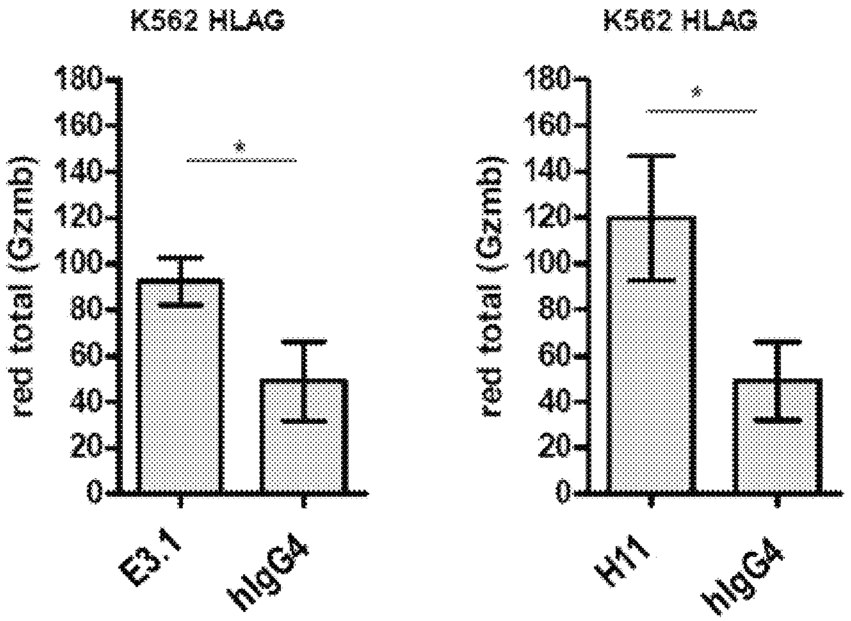
【Figure 10】
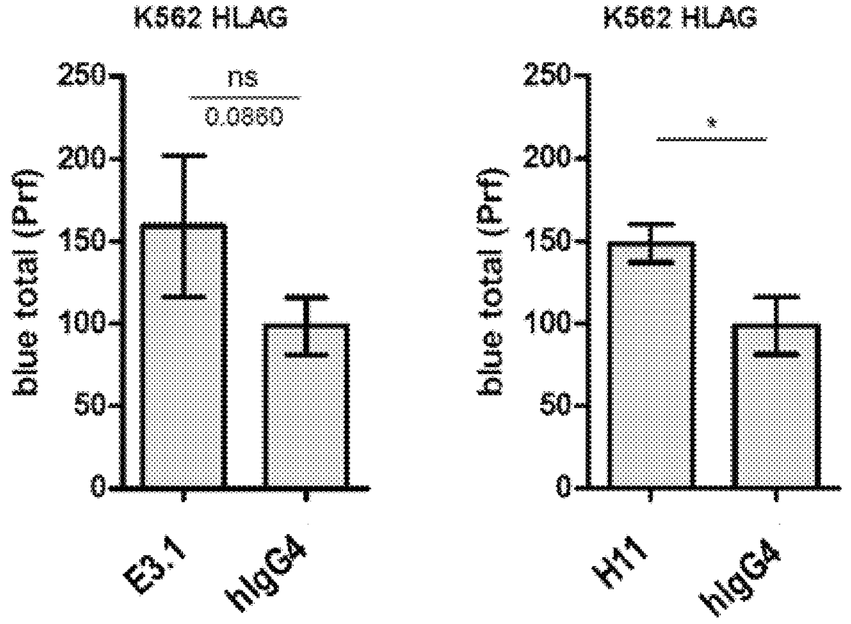

【Figure 11】
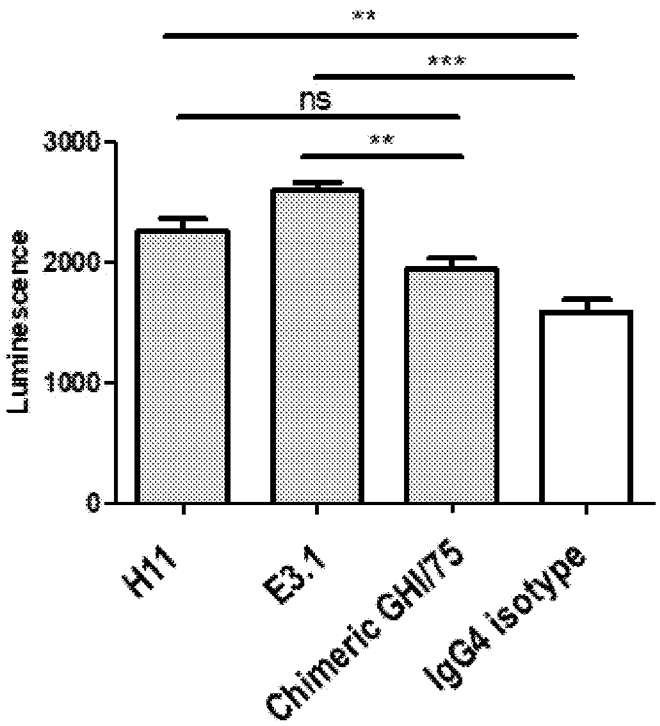

【Figure 12】
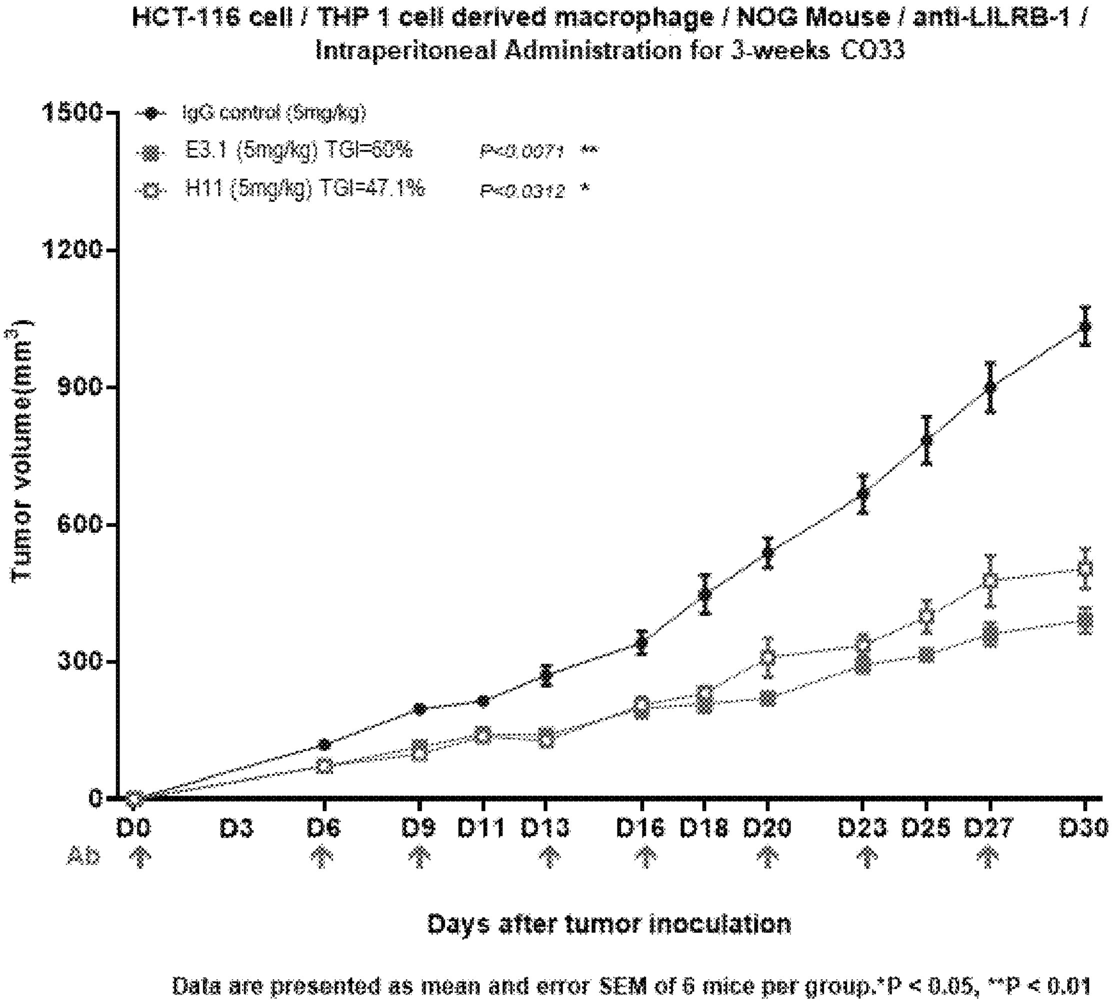

ANTI-LILRB1 ANTIBODY AND USES THEREOF

CROSS-REFERENCE TO RELATED APPLICATIONS

This application is a 35 U.S.C. 371 National Phase Entry Application from PCT/KR2020/018931 filed on Dec. 22, 2020, which claims the benefits of KR 10-2019-0173414 filed on Dec. 23, 2019 and KR 10-2020-0061907 filed on May 22, 2020 with the Korean Intellectual Property Office, the entire disclosures of which are herein incorporated by reference.

TECHNICAL FIELD

The disclosure relates to an anti-LILRB1 antibody and uses thereof. More specifically, an anti-LILRB1 antibody or an antigen-binding fragment thereof, and a use thereof for cancer therapy are provided.

The present application includes a Sequence Listing filed in electronic format. The Sequence Listing is entitled "3570-819_ST25.txt" created on Dec. 21, 2022 and is 292,811 bytes in size. The information in the electronic format of the Sequence Listing is part of the present application and is incorporated herein by reference in its entirety.

BACKGROUND OF THE INVENTION

Leukocyte immunoglobulin-like receptor subfamily B member 1 (LILRB1; also known as ILT2, CD85j, or LIR-1) is an inhibitory receptor, which is expressed in cells such as B cells, T cells, NK cells, dendritic cells, macrophages, and other immune cells. LILRB1 participates in a signal transduction mechanism of inhibiting activities of immune cells by binding classical and non-classical MHC class I.

Meanwhile, it has been reported that various cancer cells overexpress MHC class I such as HLA-G for immune evasion. It has been expected that blocking the binding of LILRB1 to MHC Class I allows recovery of the inhibited activities of immune cells, thereby exhibiting anti-cancer effects.

Therefore, it is required to develop novel agent binding to LILRB1 and blocking the binding of LILRB1 to MHC Class I and/or the interaction between LILRB1 and MHC Class I.

BRIEF SUMMARY OF THE INVENTION

This disclosure provides antibodies, which bind to LILRB1, act on LILRB1-expressing immune cells, regulate activities of the immune cells, and exhibit anti-cancer effects, and uses thereof for cancer therapies.

An embodiment provides an anti-LILRB1 antibody, which binds to LILRB1, or an antigen-binding fragment thereof. The anti-LILRB1 antibody or an antigen-binding fragment thereof may have an activity to block the binding of LILRB1 to MHC Class I and/or blocking the interaction between LILRB1 and MHC Class I. In addition, the anti-LILRB1 antibody or an antigen-binding fragment thereof may have an activity to inhibit immune evasion of cancer cells. Furthermore, the anti-LILRB1 antibody or an antigen-binding fragment thereof may have an anti-cancer effect. The anti-cancer effect may be against a cancer cell expressing or overexpressing MHC Class I on its cell surface.

Another embodiment provides a pharmaceutical composition for treatment and/or prevention of a cancer, the composition comprising the anti-LILRB1 antibody or an antigen-binding fragment thereof as an active ingredient.

Another embodiment provides a pharmaceutical composition for inhibition of binding of LILRB1 to MHC Class I and/or blocking the interaction between LILRB1 and MHC Class I, the composition comprising the anti-LILRB1 antibody or an antigen-binding fragment thereof as an active ingredient.

Another embodiment provides a pharmaceutical composition for inhibiting immune evasion of cancer cell, the composition comprising the anti-LILRB1 antibody or an antigen-binding fragment thereof as an active ingredient.

DETAILED DESCRIPTION OF THE INVENTION

An embodiment provides an anti-LILRB1 antibody, which binds to LILRB1, or an antigen-binding fragment thereof. The anti-LILRB1 antibody or an antigen-binding fragment thereof may have an activity to block the binding of LILRB1 to MHC Class I and/or blocking the interaction between LILRB1 and MHC Class I. In addition, the anti-LILRB1 antibody or an antigen-binding fragment thereof may have an activity to inhibit immune evasion of cancer cells. In addition, the anti-LILRB1 antibody or an antigen-binding fragment thereof may have an anti-cancer effect.

The anti-LILRB1 antibody or an antigen-binding fragment thereof may comprise the following complementarity determining regions (CDRs):

(1) based on the CDR definition according to Kabat numbering (Kabat, E. A., Wu, T. T., Perry, H., Gottesman, K. and Foeller, C. (1991) Sequences of Proteins of Immunological Interest, Fifth Edition. NIH Publication No. 91-3242; http://www.abysis.org/), a CDR-L1 comprising an amino acid sequence of SEQ ID NO: 1, 7, 13, 19, 25, 31, 37, 43, 49, 55, 61, 67, 73, 79, 85, 91, 97, 103, 109, or 115, a CDR-L2 comprising an amino acid sequence of SEQ ID NO: 2, 8, 14, 20, 26, 32, 38, 44, 50, 56, 62, 68, 74, 80, 86, 92, 98, 104, 110, or 116, a CDR-L3 comprising an amino acid sequence of SEQ ID NO: 3, 9, 15, 21, 27, 33, 39, 45, 51, 57, 63, 69, 75, 81, 87, 93, 99, 105, 111, or 117, a CDR-H1 comprising an amino acid sequence of SEQ ID NO: 4, 10, 16, 22, 28, 34, 40, 46, 52, 58, 64, 70, 76, 82, 88, 94, 100, 106, 112, or 118, a CDR-H2 comprising an amino acid sequence of SEQ ID NO: 5, 11, 17, 23, 29, 35, 41, 47, 53, 59, 65, 71, 77, 83, 89, 95, 101, 107, 113, or 119, and a CDR-H3 comprising an amino acid sequence of SEQ ID NO: 6, 12, 18, 24, 30, 36, 42, 48, 54, 60, 66, 72, 78, 84, 90, 96, 102, 108, 114, or 120; or (2) based on the CDR definition according to IMGT numbering (http://www.imgt.org/), a CDR-L1 comprising an amino acid sequence of SEQ ID NO: 121, 126, 131, 136, 141, 146, 151, 156, 161, 166, 171, 176, 181, 186, 191, 196, 201, 206, 211, or 216, a CDR-L2 comprising an amino acid sequence of SEQ ID NO: 122, 127, 132, 137, 142, 147, 152, 157, 162, 167, 172, 177, 182, 187, 192, 197, 202, 207, 212, or 217, a CDR-L3 comprising an amino acid sequence of SEQ ID NO: 3, 9, 15, 21, 27, 33, 39, 45, 51, 57, 63, 69, 75, 81, 87, 93, 99, 105, 111, or 117, a CDR-H1 comprising an amino acid sequence of SEQ ID NO: 123, 128, 133, 138, 143, 148, 153, 158, 163, 168, 173, 178, 183, 188, 193, 198, 203, 208, 213, or 218, a CDR-H2 comprising an amino acid sequence of SEQ ID NO: 124, 129, 134, 139, 144, 149, 154, 159, 164, 169, 174, 179, 184, 189, 194, 199, 204, 209, 214, or 219, and a CDR-H3 comprising an amino acid sequence of SEQ ID NO: 125, 130, 135, 140, 145, 150, 155, 160, 165, 170, 175, 180, 185, 190, 195, 200, 205, 210, 215, or 220.

In a specific embodiment, combinations of 6 CDRs (CDR-L1, CDR-L2, CDR-L3, CDR-H1, CDR-H2, and CDR-H3) that can be comprised in the anti-LILRB1 antibody or an antigen-binding fragment thereof provided in this disclosure are illustrated in Table 1:

TABLE 1

| | CDR | Amino Acid Sequence (N→C) (Kabat) | SEQ ID NO | Amino Acid Sequence (N→C) (IMGT) | SEQ ID NO |
|---|---|---|---|---|---|
| E3/ E3.1 | CDR-L1 | QGDSLRNFYAS | 1 | SLRNFY | 121 |
| | CDR-L2 | GKNNRPS | 2 | GKN | 122 |
| | CDR-L3 | NSRDSSGSHLTGV | 3 | NSRDSSGSHLTGV | 3 |
| | CDR-H1 | SYAMS | 4 | GFTFSSYA | 123 |
| | CDR-H2 | AISGSGGSTYYADSVKG | 5 | ISGSGGST | 124 |
| | CDR-H3 | DTYYYGSGRSNAFDI | 6 | ARDTYYYGSGRSNAFDI | 125 |
| B3 | CDR-L1 | QASQDISNYLN | 7 | QDISNY | 126 |
| | CDR-L2 | DASNLET | 8 | DAS | 127 |
| | CDR-L3 | QQYDNLP | 9 | QQYDNLP | 9 |
| | CDR-H1 | DYAMH | 10 | GFTFDDYA | 128 |
| | CDR-H2 | GISWNSGSIGYADSVKG | 11 | ISWNSGSI | 129 |
| | CDR-H3 | VGDSSGWSDAFDI | 12 | ARVGDSSGWSDAFDI | 130 |
| A10 | CDR-L1 | RASQSVSSNLA | 13 | QSVSSN | 131 |
| | CDR-L2 | GASTRAT | 14 | GAS | 132 |
| | CDR-L3 | QQYGSSPRMYT | 15 | QQYGSSPRMYT | 15 |
| | CDR-H1 | SYAIS | 16 | GGTFSSYA | 133 |
| | CDR-H2 | GIIPIFGTANYAQKFQG | 17 | IIPIFGTA | 134 |
| | CDR-H3 | GGLGELDNWFDP | 18 | ARGGLGELDNWFDP | 135 |
| G1 | CDR-L1 | SGYKLGDRYVS | 19 | KLGDRY | 136 |
| | CDR-L2 | KDSQRPS | 20 | KDS | 137 |
| | CDR-L3 | QAWDSGTGV | 21 | QAWDSGTGV | 21 |
| | CDR-H1 | SYGIS | 22 | GGTFSSYG | 138 |
| | CDR-H2 | WISAYNGNTNYAQELQG | 23 | ISAYNGNT | 139 |
| | CDR-H3 | VGVAGKLDY | 24 | ARVGVAGKLDY | 140 |
| G9 | CDR-L1 | TGSSSDVGGYNYVS | 25 | SSDVGGYNY | 141 |
| | CDR-L2 | DVSNRPS | 26 | DVS | 142 |
| | CDR-L3 | SSYTGSSTLDVL | 27 | SSYTGSSTLDVL | 27 |
| | CDR-H1 | SYWIG | 28 | GYSFTSYW | 143 |
| | CDR-H2 | IIYPGDSDTRYSPSFQG | 29 | IYPGDSDT | 144 |
| | CDR-H3 | QYYDGGYYMDV | 30 | ASQYYDGGYYMDV | 145 |
| H2 | CDR-L1 | QGDSLRNYYAS | 31 | SLRNYY | 146 |
| | CDR-L2 | GNNKRPS | 32 | GNN | 147 |
| | CDR-L3 | NSLDSTYNHPI | 33 | NSLDSTYNHPI | 33 |
| | CDR-H1 | SYDIH | 34 | GYTFTSYD | 148 |
| | CDR-H2 | WISAYNGNTNYAQKLQG | 35 | ISAYNGNT | 149 |
| | CDR-H3 | DGGDAFDI | 36 | ARDGGDAFDI | 150 |
| H11 | CDR-L1 | QGDSLRSYYAS | 37 | SLRSYY | 151 |
| | CDR-L2 | GRNNRPS | 38 | GRN | 152 |
| | CDR-L3 | KSRDSSGNHYV | 39 | KSRDSSGNHYV | 39 |
| | CDR-H1 | SYYMH | 40 | GYTFTSYY | 153 |
| | CDR-H2 | IINPSGGSTSYAQKFQG | 41 | INPSGGST | 154 |
| | CDR-H3 | DAGSSSDY | 42 | ARDAGSSSDY | 155 |
| F12 | CDR-L1 | AGTSSDIGDYDYVS | 43 | SSDIGDYDY | 156 |
| | CDR-L2 | DVSRRPS | 44 | DVS | 157 |
| | CDR-L3 | ASYTSSSVVV | 45 | ASYTSSSVVV | 45 |
| | CDR-H1 | SYWIG | 46 | GYSFTSYW | 158 |
| | CDR-H2 | IIYPGDSDTRYSPSFQG | 47 | IYPGDSDT | 159 |
| | CDR-H3 | QYYDGGYYMDV | 48 | ASQYYDGGYYMDV | 160 |
| B9 | CDR-L1 | RASQSISRYLN | 49 | QSISRY | 161 |
| | CDR-L2 | GASSLQS | 50 | GAS | 162 |
| | CDR-L3 | QQAYGFPLT | 51 | QQAYGFPLT | 51 |
| | CDR-H1 | SYAIS | 52 | GGTFSSYA | 163 |
| | CDR-H2 | GIIPIFGTANYAQKFQG | 53 | IIPIFGTA | 164 |
| | CDR-H3 | GEIAVAQNWDYYGMDV | 54 | ARGEIAVAQNWDYYGMDV | 165 |
| G11 | CDR-L1 | TGTSSDVGGYNYVS | 55 | SSDVGGYNY | 166 |
| | CDR-L2 | DVSKRPS | 56 | DVS | 167 |
| | CDR-L3 | SSYSSSSTLVV | 57 | SSYSSSSTLVV | 57 |
| | CDR-H1 | SYWIG | 58 | GYSFTSYW | 168 |
| | CDR-H2 | IIYPGDSDTRYSPSFQG | 59 | IYPGDSDT | 169 |
| | CDR-H3 | QYYDGGYYMDV | 60 | ASQYYDGGYYMDV | 170 |
| G6 | CDR-L1 | QGDSLRRYYAT | 61 | SLRRYY | 171 |
| | CDR-L2 | GQNYRPS | 62 | GQN | 172 |
| | CDR-L3 | NSRDSSGNHVV | 63 | NSRDSSGNHVV | 63 |
| | CDR-H1 | SYYMH | 64 | GYTFTSYY | 173 |
| | CDR-H2 | GIIPIFGTANYAQKFQG | 65 | IIPIFGTA | 174 |
| | CDR-H3 | GWGYSSSFDY | 66 | ARGWGYSSSFDY | 175 |
| F11 | CDR-L1 | SGSSSNIGTNTVN | 67 | SSNIGTNT | 176 |
| | CDR-L2 | SNDQRPS | 68 | SND | 177 |
| | CDR-L3 | ETWDDSLKGPV | 69 | ETWDDSLKGPV | 69 |
| | CDR-H1 | SYAMS | 70 | GFTFSSYA | 178 |
| | CDR-H2 | TISGSGDSTYYADSVKG | 71 | ISGSGDST | 179 |
| | CDR-H3 | EWELGDAFDI | 72 | AREWELGDAFDI | 180 |
| D3 | CDR-L1 | RASQSISSYLN | 73 | QSISSY | 181 |
| | CDR-L2 | AASSLQS | 74 | AAS | 182 |
| | CDR-L3 | QQSYSTRWT | 75 | QQSYSTRWT | 75 |
| | CDR-H1 | SYAMS | 76 | GSTFSSYA | 183 |
| | CDR-H2 | AISGSGGSTYYADSVKG | 77 | ISGSGGST | 184 |
| | CDR-H3 | DRGSYGYYYGMDV | 78 | AKDRGSYGYYYGMDV | 185 |
| B12 | CDR-L1 | RASQSISSYLN | 79 | QSISSY | 186 |
| | CDR-L2 | AASSLOS | 80 | AAS | 187 |
| | CDR-L3 | QQSYSTLRT | 81 | QQSYSTLRT | 81 |
| | CDR-H1 | GYYMH | 82 | GYTFTGYY | 188 |
| | CDR-H2 | WINPNSGGTNYAQKFQG | 83 | INPNSGGT | 189 |
| | CDR-H3 | AGASIVGATALDY | 84 | TRAGASIVGATALDY | 190 |
| E4 | CDR-L1 | TRSSGSIASNYVQ | 85 | SGSIASNY | 191 |
| | CDR-L2 | EDNQRPS | 86 | EDN | 192 |
| | CDR-L3 | QSYDTGNRNYV | 87 | QSYDTGNRNYV | 87 |
| | CDR-H1 | SYTIS | 88 | GGTFSSYT | 193 |
| | CDR-H2 | RIIPILGIANYAQKFQG | 89 | IIPILGIA | 194 |
| | CDR-H3 | GPSLNYAGYFDN | 90 | VRGPSLNYAGYFDN | 195 |
| E12 | CDR-L1 | QGDSLRSYYAS | 91 | SLRSYY | 196 |
| | CDR-L2 | GKEKRPS | 92 | GKE | 197 |
| | CDR-L3 | NSRGSTTDYMV | 93 | NSRGSTTDYMV | 93 |
| | CDR-H1 | SYAMH | 94 | GFTFSSYA | 198 |
| | CDR-H2 | VISYDGSNKYYADSVKG | 95 | ISYDGSNK | 199 |
| | CDR-H3 | ERGSGMDV | 96 | ARERGSGMDV | 200 |
| D1 | CDR-L1 | KASQDIDDDMN | 97 | QDIDDD | 201 |
| | CDR-L2 | EASTLVP | 98 | EAS | 202 |
| | CDR-L3 | LQHDKFPYT | 99 | LQHDKFPYT | 99 |
| | CDR-H1 | SYGIS | 100 | GYTFTSYG | 203 |
| | CDR-H2 | WINPNSGGTNYAQKFQG | 101 | INPNSGGT | 204 |
| | CDR-H3 | RGVDEGDY | 102 | ASRGVDEGDY | 205 |
| E6 | CDR-L1 | TGSSGNIASNYVQ | 103 | SGNIASNY | 206 |
| | CDR-L2 | RDDQRPS | 104 | RDD | 207 |

TABLE 1-continued

| | CDR | Amino Acid Sequence (N→C) (Kabat) | SEQ ID NO | Amino Acid Sequence (N→C) (IMGT) | SEQ ID NO |
|---|---|---|---|---|---|
| | CDR-L3 | QSYDSSSWV | 105 | QSYDSSSWV | 105 |
| | CDR-H1 | TYDIT | 106 | GYTFTTYD | 208 |
| | CDR-H2 | WMNPNSGNSRSAQKFQG | 107 | MNPNSGNS | 209 |
| | CDR-H3 | GDYSGVVLTATALDY | 108 | ATGDYSGVVLTATALDY | 210 |
| E9 | CDR-L1 | SGSSSNIGNNYVY | 109 | SSNIGNNY | 211 |
| | CDR-L2 | RNNQRPS | 110 | RNN | 212 |
| | CDR-L3 | AAWDDSLSGWV | 111 | AAWDDSLSGWV | 111 |
| | CDR-H1 | SYGMH | 112 | GFTFSSYG | 213 |
| | CDR-H2 | NIKQDGSEKYYVDSVKG | 113 | IKQDGSEK | 214 |
| | CDR-H3 | EDRIAAAGMRELDY | 114 | AREDRIAAAGMRELDY | 215 |
| A11 | CDR-L1 | RSSQSLLHSNGYNYLD | 115 | QSLLHSNGYNY | 216 |
| | CDR-L2 | LGSNRAS | 116 | LGS | 217 |
| | CDR-L3 | MQGTHWPPYT | 117 | MQGTHWPPYT | 117 |
| | CDR-H1 | SYAMT | 118 | GFSFTSYA | 218 |
| | CDR-H2 | GISSDGTTTTYADSVRG | 119 | ISSDGTTT | 219 |
| | CDR-H3 | DQLLGWDALNV | 120 | ARDQLLGWDALNV | 220 |

In an embodiment, the anti-LILRB1 antibody or an antigen-binding fragment thereof may comprise:

a light chain variable region comprising a CDR-L1, a CDR-L2, and CDR-L3, and a heavy chain variable region comprising a CDR-H1, a CDR-H2, and a CDR-H3, wherein the CDRs are as described above.

More specifically, the anti-LILRB1 antibody or an antigen-binding fragment thereof may comprise:

a light chain variable region comprising an amino acid sequence of SEQ ID NO: 221, 223, 225, 227, 229, 231, 233, 235, 237, 239, 241, 243, 245, 247, 249, 251, 253, 255, 257, 259, or 345, and a heavy chain variable region comprising an amino acid sequence of SEQ ID NO: 222, 224, 226, 228, 230, 232, 234, 236, 238, 240, 242, 244, 246, 248, 250, 252, 254, 256, 258, or 260.

In a specific embodiment, combinations of a light chain variable region and a heavy chain variable region that can be comprised in the anti-LILRB1 antibody or an antigen-binding fragment thereof provided in this disclosure are illustrated in Table 2:

TABLE 2

| | variable region | Amino acid sequence (N→C) | SEQ ID NO |
|---|---|---|---|
| E3 | light chain variable region | SYELTQDPAVSVALGQTVRITCQGDSLRNFYASWYQQKSGQAPVLVMYGKNNRPSGIPDRFSGSTSGNTASLTITGAQAEDEADYYCNSRDSSGSHLTGVFGGGTKVTVLGQPAAA | 221 |
| | heavy chain variable region | QVQLVESGGGLVQPGGSLRLSCAASGFTFSSYAMSWVRQAPGKGLEWVSAISGSGGSTYYADSVKGRFTISRDNSKNTLYLQMISLRAEDTAVYYCARDTYYYGSGRSNAFDIWGQGTLVTVSS | 222 |
| B3 | light chain variable region | DIQMTQSPSSLSASVGDRVTITCQASQDISNYLNWYQQKPGKAPKLLIYDASNLETGVPSRFSGSGSGTDFTFTISSLQPEDIATYYCQQYDNLPFGGGTKVDIKRTAAA | 223 |
| | heavy chain variable region | EVQLLESGGGLVQPGRSLRLSCAASGFTFDDYAMHWVRQAPGKGLEWVSGISWNSGSIGYADSVKGRFTISRDNSKNTLYLQMNSLRAEDTAVYYCARVGDSSGWSDAFDIWGQGTMVTVSS | 224 |
| A10 | light chain variable region | DIVMTQSPATLSVSPGERATLSCRASQSVSSNLAWYQQKPGQAPRLLIYGASTRATGIPARFSGSGSGTEFTLTISSLQSEDFAVYYCQQYGSSPRMYTFGQGTKVDIKRTAAA | 225 |
| | heavy chain variable region | QMQLVQSGAEVKKPGSSVKVSCKASGGTFSSYAISWVRQAPGQGLEWMGGIIPIFGTANYAQKFQGRVTITADKSISTAYMELSSLRSEDTAVYYCARGGLGELDNWFDPWGQGTLVTVSS | 226 |
| G1 | light chain variable region | SYELTQPPSLSVSPGQTASITCSGYKLGDRYVSWYQQKTGQSPVVVIYKDSQRPSGVPERFSGSNSGNTATLTISGTQAMDEADYYCQAWDSGTGVFGGGTKLTVLGQPAAA | 227 |
| | heavy chain variable region | EVQLVQSGAEVKKPGSSVKVSCKASGGTFSSYGISWVRQAPGQGLEWMGWISAYNGNTNYAQELQGRVTMTTDTSTSTAYMELRSLRSDDTAVYYCARVGVAGKLDYWGQGTLVTVSS | 228 |
| G9 | light chain variable region | QSALTQPASVSGSPGQSITISCTGSSSDVGGYNYVSWYQQHPGKAPKLMIYDVSNRPSGVSDRFSGSKSGNMASLTISGLQAEDEADYYCSSYTGSSTLDVLFGGGTKLTVLGQPAAA | 233 |
| | heavy chain variable region | QVQLVQPGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSS | 234 |

TABLE 2-continued

| | variable region | Amino acid sequence (N→C) | SEQ ID NO |
|---|---|---|---|
| H2 | light chain variable region | SYELTQDPAVSVALGQTVRITCQGDSLRNYYASWYQQKPGQAPILVISGNNKRPSGIPDRFSGSSSGDTASLTISGAQAEDEADYYCNSLDSTYNHPIFGGGTKVTVLGQPAAA | 235 |
| | heavy chain variable region | QVQLVQSGAEVKKPGASVKVSCKASGYTFTSYDIHWVRQATGQGLEWMGWISAYNGNTNYAQKLQGRVTMTTDTSTSTAYMELRSLRSDDTAVYYCARDGGDAFDIWGQGTLVTVSS | 236 |
| H11 | light chain variable region | SYELTQDPAASVALGQTVRITCQGDSLRSYYASWYQQKPGQAPVVVIYGRNNRPSGIPDRFSGSSSGDTASLTITGAQAEDEADYYCKSRDSSGNHYVFGTGTKLTVLGQPAAA | 231 |
| | heavy chain variable region | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDAGSSSDYWGRGTLVTVSS | 232 |
| F12 | light chain variable region | QSVLTQPASVSGSPGQSITISCAGTSSDIGDYDYVSWYQQHPGKTPKLMIYDVSRRPSGVPDRFSGSKSGNTASLTISGLQTEDEADYYCASYTSSSVVVFGGGTKLTVLGQPAAA | 237 |
| | heavy chain variable region | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSS | 238 |
| B9 | light chain variable region | DIQMTQSPSSLSASVGDRVTITCRASQSISRYLNWYQQKPGKAPKLLIYGASSLQSGVPSRFSGSGSGTDFTLTISSLQPEDFATYHCQQAYGFPLTLGGGTKVEIKRTAAA | 229 |
| | heavy chain variable region | QVQLVESGAEVKKPGSSVKVSCKASGGTFSSYAISWVRQAPGQGLEWMGGIIPIFGTANYAQKFQGRVTITADESTSTAYMELSSLRSEDTAVYYCARGEIAVAQNWDYYGMDVWGQGTLVTVSS | 230 |
| G11 | light chain variable region | QSALTQPRSVSGSPGQSVTISCTGTSSDVGGYNYVSWYQQHPGKAPKLMIYDVSKRPSGVPDRFSGSKSGNTASLTISGLQAEDEADYYCSSYSSSSTLVVFGGGTKLTVLGQPAAA | 239 |
| | heavy chain variable region | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSS | 240 |
| G6 | light chain variable region | SYELTQDPAVSVALGQTVTITCQGDSLRRYYATWYQQKPGQAPVLVIYGQNYRPSGIPDRFSGSNSGTTASLTITGAQAEDEADYYCNSRDSSGNHVVFGGGTKLTVLGQPAAA | 241 |
| | heavy chain variable region | EVQLVESGAEVKKPGASVKVSCKASGYTFTSYYMHWVRQAPGQGLEWMGGIIPIFGTANYAQKFQGRVTITADESTSTAYMELSSLRSEDTAVYYCARGWGYSSSFDYWGQGTTVTVSS | 242 |
| F11 | light chain variable region | QSVLTQPPSTSGTPGQTFSIFCSGSSSNIGTNTVNWYQQLPGTAPKLLIYSNDQRPSGVPDRFSGSKSGTSASLAISGLQSEDEADYYCETWDDSLKGPVFGGGTKVTVLGQPAAA | 243 |
| | heavy chain variable region | EVQLVESGGGLVQPGGSLKLSCAASGFTFSSYAMSWVRRAPGKGLEWVSTISGSGDSTYYADSVKGRFTISRDNSKNTLYLQMNNLRAEDTAVYYCAREWELGDAFDIWGRGTLVTVSS | 244 |
| D3 | light chain variable region | DIQMTQSPSSLSASVGDRVTITCRASQSISSYLNWYQQKPGKAPKLLIYAASSLQSGVPSRFSGSGSGTDFTLTISSLQPEDFATYYCQQSYSTRWTFGQGTKVEIKRTAAA | 245 |
| | heavy chain variable region | EVQLLESGGGVVQPGRSLRLSCAASGSTFSSYAMSWVRQAPGKGLEWVSAISGSGGSTYYADSVKGRFTISRDNSKNTLYLQMNSLRAEDTAVYYCAKDRGSYGYYYGMDVWGQGTMVTVSS | 246 |

TABLE 2-continued

| | variable region | Amino acid sequence (N→C) | SEQ ID NO |
|---|---|---|---|
| B12 | light chain variable region | DIQMTQSPSSLSASVGDRVTITCRASQSISSYLNWYQQK PGKAPKLLIYAASSLQSGVPSRFSGSGSGTDFTLTISSLQ PEDFATYYCQQSYSTLRTFGQGTKVEIKRTAAA | 247 |
| | heavy chain variable region | QVQLVQSGAEVKKPGASVKVSCKASGYTFTGYYMHWV RQAPGQGLEWMGWINPNSGGTNYAQKFQGRVTITADES TSTAYMELSSLRSEDTAVYYCTRAGASIVGATALDYWGQ GTLVTVSS | 248 |
| E4 | light chain variable region | NFMLTQPHSVSESPGKTVTISCTRSSGSIASNYVQWYQQ RPGSSPTTVIYEDNQRPSGVPDRFSGSIDSSSNSASLTIS GLKTEDEADYYCQSYDTGNRNYVFGTGTQLTVLGQPAA A | 249 |
| | heavy chain variable region | QVQLVQSGAEVKKPGSSVKVSCKASGGTFSSYTISWVR QAPGQGLEWMGRIIPILGIANYAQKFQGRVTMTRDMSTD TAYMELSSLTYDDTAVYFCVRGPSLNYAGYFDNWGQGT LVTVSS | 250 |
| E12 | light chain variable region | SYELTQDPAVSVALGQTVRITCQGDSLRSYYASWYQQKS GQAPVLVIYGKEKRPSGIPDRFSGSSSGNTASLTITGARA EDEADYYCNSRGSTTDYMVFGGGTQLTVLGQPAAA | 251 |
| | heavy chain variable region | QVQLVESGGGLVQPGGSLRLSCAASGFTFSSYAMHWVR QAPGKGLEWVAVISYDGSNKYYADSVKGRFTISRDNSKN TLYLQMNSLRAEDTAVYYCARERGSGMDVWGQGTLVTV SS | 252 |
| D1 | light chain variable region | ETTLTQSPAFMSATPGDKVNISCKASQDIDDDMNWYQQK PGEAAISIIQEASTLVPGIPPRFSGSGYGTDFTLTINNIESE DAAYYFCLQHDKFPYTFGQGTKLEIKRTAAA | 253 |
| | heavy chain variable region | EVQLVQSGAEVKKPGASVKVSCKASGYTFTSYGISWVR QAPGQGLEWMGWINPNSGGTNYAQKFQGRVTMTRDTS ISTAYMELSRLRSDDTAVYYCASRGVDEGDYWGQGTMV TVSS | 254 |
| E6 | light chain variable region | NFMLTQPHSVSESPGKTVTLSCTGSSGNIASNYVQWYQ HRPGSAPTTVIYRDDQRPSGVPDRFSGSIDSSSNSASLTI SGLRPEDEADYYCQSYDSSSWVFGGGTKLTVLGQPAAA | 255 |
| | heavy chain variable region | QVQLVQSGAEVKKPGASVKVSCKASGYTFTTYDITWVR QAPGQGLEWMGWMNPNSGNSRSAQKFQGRVSMTSDS SISTAYMELSSLRSEDTAVYYCATGDYSGVVLTATALDY WGQGTLVTVSS | 256 |
| E9 | light chain variable region | QSELTQLPSASETPGQRVTISCSGSSSNIGNNYVYWYQQ LPGTAPKLLIYRNNQRPSGVPDRFSGSKSGTSASLAISGL RSEDEADYYCAAWDDSLSGWVFGGGTKLTVLGQPAAA | 257 |
| | heavy chain variable region | QVQLVESGGGLVQPGRSLRLSCAASGFTFSSYGMHWV RQAPGKGLEWVANIKQDGSEKYYVDSVKGRFTISRDNA KNTLYLQMNSLRAEDTAVYYCAREDRIAAAGMRELDYW GQGTLVTVSS | 258 |
| A11 | light chain variable region | DIVMTQSPLSLPVTPGEPASISCRSSQSLLHSNGYNYLD WYLQKPGQSPQLLIYLGSNRASGVPDRFSGSGSGTDFT LKISRVEAEDVGVYYCMQGTHWPPYTFGQGTKVEIKRTA AA | 259 |
| | heavy chain variable region | EVQLLESGGGLEQPGGFLRLSCAASGFSFTSYAMTWVR QAPGKGLEWVSGISSDGTTTTYADSVRGRFTISRDNAKN TVYLQMNSLRDEDTAVYYCARDQLLGWDALNVWGQGT MVTVSS | 260 |
| E3.1 | light chain variable region | SYELTQDPAVSVALGQTVRITCQGDSLRNFYASWYQQKS GQAPVLVMYGKNNRPSGIPDRFSGSTSGNTASLTITGAQ AEDEADYYCNSRDSSGSHLTGVFGGGTKVTVL | 345 |
| | heavy chain variable region | QVQLVESGGGLVQPGGSLRLSCAASGFTFSSYAMSWVR QAPGKGLEWVSAISGSGGSTYYADSVKGRFTISRDNSKN TLYLQMISLRAEDTAVYYCARDTYYYGSGRSNAFDIWGQ GTLVTVSS | 222 |

In this disclosure, the expression "an antibody or an antigen-binding fragment (for example, CDR, variable region, or heavy chain/light chain) comprising, consists of, or represented by a certain amino acid sequence" may refer to an antigen-binding fragment that consists essentially of (1) the certain amino acid sequence or (2) an amino acid sequence wherein an insignificant mutation (for example, substitution, deletion, and/or addition of an amino acid residue(s); leading to no impact on the activity of the antibody) is introduced in the amino acid sequence (1).

The anti-LILRB1 antibody or an antigen-binding fragment thereof provided in this disclosure may have a binding affinity ($K_D$) to LILRB1 (for example, human LILRB1) of 10 mM or less, 5 mM or less, 1 mM or less, 0.5 mM or less, 0.2 mM, or 0.15 mM or less, for example, 0.001 nM to 10 mM, 0.005 nM to 10 mM, 0.01 nM to 10 mM, 0.05 nM to 10 mM, 0.1 nM to 10 mM, 0.5 nM to 10 mM, 1 nM to 10 mM, 0.001 nM to 5 mM, 0.005 nM to 5 mM, 0.01 nM to 5 mM, 0.05 nM to 5 mM, 0.1 nM to 5 mM, 0.5 nM to 5 mM, 1 nM to 5 mM, 0.001 nM to 1 mM, 0.005 nM to 1 mM, 0.01 nM to 1 mM, 0.05 nM to 1 mM, 0.1 nM to 1 mM, 0.5 nM to 1 mM, 1 nM to 1 mM, 0.001 nM to 0.5 mM, 0.005 nM to 0.5 mM, 0.01 nM to 0.5 mM, 0.05 nM to 0.5 mM, 0.1 nM to 0.5 mM, 0.5 nM to 0.5 mM, 1 nM to 0.5 mM, 0.001 nM to 0.2 mM, 0.005 nM to 0.2 mM, 0.01 nM to 0.2 mM, 0.05 nM to 0.2 mM, 0.1 nM to 0.2 mM, 0.5 nM to 0.2 mM, 1 nM to 0.2 mM, 0.001 nM to 0.15 mM, 0.005 nM to 0.15 mM, 0.01 nM to 0.15 mM, 0.05 nM to 0.15 mM, 0.1 nM to 0.15 mM, 0.5 nM to 0.15 mM, or 1 nM to 0.15 mM, when measured by surface plasmon resonance (SPR).

Another embodiment provides a pharmaceutical composition comprising the anti-LILRB1 antibody or an antigen-binding fragment thereof as an active ingredient. For example, the pharmaceutical composition may be a pharmaceutical composition for treating and/or preventing a cancer. The pharmaceutical composition may have an activity to inhibit the binding of LILRB1 to MHC Class I and/or the interaction between LILRB1 and MHC Class I. The cancer may be a cancer associated with the interaction between LILRB1 and MHC Class I. In an embodiment, the pharmaceutical composition may have an activity to inhibit immune evasion of a cancer cell. The cancer cell may be a cell expressing or overexpressing MHC Class I on cell surface.

Another embodiment provides a composition for blocking the binding of LILRB1 to MHC Class I and/or the interaction between LILRB1 and MHC Class I, the composition comprising the anti-LILRB1 antibody or an antigen-binding fragment thereof as an active ingredient.

Another embodiment provides a composition for inhibiting immune evasion of a cancer cell, the composition comprising the anti-LILRB1 antibody or an antigen-binding fragment thereof as an active ingredient.

Another embodiment provides a method of treating and/or preventing a cancer, comprising administering (orally or parenterally) a pharmaceutically effective amount of the anti-LILRB1 antibody or an antigen-binding fragment thereof to a subject (e.g., a mammal including human) in need of treating and/or preventing the cancer.

Another embodiment provides a method of blocking the binding of LILRB1 to MHC Class I and/or a method of blocking the interaction between LILRB1 and MHC Class I, comprising administering (orally or parenterally) a pharmaceutically effective amount of the anti-LILRB1 antibody or an antigen-binding fragment thereof to a subject (e.g., a mammal including human) in need of inhibiting the binding of LILRB1 to MHC Class I and/or the interaction between LILRB1 and MHC Class I.

Another embodiment provides a method of inhibiting immune evasion of a cancer cell, comprising administering (orally or parenterally) a pharmaceutically effective amount of the anti-LILRB1 antibody or an antigen-binding fragment thereof to a subject (e.g., a mammal including human) in need of inhibiting immune evasion of the cancer cell.

The methods provided in this disclosure may further comprise a step of identifying the subject in need of treating and/or preventing the cancer, inhibiting the binding of LILRB1 to MHC Class I and/or the interaction between LILRB1 and MHC Class I, and/or inhibiting immune evasion of the cancer cell, prior to the step of administering.

Another embodiment provides a nucleic acid molecule (polynucleotide) encoding at least one polypeptide selected from the group consisting of CDR (CDR-L1, CDR-L2, CDR-L3, CDR-H1, CDR-H2, CDR-H3, a combination of CDR-L1, CDR-L2, and CDR-L3, or a combination of CDR-H1, CDR-H2, and CDR-H3), a light chain variable region comprising CDR-L1, CDR-L2, and CDR-L3, a heavy chain variable region comprising CDR-H1, CDR-H2, and CDR-H3; a light chain comprising the light chain variable region, and a heavy chain comprising the heavy chain variable region, of the anti-LILRB1 antibody described above.

Another embodiment provides a recombinant vector comprising the nucleic acid molecule. In an embodiment, the recombinant vector may comprise a nucleic acid molecule encoding the light chain variable region or light chain, and a nucleic acid molecule encoding the heavy chain variable region or heavy chain, respectively (e.g., in two separate vectors) or all together (e.g., in one vector). The recombinant vector may be used as an expression vector.

Another embodiment provides a recombinant cell comprising the nucleic acid molecule or the recombinant vector.

Another embodiment provides a method of preparing an anti-LILRB1 antibody or an antigen-binding fragment thereof, comprising expressing the nucleic acid molecule in a cell. The step of expressing the nucleic acid molecule may comprise culturing the recombinant cell.

As described herein, the antigen-binding fragment of an anti-LILRB1 antibody may refer to a fragment which is derived from an anti-LILRB1 antibody and retain antigen (LILRB1) binding affinity of the antibody. In an embodiment, the antigen-binding fragment may be an polypeptide comprising the 6 CDRs of an anti-LILRB1 antibody as described above, and, for example, may be scFv, scFv-Fc, scFv-Ck (kappa constant region), scFv-Cλ (lambda constant region), $(scFv)_2$, Fab, Fab', or a $F(ab')_2$, but not be limited thereto. In an embodiment, the antigen-binding fragment may be scFv, a fusion polypeptide (scFv-Fc) wherein scFv is fused with a Fc region of an immunoglobulin (e.g., IgA, IgD, IgE, IgG (IgG1, IgG2, IgG3, IgG4), IgM, etc.), or a fusion polypeptide (scFv-Ck or scFv-Cλ) wherein scFv is fused with a constant region (e.g., kappa or lambda) of a light chain.

The anti-LILRB1 antibody or an antigen-binding fragment thereof may have a regulatory activity, for example, an antagonistic or agonistic activity, on LILRB1 protein. In addition, the anti-LILRB1 antibody or an antigen-binding fragment thereof may have an activity of blocking the binding of LILRB1 to MHC Class I and/or the interaction between LILRB1 and MHC Class I. In addition, the anti-LILRB1 antibody or an antigen-binding fragment thereof may have an activity of inhibiting immune evasion of a cancer cell. Furthermore, the anti-LILRB1 antibody or an antigen-binding fragment thereof may have an anti-cancer effect.

A protein LILRB1, which is an antigen of an anti-LILRB1 antibody or an antigen-binding fragment thereof provided in this disclosure, may be derived from mammal. For example, LILRB1 as an antigen may be a human LILRB1 (e.g., GenBank accession numbers AAH15731.1 (SEQ ID NO: 348), NP_001265328.2, NP_001265327.2, NP_001075108.2, NP_001075107.2, NP_001075106.2, NP_006660.4, NM_001081637.2, NM_001081638.3, NM_001081639.3, NM_001278398.2, NM_001278399.2, etc.), but not be limited thereto.

MHC Class I may be one of classes of major histocompatibility complex (MHC) molecules. In an embodiment, the MHC Class I may be a human MHC Class I and may be at least one selected from the group consisting of HLA (human leukocyte antigen)-A, HLA-B, HLA-C, HLA-E, HLA-F, and HLA-G, but not be limited thereto.

As described herein, the term "antibody" may refer to a protein that specifically binds to a specific antigen, and may be a protein produced by stimulation of an antigen in the immune system, or a protein produced by chemical synthesis or recombinant production, with no specific limitation. The antibody may be non-naturally occurring, for example, produced by recombinant or synthetic production. The antibody may be an animal antibody (e.g., a mouse antibody, etc.), a chimeric antibody, a humanized antibody, or a human antibody. The antibody may be a monoclonal or polyclonal antibody.

In the anti-LILRB1 antibody or an antigen-binding fragment thereof provided herein, the portion, except for the heavy-chain CDR and light-chain CDR portions or the heavy-chain variable and light-chain variable regions as defined above, may be derived from any subtype of immunoglobulin (e.g., IgA, IgD, IgE, IgG (IgG1, IgG2, IgG3, IgG4), IgM, and the like), and, for example, derived from the framework portions, and/or light-chain constant region and/or heavy-chain constant region. In an embodiment, the anti-LILRB1 antibody provided in this disclosure may be an antibody in a form of human IgG, for example, IgG1, IgG2, IgG3, or IgG4, but not be limited thereto.

An intact antibody (e.g., IgG type) has a structure with two full-length light chains and two full-length heavy chains, in which each light chain is linked to a corresponding heavy chain via a disulfide bond. The constant region of an antibody is divided into a heavy-chain constant region and a light-chain constant region. The heavy-chain constant region is of a gamma (γ), mu (μ), alpha (α), delta (δ), or epsilon (ε) type, and has gamma1 (γ1), gamma2 (γ2), gamma3 (γ3), gamma4 (γ4), alpha1 (α1) or alpha2 (α2) as its subclass. The light chain constant region is of either a kappa (κ) or lambda (λ) type.

As used herein, the term "heavy chain" may be intended to encompass a full-length heavy chains and fragments thereof, wherein the full-length heavy chain may comprise a variable region VH including amino acid sequences sufficient to provide specificity to antigens, three constant regions CH1, CH2, and CH3, and a hinge. The term "light chain" may be intended to encompass full-length light chains and fragments thereof, wherein the full-length light chain may comprises a variable region VL including amino acid sequences sufficient to provide specificity to antigens, and a constant region CL.

The term "complementarity determining region (CDR)" may refer to a portion that confers antigen-binding specificity in a variable region of an antibody, and may refer to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contacting residues that play an important role in the binding of an antibody to its antigen or an epitope of the antigen. As used herein, the terms "specifically binding" and "specifically recognizing" may have the same general meaning as known to one of ordinary skill in the art, and indicate that an antibody and an antigen specifically interact with each other to lead to an immunological reaction.

In this disclosure, unless differently stated, the term "antibody" may encompass not only an intact antibody but also an antigen-binding fragment of the antibody possessing an antigen-binding capability.

The term "antigen-binding fragment" used herein may refer to a polypeptide in any type, which comprises a portion (e.g., 6 CDRs as described herein) capable of binding to an antigen, and, for example, may be scFv, $(scFv)_2$, scFv-Fc, Fab, Fab', or $F(ab')_2$, but is not limited thereto. In addition, as described above, the antigen-binding fragment may be scFv, a fusion polypeptide wherein scFv is fused with a Fc region of an immunoglobulin (e.g., IgA, IgD, IgE, IgG (IgG1, IgG2, IgG3, IgG4), IgM, etc.) or a constant region (e.g., kappa or lambda).

Among the antigen-binding fragments, Fab includes light chain and heavy chain variable regions, a light chain constant region, and a first heavy chain constant region CH1.

Fab' is different from Fab in that Fab' comprises a hinge region having at least one cysteine residue at the C-terminal of CH1.

$F(ab')_2$ antibody is formed through disulfide bridging of the cysteine residues in the hinge region of Fab'.

Fv is a minimal antibody fragment composed of only a heavy chain variable region and a light chain variable region. Recombination techniques of generating an Fv fragment are widely known in the art.

Two-chain Fv comprises a heavy chain variable region and a light chain variable region which are linked to each other by a non-covalent bond. Single-chain Fv generally comprises a heavy-chain variable region and a light-chain variable region which are linked to each other by a covalent bond via a peptide linker or directly linked at the C-terminals to have a dimer structure like two-chain Fv.

The antigen-binding fragments may be obtained using protease (for example, Fab may be obtained by restrictively cleaving a whole antibody with papain, and an $F(ab')_2$ fragment may be obtained by cleaving with pepsin), or may be prepared by using a genetic recombination technique.

The term "hinge region" may refer to a region between CH1 and CH2 domains within heavy chain of an antibody, which functions to provide flexibility for the antigen-binding site in the antibody.

The anti-LILRB1 antibody may be a monoclonal or polyclonal antibody and, for example, a monoclonal antibody. A monoclonal antibody can be prepared using a method widely known in the art, for example, using a phage display technique. Alternatively, the anti-LILRB1 antibody may be constructed in the form of a mouse-derived monoclonal antibody by a conventional method.

Meanwhile, individual monoclonal antibodies can be screened using a typical ELISA (Enzyme-Linked ImmunoSorbent Assay) format, based on the binding potential against LILRB1. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to LILRB1 may be each verified.

The pharmaceutical composition may further comprise a pharmaceutically acceptable carrier, in addition to the active ingredient (the anti-LILRB1 antibody or an antigen-binding fragment thereof). The pharmaceutically acceptable carrier may be anyone selected from those commonly used for the formulation of antibodies. For example, the pharmaceutically acceptable carrier may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, mineral oil, and the like, but are not limited thereto. The pharmaceutical composition may further comprise one or more selected from the group consisting of a diluent, an excipient, a lubricant, a wetting agent, a sweetener, a flavor enhancer, an emulsifying agent, a suspension agent, preservative, and the like, which can be commonly used for manufacturing pharmaceutical composition.

The pharmaceutical composition, or the antibody or an antigen-binding fragment thereof may be administered orally or parenterally in a pharmaceutically effective amount. The parenteral administration may be intravenous injection, subcutaneous injection, muscular injection, intraperitoneal injection, endothelial administration, intranasal administration, intrapulmonary administration, rectal administration or intralesional local administration. Since proteins or peptides are digested when administered orally, the active ingredient in the compositions for oral administration may be coated or formulated to prevent digestion in stomach. In addition, the antibody or the compositions may be administered using an optional device that enables the active ingredient to be delivered to target cells (e.g., cancer cells).

The anti-LILRB1 antibody or an antigen-binding fragment thereof may be comprised in the pharmaceutical composition or administered to a subject in a pharmaceutically effective amount. As used herein, the term "pharmaceutically effective amount" may refer to an amount of an active ingredient (the antibody or fragment thereof) at which the active ingredient can exert desired effects (e.g., anti-cancer effect). The pharmaceutically effective amount may be prescribed in a variety of ways, depending on various factors, such as age, body weight, gender, pathologic conditions, diets, excretion speed, and/or reaction sensitivity of a subject, formulation types, administration time, administration interval, administration route, administration manner, and the like. For example, anti-LILRB1 antibody or an antigen-binding fragment thereof may be administered at the amount of 0.005 ug/kg to 1000 mg/kg, 0.005 ug/kg to 500 mg/kg, 0.005 ug/kg to 250 mg/kg, 0.005 ug/kg to 100 mg/kg, 0.005 ug/kg to 75 mg/kg, 0.005 ug/kg to 50 mg/kg, 0.01 ug/kg to 1000 mg/kg, 0.01 ug/kg to 500 mg/kg, 0.01 ug/kg to 250 mg/kg, 0.01 ug/kg to 100 mg/kg, 0.01 ug/kg to 75 mg/kg, 0.01 ug/kg to 50 mg/kg, 0.05 ug/kg to 1000 mg/kg, 0.05 ug/kg to 500 mg/kg, 0.05 ug/kg to 250 mg/kg, 0.05 ug/kg to 100 mg/kg, 0.05 ug/kg to 75 mg/kg, or 0.05 ug/kg to 50 mg/kg per day, but not be limited thereto. The daily dosage may be formulated into a single formulation in a unit dosage form or formulated in suitably divided dosage forms, or it may be manufactured to be contained in a multiple dosage container.

The pharmaceutical compositions may be formulated into a form of a solution in oil or an aqueous medium, a suspension, syrup, an emulsifying solution, an extract, powder, granules, a tablet, or a capsule, and may further comprise a dispersing or a stabilizing agent for the formulation.

The subject, to whom the antibody, pharmaceutical composition, or method provided in this disclosure is applied, may be selected from mammals including a mammal including primates such as humans and monkeys, rodents such as rats and mice, and the like.

The cancer may be a solid cancer or blood cancer. The cancer may be, but not limited to, one or more selected from the group consisting of lung cancer (e.g., squamous cell carcinoma of the lung, small-cell lung cancer, non-small-cell lung cancer, adenocarcinoma of the lung), peritoneal carcinoma, skin cancer, squamous cell carcinoma, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, leukemia (e.g., chronic or acute leukemia), lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, renal cell carcinoma, kidney cancer, prostate cancer, vulvar cancer, thyroid cancer, head and neck cancer, brain cancer, biliary tract cancer, gallbladder cancer, bone osteosarcoma, and the like. The cancer may be a primary cancer or a metastatic cancer. The cancer may be a cancer characterized by expression or overexpression of MHC Class I on a surface of cancer cell, and, for example, may be colon adenocarcinoma, small cell lung carcinoma, breast cancer, pancreatic cancer, malignant melanoma, bone osteosarcoma, renal cell carcinoma, or gastric cancer. The overexpression of MHC Class I may refer to an overexpression compared to that of a normal cell or a cancer cell which is non-responsive or resistant to the immunotherapy, for example, T-cell (e.g., cytotoxic T-cell) mediated immunotherapy.

As used herein, the term "treatment of cancer" may refer to all anti-cancer actions that prevent, alleviate or ameliorate the symptoms of cancer, or partially or completely remove a cancer, such as, cancer cell death, inhibition of cancer cell proliferation, inhibition of cancer metastasis, and the like.

The anti-LILRB1 antibody or an antigen-binding fragment thereof provided in this disclosure may be co-administered with another drug, for example, at least one selected from the group consisting of conventionally used agents for immunotherapy, anti-cancer agents, cytotoxic agents, and the like. Accordingly, an embodiment provides a pharmaceutical composition of combined administration for treating and/or preventing a cancer, comprising (1) an anti-LILRB1 antibody or an antigen-binding fragment thereof, and (2) at least one selected from the group consisting of agents for immunotherapy, anti-cancer agents, cytotoxic agents, and the like. Another embodiment provides a method of treating and/or preventing a cancer, comprising administering (1) an anti-LILRB1 antibody or an antigen-binding fragment thereof, and (2) at least one selected from the group consisting of agents for immunotherapy, anti-cancer agents, cytotoxic agents, and the like, to a subject in need of treating and/or preventing the cancer. The agents for immunotherapy, anti-cancer agents, and cytotoxic agents may include any drugs which are conventionally used for cancer therapy, and/or have cytotoxic activity, and for example, they may be at least one selected from the group consisting of proteins such as antibodies, nucleic acid molecules such as siRNA, and/or small molecular chemicals such as paclitaxel, docetaxel, and the like, but not limited thereto.

Another embodiment provides a polypeptide molecule comprising a heavy chain complementarity determining region (CDR-H1, CDR-H2, CDR-H3, or a combination thereof), a light chain complementarity determining region (CDR-L1, CDR-L2, CDR-L3, or a combination thereof), a combination thereof; or heavy chain variable region, light chain variable region, or a combination thereof, of the anti-LILRB1 antibody as described above. The polypeptide molecule may be used in preparing an antibody as a precursor of antibody, or comprised in a protein scaffold having an antibody-like structure (e.g., peptibody), a bispecific antibody, or a multispecific antibody, as a component thereof. In another embodiment, the polypeptide molecule may be used as a target (antigen) recognition domain or a secreted antibody, in cell therapeutics for target therapy, such as CAR-T. In another embodiment, the polypeptide molecule may be used for constructing anti-LILRB1 antibody-secreting cells as cell therapeutics.

Another embodiment provides a nucleic acid molecule encoding a heavy chain complementarity determining region (CDR-H1, CDR-H2, CDR-H3, or a combination thereof), a heavy chain variable region, or a heavy chain, of the anti-LILRB1 antibody.

Another embodiment provides a nucleic acid molecule encoding a light chain complementarity determining region (CDR-L1, CDR-L2, CDR-L3, or a combination thereof), a light chain variable region, or a light chain, of the anti-LILRB1 antibody.

Another embodiment provides a recombinant vector comprising a nucleic acid molecule encoding a heavy chain variable region or a heavy chain of the anti-LILRB1 antibody, and a light chain variable region or a light chain of the anti-LILRB1 antibody, respectively in two separate vectors or all together in one vector.

Another embodiment provides a recombinant cell comprising the nucleic acid molecule or the recombinant vector.

The term "vector" refers to a means for expressing a target gene in a host cell, as exemplified by a plasmid vector, a cosmid vector, and a viral vector such as a bacteriophage vector, a lentivirus vector, an adenovirus vector, a retrovirus vector, and an adeno-associated virus vector. The recombinant vector may be constructed from or by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), a phage (for example, λgt4λB, λ-Charon, λΔz1, M13, etc.), or a virus vector (for example, SV40, etc.), which is commonly used in the art.

In the recombinant vector, the nucleic acid molecule may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of a polynucleotide of interest.

The recombinant vector may be constructed typically as a cloning vector or an expression vector. For recombinant expression vectors, a vector generally available in the relevant art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a $pL^{\lambda}$ promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, tk promoter of HSV, etc.), and a polyadenylation sequence as a transcription termination sequence.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure may be selected from *E. coli* such as *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens* and various *Pseudomonas* species. Eukaryotic host cells that may be used for transformation may selected from, but are not limited to, *Saccharomyces cerevisiae*, insect cells, and animal cells, such as Sp2/0, CHO (Chinese hamster ovary) K1, CHO DG44, CHO S, CHO DXB11, CHO GS-KO, PER.C6, W138, BHK, COS-7, 293, HepG2, Huh7, 3T3, RIN, MDCK, etc.

The nucleic acid molecule or a recombinant vector carrying the same may be introduced (transfected) into a host cell using a method well known in the relevant art. For example, this transfection may be carried out using a $CaCl_2$ or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another embodiment provides a method of preparing the anti-LILRB1 antibody or an antigen-binding fragment thereof, comprising expressing the nucleic acid molecule or a recombinant vector in a host cell. The step of expressing may be conducted by culturing the recombinant cell comprising the nucleic acid molecule (for example, in a recombinant vector) under a condition allowing the expression of the nucleic acid molecule. The method may further comprise isolating and/or purifying the antibody or its fragment from the cell culture, after the step of expressing or culturing.

ADVANTAGEOUS EFFECTS

The anti-LILRB1 antibody or an antigen-binding fragment thereof provided in this disclosure can have high anti-cancer effect by inhibiting the immune evasion mechanism of cancer cells, allowing that the immune cells can exhibit their anti-cancer effect.

BRIEF DESCRIPTION OF DRAWINGS

FIG. 1 shows electrophoresis images showing the results of SDS-PAGE gel analysis for anti-LILRB1 antibodies purified in an example.

FIG. 2 is a sensorgram showing the results of SPR (surface plasmon resonance) assay for anti-LILRB1 antibody B3 according to an example.

FIG. 3 is a sensorgram showing the results of SPR assay for anti-LILRB1 antibody E3 according to an example.

FIG. 4*a* is a graph showing binding ability of anti-LILRB1 antibody A10 according to an example to a human natural killer cell, KHYG-1; FIG. 4*b* is a graph showing binding ability of anti-LILRB1 antibody E3 according to an example to a human natural killer cell, KHYG-1; and FIG. 4*c* is a graph showing binding ability of human IgG4 isotype control antibody to a human natural killer cell, KHYG-1.

FIG. 5 is a graph showing the level of binding of recombinant LILRB1-Fc proteins to HLA-G overexpressing cell surface measured by iQue screener, when treated with anti-LILRB1 antibodies according to an example and human IgG4 isotype control antibody, respectively.

FIG. 6 is a graph showing in vivo antitumor effects of anti-LILRB1 antibody E3 and B3 according to an example.

FIGS. 7*a* to 7*d* are flow cytometry diagrams of binding of anti-LILRB1 antibody E3.1 according to an example to cells expressing various members of human LILR family.

FIGS. 8*a* to 8*d* are flow cytometry diagrams of binding of anti-LILRB1 antibody H11 according to an example to cells expressing various members of human LILR family.

FIG. 9 shows graphs showing release level of granzyme B in a human natural killer cell, KHYG-1, when treated with anti-LILRB1 antibody E3.1 or H11 according to an example, comparing with that in the cell treated with a control antibody (human IgG4 isotype).

FIG. 10 shows graphs showing release level of perforin in a human natural killer cell, KHYG-1, when treated with anti-LILRB1 antibody E3.1 or H11 according to an example, comparing with that in the cell treated with a control antibody (human IgG4 isotype).

FIG. 11 is a graph showing results of luciferase reporter assay for evaluating ability of anti-LILRB1 antibody E3.1 or H11 according to an example to block LILRB1 signal pathway.

FIG. 12 is a graph showing in vivo anti-tumor effects of anti-LILRB1 antibody E3.1 and H11 according to an example.

Hereafter, the present invention will be described in detail by examples.

The following examples are intended merely to illustrate the invention and are not construed to restrict the invention.

Example 1: Preparation of Human Antibodies Against LILRB1

1.1. Selection of Human Antibodies Against LILRB1 Using Phage Display

In order to select antibodies that specifically recognize human LILRB1, a phage display screening was performed using a library composed of human scFv antibodies. As an antigen, human LILRB1-His (Cat. No. 8989-T2) and human LILRB1-Fc (Cat. No. 2017-T2) (RnD systems) were used respectively. Each antigen was conjugated with biotin by EZ-Link Sulfo-NHS-Biotin kit (ThermoFisher Scientific) for use.

The phage display screening was performed using total 4-types of LILRB1 antigens (LILRB1-His, LILRB1-Fc, LILRB1-His-Biotin, and LILRB1-Fc-Biotin) through solid-phase screening and solution-phase screening. Additional screenings were performed by gradually decreasing the concentration of the used antigen, competitively eluting with control antibodies against LILRB1, conducting negative selection to Fc when LILRB1-Fc is used as an antigen, etc. The selected products were confirmed for their binding to the antigen through polyclonal phage ELISA.

1.2. Screening and Analysis of Monoclonal Soluble scFvs

Genes encoding the scFvs, which were verified to bind the antigen in Example 1.1, were amplified by PCR to prepare expression vectors. For each selection, a certain number of transformants were transferred to a 96 well culture plate for screening. Antibodies in a scFv form were expressed using Autoinduction media (Studier, F. W. (2005) Protein Expression and Purification 41, 207-34) and then analyzed for their binding to the antigen by performing DELFIA immune assay (PerkinElmer). In addition, after allowing a certain amount of each scFv antibody to be captured on the surface, DELFIA for the antigen was performed to determine the ranking for antigen-antibody binding affinity.

1.3. Conversion of the Screened scFvs into IgG Antibodies

Among the clones which were confirmed to bind to the antigen in Example 1.2, a total of 376 clones were selected, and the DNA sequences of genes encoding the selected scFvs were analyzed by a general DNA sequencing to remove duplicate clones. In addition, a total of 93 clones were selected based on the ranking of the antigen-antibody binding affinity determined in Example 1.2. Genes encoding a heavy chain variable region (VH) and a light chain variable region (VL) were respectively amplified by PCR from each of the genes encoding the selected scFvs, and inserted into an expression vector (pTRIOZ-hIgG4, InvivoGen; alternatively, any one of vectors comprising CMV promoter or CMV/CHO beta-actin fusion promoter (KR10-1038126B1) and genes encoding human IgG4 heavy chain constant region and kappa or lambda light chain constant region can be used), wherein the expression vector was designed for encoding a human IgG4 antibody (IgG4 Fc: SEQ ID NO: 341, Kappa constant region: SEQ ID NO: 342, Lambda constant region: SEQ ID NO: 343). The DNA sequence of the expression vector was confirmed by sequencing.

1.4. Preparation of Selected Antibodies

The vectors constructed in Example 1.3 were purified using Plasmid Plus Maxi kit (Qiagen). The purified vectors were used for expressing antibodies in ExpiCHO-S™ cells or Expi293™ cells.

In particular, the vectors constructed in Example 1.3 were transfected into ExpiCHO-S™ cells (Gibco) ($1.5\times10^8$ cells/Culture Volume 25 mL) by adding 80 μL of ExpiFectamine™ CHO reagent (Thermo Fisher). One day post-transfection, 150 μL of ExpiCHO™ Enhancer (Thermo Fisher) and 4 mL of ExpiCHO™ Feed (Thermo Fisher) were added to the culture. On day 5, 4 mL of ExpiCHO™ Feed was added to the culture. The transfected cells were cultured under the conditions of 32° C. and 5% $CO_2$ for 7-11 days in total.

In addition, the vectors constructed in Example 1.3 were transfected into Expi293F™ cells (Gibco) ($3\times10^8$ cells/ Culture Volume 100 mL) by adding 320 μL of Expi-Fectamine™ 293 Reagent (Gibco) according to manufacturer's protocol. One day post-transfection, ExpiFectamine™ 293 Enhancer 1 (Thermo Fisher), Expi-Fectamine™ Enhancer 2 (Thermo Fisher), and glucose were added in the amount of 0.6 mL per Culture Volume 100 mL, 6 mL per Culture Volume 100 mL, and 3.6 g per 1 liter, respectively. The transfected cells were cultured under the conditions of 36.5° C. and 5% $CO_2$ for 5 days in total. The cultured cells of two types were respectively centrifuged at 4000 rpm at 4° C. for 20 minutes, and then, filtrated using 0.22 um bottle-top filter system (Corning). The culture supernatant was harvested and purified using AKTA Pure L (GE healthcare). The culture supernatant was loaded into AKTA Pure L equipped with Hitrap MabSelectSure 1 mL column (GE healthcare) at the flow rate of 1 mL/min,, and the column was washed with 20 column volumes (CV) of 1×PBS. Then, elutionbuffer (0.1 M sodium citrate pH 3.4 buffer) was loaded to the column, to elute a protein of interest. The eluate was concentrated using Amicon Ultra Filter Device (MWCO 10K, Merck), centrifuged and subjected to buffer exchange with 1×PBS buffer.

The purified antibody samples were diluted with 1×PBS, to make the final concentration about 1 mg/mL. Ten (10) μL of Reducing Loading Buffer (3×) or Non-reducing Loading Buffer (3×) and 20 μL of the purified antibody sample were mixed and left in 95° C. heating bath for 2 minutes, and then, brought out and cooled. The sample was injected into SDS-PAGE Gradient Gel (4-20% or 4-12%) equipped on an electrophoresis device at the amount of 10 μg per well and developed on the gel. In order to analyze molecular weight of the sample, Precision Plus Protein™ Dual Color Standards (BIO-RAD) was injected to another separate well. The gel was stained with Coomassie staining solution and destained to obtain gel images.

Among 93 antibodies, gel electrophoresis images for antibodies A10, B3, E3, G1, G9 and H2 were representatively shown in FIG. 1. As shown in FIG. 1, the production of antibodies having disulfide bond was confirmed.

1.5. Analysis of Binding Affinity of the Selected Antibodies

The binding affinities of the 93 antibodies, which were selected in Example 1.3, to the antigen, LILRB1, were measured using Biacore T200 (GE healthcare). An anti-human IgG (Fc) antibody (GE healthcare, Cat. No. BR-1008-39, final concentration of 25 μg/mL) was flowed at the flow rate of 5 μL/min for 360 seconds to be immobilized at 5000-7000 RU on Series S Sensor Chip CM5 (GE healthcare, Cat. No. BR-1005-30) using Amine Coupling Kit (GE healthcare, Cat. No. BR-1000-508). The antigen, human LILRB1 protein (LILRB1-His, RnD systems Cat. No. 8989-T2) was injected thereto in 4~9 different concentrations from 3.13 nM to 1600 nM at the flow rate of 30 μL/min to determine $k_a$ and $k_d$ values as shown in Table 3 and calculate $K_D$ value therefrom.

Among the 93 antibodies, 20 antibodies showing excellent binding affinities ($K_D$ values) were selected and summarized in Table 3. Among them, SPR sensorgrams for antibody B3 showing the LILRB1 binding affinity ($K_D$) of about 99.8 nM and for antibody E3 showing the LILRB1 binding affinity ($K_D$) of about 101.2 nM are shown in FIGS. 2 and 3, respectively (FIG. 2: SPR sensorgram for B3, FIG. 3: SPR sensorgram for E3):

TABLE 3

| Antigen Binding Affinities ($K_D$) of Anti-LILRB1 antibodies to human LILRB1 | | | |
|---|---|---|---|
| Clone name | $k_a$ ($\times10^5$) (1/Ms) | $k_d$ ($\times10^{-4}$) (1/s) | $K_D$ (nM) |
| A10 | 0.504 | 76.5 | 152 |
| A11 | 0.001801 | 9.814 | 5448 |
| B3 | 0.149 | 14.87 | 99.8 |
| B9 | 0.09324 | 6.16 | 66.1 |
| B12 | 1.84 | 14.42 | 7.84 |
| D1 | 1.165 | 57.44 | 49.33 |
| D3 | 0.0311 | 5.58 | 180 |
| E3 | 0.3460 | 35.00 | 101.2 |
| E4 | 0.1065 | 7.73 | 72.55 |
| E6 | 0.2679 | 16.27 | 60.73 |
| E9 | 0.105 | 10.48 | 99.86 |
| E12 | 2.331 | 102.6 | 44.01 |
| F11 | 2.72 | 6.15 | 2.26 |
| F12 | 2.811 | 9.731 | 3.462 |
| G1 | 4.33 | 14.19 | 3.28 |
| G6 | 2.58 | 152.4 | 59.06 |
| G9 | 1.43 | 4.36 | 3.05 |
| G11 | 0.454 | 20.53 | 45.23 |
| H2 | 5.865 | 95 | 16.20 |
| H11 | 2.962 | 22.57 | 7.621 |

1.6. Sequence Analysis of the Selected Antibodies

In the 20 antibodies which are analyzed for antigen binding affinity in Example 1.5, amino acid sequences of the CDRs defined according to Kabat numbering, light chain variable region, heavy chain variable region, light chain, and heavy chain, and nucleic acid sequence encoding the light chain variable region and the heavy chain variable region were analyzed by general amino acid sequencing and DNA sequencing methods and summarized in Tables 4-23:

TABLE 4

| Antibody clone E3 | | |
|---|---|---|
| | Amino acid sequence (N→C) / Nucleic acid sequence (5'→3') | SEQ ID NO |
| CDR-L1 | QGDSLRNFYAS | 1 |
| CDR-L2 | GKNNRPS | 2 |
| CDR-L3 | NSRDSSGSHLTGV | 3 |
| CDR-H1 | SYAMS | 4 |

TABLE 4-continued

| Antibody clone E3 | | |
|---|---|---|
| | Amino acid sequence (N→C) / Nucleic acid sequence (5'→3') | SEQ ID NO |
| CDR-H2 | AISGSGGSTYYADSVKG | 5 |
| CDR-H3 | DTYYYGSGRSNAFDI | 6 |
| light chain variable region | SYELTQDPAVSVALGQTVRITCQGDSLRNFYASWYQQKSG QAPVLVMYGKNNRPSGIPDRFSGSTSGNTASLTITGAQAE DEADYYCNSRDSSGSHLTGVFGGGTKVTVLGQPAAA | 221 |
| light chain variable region coding gene | TCCTATGAGCTGACTCAGGACCCTGCTGTGTCTGTGGC CTTGGGACAGACAGTCAGGATCACATGCCAGGGAGACA GCCTCAGAAACTTTTATGCAAGCTGGTACCAGCAGAAGT CAGGACAGGCCCCAGTTCTTGTCATGTATGGTAAAAACA ACCGGCCCTCAGGGATCCCAGACCGATTCTCTGGCTCC ACCTCAGGAAACACAGCTTCCTTGACCATCACTGGGGC TCAGGCGGAAGATGAGGCTGACTATTACTGTAACTCCCG GGACAGCAGTGGTAGCCATTTGACGGGCGTATTCGGCG GAGGGACCAAGGTCACCGTCCTAGGTCAGCCCGCGGC CGCA | 261 |
| heavy chain variable region | QVQLVESGGGLVQPGGSLRLSCAASGFTFSSYAMSWVR QAPGKGLEWVSAISGSGGSTYYADSVKGRFTISRDNSKN TLYLQMISLRAEDTAVYYCARDTYYYGSGRSNAFDIWGQG TLVTVSS | 222 |
| heavy chain variable region coding gene | CAGGTGCAGCTGGTGGAGTCTGGGGGAGGCTTGGTAC AGCCTGGGGGGTCCCTGAGACTCTCCTGTGCAGCCTC TGGATTCACCTTTAGCAGCTATGCCATGAGCTGGGTCCG CCAGGCTCCAGGGAAGGGGCTGGAGTGGGTCTCAGCT ATTAGTGGTAGTGGTGGTAGCACATACTACGCAGACTCC GTGAAGGGCCGGTTCACCATCTCCAGAGACAATTCCAA GAATACGCTGTATCTGCAAATGATTAGCCTGAGAGCTGA GGACACGGCTGTGTATTACTGTGCGAGAGATACGTATTA CTATGGTTCGGGGAGAAGTAATGCTTTTGATATATGGGG CCAGGGAACCCTGGTCACCGTCTCGAGT | 262 |
| light chain (Lambda) | SYELTQDPAVSVALGQTVRITCQGDSLRNFYASWYQQKSG QAPVLVMYGKNNRPSGIPDRFSGSTSGNTASLTITGAQAE DEADYYCNSRDSSGSHLTGVFGGGTKVTVLGQPAAAPSV TLFPPSSEELQANKATLVCLISDFYPGAVTVAWKADSSPV KAGVETTTPSKQSNNKYAASSYLSLTPEQWKSHRSYSCQ VTHEGSTVEKTVAPTECS | 301 |
| heavy chain | QVQLVESGGGLVQPGGSLRLSCAASGFTFSSYAMSWVR QAPGKGLEWVSAISGSGGSTYYADSVKGRFTISRDNSKN TLYLQMISLRAEDTAVYYCARDTYYYGSGRSNAFDIWGQG TLVTVSSASTKGPSVFPLAPCSRSTSESTAALGCLVKDYF PEPVTVSWNSGALTSGVHTFPAVLQSSGLYSLSSVVTVPS SSLGTKTYTCNVDHKPSNTKVDKRVESKYGPPCPPCPAP EFLGGPSVFLFPPKPKDTLMISRTPEVTCVVVDVSQEDPE VQFNWYVDGVEVHNAKTKPREEQFNSTYRVVSVLTVLHQ DWLNGKEYKCKVSNKGLPSSIEKTISKAKGQPREPQVYTL PPSQEEMTKNQVSLTCLVKGFYPSDIAVEWESNGQPENN YKTTPPVLDSDGSFFLYSRLTVDKSRWQEGNVFSCSVMH EALHNHYTQKSLSLSLGK | 302 |

TABLE 5

| Antibody clone B3 | | |
|---|---|---|
| | Amino acid sequence (N→C)/ Nucleic acid sequence (5'→3') | SEQ ID NO |
| CDR-L1 | QASQDISNYLN | 7 |
| CDR-L2 | DASNLET | 8 |
| CDR-L3 | QQYDNLP | 9 |
| CDR-H1 | DYAMH | 10 |
| CDR-H2 | GISWNSGSIGYADSVKG | 11 |

TABLE 5-continued

| Antibody clone B3 | | |
|---|---|---|
| | Amino acid sequence (N→C)/ Nucleic acid sequence (5'→3') | SEQ ID NO |
| CDR-H3 | VGDSSGWSDAFDI | 12 |
| light chain variable region | DIQMTQSPSSLSASVGDRVTITCQASQDISNYLNWYQQK PGKAPKLLIYDASNLETGVPSRFSGSGSGTDFTFTISSL QPEDIATYYCQQYDNLPFGGGTKVDIKRTAAA | 223 |
| light chain variable region coding gene | GACATCCAGATGACCCAGTCTCCATCCTCCCTGTCTGCA TCTGTAGGAGACAGAGTCACCATCACTTGCCAGGCGAGT CAGGACATTAGCAACTATTTGAATTGGTATCAGCAGAAA CCAGGGAAAGCCCCTAAGCTCCTGATCTACGATGCATCC AATTTGGAAACAGGGGTCCCATCAAGGTTCAGTGGAAGT GGATCTGGGACAGATTTTACTTTCACCATCAGCAGCCTG CAGCCTGAAGATATTGCAACATATTACTGTCAACAGTAT GATAATCTCCCTTTCGGCGGAGGGACCAAAGTGGATATC AAACGTACCGCGGCCGCA | 263 |
| heavy chain variable region | EVQLLESGGGLVQPGRSLRLSCAASGFTFDDYAMHWVRQ APGKGLEWVSGISWNSGSIGYADSVKGRFTISRDNSKNT LYLQMNSLRAEDTAVYYCARVGDSSGWSDAFDIWGQGTM VTVSS | 224 |
| heavy chain variable region coding gene | GAGGTGCAGCTGTTGGAGTCTGGGGGAGGCTTGGTACAG CCTGGCAGGTCCCTGAGACTCTCCTGTGCAGCCTCTGGA TTCACCTTTGATGATTATGCCATGCACTGGGTCCGGCAA GCTCCAGGGAAGGGCCTGGAGTGGGTCTCAGGTATTAGT TGGAATAGTGGTAGCATAGGCTACGCAGACTCCGTGAAG GGCCGATTCACCATCTCCAGAGACAATTCCAAGAACACG CTGTATCTTCAAATGAACAGTCTGAGAGCCGAGGACACG GCCGTGTATTACTGTGCGAGAGTTGGGGATAGCAGTGGC TGGTCCGATGCTTTTGATATCTGGGGCCAAGGGACAATG GTCACCGTCTCGAGT | 264 |
| light chain (Kappa) | DIQMTQSPSSLSASVGDRVTITCQASQDISNYLNWYQQK PGKAPKLLIYDASNLETGVPSRFSGSGSGTDFTFTISSL QPEDIATYYCQQYDNLPFGGGTKVDIKRTAAAPSVFIFP PSDEQLKSGTASVVCLLNNFYPREAKVQWKVDNALQSGN SQESVTEQDSKDSTYSLSSTLTLSKADYEKHKLYACEVT HQGLSSPVTKSFNRGEC | 303 |
| heavy chain | EVQLLESGGGLVQPGRSLRLSCAASGFTFDDYAMHWVRQ APGKGLEWVSGISWNSGSIGYADSVKGRFTISRDNSKNT LYLQMNSLRAEDTAVYYCARVGDSSGWSDAFDIWGQGTM VTVSSASTKGPSVFPLAPCSRSTSESTAALGCLVKDYFP EPVTVSWNSGALTSGVHTFPAVLQSSGLYSLSSVVTVPS SSLGTKTYTCNVDHKPSNTKVDKRVESKYGPPCPPCPAP EFLGGPSVFLFPPKPKDTLMISRTPEVTCVVVDVSQEDP EVQFNWYVDGVEVHNAKTKPREEQFNSTYRVVSVLTVLH QDWLNGKEYKCKVSNKGLPSSIEKTISKAKGQPREPQVY TLPPSQEEMTKNQVSLTCLVKGFYPSDIAVEWESNGQPE NNYKTTPPVLDSDGSFFLYSRLTVDKSRWQEGNVFSCSV MHEALHNHYTQKSLSLSLGK | 304 |

TABLE 6

| Antibody clone A10 | | |
|---|---|---|
| | Amino acid sequence (N→C)/ Nucleic acid sequence (5'→3') | SEQ ID NO |
| CDR-L1 | RASQSVSSNLA | 13 |
| CDR-L2 | GASTRAT | 14 |
| CDR-L3 | QQYGSSPRMYT | 15 |
| CDR-H1 | SYAIS | 16 |
| CDR-H2 | GIIPIFGTANYAQKFQG | 17 |
| CDR-H3 | GGLGELDNWFDP | 18 |

TABLE 6-continued

| Antibody clone A10 | | |
|---|---|---|
| | Amino acid sequence (N→C)/ Nucleic acid sequence (5'→3') | SEQ ID NO |
| light chain variable region | DIVMTQSPATLSVSPGERATLSCRASQSVSSNLAWYQQKPGQAPRLLIYGASTRATGIPARFSGSGSGTEFTLTISSLQSEDFAVYYCQQYGSSPRMYTFGQGTKVDIKRTAAA | 225 |
| light chain variable region coding gene | GATATTGTGATGACACAGTCTCCAGCCACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACCGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTATGGTAGCTCACCTCGGATGTACACTTTTGGCCAGGGGACCAAAGTGGATATCAAACGTACCGCGGCCGCA | 265 |
| heavy chain variable region | QMQLVQSGAEVKKPGSSVKVSCKASGGTFSSYAISWVRQAPGQGLEWMGGIIPIFGTANYAQKFQGRVTITADKSISTAYMELSSLRSEDTAVYYCARGGLGELDNWFDPWGQGTLVTVSS | 226 |
| heavy chain variable region coding gene | CAAATGCAGCTGGTGCAGTCTGGGGCTGAGGTGAAGAAGCCTGGGTCCTCGGTGAAGGTCTCCTGCAAGGCTTCTGGAGGCACCTTCAGCAGCTATGCTATCAGCTGGGTGCGACAGGCCCCTGGACAAGGGCTTGAGTGGATGGGTGGGATCATCCCTATCTTTGGTACAGCAAACTACGCACAGAAGTTCCAGGGCAGAGTCACGATTACCGCGGACAAATCCATCAGCACAGCCTACATGGAGCTGAGCAGCCTGAGATCTGAGGACACGGCCGTGTATTACTGTGCGAGAGGCGGCCTCGGGGAGTTGGACAACTGGTTCGACCCCTGGGGCCAGGGAACCCTGGTCACCGTCTCGAGT | 266 |
| light chain (Kappa) | DIVMTQSPATLSVSPGERATLSCRASQSVSSNLAWYQQKPGQAPRLLIYGASTRATGIPARFSGSGSGTEFTLTISSLQSEDFAVYYCQQYGSSPRMYTFGQGTKVDIKRTAAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC | 305 |
| heavy chain | QMQLVQSGAEVKKPGSSVKVSCKASGGTFSSYAISWVRQAPGQGLEWMGGIIPIFGTANYAQKFQGRVTITADKSISTAYMELSSLRSEDTAVYYCARGGLGELDNWFDPWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 306 |

TABLE 7

| Antibody clone G1 | | |
|---|---|---|
| | Amino acid sequence (N→C)/ Nucleic acid sequence (5'→3') | SEQ ID NO |
| CDR-L1 | SGYKLGDRYVS | 19 |
| CDR-L2 | KDSQRPS | 20 |
| CDR-L3 | QAWDSGTGV | 21 |
| CDR-H1 | SYGIS | 22 |
| CDR-H2 | WISAYNGNTNYAQELQG | 23 |
| CDR-H3 | VGVAGKLDY | 24 |
| light chain variable region | SYELTQPPSLSVSPGQTASITCSGYKLGDRYVSWYQQKTGQSPVVVIYKDSQRPSGVPERFSGSNSGNTATLTISGTQAMDEADYYCQAWDSGTGVFGGGTKLTVLGQPAAA | 227 |

TABLE 7-continued

| Antibody clone G1 | | |
|---|---|---|
| | Amino acid sequence (N→C)/ Nucleic acid sequence (5'→3') | SEQ ID NO |
| light chain variable region coding gene | TCCTATGAGCTGACTCAGCCACCCTCACTGTCCGTGTCCCCAGGACAGACAGCCAGCATCACCTGCTCAGGATATAAACTGGGAGATAGATATGTTTCCTGGTATCAGCAGAAGACAGGCCAGTCCCCTGTGGTGGTCATCTATAAAGATAGCCAGCGGCCCTCAGGGGTCCCTGAACGATTCTCTGGCTCCAACTCTGGGAACACAGCCACTCTGACCATCAGCGGGACCCAGGCTATGGATGAGGCTGACTATTACTGTCAGGCGTGGGACAGCGGCACTGGGGTATTCGGCGGAGGGACCAAGCTGACCGTCCTAGGTCAGCCCGCGGCCGCA | 267 |
| heavy chain variable region | EVQLVQSGAEVKKPGSSVKVSCKASGGTFSSYGISWVRQAPGQGLEWMGWISAYNGNTNYAQELQGRVTMTTDTSTSTAYMELRSLRSDDTAVYYCARVGVAGKLDYWGQGTLVTVSS | 228 |
| heavy chain variable region coding gene | GAAGTGCAGCTGGTGCAGTCTGGGGCTGAGGTGAAGAAGCCTGGGTCCTCGGTGAAGGTCTCCTGCAAGGCTTCTGGAGGCACCTTCAGCAGCTATGGTATCAGCTGGGTGCGACAGGCCCCTGGACAAGGGCTTGAGTGGATGGGATGGATCAGCGCTTACAATGGTAACACAAACTATGCACAGGAGCTCCAGGGCAGAGTCACCATGACCACAGACACATCCACGAGCACAGCCTATATGGAGCTGAGGAGCCTGAGATCTGACGACACGGCCGTGTATTACTGTGCGAGAGTAGGGGTGGCTGGTAAACTTGACTACTGGGGCCAAGGAACCCTGGTCACCGTCTCGAGT | 268 |
| light chain (Lambda) | SYELTQPPSLSVSPGQTASITCSGYKLGDRYVSWYQQKTGQSPVVVIYKDSQRPSGVPERFSGSNSGNTATLTISGTQAMDEADYYCQAWDSGTGVFGGGTKLTVLGQPAAAPSVTLFPPSSEELQANKATLVCLISDFYPGAVTVAWKEDSSPVKAGVETTTPSKQSNNKYAASSYLSLTPEQWKSHRSYSCQVTHEGSTVEKTVAPTECS | 307 |
| heavy chain | EVQLVQSGAEVKKPGSSVKVSCKASGGTFSSYGISWVRQAPGQGLEWMGWISAYNGNTNYAQELQGRVTMTTDTSTSTAYMELRSLRSDDTAVYYCARVGVAGKLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 308 |

TABLE 8

| Antibody clone G9 | | |
|---|---|---|
| | Amino acid sequence (N→C)/ Nucleic acid sequence (5'→3') | SEQ ID NO |
| CDR-L1 | TGSSSDVGGYNYVS | 25 |
| CDR-L2 | DVSNRPS | 26 |
| CDR-L3 | SSYTGSSTLDVL | 27 |
| CDR-H1 | SYWIG | 28 |
| CDR-H2 | IIYPGDSDTRYSPSFQG | 29 |
| CDR-H3 | QYYDGGYYMDV | 30 |
| light chain variable region | QSALTQPASVSGSPGQSITISCTGSSSDVGGYNYVSWYQQHPGKAPKLMIYDVSNRPSGVSDRFSGSKSGNMASLTISGLQAEDEADYYCSSYTGSSTLDVLFGGGTKLTVLGQPAAA | 233 |

TABLE 8-continued

| Antibody clone G9 | | |
|---|---|---|
| | Amino acid sequence (N→C)/<br>Nucleic acid sequence (5'→3') | SEQ ID NO |
| light chain variable region coding gene | CAGTCTGCGCTGACTCAGCCTGCCTCCGTGTCTGGGTCT<br>CCTGGACAGTCGATCACCATCTCCTGCACTGGAAGCAGC<br>AGTGACGTTGGTGGTTATAACTATGTCTCCTGGTACCAG<br>CAACACCCAGGCAAAGCCCCCAAACTCATGATTTATGAT<br>GTCAGTAATCGGCCCTCAGGGGTTTCTGATCGCTTCTCT<br>GGCTCCAAGTCTGGCAACATGGCCTCCCTGACCATCTCT<br>GGGCTCCAGGCTGAGGACGAGGCTGATTATTACTGCAGC<br>TCATATACAGGAAGCAGCACTCTCGACGTGCTATTCGGC<br>GGAGGGACCAAGCTGACCGTCCTAGGTCAGCCCGCGGCC<br>GCA | 269 |
| heavy chain variable region | QVQLVQPGAEVKKPGESLKISCKGSGYSFTSYWIGWVRQ<br>MPGKGLEWMGIIYPGDSDTRYSPSFQGQVTISADKSIST<br>AYLQWSSLKASDTAMYYCASQYYDGGYYMDVWGQGTLVT<br>VSS | 234 |
| heavy chain variable region coding gene | CAGGTGCAGCTGGTGCAGCCTGGAGCAGAGGTGAAAAAG<br>CCGGGGGAGTCTCTGAAGATCTCCTGTAAGGGTTCTGGA<br>TACAGCTTTACCAGCTACTGGATCGGCTGGGTGCGCCAG<br>ATGCCCGGGAAGGGCCTGGAGTGGATGGGGATCATCTAT<br>CCTGGTGACTCTGATACCAGATACAGCCCGTCCTTCCAA<br>GGCCAGGTCACCATCTCAGCCGACAAGTCCATCAGCACC<br>GCCTACCTGCAGTGGAGCAGCCTGAAGGCCTCGGACACC<br>GCCATGTATTACTGTGCGAGTCAATATTACGATGGGGGT<br>TACTACATGGACGTCTGGGGCCAGGGAACCCTGGTCACC<br>GTCTCGAGT | 270 |
| light chain (Lambda) | QSALTQPASVSGSPGQSITISCTGSSSDVGGYNYVSWYQ<br>QHPGKAPKLMIYDVSNRPSGVSDRFSGSKSGNMASLTIS<br>GLQAEDEADYYCSSYTGSSTLDVLFGGGTKLTVLGQPAA<br>APSVTLFPPSSEELQANKATLVCLISDFYPGAVTVAWKA<br>DSSPVKAGVETTTPSKQSNNKYAASSYLSLTPEQWKSHR<br>SYSCQVTHEGSTVEKTVAPTECS | 309 |
| heavy chain | QVQLVQPGAEVKKPGESLKISCKGSGYSFTSYWIGWVRQ<br>MPGKGLEWMGIIYPGDSDTRYSPSFQGQVTISADKSIST<br>AYLQWSSLKASDTAMYYCASQYYDGGYYMDVWGQGTLVT<br>VSSASTKGPSVFPLAPCSRSTSESTAALGCLVKDYFPEP<br>VTVSWNSGALTSGVHTFPAVLQSSGLYSLSSVVTVPSSS<br>LGTKTYTCNVDHKPSNTKVDKRVESKYGPPCPPCPAPEF<br>LGGPSVFLFPPKPKDTLMISRTPEVTCVVVDVSQEDPEV<br>QFNWYVDGVEVHNAKTKPREEQFNSTYRVVSVLTVLHQD<br>WLNGKEYKCKVSNKGLPSSIEKTISKAKGQPREPQVYTL<br>PPSQEEMTKNQVSLTCLVKGFYPSDIAVEWESNGQPENN<br>YKTTPPVLDSDGSFFLYSRLTVDKSRWQEGNVFSCSVMH<br>EALHNHYTQKSLSLSLGK | 310 |

TABLE 9

| Antibody clone H2 | | |
|---|---|---|
| | Amino acid sequence (N→C)/<br>Nucleic acid sequence (5'→3') | SEQ ID NO |
| CDR-L1 | QGDSLRNYYAS | 31 |
| CDR-L2 | GNNKRPS | 32 |
| CDR-L3 | NSLDSTYNHPI | 33 |
| CDR-H1 | SYDIH | 34 |
| CDR-H2 | WISAYNGNTNYAQKLQG | 35 |
| CDR-H3 | DGGDAFDI | 36 |
| light chain variable region | SYELTQDPAVSVALGQTVRITCQGDSLRNYYASWYQQKP<br>GQAPILVISGNNKRPSGIPDRFSGSSSGDTASLTISGAQ<br>AEDEADYYCNSLDSTYNHPIFGGGTKVTVLGQPAAA | 235 |

TABLE 9-continued

| Antibody clone H2 | | |
|---|---|---|
| | Amino acid sequence (N→C)/ Nucleic acid sequence (5'→3') | SEQ ID NO |
| light chain variable region coding gene | TCCTATGAGCTGACTCAGGACCCTGCTGTGTCGGTGGCCTTGGGACAGACAGTCAGGATCACATGCCAAGGAGACAGCCTCAGAAACTATTATGCAAGCTGGTACCAGCAGAAGCCAGGACAGGCCCCTATTCTTGTCATCTCTGGTAACAACAAACGGCCCTCGGGGATCCCAGACCGATTCTCTGGCTCCAGCTCAGGAGACACAGCTTCCTTGACCATCTCTGGGGCTCAGGCGGAAGATGAGGCTGACTATTACTGTAACTCCCTAGACAGCACTTATAACCATCCGATATTCGGCGGAGGGACCAAGGTCACCGTCCTAGGTCAGCCCGCGGCCGCA | 271 |
| heavy chain variable region | QVQLVQSGAEVKKPGASVKVSCKASGYTFTSYDIHWVRQATGQGLEWMGWISAYNGNTNYAQKLQGRVTMTTDTSTSTAYMELRSLRSDDTAVYYCARDGGDAFDIWGQGTLVTVSS | 236 |
| heavy chain variable region coding gene | CAGGTCCAGCTTGTGCAGTCTGGGGCTGAGGTGAAGAAGCCTGGGGCCTCAGTGAAGGTCTCCTGCAAGGCTTCTGGATACACCTTCACCAGTTATGATATCCACTGGGTGCGACAGGCCACTGGACAAGGGCTTGAGTGGATGGGATGGATCAGCGCTTACAATGGTAACACAAACTATGCACAGAAGCTCCAGGGCAGAGTCACCATGACCACAGACACATCCACGAGCACAGCCTACATGGAGCTGAGGAGCCTGAGATCTGACGACACGGCCGTGTATTACTGTGCGAGAGATGGGGGTGATGCTTTTGATATCTGGGGCCAAGGAACCCTGGTCACCGTCTCGAGT | 272 |
| light chain (Lambda) | SYELTQDPAVSVALGQTVRITCQGDSLRNYYASWYQQKPGQAPILVISGNNKRPSGIPDRFSGSSSGDTASLTISGAQAEDEADYYCNSLDSTYNHPIFGGGTKVTVLGQPAAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 311 |
| heavy chain | QVQLVQSGAEVKKPGASVKVSCKASGYTFTSYDIHWVRQATGQGLEWMGWISAYNGNTNYAQKLQGRVTMTTDTSTSTAYMELRSLRSDDTAVYYCARDGGDAFDIWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 312 |

TABLE 10

| Antibody clone H11 | | |
|---|---|---|
| | Amino acid sequence (N→C)/ Nucleic acid sequence (5'→3') | SEQ ID NO |
| CDR-L1 | QGDSLRSYYAS | 37 |
| CDR-L2 | GRNNRPS | 38 |
| CDR-L3 | KSRDSSGNHYV | 39 |
| CDR-H1 | SYYMH | 40 |
| CDR-H2 | IINPSGGSTSYAQKFQG | 41 |
| CDR-H3 | DAGSSSDY | 42 |
| light chain variable region | SYELTQDPAASVALGQTVRITCQGDSLRSYYASWYQQKPGQAPVVVIYGRNNRPSGIPDRFSGSSSGDTASLTITGAQAEDEADYYCKSRDSSGNHYVFGTGTKLTVLGQPAAA | 231 |

TABLE 10-continued

| Antibody clone H11 | | |
|---|---|---|
| | Amino acid sequence (N→C)/ Nucleic acid sequence (5'→3') | SEQ ID NO |
| light chain variable region coding gene | TCCTATGAGCTGACTCAGGACCCTGCTGCGTCTGTGGCCTTGGGACAGACAGTCAGGATCACATGCCAAGGAGACAGCCTCAGAAGCTATTATGCAAGCTGGTACCAGCAGAAGCCAGGACAGGCCCCTGTAGTTGTCATCTATGGTAGAAACAACCGGCCCTCAGGGATCCCAGACCGATTCTCTGGCTCCAGCTCAGGAGACACAGCTTCCTTGACCATCACTGGGGCTCAGGCGGAAGATGAGGCTGACTATTACTGTAAGTCCCGGGACAGCAGTGGTAACCATTATGTCTTCGGAACTGGGACCAAGCTGACCGTCCTAGGTCAGCCCGCGGCCGCA | 273 |
| heavy chain variable region | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDAGSSSDYWGRGTLVTVSS | 232 |
| heavy chain variable region coding gene | CAGGTGCAGCTGGTGCAGTCTGGGGCTGAGGTGAAGAAGCCTGGGGCCTCAGTGAAGGTTTCCTGCAAGGCATCTGGATACACCTTCACCAGCTACTATATGCACTGGGTGCGACAGGCCCCTGGACAAGGGCTTGAGTGGATGGGAATAATCAACCCTAGTGGTGGTAGCACAAGCTACGCACAGAAGTTCCAGGGCAGAGTCACCATGACCAGGGACACGTCCACGAGCACAGTCTACATGGAGCTGAGCAGCCTGAGATCTGAGGACACGGCCGTGTATTACTGTGCGAGAGATGCCGGCAGCTCGTCCGATTACTGGGGCCGTGGCACCCTGGTCACCGTCTCGAGT | 274 |
| light chain (Lambda) | SYELTQDPAASVALGQTVRITCQGDSLRSYYASWYQQKPGQAPVVVIYGRNNRPSGIPDRFSGSSSGDTASLTITGAQAEDEADYYCKSRDSSGNHYVFGTGTKLTVLGQPAAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 313 |
| heavy chain | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDAGSSSDYWGRGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 314 |

TABLE 11

| Antibody clone F12 | | |
|---|---|---|
| | Amino acid sequence (N→C)/ Nucleic acid sequence (5'→3') | SEQ ID NO |
| CDR-L1 | AGTSSDIGDYDYVS | 43 |
| CDR-L2 | DVSRRPS | 44 |
| CDR-L3 | ASYTSSSVVV | 45 |
| CDR-H1 | SYWIG | 46 |
| CDR-H2 | IIYPGDSDTRYSPSFQG | 47 |
| CDR-H3 | QYYDGGYYMDV | 48 |
| light chain variable region | QSVLTQPASVSGSPGQSITISCAGTSSDIGDYDYVSWYQQHPGKTPKLMIYDVSRRPSGVPDRFSGSKSGNTASLTISGLQTEDEADYYCASYTSSSVVVFGGGTKLTVLGQPAAA | 237 |

TABLE 11-continued

| Antibody clone F12 | | |
|---|---|---|
| | Amino acid sequence (N→C)/ Nucleic acid sequence (5'→3') | SEQ ID NO |
| light chain variable region coding gene | CAGTCTGTGCTGACTCAGCCTGCCTCCGTGTCTGGGTCTCCTGGACAGTCGATCACCATCTCCTGCGCTGGAACCAGCAGTGACATTGGTGATTATGACTATGTCTCCTGGTACCAACAGCACCCAGGCAAGACTCCCAAACTCATGATTTATGATGTCAGTAGGCGGCCCTCAGGGGTCCCTGATCGCTTCTCTGGCTCCAAGTCTGGCAACACGGCCTCCCTGACCATCTCTGGGCTCCAGACTGAGGACGAGGCTGATTATTACTGCGCCTCATATACAAGCAGCAGCGTCGTGGTCTTCGGCGGAGGGACCAAGCTGACCGTCCTAGGTCAGCCCGCGGCCGCA | 275 |
| heavy chain variable region | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSS | 238 |
| heavy chain variable region coding gene | CAGGTGCAGCTGGTGCAGTCTGGAGCAGAGGTGAAAAAGCCCGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGTCAATATTACGATGGGGGTTACTACATGGACGTCTGGGGCCAGGGCACCCTGGTCACCGTCTCGAGT | 276 |
| light chain (Lambda) | QSVLTQPASVSGSPGQSITISCAGTSSDIGDYDYVSWYQQHPGKTPKLMIYDVSRRPSGVPDRFSGSKSGNTASLTISGLQTEDEADYYCASYTSSSVVVFGGGTKLTVLGQPAAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 315 |
| heavy chain | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 316 |

TABLE 12

| Antibody clone B9 | | |
|---|---|---|
| | Amino acid sequence (N→C)/ Nucleic acid sequence (5'→3') | SEQ ID NO |
| CDR-L1 | RASQSISRYLN | 49 |
| CDR-L2 | GASSLQS | 50 |
| CDR-L3 | QQAYGFPLT | 51 |
| CDR-H1 | SYAIS | 52 |
| CDR-H2 | GIIPIFGTANYAQKFQG | 53 |
| CDR-H3 | GEIAVAQNWDYYGMDV | 54 |
| light chain variable region | DIQMTQSPSSLSASVGDRVTITCRASQSISRYLNWYQQKPGKAPKLLIYGASSLQSGVPSRFSGSGSGTDFTLTISSLQPEDFATYHCQQAYGFPLTLGGGTKVEIKRTAA | 229 |

TABLE 12-continued

| Antibody clone B9 | | |
|---|---|---|
| | Amino acid sequence (N→C)/ Nucleic acid sequence (5'→3') | SEQ ID NO |
| light chain variable region coding gene | GACATCCAGATGACCCAGTCTCCATCCTCCCTGTCTGCA TCTGTAGGAGACAGAGTCACCATCACTTGCCGGGCAAGT CAGAGCATTAGCAGGTATTTAAATTGGTATCAGCAGAAA CCAGGGAAAGCCCCCAAGCTCCTGATCTATGGTGCATCC AGTTTGCAAAGTGGGGTCCCATCAAGGTTCAGTGGCAGT GGATCTGGGACAGATTTCACTCTCACCATCAGCAGTCTG CAGCCTGAAGATTTCGCAACTTACCATTGTCAACAGGCT TACGGTTTCCCCCTCACTCTCGGGGGAGGGACCAAGGTG GAGATCAAACGTACCGCGGCCGCA | 277 |
| heavy chain variable region | QVQLVESGAEVKKPGSSVKVSCKASGGTFSSYAISWVRQ APGQGLEWMGGIIPIFGTANYAQKFQGRVTITADESTST AYMELSSLRSEDTAVYYCARGEIAVAQNWDYYGMDVWGQ GTLVTVSS | 230 |
| heavy chain variable region coding gene | CAGGTGCAGCTGGTGGAGTCTGGGGCTGAGGTGAAGAAG CCTGGGTCCTCGGTGAAGGTCTCCTGCAAGGCTTCTGGA GGCACCTTCAGCAGCTATGCTATCAGCTGGGTGCGACAG GCCCCTGGACAAGGGCTTGAGTGGATGGGAGGGATCATC CCTATCTTTGGTACAGCAAACTACGCACAGAAGTTCCAG GGCAGAGTCACGATTACCGCGGACGAATCCACGAGCACA GCCTACATGGAGCTGAGCAGCCTGAGATCTGAGGACACG GCCGTGTATTACTGTGCGAGAGGGGAAATAGCAGTGGCT CAAAACTGGGACTACTACGGTATGGACGTCTGGGGCCAG GGCACCCTGGTCACCGTCTCGAGT | 278 |
| light chain (Kappa) | DIQMTQSPSSLSASVGDRVTITCRASQSISRYLNWYQQK PGKAPKLLIYGASSLQSGVPSRFSGSGSGTDFTLTISSL QPEDFATYHCQQAYGFPLTLGGGTKVEIKRTAAPSVFI FPPSDEQLKSGTASVVCLLNNFYPREAKVQWKVDNALQS GNSQESVTEQDSKDSTYSLSSTLTLSKADYEKHKLYACE VTHQGLSSPVTKSFNRGEC | 317 |
| heavy chain | QVQLVESGAEVKKPGSSVKVSCKASGGTFSSYAISWVRQ APGQGLEWMGGIIPIFGTANYAQKFQGRVTITADESTST AYMELSSLRSEDTAVYYCARGEIAVAQNWDYYGMDVWGQ GTLVTVSSASTKGPSVFPLAPCSRSTSESTAALGCLVKD YFPEPVTVSWNSGALTSGVHTFPAVLQSSGLYSLSSVVT VPSSSLGTKTYTCNVDHKPSNTKVDKRVESKYGPPCPPC PAPEFLGGPSVFLFPPKPKDTLMISRTPEVTCVVVDVSQ EDPEVQFNWYVDGVEVHNAKTKPREEQFNSTYRVVSVLT VLHQDWLNGKEYKCKVSNKGLPSSIEKTISKAKGQPREP QVYTLPPSQEEMTKNQVSLTCLVKGFYPSDIAVEWESNG QPENNYKTTPPVLDSDGSFFLYSRLTVDKSRWQEGNVFS CSVMHEALHNHYTQKSLSLSLGK | 318 |

TABLE 13

| Antibody clone G11 | | |
|---|---|---|
| | Amino acid sequence (N→C)/ Nucleic acid sequence (5'→3') | SEQ ID NO |
| CDR-L1 | TGTSSDVGGYNYVS | 55 |
| CDR-L2 | DVSKRPS | 56 |
| CDR-L3 | SSYSSSSTLVV | 57 |
| CDR-H1 | SYWIG | 58 |
| CDR-H2 | IIYPGDSDTRYSPSFQG | 59 |
| CDR-H3 | QYYDGGYYMDV | 60 |
| light chain variable region | QSALTQPRSVSGSPGQSVTISCTGTSSDVGGYNYVSWYQ QHPGKAPKLMIYDVSKRPSGVPDRFSGSKSGNTASLTIS GLQAEDEADYYCSSYSSSSTLVVFGGGTKLTVLGQPAAA | 239 |

TABLE 13-continued

| Antibody clone G11 | | |
|---|---|---|
| | Amino acid sequence (N→C)/ Nucleic acid sequence (5'→3') | SEQ ID NO |
| light chain variable region coding gene | CAGTCTGCGCTGACTCAGCCTCGCTCAGTGTCCGGGTCTCCTGGACAGTCAGTCACCATCTCCTGCACTGGAACCAGCAGTGATGTTGGTGGTTATAACTATGTCTCCTGGTACCAACAGCACCCAGGCAAAGCCCCCAAACTCATGATTTATGATGTCAGTAAGCGGCCCTCAGGGGTCCCTGATCGCTTCTCTGGCTCCAAGTCTGGCAACACGGCCTCCCTGACAATCTCTGGGCTCCAGGCTGAGGACGAGGCTGATTATTACTGCAGCTCATATTCAAGCAGCAGCACTCTCGTGGTTTTCGGCGGAGGGACCAAGCTGACCGTCCTAGGTCAGCCCGCGGCCGCA | 279 |
| heavy chain variable region | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSS | 240 |
| heavy chain variable region coding gene | CAGGTCCAGCTGGTACAGTCTGGAGCAGAGGTGAAAAAGCCGGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGTCAATATTACGATGGGGGTTACTACATGGACGTCTGGGGCCAGGGAACCCTGGTCACCGTCTCGAGT | 280 |
| light chain (Lambda) | QSALTQPRSVSGSPGQSVTISCTGTSSDVGGYNYVSWYQQHPGKAPKLMIYDVSKRPSGVPDRFSGSKSGNTASLTISGLQAEDEADYYCSSYSSSSTLVVFGGGTKLTVLGQPAAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 319 |
| heavy chain | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCASQYYDGGYYMDVWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 320 |

TABLE 14

| Antibody clone G6 | | |
|---|---|---|
| | Amino acid sequence (N→C)/ Nucleic acid sequence (5'→3') | SEQ ID NO |
| CDR-L1 | QGDSLRRYYAT | 61 |
| CDR-L2 | GQNYRPS | 62 |
| CDR-L3 | NSRDSSGNHVV | 63 |
| CDR-H1 | SYYMH | 64 |
| CDR-H2 | GIIPIFGTANYAQKFQG | 65 |
| CDR-H3 | GWGYSSSFDY | 66 |
| light chain variable region | SYELTQDPAVSVALGQTVTITCQGDSLRRYYATWYQQKPGQAPVLVIYGQNYRPSGIPDRFSGSNSGTTASLTITGAQAEDEADYYCNSRDSSGNHVVFGGGTKLTVLGQPAAA | 241 |

TABLE 14-continued

| Antibody clone G6 | | |
|---|---|---|
| | Amino acid sequence (N→C)/ Nucleic acid sequence (5'→3') | SEQ ID NO |
| light chain variable region coding gene | TCCTATGAGCTGACTCAGGACCCTGCTGTGTCTGTGGCC TTGGGACAGACAGTCACGATCACATGCCAAGGAGACAGC CTCAGAAGGTATTATGCAACCTGGTACCAGCAGAAGCCA GGACAGGCCCCTGTCCTTGTCATCTATGGTCAAAACTAC CGGCCCTCGGGGATCCCAGACCGATTCTCTGGCTCCAAC TCAGGAACCACAGCTTCCTTGACCATCACTGGGGCTCAG GCGGAAGATGAGGCTGACTATTACTGTAACTCCCGGGAC AGCAGTGGTAACCATGTGGTATTCGGCGGAGGGACCAAG CTGACCGTCCTAGGTCAGCCCGCGGCCGCA | 281 |
| heavy chain variable region | EVQLVESGAEVKKPGASVKVSCKASGYTFTSYYMHWVRQ APGQGLEWMGGIIPIFGTANYAQKFQGRVTITADESTST AYMELSSLRSEDTAVYYCARGWGYSSSFDYWGQGTTVTV SS | 242 |
| heavy chain variable region coding gene | GAGGTGCAGCTGGTGGAGTCTGGGGCTGAGGTGAAGAAG CCTGGGGCCTCAGTGAAGGTTTCCTGCAAGGCATCTGGA TACACCTTCACCAGCTACTATATGCACTGGGTGCGACAG GCCCCTGGACAAGGGCTTGAGTGGATGGGAGGGATCATC CCTATCTTTGGTACAGCAAACTACGCACAGAAGTTCCAG GGCAGAGTCACGATTACCGCGGACGAATCCACGAGCACA GCCTACATGGAGCTGAGCAGCCTGAGATCTGAGGACACG GCCGTGTACTACTGTGCGAGAGGGTGGGGGTATAGCAGC TCGTTTGACTACTGGGGGCAAGGGACCACGGTCACCGTC TCGAGT | 282 |
| light chain (Lambda) | SYELTQDPAVSVALGQTVTITCQGDSLRRYYATWYQQKP GQAPVLVIYGQNYRPSGIPDRFSGSNSGTTASLTITGAQ AEDEADYYCNSRDSSGNHVVFGGGTKLTVLGQPAAAPSV TLFPPSSEELQANKATLVCLISDFYPGAVTVAWKADSSP VKAGVETTTPSKQSNNKYAASSYLSLTPEQWKSHRSYSC QVTHEGSTVEKTVAPTECS | 321 |
| heavy chain | EVQLVESGAEVKKPGASVKVSCKASGYTFTSYYMHWVRQ APGQGLEWMGGIIPIFGTANYAQKFQGRVTITADESTST AYMELSSLRSEDTAVYYCARGWGYSSSFDYWGQGTTVTV SSASTKGPSVFPLAPCSRSTSESTAALGCLVKDYFPEPV TVSWNSGALTSGVHTFPAVLQSSGLYSLSSVVTVPSSSL GTKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLP PSQEEMTKNQVSLTCLVKGFYPSDIAVEWESNGQPENNY KTTPPVLDSDGSFFLYSRLTVDKSRWQEGNVFSCSVMHE ALHNHYTQKSLSLSLGK | 322 |

TABLE 15

| Antibody clone F11 | | |
|---|---|---|
| | Amino acid sequence (N→C)/ Nucleic acid sequence (5'→3') | SEQ ID NO |
| CDR-L1 | SGSSSNIGTNTVN | 67 |
| CDR-L2 | SNDQRPS | 68 |
| CDR-L3 | ETWDDSLKGPV | 69 |
| CDR-H1 | SYAMS | 70 |
| CDR-H2 | TISGSGDSTYYADSVKG | 71 |
| CDR-H3 | EWELGDAFDI | 72 |
| light chain variable region | QSVLTQPPSTSGTPGQTFSIFCSGSSSNIGTNTVNWYQQ LPGTAPKLLIYSNDQRPSGVPDRFSGSKSGTSASLAISG LQSEDEADYYCETWDDSLKGPVFGGGTKVTVLGQPAAA | 243 |

TABLE 15-continued

| Antibody clone F11 | | |
|---|---|---|
| | Amino acid sequence (N→C)/ Nucleic acid sequence (5'→3') | SEQ ID NO |
| light chain variable region coding gene | CAGTCTGTGCTGACTCAGCCACCCTCAACGTCTGGGACC CCCGGGCAGACGTTCTCCATTTTTTGTTCTGGAAGCAGT TCGAACATCGGAACTAATACTGTTAATTGGTACCAGCAG CTCCCAGGAACGGCCCCCAAACTCCTCATCTATAGTAAT GATCAGCGGCCCTCAGGGGTCCCTGACCGATTCTCTGGC TCCAAGTCTGGCACCTCAGCCTCCCTGGCCATCAGTGGG CTCCAGTCTGAGGATGAGGCTGATTATTACTGTGAAACA TGGGATGACAGCCTGAAAGGCCCGGTGTTCGGCGGGGGG ACCAAGGTCACCGTCCTAGGTCAGCCCGCGGCCGCA | 283 |
| heavy chain variable region | EVQLVESGGGLVQPGGSLKLSCAASGFTFSSYAMSWVRR APGKGLEWVSTISGSGDSTYYADSVKGRFTISRDNSKNT LYLQMNNLRAEDTAVYYCAREWELGDAFDIWGRGTLVTV SS | 244 |
| heavy chain variable region coding gene | GAGGTGCAGCTGGTGGAGTCTGGGGGAGGCTTGGTCCAG CCTGGGGGGTCCCTGAAACTCTCCTGTGCAGCGTCTGGA TTCACCTTTAGCAGCTATGCCATGAGCTGGGTCCGCCGG GCTCCAGGGAAGGGGCTGGAGTGGGTCTCAACTATTAGT GGTAGTGGTGATAGCACATACTACGCAGACTCCGTGAAG GGCCGGTTCACCATCTCCAGAGACAATTCCAAGAACACG CTGTATCTGCAAATGAACAACCTGAGAGCCGAGGACACG GCCGTATATTACTGTGCGAGAGAATGGGAACTAGGCGAT GCTTTTGATATCTGGGGCCGTGGCACCCTGGTCACCGTC TCGAGT | 284 |
| light chain (Lambda) | QSVLTQPPSTSGTPGQTFSIFCSGSSSNIGTNTVNWYQQ LPGTAPKLLIYSNDQRPSGVPDRFSGSKSGTSASLAISG LQSEDEADYYCETWDDSLKGPVFGGGTKVTVLGQPAAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS | 323 |
| heavy chain | EVQLVESGGGLVQPGGSLKLSCAASGFTFSSYAMSWVRR APGKGLEWVSTISGSGDSTYYADSVKGRFTISRDNSKNT LYLQMNNLRAEDTAVYYCAREWELGDAFDIWGRGTLVTV SSASTKGPSVFPLAPCSRSTSESTAALGCLVKDYFPEPV TVSWNSGALTSGVHTFPAVLQSSGLYSLSSVVTVPSSSL GTKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLP PSQEEMTKNQVSLTCLVKGFYPSDIAVEWESNGQPENNY KTTPPVLDSDGSFFLYSRLTVDKSRWQEGNVFSCSVMHE ALHNHYTQKSLSLSLGK | 324 |

TABLE 16

| Antibody clone D3 | | |
|---|---|---|
| | Amino acid sequence (N→C)/ Nucleic acid sequence (5'→3') | SEQ ID NO |
| CDR-L1 | RASQSISSYLN | 73 |
| CDR-L2 | AASSLQS | 74 |
| CDR-L3 | QQSYSTRWT | 75 |
| CDR-H1 | SYAMS | 76 |
| CDR-H2 | AISGSGGSTYYADSVKG | 77 |
| CDR-H3 | DRGSYGYYYGMDV | 78 |
| light chain variable region | DIQMTQSPSSLSASVGDRVTITCRASQSISSYLNWYQQK PGKAPKLLIYAASSLQSGVPSRFSGSGSGTDFTLTISSL QPEDFATYYCQQSYSTRWTFGQGTKVEIKRTAA | 245 |

TABLE 16-continued

| Antibody clone D3 | | |
|---|---|---|
| | Amino acid sequence (N→C)/ Nucleic acid sequence (5'→3') | SEQ ID NO |
| light chain variable region coding gene | GACATCCAGATGACCCAGTCTCCATCCTCCCTGTCTGCA TCTGTAGGAGACAGAGTCACCATCACTTGCCGGGCAAGT CAGAGCATTAGCAGCTATTTAAATTGGTATCAGCAGAAA CCAGGGAAAGCCCCTAAGCTCCTGATCTATGCTGCATCC AGTTTGCAAAGTGGGGTCCCATCAAGGTTCAGTGGCAGT GGATCTGGGACAGATTTCACTCTCACCATCAGCAGTCTG CAACCTGAAGATTTTGCAACTTACTACTGTCAACAGAGT TACAGTACCCGGTGGACGTTCGGCCAAGGGACCAAGGTG GAAATCAAACGTACCGCGGCCGCA | 285 |
| heavy chain variable region | EVQLLESGGGVVQPGRSLRLSCAASGSTFSSYAMSWVRQ APGKGLEWVSAISGSGGSTYYADSVKGRFTISRDNSKNT LYLQMNSLRAEDTAVYYCAKDRGSYGYYYGMDVWGQGTM VTVSS | 246 |
| heavy chain variable region coding gene | GAGGTGCAGCTGTTGGAGTCTGGGGGAGGCGTGGTCCAG CCTGGGAGGTCCCTGAGACTCTCCTGTGCAGCCTCTGGA TCCACCTTTAGCAGCTATGCCATGAGCTGGGTCCGCCAG GCTCCAGGGAAGGGGCTGGAGTGGGTCTCAGCTATTAGT GGTAGTGGTGGTAGCACATACTACGCAGACTCCGTGAAG GGCCGGTTCACCATCTCCAGAGACAATTCCAAGAACACG CTGTATCTGCAAATGAACAGCCTGAGAGCCGAGGACACG GCCGTATATTACTGTGCGAAAGACAGAGGCAGCTATGGT TACTACTACGGTATGGACGTCTGGGGCCAAGGGACAATG GTCACCGTCTCGAGT | 286 |
| light chain (Kappa) | DIQMTQSPSSLSASVGDRVTITCRASQSISSYLNWYQQK PGKAPKLLIYAASSLQSGVPSRFSGSGSGTDFTLTISSL QPEDFATYYCQQSYSTRWTFGQGTKVEIKRTAAAPSVTL FPPSSEELQANKATLVCLISDFYPGAVTVAWKADSSPVK AGVETTTPSKQSNNKYAASSYLSLTPEQWKSHRSYSCQV THEGSTVEKTVAPTECS | 325 |
| heavy chain | EVQLLESGGGVVQPGRSLRLSCAASGSTFSSYAMSWVRQ APGKGLEWVSAISGSGGSTYYADSVKGRFTISRDNSKNT LYLQMNSLRAEDTAVYYCAKDRGSYGYYYGMDVWGQGTM VTVSSASTKGPSVFPLAPCSRSTSESTAALGCLVKDYFP EPVTVSWNSGALTSGVHTFPAVLQSSGLYSLSSVVTVPS SSLGTKTYTCNVDHKPSNTKVDKRVESKYGPPCPPCPAP EFLGGPSVFLFPPKPKDTLMISRTPEVTCVVVDVSQEDP EVQFNWYVDGVEVHNAKTKPREEQFNSTYRVVSVLTVLH QDWLNGKEYKCKVSNKGLPSSIEKTISKAKGQPREPQVY TLPPSQEEMTKNQVSLTCLVKGFYPSDIAVEWESNGQPE NNYKTTPPVLDSDGSFFLYSRLTVDKSRWQEGNVFSCSV MHEALHNHYTQKSLSLSLGK | 326 |

TABLE 17

| Antibody clone B12 | | |
|---|---|---|
| | Amino acid sequence (N→C)/ Nucleic acid sequence (5'→3') | SEQ ID NO |
| CDR-L1 | RASQSISSYLN | 79 |
| CDR-L2 | AASSLQS | 80 |
| CDR-L3 | QQSYSTLRT | 81 |
| CDR-H1 | GYYMH | 82 |
| CDR-H2 | WINPNSGGTNYAQKFQG | 83 |
| CDR-H3 | AGASIVGATALDY | 84 |
| light chain variable region | DIQMTQSPSSLSASVGDRVTITCRASQSISSYLNWYQQK PGKAPKLLIYAASSLQSGVPSRFSGSGSGTDFTLTISSL QPEDFATYYCQQSYSTLRTFGQGTKVEIKRTAA | 247 |

TABLE 17-continued

| Antibody clone B12 | | |
|---|---|---|
| | Amino acid sequence (N→C)/ Nucleic acid sequence (5'→3') | SEQ ID NO |
| light chain variable region coding gene | GACATCCAGATGACCCAGTCTCCATCCTCCCTGTCTGCA TCTGTAGGAGACAGAGTCACCATCACTTGCCGGGCAAGT CAGAGCATTAGCAGCTATTTAAATTGGTATCAGCAGAAA CCAGGGAAAGCCCCTAAGCTCCTGATCTATGCTGCATCC AGTTTGCAAAGTGGGGTCCCATCAAGGTTCAGTGGCAGT GGATCTGGGACAGATTTCACTCTCACCATCAGCAGTCTG CAACCTGAAGATTTTGCAACTTACTACTGTCAACAGAGT TACAGTACCCTCCGGACGTTCGGCCAAGGGACCAAGGTG GAGATCAAACGTACCGCGGCCGCA | 287 |
| heavy chain variable region | QVQLVQSGAEVKKPGASVKVSCKASGYTFTGYYMHWVRQ APGQGLEWMGWINPNSGGTNYAQKFQGRVTITADESTST AYMELSSLRSEDTAVYYCTRAGASIVGATALDYWGQGTL VTVSS | 248 |
| heavy chain variable region coding gene | CAGGTCCAGCTGGTACAGTCTGGGGCTGAGGTGAAGAAG CCTGGGGCCTCAGTGAAGGTCTCCTGCAAGGCTTCTGGA TACACCTTCACCGGCTACTATATGCACTGGGTGCGACAG GCCCCTGGACAAGGGCTTGAGTGGATGGGATGGATCAAC CCTAACAGTGGTGGCACAAACTACGCACAGAAGTTCCAG GGCAGAGTCACGATTACCGCGGACGAATCCACGAGCACA GCCTACATGGAGCTGAGCAGCCTGAGATCTGAGGACACG GCCGTGTATTACTGTACGAGAGCCGGTGCTTCTATAGTG GGAGCTACCGCGCTTGACTACTGGGGCCAGGGAACCCTG GTCACCGTCTCGAGT | 288 |
| light chain (Kappa) | DIQMTQSPSSLSASVGDRVTITCRASQSISSYLNWYQQK PGKAPKLLIYAASSLQSGVPSRFSGSGSGTDFTLTISSL QPEDFATYYCQQSYSTLRTFGQGTKVEIKRTAAPSVFI FPPSDEQLKSGTASVVCLLNNFYPREAKVQWKVDNALQS GNSQESVTEQDSKDSTYSLSSTLTLSKADYEKHKLYACE VTHQGLSSPVTKSFNRGEC | 327 |
| heavy chain | QVQLVQSGAEVKKPGASVKVSCKASGYTFTGYYMHWVRQ APGQGLEWMGWINPNSGGTNYAQKFQGRVTITADESTST AYMELSSLRSEDTAVYYCTRAGASIVGATALDYWGQGTL VTVSSASTKGPSVFPLAPCSRSTSESTAALGCLVKDYFP EPVTVSWNSGALTSGVHTFPAVLQSSGLYSLSSVVTVPS SSLGTKTYTCNVDHKPSNTKVDKRVESKYGPPCPPCPAP EFLGGPSVFLFPPKPKDTLMISRTPEVTCVVVDVSQEDP EVQFNWYVDGVEVHNAKTKPREEQFNSTYRVVSVLTVLH QDWLNGKEYKCKVSNKGLPSSIEKTISKAKGQPREPQVY TLPPSQEEMTKNQVSLTCLVKGFYPSDIAVEWESNGQPE NNYKTTPPVLDSDGSFFLYSRLTVDKSRWQEGNVFSCSV MHEALHNHYTQKSLSLSLGK | 328 |

TABLE 18

| Antibody clone E4 | | |
|---|---|---|
| | Amino acid sequence (N→C)/ Nucleic acid sequence (5'→3') | SEQ ID NO |
| CDR-L1 | TRSSGSIASNYVQ | 85 |
| CDR-L2 | EDNQRPS | 86 |
| CDR-L3 | QSYDTGNRNYV | 87 |
| CDR-H1 | SYTIS | 88 |
| CDR-H2 | RIIPILGIANYAQKFQG | 89 |
| CDR-H3 | GPSLNYAGYFDN | 90 |
| light chain variable region | NFMLTQPHSVSESPGKTVTISCTRSSGSIASNYVQWYQQR PGSSPTTVIYEDNQRPSGVPDRFSGSIDSSSNSASLTISG LKTEDEADYYCQSYDTGNRNYVFGTGTQLTVLGQPAAA | 249 |

TABLE 18-continued

| Antibody clone E4 | | |
|---|---|---|
| | Amino acid sequence (N→C)/<br>Nucleic acid sequence (5'→3') | SEQ ID NO |
| light chain variable region coding gene | AATTTTATGCTGACTCAGCCCCACTCTGTGTCGGAGTCTC<br>CGGGAAAGACGGTAACCATCTCCTGCACCCGCAGCAGTGG<br>CAGCATTGCCAGCAACTATGTGCAGTGGTACCAGCAGCGC<br>CCGGGCAGTTCCCCCACCACTGTGATCTATGAGGATAACC<br>AAAGACCCTCTGGGGTCCCTGATCGGTTCTCTGGCTCCAT<br>CGACAGCTCCTCCAACTCTGCCTCCCTCACCATCTCTGGA<br>CTGAAGACTGAGGACGAGGCTGACTACTACTGTCAGTCTT<br>ATGATACCGGCAATCGGAATTATGTCTTCGGAACTGGGAC<br>CCAGCTCACCGTCCTAGGTCAGCCCGCGGCCGCA | 289 |
| heavy chain variable region | QVQLVQSGAEVKKPGSSVKVSCKASGGTFSSYTISWVRQA<br>PGQGLEWMGRIIPILGIANYAQKFQGRVTMTRDMSTDTAY<br>MELSSLTYDDTAVYFCVRGPSLNYAGYFDNWGQGTLVTVS<br>S | 250 |
| heavy chain variable region coding gene | CAGGTGCAGCTGGTGCAATCTGGGGCTGAGGTGAAGAAGC<br>CTGGGTCCTCGGTGAAGGTCTCCTGCAAGGCTTCTGGAGG<br>CACCTTCAGCAGCTATACTATCAGCTGGGTGCGACAGGCC<br>CCTGGACAAGGGCTTGAGTGGATGGGAAGGATCATCCCTA<br>TCCTTGGTATAGCAAACTACGCACAGAAGTTCCAGGGCAG<br>AGTCACCATGACCAGGGACATGTCCACAGACACAGCCTAC<br>ATGGAGTTGAGCAGCCTGACATATGATGACACGGCCGTAT<br>ATTTTTGTGTGAGAGGCCCTAGTCTTAATTATGCCGGCTA<br>TTTTGACAACTGGGGCCAGGGCACCCTGGTCACCGTCTCG<br>AGT | 290 |
| light chain (Lambda) | NFMLTQPHSVSESPGKTVTISCTRSSGSIASNYVQWYQQR<br>PGSSPTTVIYEDNQRPSGVPDRFSGSIDSSSNSASLTISG<br>LKTEDEADYYCQSYDTGNRNYVFGTGTQLTVLGQPAAAPS<br>VTLFPPSSEEIQANKATLVCLISDFYPGAVTVAWKADSSP<br>VKAGVETTTPSKQSNNKYAASSYLSLTPEQWKSHRSYSCQ<br>VTHEGSTVEKTVAPTECS | 329 |
| heavy chain | QVQLVQSGAEVKKPGSSVKVSCKASGGTFSSYTISWVRQA<br>PGQGLEWMGRIIPILGIANYAQKFQGRVTMTRDMSTDTAY<br>MELSSLTYDDTAVYFCVRGPSLNYAGYFDNWGQGTLVTVS<br>SASTKGPSVFPLAPCSRSTSESTAALGCLVKDYFPEPVTV<br>SWNSGALTSGVHTFPAVLQSSGLYSLSSVVTVPSSSLGTK<br>TYTCNVDHKPSNTKVDKRVESKYGPPCPPCPAPEFLGGPS<br>VFLFPPKPKDTLMISRTPEVTCVVVDVSQEDPEVQFNWYV<br>DGVEVHNAKTKPREEQFNSTYRVVSVLTVLHQDWLNGKEY<br>KCKVSNKGLPSSIEKTISKAKGQPREPQVYTLPPSQEEMT<br>KNQVSLTCLVKGFYPSDIAVEWESNGQPENNYKTTPPVLD<br>SDGSFFLYSRLTVDKSRWQEGNVFSCSVMHEALHNHYTQK<br>SLSLSLGK | 330 |

TABLE 19

| Antibody clone E12 | | |
|---|---|---|
| | Amino acid sequence (N→C)/<br>Nucleic acid sequence (5'→3') | SEQ ID NO |
| CDR-L1 | QGDSLRSYYAS | 91 |
| CDR-L2 | GKEKRPS | 92 |
| CDR-L3 | NSRGSTTDYMV | 93 |
| CDR-H1 | SYAMH | 94 |
| CDR-H2 | VISYDGSNKYYADSVKG | 95 |
| CDR-H3 | ERGSGMDV | 96 |
| light chain variable region | SYELTQDPAVSVALGQTVRITCQGDSLRSYYASWYQQKS<br>GQAPVLVIYGKEKRPSGIPDRFSGSSSGNTASLTITGAR<br>AEDEADYYCNSRGSTTDYMVFGGGTQLTVLGQPAAA | 251 |

TABLE 19-continued

| Antibody clone E12 | | |
|---|---|---|
| | Amino acid sequence (N→C)/<br>Nucleic acid sequence (5'→3') | SEQ ID NO |
| light chain variable region coding gene | TCCTATGAGCTGACTCAGGACCCTGCTGTGTCTGTGGCC<br>TTGGGACAGACAGTCAGGATCACATGCCAAGGAGACAGC<br>CTCAGAAGCTATTATGCAAGCTGGTACCAGCAGAAGTCA<br>GGACAGGCCCCTGTACTTGTCATCTATGGTAAAGAAAAG<br>CGCCCCTCAGGGATCCCAGACCGATTCTCTGGCTCCAGC<br>TCAGGAAACACAGCTTCCTTGACCATCACTGGGGCTCGG<br>GGGGAAGATGAGGCTGACTATTACTGTAACTCCCGGGGC<br>AGCACTACTGACTATATGGTGTTCGGGGGGGGGACCCAG<br>CTCACCGTCCTAGGTCAGCCCGCGGCCGCA | 291 |
| heavy chain variable region | QVQLVESGGGLVQPGGSLRLSCAASGFTFSSYAMHWVRQ<br>APGKGLEWVAVISYDGSNKYYADSVKGRFTISRDNSKNT<br>LYLQMNSLRAEDTAVYYCARERGSGMDVWGQGTLVTVSS | 252 |
| heavy chain variable region coding gene | CAGGTGCAGCTGGTGGAGTCCGGGGGAGGCTTAGTTCAG<br>CCTGGGGGGTCCCTGAGACTCTCCTGTGCAGCCTCTGGA<br>TTCACCTTCAGTAGCTATGCTATGCACTGGGTCCGCCAG<br>GCTCCAGGCAAGGGGCTGGAGTGGGTGGCAGTTATATCA<br>TATGATGGAAGCAATAAATACTACGCAGACTCCGTGAAG<br>GGCCGATTCACCATCTCCAGAGACAATTCCAAGAACACG<br>CTGTATCTGCAAATGAACAGCCTGAGAGCTGAGGACACG<br>GCTGTGTATTACTGTGCGAGAGAACGGGGAAGTGGTATG<br>GACGTCTGGGGCCAAGGAACCCTGGTCACCGTCTCGAGT | 292 |
| light chain (Lambda) | SYELTQDPAVSVALGQTVRITCQGDSLRSYYASWYQQKS<br>GQAPVLVIYGKEKRPSGIPDRFSGSSSGNTASLTITGAR<br>AEDEADYYCNSRGSTTDYMVFGGGTQLTVLGQPAAAPSV<br>TLFPPSSEELQANKATLVCLISDFYPGAVTVAWKADSSP<br>VKAGVETTTPSKQSNNKYAASSYLSLTPEQWKSHRSYSC<br>QVTHEGSTVEKTVAPTECS | 331 |
| heavy chain | QVQLVESGGGLVQPGGSLRLSCAASGFTFSSYAMHWVRQ<br>APGKGLEWVAVISYDGSNKYYADSVKGRFTISRDNSKNT<br>LYLQMNSLRAEDTAVYYCARERGSGMDVWGQGTLVTVSS<br>ASTKGPSVFPLAPCSRSTSESTAALGCLVKDYFPEPVTV<br>SWNSGALTSGVHTFPAVLQSSGLYSLSSVVTVPSSSLGT<br>KTYTCNVDHKPSNTKVDKRVESKYGPPCPPCPAPEFLGG<br>PSVFLFPPKPKDTLMISRTPEVTCVVVDVSQEDPEVQFN<br>WYVDGVEVHNAKTKPREEQFNSTYRVVSVLTVLHQDWLN<br>GKEYKCKVSNKGLPSSIEKTISKAKGQPREPQVYTLPPS<br>QEEMTKNQVSLTCLVKGFYPSDIAVEWESNGQPENNYKT<br>TPPVLDSDGSFFLYSRLTVDKSRWQEGNVFSCSVMHEAL<br>HNHYTQKSLSLSLGK | 332 |

TABLE 20

| Antibody clone D1 | | |
|---|---|---|
| | Amino acid sequence (N→C)/<br>Nucleic acid sequence (5'→3') | SEQ ID NO |
| CDR-L1 | KASQDIDDDMN | 97 |
| CDR-L2 | EASTLVP | 98 |
| CDR-L3 | LQHDKFPYT | 99 |
| CDR-H1 | SYGIS | 100 |
| CDR-H2 | WINPNSGGTNYAQKFQG | 101 |
| CDR-H3 | RGVDEGDY | 102 |
| light chain variable region | ETTLTQSPAFMSATPGDKVNISCKASQDIDDDMNWYQQK<br>PGEAAISIIQEASTLVPGIPPRFSGSGYGTDFTLTINNI<br>ESEDAAYYFCLQHDKFPYTFGQGTKLEIKRTAAA | 253 |

TABLE 20-continued

| Antibody clone D1 | | |
|---|---|---|
| | Amino acid sequence (N→C)/ Nucleic acid sequence (5'→3') | SEQ ID NO |
| light chain variable region coding gene | GAAACGACACTCACGCAGTCTCCAGCATTCATGTCAGCG ACTCCAGGAGACAAAGTCAACATCTCCTGCAAAGCCAGC CAAGACATTGATGATGATATGAACTGGTACCAACAGAAA CCAGGAGAAGCTGCTATTTCCATTATTCAAGAAGCTAGT ACTCTCGTTCCTGGAATCCCACCTCGATTCAGTGGCAGC GGGTATGGAACAGATTTTACCCTCACAATTAATAACATA GAATCTGAGGATGCTGCATATTACTTCTGTCTACAACAT GATAAGTTCCCGTACACTTTTGGCCAGGGGACCAAGCTG GAGATCAAACGTACCGCGGCCGCA | 293 |
| heavy chain variable region | EVQLVQSGAEVKKPGASVKVSCKASGYTFTSYGISWVRQ APGQGLEWMGWINPNSGGTNYAQKFQGRVTMTRDTSIST AYMELSRLRSDDTAVYYCASRGVDEGDYWGQGTMVTVSS | 254 |
| heavy chain variable region coding gene | GAAGTGCAGCTGGTGCAGTCTGGAGCTGAGGTGAAGAAG CCTGGGGCCTCAGTGAAGGTCTCCTGCAAGGCTTCTGGT TACACCTTTACCAGCTATGGTATCAGCTGGGTGCGACAG GCCCCTGGACAAGGGCTTGAGTGGATGGGATGGATCAAC CCTAACAGTGGTGGCACAAACTATGCACAGAAGTTTCAG GGCAGGGTCACCATGACCAGGGACACGTCCATCAGCACA GCCTACATGGAGCTGAGCAGGCTGAGATCTGACGACACG GCCGTGTATTACTGTGCGAGTCGGGGGGTTGATGAGGGG GACTACTGGGGCCAAGGGACAATGGTCACCGTCTCGAGT | 294 |
| light chain (Kappa) | ETTLTQSPAFMSATPGDKVNISCKASQDIDDDMNWYQQK PGEAAISIIQEASTLVPGIPPRFSGSGYGTDFTLTINNI ESEDAAYYFCLQHDKFPYTFGQGTKLEIKRTAAAPSVFI FPPSDEQLKSGTASVVCLLNNFYPREAKVQWKVDNALQS GNSQESVTEQDSKDSTYSLSSTLTLSKADYEKHKLYACE VTHQGLSSPVTKSFNRGEC | 333 |
| heavy chain | EVQLVQSGAEVKKPGASVKVSCKASGYTFTSYGISWVRQ APGQGLEWMGWINPNSGGTNYAQKFQGRVTMTRDTSIST AYMELSRLRSDDTAVYYCASRGVDEGDYWGQGTMVTVSS ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLGK | 334 |

TABLE 21

| Antibody clone E6 | | |
|---|---|---|
| | Amino acid sequence (N→C)/ Nucleic acid sequence (5'→3') | SEQ ID NO |
| CDR-L1 | TGSSGNIASNYVQ | 103 |
| CDR-L2 | RDDQRPS | 104 |
| CDR-L3 | QSYDSSSWV | 105 |
| CDR-H1 | TYDIT | 106 |
| CDR-H2 | WMNPNSGNSRSAQKFQG | 107 |
| CDR-H3 | GDYSGVVLTATALDY | 108 |
| light chain variable region | NFMLTQPHSVSESPGKTVTLSCTGSSGNIASNYVQWYQH RPGSAPTTVIYRDDQRPSGVPDRFSGSIDSSSNSASLTI SGLRPEDEADYYCQSYDSSSWVFGGGTKLTVLGQPAAA | 255 |

TABLE 21-continued

| Antibody clone E6 | | |
|---|---|---|
| | Amino acid sequence (N→C)/ Nucleic acid sequence (5'→3') | SEQ ID NO |
| light chain variable region coding gene | AATTTTATGCTGACTCAGCCCCACTCTGTGTCGGAGTCT CCGGGGAAGACGGTTACCCTCTCCTGCACCGGCAGCAGC GGCAACATTGCCAGTAACTATGTGCAGTGGTACCAGCAC CGCCCGGGCAGTGCCCCCACCACTGTGATCTACCGGGAT GACCAAAGACCCTCTGGAGTCCCTGATCGCTTCTCTGGC TCCATCGACAGTTCATCCAACTCTGCCTCCCTCACGATC TCTGGACTGAGGCCTGAGGACGAGGCTGACTATTACTGT CAGTCTTATGATAGCAGCTCTTGGGTGTTCGGCGGAGGG ACCAAGCTGACCGTCCTAGGTCAGCCCGCGGCCGCA | 295 |
| heavy chain variable region | QVQLVQSGAEVKKPGASVKVSCKASGYTFTTYDITWVRQ APGQGLEWMGWMNPNSGNSRSAQKFQGRVSMTSDSSIST AYMELSSLRSEDTAVYYCATGDYSGVVLTATALDYWGQG TLVTVSS | 256 |
| heavy chain variable region coding gene | CAGGTCCAGCTTGTGCAGTCTGGAGCAGAGGTGAAGAAG CCTGGGGCCTCAGTGAAGGTCTCCTGCAAGGCTTCTGGA TACACCTTCACCACTTATGATATCACCTGGGTGCGACAG GCCCCTGGACAAGGCCTTGAGTGGATGGGATGGATGAAC CCGAACAGTGGTAACTCACGCTCTGCACAGAAGTTCCAG GGCAGAGTCAGCATGACCAGTGACTCCTCCATAAGCACA GCCTACATGGAGCTGAGCAGCCTGAGATCTGAGGACACG GCCGTGTATTACTGTGCAACAGGAGACTACTCGGGTGTG GTACTAACTGCAACAGCACTTGACTACTGGGGCCAGGGA ACCCTGGTCACCGTCTCGAGT | 296 |
| light chain (Lambda) | NFMLTQPHSVSESPGKTVTLSCTGSSGNIASNYVQWYQH RPGSAPTTVIYRDDQRPSGVPDRFSGSIDSSSNSASLTI SGLRPEDEADYYCQSYDSSSWVFGGGTKLTVLGQPAAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS | 335 |
| heavy chain | QVQLVQSGAEVKKPGASVKVSCKASGYTFTTYDITWVRQ APGQGLEWMGWMNPNSGNSRSAQKFQGRVSMTSDSSIST AYMELSSLRSEDTAVYYCATGDYSGVVLTATALDYWGQG TLVTVSSASTKGPSVFPLAPCSRSTSESTAALGCLVKDY FPEPVTVSWNSGALTSGVHTFPAVLQSSGLYSLSSVVTV PSSSLGTKTYTCNVDHKPSNTKVDKRVESKYGPPCPPCP APEFLGGPSVFLFPPKPKDTLMISRTPEVTCVVVDVSQE DPEVQFNWYVDGVEVHNAKTKPREEQFNSTYRVVSVLTV LHQDWLNGKEYKCKVSNKGLPSSIEKTISKAKGQPREPQ VYTLPPSQEEMTKNQVSLTCLVKGFYPSDIAVEWESNGQ PENNYKTTPPVLDSDGSFFLYSRLTVDKSRWQEGNVFSC SVMHEALHNHYTQKSLSLSLGK | 336 |

TABLE 22

| Antibody clone E9 | | |
|---|---|---|
| | Amino acid sequence (N→C)/ Nucleic acid sequence (5'→3') | SEQ ID NO |
| CDR-L1 | SGSSSNIGNNYVY | 109 |
| CDR-L2 | RNNQRPS | 110 |
| CDR-L3 | AAWDDSLSGWV | 111 |
| CDR-H1 | SYGMH | 112 |
| CDR-H2 | NIKQDGSEKYYVDSVKG | 113 |
| CDR-H3 | EDRIAAAGMRELDY | 114 |
| light chain variable region | QSELTQLPSASETPGQRVTISCSGSSSNIGNNYVYWYQQ LPGTAPKLLIYRNNQRPSGVPDRFSGSKSGTSASLAISG LRSEDEADYYCAAWDDSLSGWVFGGGTKLTVLGQPAAA | 257 |

TABLE 22-continued

| Antibody clone E9 | | |
|---|---|---|
| | Amino acid sequence (N→C)/<br>Nucleic acid sequence (5'→3') | SEQ ID NO |
| light chain variable region coding gene | CAGTCTGAGCTGACTCAGCTACCCTCAGCGTCTGAGACC CCCGGGCAGAGGGTCACCATCTCTTGTTCTGGAAGCAGC TCCAACATCGGAAATAATTATGTATACTGGTACCAGCAA CTCCCCGGAACGGCCCCCAAACTCCTCATCTATAGGAAT AATCAGCGGCCCTCAGGGGTCCCTGACCGATTCTCTGGC TCCAAGTCTGGCACCTCAGCCTCCCTGGCCATCAGTGGG CTCCGGTCCGAGGATGAGGCTGATTATTACTGTGCAGCA TGGGATGACAGCCTGAGTGGTTGGGTGTTCGGCGGAGGG ACCAAGCTGACCGTCCTAGGTCAGCCCGCGGCCGCA | 297 |
| heavy chain variable region | QVQLVESGGGLVQPGRSLRLSCAASGFTFSSYGMHWVRQ APGKGLEWVANIKQDGSEKYYVDSVKGRFTISRDNAKNT LYLQMNSLRAEDTAVYYCAREDRIAAAGMRELDYWGQGT LVTVSS | 258 |
| heavy chain variable region coding gene | CAGGTGCAGCTGGTGGAGTCTGGGGGAGGCTTGGTACAG CCTGGGAGGTCCCTGAGACTCTCCTGTGCAGCGTCTGGA TTCACCTTCAGTAGCTATGGCATGCACTGGGTCCGCCAG GCTCCAGGGAAGGGGCTGGAGTGGGTGGCCAACATAAAG CAAGATGGAAGTGAGAAATACTATGTGGACTCTGTGAAG GGCCGATTCACCATCTCCAGAGACAACGCCAAGAACACG CTGTATCTCCAAATGAACAGCCTGAGAGCTGAGGACACG GCTGTGTATTACTGTGCGAGAGAGGACCGTATAGCAGCA GCTGGGATGCGGGAGTTGGACTACTGGGGCCAGGGCACC CTGGTCACCGTCTCGAGT | 298 |
| light chain (Lambda) | QSELTQLPSASETPGQRVTISCSGSSSNIGNNYVYWYQQ LPGTAPKLLIYRNNQRPSGVPDRFSGSKSGTSASLAISG LRSEDEADYYCAAWDDSLSGWVFGGGTKLTVLGQPAAAP SVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS | 337 |
| heavy chain | QVQLVESGGGLVQPGRSLRLSCAASGFTFSSYGMHWVRQ APGKGLEWVANIKQDGSEKYYVDSVKGRFTISRDNAKNT LYLQMNSLRAEDTAVYYCAREDRIAAAGMRELDYWGQGT LVTVSSASTKGPSVFPLAPCSRSTSESTAALGCLVKDYF PEPVTVSWNSGALTSGVHTFPAVLQSSGLYSLSSVVTVP SSSLGTKTYTCNVDHKPSNTKVDKRVESKYGPPCPPCPA PEFLGGPSVFLFPPKPKDTLMISRTPEVTCVVVDVSQED PEVQFNWYVDGVEVHNAKTKPREEQFNSTYRVVSVLTVL HQDWLNGKEYKCKVSNKGLPSSIEKTISKAKGQPREPQV YTLPPSQEEMTKNQVSLTCLVKGFYPSDIAVEWESNGQP ENNYKTTPPVLDSDGSFFLYSRLTVDKSRWQEGNVFSCS VMHEALHNHYTQKSLSLSLGK | 338 |

TABLE 23

| Antibody clone A11 | | |
|---|---|---|
| | Amino acid sequence (N→C)/<br>Nucleic acid sequence (5'→3') | SEQ ID NO |
| CDR-L1 | RSSQSLLHSNGYNYLD | 115 |
| CDR-L2 | LGSNRAS | 116 |
| CDR-L3 | MQGTHWPPYT | 117 |
| CDR-H1 | SYAMT | 118 |
| CDR-H2 | GISSDGTTTTYADSVRG | 119 |
| CDR-H3 | DQLLGWDALNV | 120 |
| light chain variable region | DIVMTQSPLSLPVTPGEPASISCRSSQSLLHSNGYNYLD WYLQKPGQSPQLLIYLGSNRASGVPDRFSGSGSGTDFTL KISRVEAEDVGVYYCMQGTHWPPYTFGQGTKVEIKRTAA A | 259 |

TABLE 23-continued

| Antibody clone A11 | | |
|---|---|---|
| | Amino acid sequence (N→C)/ Nucleic acid sequence (5'→3') | SEQ ID NO |
| light chain variable region coding gene | GATATTGTGATGACCCAGTCTCCACTCTCCCTGCCCGTC ACCCCTGGAGAGCCGGCCTCCATCTCCTGCAGGTCTAGT CAGAGCCTCCTGCATAGTAATGGATACAACTATTTGGAT TGGTACCTGCAGAAGCCAGGGCAGTCTCCACAGCTCCTG ATCTATTTGGGTTCTAACCGGGCCTCCGGGGTCCCTGAC AGGTTCAGTGGCAGTGGATCAGGCACAGATTTTACACTG AAAATCAGCAGAGTGGAGGCTGAGGATGTTGGGGTTTAT TACTGCATGCAAGGTACACACTGGCCTCCGTACACCTTT GGCCAGGGGACCAAGGTGGAGATCAAACGTACCGCGGCC GCA | 299 |
| heavy chain variable region | EVQLLESGGGLEQPGGFLRLSCAASGFSFTSYAMTWVRQ APGKGLEWVSGISSDGTTTTYADSVRGRFTISRDNAKNT VYLQMNSLRDEDTAVYYCARDQLLGWDALNVWGQGTMVT VSS | 260 |
| heavy chain variable region coding gene | GAGGTGCAGCTGTTGGAGTCTGGGGGAGGCTTGGAACAG CCTGGGGGGTTCCTGAGACTCTCCTGTGCAGCCTCTGGA TTCTCCTTTACCAGCTACGCCATGACCTGGGTCCGCCAG GCTCCAGGGAAGGGGCTGGAGTGGGTCTCAGGTATTAGT AGTGATGGGACCACTACAACCTACGCGGACTCCGTGAGG GGCCGGTTCACCATCTCCAGAGACAACGCCAAGAACACG GTGTATCTCCAAATGAACAGTCTGAGAGACGAGGACACG GCTGTGTATTATTGTGCAAGAGATCAATTGTTGGGCTGG GATGCTCTGAATGTCTGGGGCCAAGGGACAATGGTCACC GTCTCGAGT | 300 |
| light chain (Kappa) | DIVMTQSPLSLPVTPGEPASISCRSSQSLLHSNGYNYLD WYLQKPGQSPQLLIYLGSNRASGVPDRFSGSGSGTDFTL KISRVEAEDVGVYYCMQGTHWPPYTFGQGTKVEIKRTAA APSVFIFPPSDEQLKSGTASVVCLLNNFYPREAKVQWKV DNALQSGNSQESVTEQDSKDSTYSLSSTLTLSKADYEKH KLYACEVTHQGLSSPVTKSFNRGEC | 339 |
| heavy chain | EVQLLESGGGLEQPGGFLRLSCAASGFSFTSYAMTWVRQ APGKGLEWVSGISSDGTTTTYADSVRGRFTISRDNAKNT VYLQMNSLRDEDTAVYYCARDQLLGWDALNVWGQGTMVT VSSASTKGPSVFPLAPCSRSTSESTAALGCLVKDYFPEP VTVSWNSGALTSGVHTFPAVLQSSGLYSLSSVVTVPSSS LGTKTYTCNVDHKPSNTKVDKRVESKYGPPCPPCPAPEF LGGPSVFLFPPKPKDTLMISRTPEVTCVVVDVSQEDPEV QFNWYVDGVEVHNAKTKPREEQFNSTYRVVSVLTVLHQD WLNGKEYKCKVSNKGLPSSIEKTISKAKGQPREPQVYTL PPSQEEMTKNQVSLTCLVKGFYPSDIAVEWESNGQPENN YKTTPPVLDSDGSFFLYSRLTVDKSRWQEGNVFSCSVMH EALHNHYTQKSLSLSLGK | 340 |

Example 2: Assay of In Vitro Biological Activities of the Selected Antibodies

2.1. Natural Killer Cell (NK Cell) Surface Binding Assay

In order to test whether or not 93 antibodies selected in Example 1.4 bind LILRB1 expressed on surface of immune cells, natural killer cell (NK cell) surface binding assay was performed. A human NK cell, KHYG-1 cell (JCRB) was cultured in RPMI 1640 medium (Gibco) supplemented with 10% (w/v) of FBS (Gibco) and 100 U/mL of interleukin-2 (Novartis). KHYG-1 cells were added to a U-bottom 96-well tissue culture plate (BD Falcon) at the amount of $5\times10^4$ cells/well. Each of the selected antibodies was added to the well to the final concentration of 50 μg/mL per well and incubated at 4° C. for 1 hour.

In order to see the level of LILRB1-specific binding of the selected antibodies, a human IgG4 isotype control antibody (Biolegend) was treated in the same manner. After washing with FACS buffer, the cells were treated with an anti-human Fc-biotin antibody (life technologies) and incubated at 4° C. for 1 hour. After washing with FACS buffer, the cells were treated with streptavidin PE (BD Pharmigen) and incubated at 4° C. for 30 minutes. After washing with FACS buffer, the cells were resuspended and subjected to analysis using iQue screener (Sartorius).

Among the obtained results, the results for antibodies A10, E3, E4, F12, G1, G9, G11, H2 and H11 are representatively compared with that of human IgG4 isotype (control), which are shown in Table 24. The flow cytometry diagrams for A10, E3 and human IgG4 isotype (control) are shown in FIGS. 4*a* (A10), 4*b* (E3), and 4*c* (isotype IgG4), respectively:

TABLE 24

| | Mean Fluorescence Intensity | % of population 2 |
|---|---|---|
| human IgG4 isotype control | 142917.2 | 2.95 |

TABLE 24-continued

| | Mean Fluorescence Intensity | % of population 2 |
|---|---|---|
| A10 | 222660.2 | 28.68 |
| E3 | 268702.2 | 40.22 |
| E4 | 272295.5 | 43.25 |
| F12 | 262012.7 | 38.02 |
| G1 | 321051.7 | 56.23 |
| G9 | 263079.3 | 41.32 |
| G11 | 262771.9 | 40.11 |
| H2 | 238570.9 | 29.00 |
| H11 | 244818.2 | 32.59 |

As shown in Table 24 and FIGS. 4*a*~4*c*, the tested antibodies show higher level of binding to human NK cells (surface), compared to that of human IgG4 isotype control antibody.

2.2. Analysis of Inhibition of LILRB1 Binding to HLA-G by the Selected Antibodies In order to test whether or not the antibodies selected in Example 1.5 exert an inhibitory effect on binding of LILRB1 to its ligand, HLA-G, the degree of blocking by the selected antibodies was analyzed.

For this purpose, JEG-3 cells (ATCC cat #HTB-36), which show high expression level of HLA-G, were used. JEG-3 cells were cultured in MEM medium (Gibco) supplemented with 10% (v/v) of FBS (Gibco) and 1% (v/v) of pen-strep (Gibco). The JEG-3 cells were added to U-bottom 96-well tissue culture plate (BD Falcon) at the amount of $5\times10^4$ cells/well. The well plate was washed with 1×PBS buffer. Each of the antibodies selected in Example 1.5 (A10, E3, F12, G1, G9, H2 and H11) and LILRB1-Fc (RnD systems) were mixed in FACS buffer (1×PBS+1% BSA+1 mM EDTA) to the final concentrations of 10 μg/mL and 5 μg/mL, respectively. The cells were treated with 100 μL of the mixture solution per well and incubated on ice for 2 hours. An anti-LILRB1 antibody (clone HP-F1, Abcam) as a positive control and an anti-lysozyme IgG4 antibody (clone D1.3) as a negative control were treated in the same manner. After washing with FACS buffer twice, the cells were treated with PE-anti-hulgG-Fc antibody (Biolegend, 10 μg/mL) and incubated on ice for one hour. After washing with FACS buffer twice, the cells were resuspended in 100 μL of the same buffer and subjected to analysis using iQue screener (Sartorius).

The obtained results are shown in FIG. 5. As shown in FIG. 5, all the tested antibodies A10, E3, F12, G1, G9, H2 and H11 effectively inhibit the binding of LILRB1-Fc to HLA-G-overexpressing cell line.

2.3. Assay of Cancer Cell Lysis by NK Cells

In order to test whether or not the selected antibodies increase the degree of cancer cell lysis by NK cells, the cell death rate of HLA-G-overexpressing HEK293 cell by NK cell KHYG-1 was analyzed. KHYG-1 cells (JCRB) were addeded to 96-well tissue culture plate (BD Falcon) at the amount of $2\times10^4$ cells/well ($4\times10^4$ cells/mL, total volume 50 μL). The cells were treated with each antibody (Table 25) to the final concentration of 20 μg/mL per well, and left at 37° C. for one hour.

As a negative control, a human IgG4 isotype control antibody (Biolegend) was treated in the same manner.

HLA-G-overexpressing HEK293 cells (which were prepared by transduction of HEK293 cells (American Typo Culture Collection) with lentivirus constructed for expressing HLA-G) were stained with IncuCyte CytoLight Rapid Red Reagent (Sartorius) according to the manufacturer's protocol. After one hour, the HLA-G-overexpressing HEK293 cells were added to the plate at the amount of $1\times10^4$ cells/well ($2\times10^4$ cells/mL, total volume 50 μL). The plate was placed in IncuCyte S3 (Sartorius) equipped in an incubator under the condition of 37° C. and 5% $CO_2$, and images thereof were taken for 72 hours. Red area confluence indicating the density of live HLA-G-overexpressing HEK293 cells was measured, and cell viability was calculated. The obtained cell viabilities are shown in Table 25 (wherein the cell viabilities are shown as a relative value to that of control antibody (cell viability of IgG4 isotype-treated well=1)):

$$\text{Relative cell viability (IgG4 Isotype = 1)} = \frac{\text{Normalized red area confluence value of antibody}}{\text{Normalized red area confluence value of IgG4 Isotype}}$$

TABLE 25

| Antibody | Relative cell viability (IgG4 isotype = 1) |
|---|---|
| human IgG4 Isotype control | 1.00 |
| A10 | 0.70 |
| B9 | 0.81 |
| D3 | 0.83 |
| E1 | 0.82 |
| E3 | 0.64 |
| F12 | 0.81 |
| G1 | 0.64 |
| G6 | 0.78 |
| G9 | 0.77 |
| G11 | 0.82 |
| H2 | 0.78 |
| H11 | 0.60 |

As shown in Table 25, all the tested antibodies including A10, B9, D3, E1, E3, F12, G1, G6, G9, G11, H2 and H11 increase cell death of HLA-G-overexpressing HEK293 cells by KHYG-1, compared to that of human IgG4 isotype control antibody.

Example 3: Assay of In Vivo Biological Activities of the Selected Antibodies

Among the antibodies selected in Example 1.5, two antibodies (E3 and B3) were tested for their in vivo anti-cancer efficacies. For this purpose, it was tested whether or not administration of the two antibodies reduces tumor size where the tumor was generated by engrafting human colorectal carcinoma cells (Bioware Brite Cell Line HCT116 Red-Fluc colorectal carcinoma cells (PerkinElmer)) and THP-1 derived macrophages to the mice. As a negative control, human colon cancer xenograft mice prepared as above were treated with a human IgG1 isotype control antibody (BioXcell, Cat. No. BP0297). Hereinafter, the processes are described in detail:

Preparation of THP-1 Derived Macrophages

The THP-1 derived macrophages used above were prepared by differentiating THP-1 cells (ATCC) with 150 nM phorbol 12-myristate 13-acetate (PMA, Sigma), 20 ng/ml of interferon gamma (Peprotech) and 10 pg/ml of lipopolysaccharide (LPS, Sigma).

Measurement of Anti-Cancer Efficacy in Mouse Model 5-week old female CIEA NOG mice [NOG immunodeficient mouse] (Central Institute for Experimental Animals, Japan) were subcutaneously injected with a mixture of $3\times10^6$ cells of HCT116 Red-Fluc colorectal carcinoma cells, $3\times10^6$ cells of THP-1 derived macrophages and each of two test antibodies (E3 or B3 antibody; 20 µg per mouse). From the $4^{th}$ day after tumor grafting, the antibody was administered to the mouse model at the dosage of 5 mg/kg by intraperitoneal injection twice a week. Then, the size ($mm^3$) of the grafted tumor was measured and shown in FIG. 6. As shown in FIG. 6, all the tested antibodies, particularly antibody E3, exhibit statistically significant effect of inhibiting tumor growth in mouse models grafted with HCT116 colon cancer cells and THP-1 derived macrophages.

Example 4: Preparation of Anti-LILRB1 Antibody (E3.1)

The nucleic acid sequence encoding the full-length heavy chain (SEQ ID NO: 302) of antibody E3, which was confirmed to have particularly significant effect in Example 3, was amplified by PCR. The nucleic acid sequence encoding the region from Ser1 to Leu110 of the light chain variable region (VL) (SEQ ID NO: 221) of antibody E3 was amplified by PCR and ligated to a nucleic acid sequence encoding the lambda constant region (Lambda CL.1, SEQ ID NO: 344) to amplify the nucleic acid sequence encoding lambda light chain by PCR. The amplified sequences were inserted into an expression vector (pTRIOZ-hIgG4, InvivoGen; alternatively, any one of vectors comprising CMV promoter or CMV/CHO beta-actin fusion promoter (KR10-1038126B1) and genes encoding human IgG4 heavy chain constant region and lambda light chain constant region, can be used), wherein the expression vector was designed for encoding a human IgG4 antibody. The DNA sequence of the expression vector was confirmed by sequencing.

An antibody (E3.1) was prepared using the constructed expression vector referring to Example 1.4, and the sequence of the antibody was analyzed referring to Example 1.6 and summarized in Table 26:

TABLE 26

| Antibody clone E3.1 | | |
|---|---|---|
| | amino acid sequence (N→C)/<br>nucleic acid sequence (5'→3') | SEQ ID NO |
| CDR-L1 | QGDSLRNFYAS | 1 |
| CDR-L2 | GKNNRPS | 2 |
| CDR-L3 | NSRDSSGSHLTGV | 3 |
| CDR-H1 | SYAMS | 4 |
| CDR-H2 | AISGSGGSTYYADSVKG | 5 |
| CDR-H3 | DTYYYGSGRSNAFDI | 6 |
| light chain variable region | SYELTQDPAVSVALGQTVRITCQGDSLRNFYASWYQQ<br>KSGQAPVLVMYGKNNRPSGIPDRFSGSTSGNTASLTI<br>TGAQAEDEADYYCNSRDSSGSHLTGVFGGGTKVTVL | 345 |
| light chain variable region coding gene | TCCTATGAGCTGACTCAGGACCCTGCTGTGTCTGTGG<br>CCTTGGGACAGACAGTCAGGATCACATGCCAGGGAGA<br>CAGCCTCAGAAACTTTTATGCAAGCTGGTACCAGCAG<br>AAGTCAGGACAGGCCCCAGTTCTTGTCATGTATGGTA<br>AAAACAACCGGCCCTCAGGGATCCCAGACCGATTCTC<br>TGGCTCCACCTCAGGAAACACAGCTTCCTTGACCATC<br>ACTGGGGCTCAGGCGGAAGATGAGGCTGACTATTACT<br>GTAACTCCCGGGACAGCAGTGGTAGCCATTTGACGGG<br>CGTATTCGGCGGAGGGACCAAGGTCACCGTCCTA | 346 |
| heavy chain variable region | QVQLVESGGGLVQPGGSLRLSCAASGFTFSSYAMSWV<br>RQAPGKGLEWVSAISGSGGSTYYADSVKGRFTISRDN<br>SKNTLYLQMISLRAEDTAVYYCARDTYYYGSGRSNAF<br>DIWGQGTLVTVSS | 222 |
| heavy chain variable region coding gene | CAGGTGCAGCTGGTGGAGTCTGGGGGAGGCTTGGTAC<br>AGCCTGGGGGGTCCCTGAGACTCTCCTGTGCAGCCTC<br>TGGATTCACCTTTAGCAGCTATGCCATGAGCTGGGTC<br>CGCCAGGCTCCAGGGAAGGGGCTGGAGTGGGTCTCAG<br>CTATTAGTGGTAGTGGTGGTAGCACATACTACGCAGA<br>CTCCGTGAAGGGCCGGTTCACCATCTCCAGAGACAAT<br>TCCAAGAATACGCTGTATCTGCAAATGATTAGCCTGA<br>GAGCTGAGGACACGGCTGTGTATTACTGTGCGAGAGA<br>TACGTATTACTATGGTTCGGGGAGAAGTAATGCTTTT<br>GATATATGGGGCCAGGGAACCCTGGTCACCGTCTCGA<br>GT | 262 |

TABLE 26-continued

| Antibody clone E3.1 | | |
|---|---|---|
| | amino acid sequence (N→C)/ nucleic acid sequence (5'→3') | SEQ ID NO |
| light chain (Lambda) | SYELTQDPAVSVALGQTVRITCQGDSLRNFYASWYQQ KSGQAPVLVMYGKNNRPSGIPDRFSGSTSGNTASLTI TGAQAEDEADYYCNSRDSSGSHLTGVFGGGTKVTVLG QPKANPTVTLFPPSSEELQANKATLVCLISDFYPGAV TVAWKADGSPVKAGVETTKPSKQSNNKYAASSYLSLT PEQWKSHRSYSCQVTHEGSTVEKTVAPTECS | 347 |
| heavy chain | QVQLVESGGGLVQPGGSLRLSCAASGFTFSSYAMSWV RQAPGKGLEWVSAISGSGGSTYYADSVKGRFTISRDN SKNTLYLQMISLRAEDTAVYYCARDTYYYGSGRSNAF DIWGQGTLVTVSSASTKGPSVFPLAPCSRSTSESTAA LGCLVKDYFPEPVTVSWNSGALTSGVHTFPAVLQSSG LYSLSSVVTVPSSSLGTKTYTCNVDHKPSNTKVDKRV ESKYGPPCPPCPAPEFLGGPSVFLFPPKPKDTLMISR TPEVTCVVVDVSQEDPEVQFNWYVDGVEVHNAKTKPR EEQFNSTYRVVSVLTVLHQDWLNGKEYKCKVSNKGLP SSIEKTISKAKGQPREPQVYTLPPSQEEMTKNQVSLT CLVKGFYPSDIAVEWESNGQPENNYKTTPPVLDSDGS FFLYSRLTVDKSRWQEGNVFSCSVMHEALHNHYTQKS LSLSLGK | 302 |

Example 5: Generation of Human LILR-Overexpressing Cell Lines

The nucleic acid sequences encoding the full-length human LILR family proteins (Table 27) were amplified by PCR, and each of the amplified sequences was inserted into an expression vector (pTRIOZ-hIgG4, InvivoGen; alternatively, any one of vectors comprising CMV promoter or CMV/CHO beta-actin fusion promoter (KR10-1038126B1) and genes encoding human IgG4 heavy chain constant region and lambda light chain constant region, can be used). The DNA sequence of the expression vector was confirmed by sequencing. The constructed vector was transfected into CHO cells, to generate 11 stable cell lines overexpressing each LILR protein on its surface.

TABLE 27

| Protein | Genbank Accession No. | amino acid sequence (N→C) | SEQ ID NO | Antibody |
|---|---|---|---|---|
| LILRB1 | AAH15731 | MTPILTVLICLGLSLGPRTHVQAGHL PKPTLWAEPGSVITQGSPVTLRCQGG QETQEYRLYREKKTAPWITRIPQELV KKGQFPIPSITWEHAGRYRCYYGSDT AGRSESSDPLELVVTGAYIKPTLSAQ PSPVVNSGGNVTLQCDSQVAFDGFIL CKEGEDEHPQCLNSQPHARGSSRAIF SVGPVSPSRRWWYRCYAYDSNSPYEW SLPSDLLELLVLGVSKKPSLSVQPGP IVAPEETLTLQCGSDAGYNRFVLYKD GERDFLQLAGAQPQAGLSQANFTLGP VSRSYGGQYRCYGAHNLSSEWSAPSD PLDILIAGQFYDRVSLSVQPGPTVAS GENVTLLCQSQGWMQTFLLTKEGAAD DPWRLRSTYQSQKYQAEFPMGPVTSA HAGTYRCYGSQSSKPYLLTHPSDPLE LVVSGPSGGPSSPTTGPTSTSGPEDQ PLTPTGSDPQSGLGRHLGVVIGILVA VILLLLLLLLFLILRHRRQGKHWTS TQRKADFQHPAGAVGPEPTDRGLQWR SSPAADAQEENLYAAVKHTQPEDGVE MDTRSPHDEDPQAVTYAEVKHSRPRR EMASPPSPLSGEFLDTKDRQAEEDRQ MDTEAAASEAPQDVTYAQLHSLTLRR KATEPPPSQEGPSPAVPSIYATLAIH | 348 | Human LILRB1 antibody (ab185796, Abcam) |
| LILRB2 | AAH36827 | MTPIVTVLICLGLSLGPRTHVQTGTI PKPTLWAEPDSVITQGSPVTLSCQGS LEAQEYRLYREKKSASWITRIRPELV KNGQFHIPSITWEHTGRYGCQYYSRA RWSELSDPLVLVMTGAYPKPTLSAQP SPVVTSGGRVTLQCESQVAFGGFILC KEGEDEHPQCLNSQPHARGSSRAIFS VGPVSPNRRWSHRCYGYDLNSPYVWS | 349 | Human LILRB2/ CD85d/ ILT4 antibody (MAB2078, R&D Systems) |

TABLE 27-continued

| Protein | Genbank Accession No. | amino acid sequence (N→C) | SEQ ID NO | Antibody |
|---|---|---|---|---|
| | | SPSDLLELLVPGVSKKPSLSVQPGPV VAPGESLTLQCVSDVGYDRFVLYKEG ERDLRQLPGRQPQAGLSQANFTLGPV SRSYGGQYRCYGAYNLSSEWSAPSDP LDILITGQIHGTPFISVQPGPTVASG ENVTLLCQSWRQFHTFLLTKAGAADA PLRLRSIHEYPKYQAEFPMSPVTSAH AGTYRCYGSLNSDPYLLSHPSEPLEL VVSGPSMGSSPPPTGPISTPAGPEDQ PLTPTGSDPQSGLGRHLGVVIGILVA VVLLLLLLLLLFLILRHRRQGKHWTS TQRKADFQHPAGAVGPEPTDRGLQWR SSPAADAQEENLYAAVKDTQPEDGVE MDTRAAASEAPQDVTYAQLHSLTLRR KATEPPPSQEGEPPAEPSIYATLAIH | | |
| LILRB3 | XP_006726377 | MTPALTALLCLGLSLGPRTRVQAGPF PKPTLWAEPGSVISWGSPVTIWCQGS LEAQEYRLDKEGSPEPLDRNNPLEPK NKARFSIPSMTEHHAGRYRCHYYSSA GWSEPSDPLELVMTGFYNKPTLSALP SPVVASGGNMTLRCGSQKGYHHFVLM KEGEHQLPRTLDSQQLHSGGFQALFP VGPVNPSHRWRFTCYYYYMNTPQVWS HPSDPLEILPSGVSRKPSLLTLQGPV LAPGQSLTLQCGSDVGYDRFVLYKEG ERDFLQRPGQQPQAGLSQANFTLGPV SPSHGGQYRCYGAHNLSSEWSAPSDP LNILMAGQIYDTVSLSAQPGPTVASG ENVTLLCQSWWQFDTFLLTKEGAAHP PLRLRSMYGAHKYQAEFPMSPVTSAH AGTYRCYGSYSSNPHLLSFPSEPLEL MVSGHSGGSSLPPTGPPSTPGLGRYL EVLIGVSVAFVLLLFLLLFLLLRRQR HSKHRTSDQRKTDFQRPAGAAETEPK DRGLLRRSSPAADVQEENLYAAVKDT QSEDRVELDSQSPHDEDPQAVTYAPV KHSSPRREMASPPSSLSGEFLDTKDR QVEEDRQMDTEAAASEASQDVTYAQL HSLTLRRKATEPPPSQEGEPPAEPSI YATLAIH | 350 | Human LILRB3/ CD85a/ ILT5 antibody (MAB1806, R&D Systems) |
| LILRB4 | NP_001265355 | MIPTFTALLCLGLSLGPRTHMQAGPL PKPTLWAEPGSVISWGNSVTIWCQGT LEAREYRLDKEESPAPWDRQNPLEPK NKARFSIPSMTEDYAGRYRCYYRSPV GWSQPSDPLELVMTGAYSKPTLSALP SPLVTSGKSVTLLCQSRSPMDTFLLI KERAAHPLLHLRSEHGAQQHQAEFPM SPVTSVHGGTYRCFSSHGFSHYLLSH PSDPLELIVSGSLEGPRPSPTRSVST AAGPEDQPLMPTGSVPHSGLRRHWEV LIGVLVVSILLLSLLLFLLLQHWRQG KHRTLAQRQADFORPPGAAEPEPKDG GLQRRSSPAADVQGENFCAAVKNTQP EDGVEMDTRQSPHDEDPQAVTYAKVK HSRPRREMASPPSPLSGEFLDTKDRQ AEEDRQMDTEAAASEAPQDVTYARLH SFTLRQKATEPPPSQEGASPAEPSVY ATLAIH | 351 | Human LILRB4/ CD85k/ ILT3 antibody (MAB24251, R&D Systems) |
| LILRB5 | NP_006831 | MTLTLSVLICLGLSVGPRTCVQAGTL PKPTLWAEPASVIARGKPVTLWCQGP LETEEYRLDKEGLPWARKRONPLEPG AKAKFHIPSTVYDSAGRYRCYYETPA GWSEPSDPLELVATGFYAEPTLLALP SPVVASGGNVTLQCDTLDGLLTFVLV EEEQKLPRTLYSQKLPKGPSQALFPV GPVTPSCRWRFRCYYYYRKNPQVWSN PSDLLEILVPGVSRKPSLLIPQGSVV ARGGSLTLQCRSDVGYDIFVLYKEGE HDLVQGSGQQPQAGLSQANFTLGPVS RSHGGQYRCYGAHNLSPRWSAPSDPL DILIAGLIPDIPALSVQPGPKVASGE NVTLLCQSWHQIDTFFLTKEGAAHPP LCLKSKYQSYRHQAEFSMSPVTSAQG | 352 | Human LILRB5/ CD85c/ LIR-8 antibody (MAB3065, R&D Systems) |

TABLE 27-continued

| Protein | Genbank Accession No. | amino acid sequence (N→C) | SEQ ID NO | Antibody |
|---|---|---|---|---|
| | | GTYRCYSAIRSYPYLLSSPSYPQELV VSGPSGDPSLSPTGSTPTPGPEDQPL TPTGLDPQSGLGRHLGVVTGVSVAFV LLLFLLLFLLLRHRHQSKHRTSAHFY RPAGAAGPEPKDQGLQKRASPVADIQ EEILNAAVKDTQPKDGVEMDARAAAS EAPQDVTYAQLHSLTLRREATEPPPS QEREPPAEPSIYAPLAIH | | |
| LILRA1 | NP_006854 | MTPIVTVLICLRLSLGPRTHVQAGTL PKPTLWAEPGSVITQGSPVTLWCQGI LETQEYRLYREKKTAPWITRIPQEIV KKGQFPIPSITWEHTGRYRCFYGSHT AGWSEPSDPLELVVTGAYIKPTLSAL PSPVVTSGGNVTLHCVSQVAFGSFIL CKEGEDEHPQCLNSQPRTHGWSRAIF SVGPVSPSRRWSYRCYAYDSNSPHVW SLPSDLLELLVLGVSKKPSLSVQPGP IVAPGESLTLQCVSDVSYDRFVLYKE GERDFLQLPGPQPQAGLSQANFTLGP VSRSYGGQYRCSGAYNLSSEWSAPSD PLDILIAGQFRGRPFISVHPGPTVAS GENVTLLCQSWGPFHTFLLTKAGAAD APLRLRSIHEYPKYQAEFPMSPVTSA HSGTYRCYGSLSSNPYLLSHPSDSLE LMVSGAAETLSPPQNKSDSKAGAANT LSPSQNKTASHPQDYTVENLIRMGIA GLVLVVLGILLFEAQHSQRSL | 353 | Human LILRA1/ LILRB1 antibody (MAB30851, R&D Systems) |
| LILRA2 | AAH17412 | MTPILTVLICLGLSLGPRTHVQAGHL PKPTLWAEPGSVIIQGSPVTLRCQGS LQAEEYHLYRENKSASWVRRIQEPGK NGQFPIPSITWEHAGRYHCQYYSHNH SSEYSDPLELVVTGAYSKPTLSALPS PVVTLGGNVTLQCVSQVAFDGFILCK EGEDEHPQRLNSHSHARGWSWAIFSV GPVSPSRRWSYRCYAYDSNSPYVWSL PSDLLELLVPGVSKKPSLSVQPGPMV APGESLTLQCVSDVGYDRFVLYKEGE RDFLQRPGWQPQAGLSQANFTLGPVS PSHGGQYRCYSAHNLSSEWSAPSDPL DILITGQFYDRPSLSVQPVPTVAPGK NVTLLCQSRGQFHTFLLTKEGAGHPP LHLRSEHQAQQNQAEFRMGPVTSAHV GTYRCYSSLSSNPYLLSLPSDPLELV VSASLGQHPQDYTVENLIRMGVAGLV LVVLGILLFEAQHSQRSLQDAAGR | 354 | Human LILRA2/ CD85h/ ILT1 antibody (MAB6364, R&D Systems) |
| LILRA3 | AAH28208 | MTSILTVLICLGLSLDPRTHVQAGPL PKPTLWAEPGSVITQGSPVTLRCQGS LETQEYHLYREKKTALWITRIPQELV KKGQFPILSITWEHAGRYCCIYGSHT VGLSESSDPLELVVTGAYSKPTLSAL PSPVVTSGGNVTIQCDSQVAFDGFIL CKEGEDEHPQCLNSHSHARGSSRAIF SVGPVSPSRRWSYRCYGYDSRAPYVW SLPSDLLGLLVPGVSKKPSLSVQPGP VVAPGEKLTFQCGSDAGYDRFVLYKE WGRDFLQRPGRQPQAGLSQANFTLGP VSRSYGGQYTCSGAYNLSSEWSAPSD PLDILITGQIRARPFLSVRPGPTVAS GENVTLLCQSQGGMHTFLLTKEGAAD SPLRLKSKRQSHKYQAEFPMSPVTSA HAGTYRCYGSLSSNPYLLTHPSDPLE LVVSGAAETLSPPQNKSDSKAGE | 355 | Human LILRA3/ CD85e antibody (PA5-47349, Invitrogen) |
| LILRA4 | NP_036408 | MTLILTSLLFFGLSLGPRTRVQAENL PKPILWAEPGPVITWHNPVTIWCQGT LEAQGYRLDKEGNSMSRHILKTLESE NKVKLSIPSMMWEHAGRYHCYYQSPA GWSEPSDPLELVVTAYSRPTLSALPS PVVTSGVNVTLRCASRLGLGRFTLIE EGDHRLSWTLNSHQHNHGKFQALFPM GPLTFSNRGTFRCYGYENNTPYVWSE PSDPLQLLVSGVSRKPSLLTLQGPVV TPGENLTLQCGSDVGYIRYTLYKEGA | 356 | CD85g (ILT7) antibody (16-5179-82, Invitrogen) |

TABLE 27-continued

| Protein | Genbank Accession No. | amino acid sequence (N→C) | SEQ ID NO | Antibody |
|---|---|---|---|---|
| | | DGLPQRPGRQPQAGLSQANFTLSPVS RSYGGQYRCYGAHNVSSEWSAPSDPL DILIAGQISDRPSLSVQPGPTVTSGE KVTLLCQSWDPMFTFLLTKEGAAHPP LRLRSMYGAHKYQAEFPMSPVTSAHA GTYRCYGSRSSNPYLLSHPSEPLELV VSGATETLNPAQKKSDSKTAPHLQDY TVENLIRMGVAGLVLLFLGILLFEAQ HSQRSPPRCSQEANSRKDNAPFRVVE PWEQI | | |
| LILRA5 | NP_067073 | MAPWSHPSAQLQPVGGDAVSPALMVL LCLGLSLGPRTHVQAGNLSKATLWAE PGSVISRGNSVTIRCQGTLEAQEYRL VKEGSPEPWDTQNPLEPKNKARFSIP SMTEHHAGRYRCYYYSPAGWSEPSDP LELVVTGFYNKPTLSALPSPVVTSGE NVTLQCGSRLRFDRFILTEEGDHKLS WTLDSQLTPSGQFQALFPVGPVTPSH RWMLRCYGSRRHILQVWSEPSDLLEI PVSGAADNLSPSQNKSDSGTASHLQD YAVENLIRMGMAGLILVVLGILIFQD WHSQRSPQAAAGR | 357 | Human LILRA5/ CD85f antibody (MAB6754, R&D Systems) |
| LILRA6 | NP_001347096 | MTPALTALLCLGLSLGPRTRVQAGPF PKPTLWAEPGSVISWGSPVTIWCQGS LEAQEYQLDKEGSPEPLDRNNPLEPK NKARFSIPSMTQHHAGRYRCHYYSSA GWSEPSDPLELVMTGFYNKPTLSALP SPVVASGGNMTLRCGSQKGYHHFVLM KEGEHQLPRTLDSQQLHSGGFQALFP VGPVTPSHRWRFTCYYYYTNTPRVWS HPSDPLEILPSGVSRKPSLLTLQGPV LAPGQSLTLQCGSDVGYDRFVLYKEG ERDFLQRPGQQPQAGLSQANFTLGPV SPSHGGQYRCYGAHNLSSEWSAPSDP LNILMAGQIYDTVSLSAQPGPTVASG ENVTLLCQSRGYFDTFLLTKEGAAHP PLRLRSMYGAHKYQAEFPMSPVTSAH AGTYRCYGSYSSNPHLLSFPSEPLEL MVSGHSGGSSLPPTGPPSTPASHAKD YTVENLIRMGMAGLVLVFLGILLFEA QHSQRNPQDAAGR | 358 | Human LILRA6/ CD85b antibody (MAB86 56, R&D Systems) |

Example 6: Determination of $EC_{50}$ for Binding of the Selected Antibodies to LILRB1 Overexpressing Cell Surface In order to determine $EC_{50}$ values of the antibodies prepared in Examples 1 and 4 for binding to human LILRB1-overexpressing cell lines, a cell surface binding assay was performed. Representing the prepared antibodies, $EC_{50}$ values of E3.1 and H11 antibodies were measured. The CHO cells prepared in Example 5, which overexpress LILRB1 on surface, were added to U-bottom 96-well tissue culture plate (BD Falcon) at the amount of $1\times10^5$ cells/well. Threefold serial dilutions of E3.1 and H11 antibodies were prepared starting from the final concentrations of 600 ug/mL and 27 ug/mL, respectively. The cells were treated with each of the diluted antibodies and incubated at 4° C. for 60 minutes. After washing with FACS buffer, the cells were treated with anti-human Fc-biotin antibody (Invitrogen) and incubated at 4° C. for 30 minutes. After washing with FACS buffer, the cells were treated with streptavidin (BD Pharmigen) labeled with PE fluorescence and incubated at 4° C. for 30 minutes. After washing with FACS buffer, the cells were resuspended and subjected to analysis using iQue screener (Sartorius). $EC_{50}$ values were calculated using nonlinear regression formula of GraphPad Prism software, and the obtained results are shown in Table 28:

TABLE 28

| | E3.1 | H11 |
|---|---|---|
| $EC_{50}$ (nM) | 7.154 | 0.376 |

Example 7: Assessment of Cross-Reactivity of the Selected Antibodies to Human LILR Family-Overexpressing Cell Lines In order to confirm whether or not the selected antibodies bind to human LILR family proteins other than LILRB1, a cell surface binding assay was performed. The CHO cells (prepared in Example 5) expressing each of various LILR family proteins on surface were added to U-bottom 96-well tissue culture plate (BD Falcon) at the amount of $1\times10^5$ cells/well. The cells in each well were treated with the selected antibody in the final concentration of 20 ug/mL and incubated at 4° C. for 60 minutes. After washing with FACS buffer, the cells were treated with anti-human Fc-biotin antibody (Invitrogen) and incubated at 4° C. for 30 minutes. After washing with FACS buffer, the cells were treated with streptavidin (BD Pharmigen) labeled with PE or FITC fluorescence and incubated at 4° C. for 30 minutes. After washing with FACS buffer, the cells were resuspended and subjected to analysis using iQue screener (Sartorius). The cells treated with each LILR protein specific antibody (Table 27) were used as a positive control, and the cells treated with human IgG4 isotype control antibody (Biolegend) were used as a negative control.

The results obtained for antibody E3.1 are shown in FIGS. 7*a* to 7*d* (E3.1: red; LILR-specific antibody: blue; Isotype (hIgG4) control: gray), and the results obtained for antibody H11 are shown in FIGS. 8*a* to 8*d* (H11: red; LILR-specific antibody: blue; Isotype (hIgG4) control: gray). As shown in FIGS. 7*a* to 7*d* and FIGS. 8*a* to 8*d*, the E3.1 and H11 antibodies do not bind at all or hardly bind to LILRs other than LILRB1. These results indicate that the antibodies provided by the examples have binding abilities specifically to LILRB1.

Example 8: Measurement of Release of Granzyme B and Perforin by Enzyme-Linked Immune Absorbent Spot (ELISPOT) Assay In order to confirm whether the E3.1 and H11 antibodies increase the level of cytotoxicity of NK cells, an enzyme-linked immune absorbent spot (ELISPOT) assay was performed. The level of cytotoxicity was determined by the release of cytotoxic granules, granzyme B and perforin, in NK cells.

$5\times10^3$ cells of LILRB1-expressing KHYG-1 cell lines (JCRB) and $5\times10^3$ cells of HLA-G-overexpressing K562 cells (which were prepared by transduction of K562 cells (American Type Culture Collection) with lentivirus constructed for expressing HLA-G) were co-cultured in U-bottom 96-well tissue culture plate. Each antibody (E3.1, H11 or human IgG4 isotype control antibody) was added thereto with final concentration of 50 ug/mL per each well and left incubated at 37° C. for 30 minutes. The co-cultured cells were transferred onto 96 well plates (Immunospot, Cat. HGZBPFN-2M) (PVDF membrane) for ELISPOT, which were coated with anti-perforin antibody and anti-granzyme B antibody, respectively, and further incubated at 37° C. for 8 hours. The PVDF membranes were washed with a washing solution (0.05% tween 20 in PBS), then treated with anti-granzyme B-HRP and anti-perforin-biotin antibodies. Then, detection processes were performed according to the manufacturer's protocol. The PVDF membranes were dried at room temperature for 24 hours, and the number of spots for granzyme B and perforin were counted by ELISPOT analyzer (Immunospot).

The results are shown in FIG. 9 (granzyme b; Gzmb) and FIG. 10 (perforin; Prf), respectively (Y-axis indicates the total number of spots). As shown in FIG. 9 and FIG. 10, the release levels of both of granzyme B and perforin are significantly increased in E3.1 or H11 antibody-treated group, as compared with the human IgG4 isotype control antibody-treated group. Unpaired T-test was performed, and all experiments were performed three times under the same conditions for the reliability of the experiment, and the results are shown as average values.

Example 9: Preparation of Chimeric GHI/75 Antibody

In order to see if antibodies provided by the examples show higher efficacy compared to pre-existing antibodies, a chimeric GHI/75 antibody comprising a variable region of GHI/75 antibody (Biolegend, cat #333721), which is a mouse-derived anti-human LILRB1 antibody, and a constant region of human antibody was prepared.

More specifically, the amino acid sequence of the GHI/75 antibody was analyzed through peptide mapping, and a vector, in which the nucleic acid sequence corresponding to the variable region (VH and VL domain) of a human IgG4 antibody was replaced by the nucleic acid sequence corresponding to the variable region (VH and VL domain) of mouse GHI/75 antibody, was prepared. In the vector, the region corresponding to upper hinge of human IgG4 was substituted with the nucleic acid sequence corresponding to the amino acid sequence (EPKSCDKTHT; SEQ ID NO: 359) of human IgG1 upper hinge. The vector was expressed as described in Example 1.4, and the obtained antibody was purified and used as a comparative antibody in examples below.

Example 10: Measurement of Inhibitory Effect of the Selected Antibodies on LILRB1 Signaling Using IL-2 Promoter Luciferase Assay In order to confirm whether the antibodies prepared in Examples 1 and 4 inhibit signaling by LILRB1, a luciferase reporter assay was performed. Among the antibodies prepared in Examples 1 and 4, the assay was performed representatively for E3.1 and H11 antibodies, and the chimeric GHI/75 antibody prepared in Example 9 was used for comparison. Jurkat cells expressing LILRB1 and interleukin 2 (IL-2) promoter luciferase (which were prepared by inserting IL-2 promoter luciferase vector (Promega) into Jurkat cell line (American Type Culture Collection) followed by transduction with lentivirus constructed for expressing LILRB1) and HLA-G-overexpressing K562 cells were used. Ninety six-well plates were coated with anti-CD3 antibody (Biolegend) by incubating with the antibody overnight at 4° C. On the next day, Jurkat cells expressing LILRB1 and IL-2 promoter luciferase were added to U-bottom 96-well plates at the amount of $1\times10^5$ cells/well, and the plates were treated with each antibody (E3.1, H11, chimeric GHI/75 or human IgG4 isotype (control)) to the final concentration of 20 ug/mL and incubated at 37° C. for one hour. HLA-G-overexpressing K562 cells ($1\times10^5$ cells/well) were added to the plates and incubated at 37° C. for 30 minutes. The obtained suspension was transferred to the plate coated with anti-CD3 antibody, and anti-CD28 antibody (Biolegend) was added thereto to the final concentration of 10 ug/mL. The plate was incubated at 37° C. for 6 hours. Steady-Glo® solution (Promega) was added to each well, and the luminescence intensity was recorded using a luminometer (Envision, PerkinElmer).

The results are shown in FIG. 11. As shown in FIGS. 11, E3.1 and H11 antibodies provided in examples exhibit considerably increased LILRB1 signaling inhibitory activity compared to human IgG4 isotype control antibody and the chimeric GHI/75 control antibody.

Example 11: Analysis of Anti-Cancer Effect of Selected Antibodies in Mouse Model For analysis of anti-cancer effects of selected antibodies, referring to Example 3, a mixture of $3\times10^6$ cells of HCT116 Red-Fluc colorectal carcinoma cells, $3\times10^6$ cells of THP-1 derived macrophages and an antibody (20 μg/mouse) was subcutaneously injected to 5-week old female CIEA NOG mice (NOG immunodeficient mouse; Central Institute for Experimental Animals, Japan) The antibody used was E3.1 or H11 antibody, and human IgG4 isotype was used as a control antibody for comparison. From the 4$^{th}$ day after grafting tumor cells, the antibody was administered to the mouse model at the dosage of 5 mg/kg by intraperitoneal injection twice a week, and the tumor volume was measured and shown in FIG. 12. As shown in FIGS. 12, E3.1 and H11 antibodies exhibit significant effect of inhibiting tumor growth in mouse models grafted with HCT116 colon cancer cells and THP-1 derived macrophages compared to the control antibody.

The invention claimed is:

1. An anti-LILRB1 antibody or an antigen-binding fragment thereof, comprising:

(1) the CDR-L1 comprising the amino acid sequence of SEQ ID NO: 1, the CDR-L2 comprising the amino acid sequence of SEQ ID NO: 2, the CDR-L3 comprising the amino acid sequence of SEQ ID NO: 3, the CDR-H1 comprising the amino acid sequence of SEQ ID NO: 4, the CDR-H2 comprising the amino acid sequence of SEQ ID NO: 5, and the CDR-H3 comprising the amino acid sequence of SEQ ID NO: 6;

(2) the CDR-L1 comprising the amino acid sequence of SEQ ID NO: 7, the CDR-L2 comprising the amino acid sequence of SEQ ID NO: 8, the CDR-L3 comprising the amino acid sequence of SEQ ID NO: 9, the CDR-H1 comprising the amino acid sequence of SEQ ID NO: 10, the CDR-H2 comprising the amino acid sequence of SEQ ID NO: 11, and the CDR-H3 comprising the amino acid sequence of SEQ ID NO: 12;

(3) the CDR-L1 comprising the amino acid sequence of SEQ ID NO: 13, the CDR-L2 comprising the amino acid sequence of SEQ ID NO: 14, the CDR-L3 comprising the amino acid sequence of SEQ ID NO: 15, the CDR-H1 comprising the amino acid sequence of SEQ ID NO: 16, the CDR-H2 comprising the amino acid sequence of SEQ ID NO: 17, and the CDR-H3 comprising the amino acid sequence of SEQ ID NO: 18;

(4) the CDR-L1 comprising the amino acid sequence of SEQ ID NO: 19, the CDR-L2 comprising the amino acid sequence of SEQ ID NO: 20, the CDR-L3 comprising the amino acid sequence of SEQ ID NO: 21, the CDR-H1 comprising the amino acid sequence of SEQ ID NO: 22, the CDR-H2 comprising the amino acid sequence of SEQ ID NO: 23, and the CDR-H3 comprising the amino acid sequence of SEQ ID NO: 24;

(5) the CDR-L1 comprising the amino acid sequence of SEQ ID NO: 25, the CDR-L2 comprising the amino acid sequence of SEQ ID NO: 26, the CDR-L3 comprising the amino acid sequence of SEQ ID NO: 27, the CDR-H1 comprising the amino acid sequence of SEQ ID NO: 28, the CDR-H2 comprising the amino acid sequence of SEQ ID NO: 29, and the CDR-H3 comprising the amino acid sequence of SEQ ID NO: 30;

(6) the CDR-L1 comprising the amino acid sequence of SEQ ID NO: 31, the CDR-L2 comprising the amino acid sequence of SEQ ID NO: 32, the CDR-L3 comprising the amino acid sequence of SEQ ID NO: 33, the CDR-H1 comprising the amino acid sequence of SEQ ID NO: 34, the CDR-H2 comprising the amino acid sequence of SEQ ID NO: 35, and the CDR-H3 comprising the amino acid sequence of SEQ ID NO: 36;

(7) the CDR-L1 comprising the amino acid sequence of SEQ ID NO: 37, the CDR-L2 comprising the amino acid sequence of SEQ ID NO: 38, the CDR-L3 comprising the amino acid sequence of SEQ ID NO: 39, the CDR-H1 comprising the amino acid sequence of SEQ ID NO: 40, the CDR-H2 comprising the amino acid sequence of SEQ ID NO: 41, and the CDR-H3 comprising the amino acid sequence of SEQ ID NO: 42;

(8) the CDR-L1 comprising the amino acid sequence of SEQ ID NO: 43, the CDR-L2 comprising the amino acid sequence of SEQ ID NO: 44, the CDR-L3 comprising the amino acid sequence of SEQ ID NO: 45, the CDR-H1 comprising the amino acid sequence of SEQ ID NO: 46, the CDR-H2 comprising the amino acid sequence of SEQ ID NO: 47, and the CDR-H3 comprising the amino acid sequence of SEQ ID NO: 48;

(9) the CDR-L1 comprising the amino acid sequence of SEQ ID NO: 49, the CDR-L2 comprising the amino acid sequence of SEQ ID NO: 50, the CDR-L3 comprising the amino acid sequence of SEQ ID NO: 51, the CDR-H1 comprising the amino acid sequence of SEQ ID NO: 52, the CDR-H2 comprising the amino acid sequence of SEQ ID NO: 53, and the CDR-H3 comprising the amino acid sequence of SEQ ID NO: 54;

(10) the CDR-L1 comprising the amino acid sequence of SEQ ID NO: 55, the CDR-L2 comprising the amino acid sequence of SEQ ID NO: 56, the CDR-L3 comprising the amino acid sequence of SEQ ID NO: 57, the CDR-H1 comprising the amino acid sequence of SEQ ID NO: 58, the CDR-H2 comprising the amino acid sequence of SEQ ID NO: 59, and the CDR-H3 comprising the amino acid sequence of SEQ ID NO: 60;

(11) the CDR-L1 comprising the amino acid sequence of SEQ ID NO: 61, the CDR-L2 comprising the amino acid sequence of SEQ ID NO: 62, the CDR-L3 comprising the amino acid sequence of SEQ ID NO: 63, the CDR-H1 comprising the amino acid sequence of SEQ ID NO: 64, the CDR-H2 comprising the amino acid sequence of SEQ ID NO: 65, and the CDR-H3 comprising the amino acid sequence of SEQ ID NO: 66;

(12) the CDR-L1 comprising the amino acid sequence of SEQ ID NO: 67, the CDR-L2 comprising the amino acid sequence of SEQ ID NO: 68, the CDR-L3 comprising the amino acid sequence of SEQ ID NO: 69, the CDR-H1 comprising the amino acid sequence of SEQ ID NO: 70, the CDR-H2 comprising the amino acid sequence of SEQ ID NO: 71, and the CDR-H3 comprising the amino acid sequence of SEQ ID NO: 72;

(13) the CDR-L1 comprising the amino acid sequence of SEQ ID NO: 73, the CDR-L2 comprising the amino acid sequence of SEQ ID NO: 74, the CDR-L3 comprising the amino acid sequence of SEQ ID NO: 75, the CDR-H1 comprising the amino acid sequence of SEQ ID NO: 76, the CDR-H2 comprising the amino acid sequence of SEQ ID NO: 77, and the CDR-H3 comprising the amino acid sequence of SEQ ID NO: 78;

(14) the CDR-L1 comprising the amino acid sequence of SEQ ID NO: 79, the CDR-L2 comprising the amino acid sequence of SEQ ID NO: 80, the CDR-L3 comprising the amino acid sequence of SEQ ID NO: 81, the CDR-H1 comprising the amino acid sequence of SEQ ID NO: 82, the CDR-H2 comprising the amino acid sequence of SEQ ID NO: 83, and the CDR-H3 comprising the amino acid sequence of SEQ ID NO: 84;

(15) the CDR-L1 comprising the amino acid sequence of SEQ ID NO: 85, the CDR-L2 comprising the amino acid sequence of SEQ ID NO: 86, the CDR-L3 comprising the amino acid sequence of SEQ ID NO: 87, the CDR-H1 comprising the amino acid sequence of SEQ ID NO: 88, the CDR-H2 comprising the amino acid sequence of SEQ ID NO: 89, and the CDR-H3 comprising the amino acid sequence of SEQ ID NO: 90;

(16) the CDR-L1 comprising the amino acid sequence of SEQ ID NO: 91, the CDR-L2 comprising the amino acid sequence of SEQ ID NO: 92, the CDR-L3 comprising the amino acid sequence of SEQ ID NO: 93, the CDR-H1 comprising the amino acid sequence of SEQ ID NO: 94, the CDR-H2 comprising the amino acid sequence of SEQ ID NO: 95, and the CDR-H3 comprising the amino acid sequence of SEQ ID NO: 96;

(17) the CDR-L1 comprising the amino acid sequence of SEQ ID NO: 97, the CDR-L2 comprising the amino acid sequence of SEQ ID NO: 98, the CDR-L3 comprising the amino acid sequence of SEQ ID NO: 99, the CDR-H1 comprising the amino acid sequence of SEQ ID NO: 100, the CDR-H2 comprising the amino acid sequence of SEQ ID NO: 101, and the CDR-H3 comprising the amino acid sequence of SEQ ID NO: 102;

(18) the CDR-L1 comprising the amino acid sequence of SEQ ID NO: 103, the CDR-L2 comprising the amino acid sequence of SEQ ID NO: 104, the CDR-L3 comprising the amino acid sequence of SEQ ID NO: 105, the CDR-H1 comprising the amino acid sequence of SEQ ID NO: 106, the CDR-H2 comprising the amino acid sequence of SEQ ID NO: 107, and the CDR-H3 comprising the amino acid sequence of SEQ ID NO: 108;

(19) the CDR-L1 comprising the amino acid sequence of SEQ ID NO: 109, the CDR-L2 comprising the amino acid sequence of SEQ ID NO: 110, the CDR-L3 comprising the amino acid sequence of SEQ ID NO: 111, the CDR-H1 comprising the amino acid sequence of SEQ ID NO: 112, the CDR-H2 comprising the amino acid sequence of SEQ ID NO: 113, and the CDR-H3 comprising the amino acid sequence of SEQ ID NO: 114; or

(20) the CDR-L1 comprising the amino acid sequence of SEQ ID NO: 115, the CDR-L2 comprising the amino acid sequence of SEQ ID NO: 116, the CDR-L3 comprising the amino acid sequence of SEQ ID NO: 117, the CDR-H1 comprising the amino acid sequence of SEQ ID NO: 118, the CDR-H2 comprising the amino acid sequence of SEQ ID NO: 119, and the CDR-H3 comprising the amino acid sequence of SEQ ID NO: 120.

2. The anti-LILRB1 antibody or an antigen-binding fragment thereof of claim 1, comprising:

a light chain variable region and a heavy chain variable region comprising:

a) SEQ ID NOs: 221 and 222,
b) SEQ ID NOs: 223 and 224,
c) SEQ ID NOs: 225 and 226,
d) SEQ ID NOs: 227 and 228,
e) SEQ ID NOs: 233 and 234,
f) SEQ ID NOs: 235 and 236,
g) SEQ ID NOs: 231 and 232,
h) SEQ ID NOs: 237 and 238,
i) SEQ ID NOs: 229 and 230,
j) SEQ ID NOs: 239 and 240,
k) SEQ ID NOs: 241 and 242,
l) SEQ ID NOs: 243 and 244,
m) SEQ ID NOs: 245 and 246,
n) SEQ ID NOs: 247 and 248,
o) SEQ ID NOs: 249 and 250,
p) SEQ ID NOs: 251 and 252,
q) SEQ ID NOs: 253 and 254,
r) SEQ ID NOs: 255 and 256,
s) SEQ ID NOs: 257 and 258,
t) SEQ ID NOs: 259 and 260, or
u) SEQ ID NOs: 345 and 222, respectively.

3. The anti-LILRB1 antibody or an antigen-binding fragment thereof of claim 1, wherein the antibody is a human IgG1 or IgG4 antibody.

4. The anti-LILRB1 antibody or an antigen-binding fragment thereof of claim 1, wherein the antigen-binding fragment is a scFv, $(scFv)_2$, Fab, Fab', $F(ab')_2$, a fusion polypeptide comprising a scFv fused with an immunoglobulin Fc, or a fusion polypeptide comprising scFv fused with a constant region of a light chain.

5. A pharmaceutical composition for treating a cancer, comprising the anti-LILRB1 antibody or an antigen-binding fragment thereof of any one of claim 1, and a pharmaceutically acceptable carrier.

6. The pharmaceutical composition of claim 5, wherein the cancer is characterized by overexpression of MHC Class I.

7. A nucleic acid molecule encoding the antibody or an antigen-binding fragment thereof of claim 1.

8. A recombinant vector comprising the nucleic acid molecule of claim 7.

9. A recombinant cell comprising the recombinant vector of claim 8.

10. A method of preparing an anti-LILRB1 antibody or an antigen-binding fragment thereof, comprising culturing the recombinant cell of claim 9.

11. The pharmaceutical composition of claim 6, wherein the cancer is colon adenocarcinoma, small cell lung carcinoma, breast cancer, pancreatic cancer, malignant melanoma, bone osteosarcoma, renal cell carcinoma, or gastric cancer.

12. A method for treating a cancer, comprising administering to a subject in need thereof a pharmaceutically effective amount of the anti-LILRB1 antibody or an antigen-binding fragment thereof of claim 1.

13. The method of claim 12, wherein the cancer is characterized by overexpression of MHC Class I.

14. The method of claim 13, wherein the cancer is colon adenocarcinoma, small cell lung carcinoma, breast cancer, pancreatic cancer, malignant melanoma, bone osteosarcoma, renal cell carcinoma, or gastric cancer.

* * * * *

SEQUENCE LISTING

```
<160> NUMBER OF SEQ ID NOS: 359

<210> SEQ ID NO 1
<211> LENGTH: 11
<212> TYPE: PRT
<213> ORGANISM: Artificial Sequence
<220> FEATURE:
<223> OTHER INFORMATION: CDR-L1 of E3 or E3.1 (Kabat)

<400> SEQUENCE: 1

Gln Gly Asp Ser Leu Arg Asn Phe Tyr Ala Ser
1               5                   10


<210> SEQ ID NO 2
<211> LENGTH: 7
<212> TYPE: PRT
<213> ORGANISM: Artificial Sequence
<220> FEATURE:
<223> OTHER INFORMATION: CDR-L2 of E3 or E3.1 (Kabat)

<400> SEQUENCE: 2

Gly Lys Asn Asn Arg Pro Ser
1               5


<210> SEQ ID NO 3
<211> LENGTH: 13
<212> TYPE: PRT
<213> ORGANISM: Artificial Sequence
<220> FEATURE:
<223> OTHER INFORMATION: CDR-L3 of E3 or E3.1 (Kabat)

<400> SEQUENCE: 3

Asn Ser Arg Asp Ser Ser Gly Ser His Leu Thr Gly Val
1               5                   10


<210> SEQ ID NO 4
<211> LENGTH: 5
<212> TYPE: PRT
<213> ORGANISM: Artificial Sequence
<220> FEATURE:
<223> OTHER INFORMATION: CDR-H1 of E3 or E3.1 (Kabat)

<400> SEQUENCE: 4

Ser Tyr Ala Met Ser
1               5


<210> SEQ ID NO 5
<211> LENGTH: 17
<212> TYPE: PRT
<213> ORGANISM: Artificial Sequence
<220> FEATURE:
<223> OTHER INFORMATION: CDR-H2 of E3 or E3.1 (Kabat)

<400> SEQUENCE: 5

Ala Ile Ser Gly Ser Gly Gly Ser Thr Tyr Tyr Ala Asp Ser Val Lys
1               5                   10                  15

Gly


<210> SEQ ID NO 6
<211> LENGTH: 15
```

```
<212> TYPE: PRT
<213> ORGANISM: Artificial Sequence
<220> FEATURE:
<223> OTHER INFORMATION: CDR-H3 of E3 or E3.1 (Kabat)

<400> SEQUENCE: 6

Asp Thr Tyr Tyr Tyr Gly Ser Gly Arg Ser Asn Ala Phe Asp Ile
1               5                   10                  15


<210> SEQ ID NO 7
<211> LENGTH: 11
<212> TYPE: PRT
<213> ORGANISM: Artificial Sequence
<220> FEATURE:
<223> OTHER INFORMATION: CDR-L1 of B3 (Kabat)

<400> SEQUENCE: 7

Gln Ala Ser Gln Asp Ile Ser Asn Tyr Leu Asn
1               5                   10


<210> SEQ ID NO 8
<211> LENGTH: 7
<212> TYPE: PRT
<213> ORGANISM: Artificial Sequence
<220> FEATURE:
<223> OTHER INFORMATION: CDR-L2 of B3 (Kabat)

<400> SEQUENCE: 8

Asp Ala Ser Asn Leu Glu Thr
1               5


<210> SEQ ID NO 9
<211> LENGTH: 7
<212> TYPE: PRT
<213> ORGANISM: Artificial Sequence
<220> FEATURE:
<223> OTHER INFORMATION: CDR-L3 of B3 (Kabat)

<400> SEQUENCE: 9

Gln Gln Tyr Asp Asn Leu Pro
1               5


<210> SEQ ID NO 10
<211> LENGTH: 5
<212> TYPE: PRT
<213> ORGANISM: Artificial Sequence
<220> FEATURE:
<223> OTHER INFORMATION: CDR-H1 of B3 (Kabat)

<400> SEQUENCE: 10

Asp Tyr Ala Met His
1               5


<210> SEQ ID NO 11
<211> LENGTH: 17
<212> TYPE: PRT
<213> ORGANISM: Artificial Sequence
<220> FEATURE:
<223> OTHER INFORMATION: CDR-H2 of B3 (Kabat)

<400> SEQUENCE: 11

Gly Ile Ser Trp Asn Ser Gly Ser Ile Gly Tyr Ala Asp Ser Val Lys
1               5                   10                  15

Gly


<210> SEQ ID NO 12
```

<211> LENGTH: 13
<212> TYPE: PRT
<213> ORGANISM: Artificial Sequence
<220> FEATURE:
<223> OTHER INFORMATION: CDR-H3 of B3 (Kabat)

<400> SEQUENCE: 12

Val Gly Asp Ser Ser Gly Trp Ser Asp Ala Phe Asp Ile
1 5 10

<210> SEQ ID NO 13
<211> LENGTH: 11
<212> TYPE: PRT
<213> ORGANISM: Artificial Sequence
<220> FEATURE:
<223> OTHER INFORMATION: CDR-L1 of A10 (Kabat)

<400> SEQUENCE: 13

Arg Ala Ser Gln Ser Val Ser Ser Asn Leu Ala
1 5 10

<210> SEQ ID NO 14
<211> LENGTH: 7
<212> TYPE: PRT
<213> ORGANISM: Artificial Sequence
<220> FEATURE:
<223> OTHER INFORMATION: CDR-L2 of A10 (Kabat)

<400> SEQUENCE: 14

Gly Ala Ser Thr Arg Ala Thr
1 5

<210> SEQ ID NO 15
<211> LENGTH: 11
<212> TYPE: PRT
<213> ORGANISM: Artificial Sequence
<220> FEATURE:
<223> OTHER INFORMATION: CDR-L3 of A10 (Kabat)

<400> SEQUENCE: 15

Gln Gln Tyr Gly Ser Ser Pro Arg Met Tyr Thr
1 5 10

<210> SEQ ID NO 16
<211> LENGTH: 5
<212> TYPE: PRT
<213> ORGANISM: Artificial Sequence
<220> FEATURE:
<223> OTHER INFORMATION: CDR-H1 of A10 (Kabat)

<400> SEQUENCE: 16

Ser Tyr Ala Ile Ser
1 5

<210> SEQ ID NO 17
<211> LENGTH: 17
<212> TYPE: PRT
<213> ORGANISM: Artificial Sequence
<220> FEATURE:
<223> OTHER INFORMATION: CDR-H2 of A10 (Kabat)

<400> SEQUENCE: 17

Gly Ile Ile Pro Ile Phe Gly Thr Ala Asn Tyr Ala Gln Lys Phe Gln
1 5 10 15

Gly

```
<210> SEQ ID NO 18
<211> LENGTH: 12
<212> TYPE: PRT
<213> ORGANISM: Artificial Sequence
<220> FEATURE:
<223> OTHER INFORMATION: CDR-H3 of A10 (Kabat)

<400> SEQUENCE: 18

Gly Gly Leu Gly Glu Leu Asp Asn Trp Phe Asp Pro
1               5                   10


<210> SEQ ID NO 19
<211> LENGTH: 11
<212> TYPE: PRT
<213> ORGANISM: Artificial Sequence
<220> FEATURE:
<223> OTHER INFORMATION: CDR-L1 of G1 (Kabat)

<400> SEQUENCE: 19

Ser Gly Tyr Lys Leu Gly Asp Arg Tyr Val Ser
1               5                   10


<210> SEQ ID NO 20
<211> LENGTH: 7
<212> TYPE: PRT
<213> ORGANISM: Artificial Sequence
<220> FEATURE:
<223> OTHER INFORMATION: CDR-L2 of G1 (Kabat)

<400> SEQUENCE: 20

Lys Asp Ser Gln Arg Pro Ser
1               5


<210> SEQ ID NO 21
<211> LENGTH: 9
<212> TYPE: PRT
<213> ORGANISM: Artificial Sequence
<220> FEATURE:
<223> OTHER INFORMATION: CDR-L3 of G1 (Kabat)

<400> SEQUENCE: 21

Gln Ala Trp Asp Ser Gly Thr Gly Val
1               5


<210> SEQ ID NO 22
<211> LENGTH: 5
<212> TYPE: PRT
<213> ORGANISM: Artificial Sequence
<220> FEATURE:
<223> OTHER INFORMATION: CDR-H1 of G1 (Kabat)

<400> SEQUENCE: 22

Ser Tyr Gly Ile Ser
1               5


<210> SEQ ID NO 23
<211> LENGTH: 17
<212> TYPE: PRT
<213> ORGANISM: Artificial Sequence
<220> FEATURE:
<223> OTHER INFORMATION: CDR-H2 of G1 (Kabat)

<400> SEQUENCE: 23

Trp Ile Ser Ala Tyr Asn Gly Asn Thr Asn Tyr Ala Gln Glu Leu Gln
1               5                   10                  15

Gly
```

<210> SEQ ID NO 24
<211> LENGTH: 9
<212> TYPE: PRT
<213> ORGANISM: Artificial Sequence
<220> FEATURE:
<223> OTHER INFORMATION: CDR-H3 of G1 (Kabat)

<400> SEQUENCE: 24

Val Gly Val Ala Gly Lys Leu Asp Tyr
1 5

<210> SEQ ID NO 25
<211> LENGTH: 14
<212> TYPE: PRT
<213> ORGANISM: Artificial Sequence
<220> FEATURE:
<223> OTHER INFORMATION: CDR-L1 of G9 (Kabat)

<400> SEQUENCE: 25

Thr Gly Ser Ser Ser Asp Val Gly Gly Tyr Asn Tyr Val Ser
1 5 10

<210> SEQ ID NO 26
<211> LENGTH: 7
<212> TYPE: PRT
<213> ORGANISM: Artificial Sequence
<220> FEATURE:
<223> OTHER INFORMATION: CDR-L2 of G9 (Kabat)

<400> SEQUENCE: 26

Asp Val Ser Asn Arg Pro Ser
1 5

<210> SEQ ID NO 27
<211> LENGTH: 12
<212> TYPE: PRT
<213> ORGANISM: Artificial Sequence
<220> FEATURE:
<223> OTHER INFORMATION: CDR-L3 of G9 (Kabat)

<400> SEQUENCE: 27

Ser Ser Tyr Thr Gly Ser Ser Thr Leu Asp Val Leu
1 5 10

<210> SEQ ID NO 28
<211> LENGTH: 5
<212> TYPE: PRT
<213> ORGANISM: Artificial Sequence
<220> FEATURE:
<223> OTHER INFORMATION: CDR-H1 of G9 (Kabat)

<400> SEQUENCE: 28

Ser Tyr Trp Ile Gly
1 5

<210> SEQ ID NO 29
<211> LENGTH: 17
<212> TYPE: PRT
<213> ORGANISM: Artificial Sequence
<220> FEATURE:
<223> OTHER INFORMATION: CDR-H2 of G9 (Kabat)

<400> SEQUENCE: 29

Ile Ile Tyr Pro Gly Asp Ser Asp Thr Arg Tyr Ser Pro Ser Phe Gln
1 5 10 15

Gly

<210> SEQ ID NO 30
<211> LENGTH: 11
<212> TYPE: PRT
<213> ORGANISM: Artificial Sequence
<220> FEATURE:
<223> OTHER INFORMATION: CDR-H3 of G9 (Kabat)

<400> SEQUENCE: 30

```
Gln Tyr Tyr Asp Gly Gly Tyr Tyr Met Asp Val
1               5                   10
```

<210> SEQ ID NO 31
<211> LENGTH: 11
<212> TYPE: PRT
<213> ORGANISM: Artificial Sequence
<220> FEATURE:
<223> OTHER INFORMATION: CDR-L1 of H2 (Kabat)

<400> SEQUENCE: 31

```
Gln Gly Asp Ser Leu Arg Asn Tyr Tyr Ala Ser
1               5                   10
```

<210> SEQ ID NO 32
<211> LENGTH: 7
<212> TYPE: PRT
<213> ORGANISM: Artificial Sequence
<220> FEATURE:
<223> OTHER INFORMATION: CDR-L2 of H2 (Kabat)

<400> SEQUENCE: 32

```
Gly Asn Asn Lys Arg Pro Ser
1               5
```

<210> SEQ ID NO 33
<211> LENGTH: 11
<212> TYPE: PRT
<213> ORGANISM: Artificial Sequence
<220> FEATURE:
<223> OTHER INFORMATION: CDR-L3 of H2 (Kabat)

<400> SEQUENCE: 33

```
Asn Ser Leu Asp Ser Thr Tyr Asn His Pro Ile
1               5                   10
```

<210> SEQ ID NO 34
<211> LENGTH: 5
<212> TYPE: PRT
<213> ORGANISM: Artificial Sequence
<220> FEATURE:
<223> OTHER INFORMATION: CDR-H1 of H2 (Kabat)

<400> SEQUENCE: 34

```
Ser Tyr Asp Ile His
1               5
```

<210> SEQ ID NO 35
<211> LENGTH: 17
<212> TYPE: PRT
<213> ORGANISM: Artificial Sequence
<220> FEATURE:
<223> OTHER INFORMATION: CDR-H2 of H2 (Kabat)

<400> SEQUENCE: 35

```
Trp Ile Ser Ala Tyr Asn Gly Asn Thr Asn Tyr Ala Gln Lys Leu Gln
1               5                   10                  15
```

Gly

<210> SEQ ID NO 36
<211> LENGTH: 8
<212> TYPE: PRT
<213> ORGANISM: Artificial Sequence
<220> FEATURE:
<223> OTHER INFORMATION: CDR-H3 of H2 (Kabat)

<400> SEQUENCE: 36

Asp Gly Gly Asp Ala Phe Asp Ile
1               5

<210> SEQ ID NO 37
<211> LENGTH: 11
<212> TYPE: PRT
<213> ORGANISM: Artificial Sequence
<220> FEATURE:
<223> OTHER INFORMATION: CDR-L1 of H11 (Kabat)

<400> SEQUENCE: 37

Gln Gly Asp Ser Leu Arg Ser Tyr Tyr Ala Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: CDR-L2 of H11 (Kabat)

<400> SEQUENCE: 38

Gly Arg Asn Asn Arg Pro Ser
1               5

<210> SEQ ID NO 39
<211> LENGTH: 11
<212> TYPE: PRT
<213> ORGANISM: Artificial Sequence
<220> FEATURE:
<223> OTHER INFORMATION: CDR-L3 of H11 (Kabat)

<400> SEQUENCE: 39

Lys Ser Arg Asp Ser Ser Gly Asn His Tyr Val
1               5                   10

<210> SEQ ID NO 40
<211> LENGTH: 5
<212> TYPE: PRT
<213> ORGANISM: Artificial Sequence
<220> FEATURE:
<223> OTHER INFORMATION: CDR-H1 of H11 (Kabat)

<400> SEQUENCE: 40

Ser Tyr Tyr Met His
1               5

<210> SEQ ID NO 41
<211> LENGTH: 17
<212> TYPE: PRT
<213> ORGANISM: Artificial Sequence
<220> FEATURE:
<223> OTHER INFORMATION: CDR-H2 of H11 (Kabat)

<400> SEQUENCE: 41

Ile Ile Asn Pro Ser Gly Gly Ser Thr Ser Tyr Ala Gln Lys Phe Gln
1               5                   10                  15

Gly

<210> SEQ ID NO 42
<211> LENGTH: 8
<212> TYPE: PRT
<213> ORGANISM: Artificial Sequence
<220> FEATURE:
<223> OTHER INFORMATION: CDR-H3 of H11 (Kabat)

<400> SEQUENCE: 42

Asp Ala Gly Ser Ser Ser Asp Tyr
1               5

<210> SEQ ID NO 43
<211> LENGTH: 14
<212> TYPE: PRT
<213> ORGANISM: Artificial Sequence
<220> FEATURE:
<223> OTHER INFORMATION: CDR-L1 of F12 (Kabat)

<400> SEQUENCE: 43

Ala Gly Thr Ser Ser Asp Ile Gly Asp Tyr Asp Tyr Val Ser
1               5                   10

<210> SEQ ID NO 44
<211> LENGTH: 7
<212> TYPE: PRT
<213> ORGANISM: Artificial Sequence
<220> FEATURE:
<223> OTHER INFORMATION: CDR-L2 of F12 (Kabat)

<400> SEQUENCE: 44

Asp Val Ser Arg Arg Pro Ser
1               5

<210> SEQ ID NO 45
<211> LENGTH: 10
<212> TYPE: PRT
<213> ORGANISM: Artificial Sequence
<220> FEATURE:
<223> OTHER INFORMATION: CDR-L3 of F12 (Kabat)

<400> SEQUENCE: 45

Ala Ser Tyr Thr Ser Ser Ser Val Val Val
1               5                   10

<210> SEQ ID NO 46
<211> LENGTH: 5
<212> TYPE: PRT
<213> ORGANISM: Artificial Sequence
<220> FEATURE:
<223> OTHER INFORMATION: CDR-H1 of F12 (Kabat)

<400> SEQUENCE: 46

Ser Tyr Trp Ile Gly
1               5

<210> SEQ ID NO 47
<211> LENGTH: 17
<212> TYPE: PRT
<213> ORGANISM: Artificial Sequence
<220> FEATURE:
<223> OTHER INFORMATION: CDR-H2 of F12 (Kabat)

<400> SEQUENCE: 47

Ile Ile Tyr Pro Gly Asp Ser Asp Thr Arg Tyr Ser Pro Ser Phe Gln 1 5 10 15

Gly

<210> SEQ ID NO 48
<211> LENGTH: 11
<212> TYPE: PRT
<213> ORGANISM: Artificial Sequence
<220> FEATURE:
<223> OTHER INFORMATION: CDR-H3 of F12 (Kabat)

<400> SEQUENCE: 48

Gln Tyr Tyr Asp Gly Gly Tyr Tyr Met Asp Val
1 5 10

<210> SEQ ID NO 49
<211> LENGTH: 11
<212> TYPE: PRT
<213> ORGANISM: Artificial Sequence
<220> FEATURE:
<223> OTHER INFORMATION: CDR-L1 of B9 (Kabat)

<400> SEQUENCE: 49

Arg Ala Ser Gln Ser Ile Ser Arg Tyr Leu Asn
1 5 10

<210> SEQ ID NO 50
<211> LENGTH: 7
<212> TYPE: PRT
<213> ORGANISM: Artificial Sequence
<220> FEATURE:
<223> OTHER INFORMATION: CDR-L2 of B9 (Kabat)

<400> SEQUENCE: 50

Gly Ala Ser Ser Leu Gln Ser
1 5

<210> SEQ ID NO 51
<211> LENGTH: 9
<212> TYPE: PRT
<213> ORGANISM: Artificial Sequence
<220> FEATURE:
<223> OTHER INFORMATION: CDR-L3 of B9 (Kabat)

<400> SEQUENCE: 51

Gln Gln Ala Tyr Gly Phe Pro Leu Thr
1 5

<210> SEQ ID NO 52
<211> LENGTH: 5
<212> TYPE: PRT
<213> ORGANISM: Artificial Sequence
<220> FEATURE:
<223> OTHER INFORMATION: CDR-H1 of B9 (Kabat)

<400> SEQUENCE: 52

Ser Tyr Ala Ile Ser
1 5

<210> SEQ ID NO 53
<211> LENGTH: 17
<212> TYPE: PRT
<213> ORGANISM: Artificial Sequence
<220> FEATURE:
<223> OTHER INFORMATION: CDR-H2 of B9 (Kabat)

<400> SEQUENCE: 53

Gly Ile Ile Pro Ile Phe Gly Thr Ala Asn Tyr Ala Gln Lys Phe Gln
1 5 10 15

Gly

<210> SEQ ID NO 54
<211> LENGTH: 16
<212> TYPE: PRT
<213> ORGANISM: Artificial Sequence
<220> FEATURE:
<223> OTHER INFORMATION: CDR-H3 of B9 (Kabat)

<400> SEQUENCE: 54

Gly Glu Ile Ala Val Ala Gln Asn Trp Asp Tyr Tyr Gly Met Asp Val
1 5 10 15

<210> SEQ ID NO 55
<211> LENGTH: 14
<212> TYPE: PRT
<213> ORGANISM: Artificial Sequence
<220> FEATURE:
<223> OTHER INFORMATION: CDR-L1 of G11 (Kabat)

<400> SEQUENCE: 55

Thr Gly Thr Ser Ser Asp Val Gly Gly Tyr Asn Tyr Val Ser
1 5 10

<210> SEQ ID NO 56
<211> LENGTH: 7
<212> TYPE: PRT
<213> ORGANISM: Artificial Sequence
<220> FEATURE:
<223> OTHER INFORMATION: CDR-L2 of G11 (Kabat)

<400> SEQUENCE: 56

Asp Val Ser Lys Arg Pro Ser
1 5

<210> SEQ ID NO 57
<211> LENGTH: 11
<212> TYPE: PRT
<213> ORGANISM: Artificial Sequence
<220> FEATURE:
<223> OTHER INFORMATION: CDR-L3 of G11 (Kabat)

<400> SEQUENCE: 57

Ser Ser Tyr Ser Ser Ser Ser Thr Leu Val Val
1 5 10

<210> SEQ ID NO 58
<211> LENGTH: 5
<212> TYPE: PRT
<213> ORGANISM: Artificial Sequence
<220> FEATURE:
<223> OTHER INFORMATION: CDR-H1 of G11 (Kabat)

<400> SEQUENCE: 58

Ser Tyr Trp Ile Gly
1 5

<210> SEQ ID NO 59
<211> LENGTH: 17
<212> TYPE: PRT
<213> ORGANISM: Artificial Sequence
<220> FEATURE:
<223> OTHER INFORMATION: CDR-H2 of G11 (Kabat)

<400> SEQUENCE: 59

Ile Ile Tyr Pro Gly Asp Ser Asp Thr Arg Tyr Ser Pro Ser Phe Gln
1 5 10 15

Gly

<210> SEQ ID NO 60
<211> LENGTH: 11
<212> TYPE: PRT
<213> ORGANISM: Artificial Sequence
<220> FEATURE:
<223> OTHER INFORMATION: CDR-H3 of G11 (Kabat)

<400> SEQUENCE: 60

Gln Tyr Tyr Asp Gly Gly Tyr Tyr Met Asp Val
1 5 10

<210> SEQ ID NO 61
<211> LENGTH: 11
<212> TYPE: PRT
<213> ORGANISM: Artificial Sequence
<220> FEATURE:
<223> OTHER INFORMATION: CDR-L1 of G6 (Kabat)

<400> SEQUENCE: 61

Gln Gly Asp Ser Leu Arg Arg Tyr Tyr Ala Thr
1 5 10

<210> SEQ ID NO 62
<211> LENGTH: 7
<212> TYPE: PRT
<213> ORGANISM: Artificial Sequence
<220> FEATURE:
<223> OTHER INFORMATION: CDR-L2 of G6 (Kabat)

<400> SEQUENCE: 62

Gly Gln Asn Tyr Arg Pro Ser
1 5

<210> SEQ ID NO 63
<211> LENGTH: 11
<212> TYPE: PRT
<213> ORGANISM: Artificial Sequence
<220> FEATURE:
<223> OTHER INFORMATION: CDR-L3 of G6 (Kabat)

<400> SEQUENCE: 63

Asn Ser Arg Asp Ser Ser Gly Asn His Val Val
1 5 10

<210> SEQ ID NO 64
<211> LENGTH: 5
<212> TYPE: PRT
<213> ORGANISM: Artificial Sequence
<220> FEATURE:
<223> OTHER INFORMATION: CDR-H1 of G6 (Kabat)

<400> SEQUENCE: 64

Ser Tyr Tyr Met His
1 5

<210> SEQ ID NO 65
<211> LENGTH: 17
<212> TYPE: PRT
<213> ORGANISM: Artificial Sequence
<220> FEATURE:
<223> OTHER INFORMATION: CDR-H2 of G6 (Kabat)

<400> SEQUENCE: 65

Gly Ile Ile Pro Ile Phe Gly Thr Ala Asn Tyr Ala Gln Lys Phe Gln
1 5 10 15

Gly

<210> SEQ ID NO 66
<211> LENGTH: 10
<212> TYPE: PRT
<213> ORGANISM: Artificial Sequence
<220> FEATURE:
<223> OTHER INFORMATION: CDR-H3 of G6 (Kabat)

<400> SEQUENCE: 66

Gly Trp Gly Tyr Ser Ser Ser Phe Asp Tyr
1 5 10

<210> SEQ ID NO 67
<211> LENGTH: 13
<212> TYPE: PRT
<213> ORGANISM: Artificial Sequence
<220> FEATURE:
<223> OTHER INFORMATION: CDR-L1 of F11 (Kabat)

<400> SEQUENCE: 67

Ser Gly Ser Ser Ser Asn Ile Gly Thr Asn Thr Val Asn
1 5 10

<210> SEQ ID NO 68
<211> LENGTH: 7
<212> TYPE: PRT
<213> ORGANISM: Artificial Sequence
<220> FEATURE:
<223> OTHER INFORMATION: CDR-L2 of F11 (Kabat)

<400> SEQUENCE: 68

Ser Asn Asp Gln Arg Pro Ser
1 5

<210> SEQ ID NO 69
<211> LENGTH: 11
<212> TYPE: PRT
<213> ORGANISM: Artificial Sequence
<220> FEATURE:
<223> OTHER INFORMATION: CDR-L3 of F11 (Kabat)

<400> SEQUENCE: 69

Glu Thr Trp Asp Asp Ser Leu Lys Gly Pro Val
1 5 10

<210> SEQ ID NO 70
<211> LENGTH: 5
<212> TYPE: PRT
<213> ORGANISM: Artificial Sequence
<220> FEATURE:
<223> OTHER INFORMATION: CDR-H1 of F11 (Kabat)

<400> SEQUENCE: 70

Ser Tyr Ala Met Ser
1 5

<210> SEQ ID NO 71
<211> LENGTH: 17
<212> TYPE: PRT
<213> ORGANISM: Artificial Sequence
<220> FEATURE:
<223> OTHER INFORMATION: CDR-H2 of F11 (Kabat)

<400> SEQUENCE: 71

Thr Ile Ser Gly Ser Gly Asp Ser Thr Tyr Tyr Ala Asp Ser Val Lys
1 5 10 15

Gly

<210> SEQ ID NO 72
<211> LENGTH: 10
<212> TYPE: PRT
<213> ORGANISM: Artificial Sequence
<220> FEATURE:
<223> OTHER INFORMATION: CDR-H3 of F11 (Kabat)

<400> SEQUENCE: 72

Glu Trp Glu Leu Gly Asp Ala Phe Asp Ile
1 5 10

<210> SEQ ID NO 73
<211> LENGTH: 11
<212> TYPE: PRT
<213> ORGANISM: Artificial Sequence
<220> FEATURE:
<223> OTHER INFORMATION: CDR-L1 of D3 (Kabat)

<400> SEQUENCE: 73

Arg Ala Ser Gln Ser Ile Ser Ser Tyr Leu Asn
1 5 10

<210> SEQ ID NO 74
<211> LENGTH: 7
<212> TYPE: PRT
<213> ORGANISM: Artificial Sequence
<220> FEATURE:
<223> OTHER INFORMATION: CDR-L2 of D3 (Kabat)

<400> SEQUENCE: 74

Ala Ala Ser Ser Leu Gln Ser
1 5

<210> SEQ ID NO 75
<211> LENGTH: 9
<212> TYPE: PRT
<213> ORGANISM: Artificial Sequence
<220> FEATURE:
<223> OTHER INFORMATION: CDR-L3 of D3 (Kabat)

<400> SEQUENCE: 75

Gln Gln Ser Tyr Ser Thr Arg Trp Thr
1 5

<210> SEQ ID NO 76
<211> LENGTH: 5
<212> TYPE: PRT
<213> ORGANISM: Artificial Sequence
<220> FEATURE:
<223> OTHER INFORMATION: CDR-H1 of D3 (Kabat)

<400> SEQUENCE: 76

Ser Tyr Ala Met Ser
1 5

<210> SEQ ID NO 77
<211> LENGTH: 17
<212> TYPE: PRT
<213> ORGANISM: Artificial Sequence
<220> FEATURE:

<223> OTHER INFORMATION: CDR-H2 of D3 (Kabat)

<400> SEQUENCE: 77

Ala Ile Ser Gly Ser Gly Gly Ser Thr Tyr Tyr Ala Asp Ser Val Lys
1 5 10 15

Gly

<210> SEQ ID NO 78
<211> LENGTH: 13
<212> TYPE: PRT
<213> ORGANISM: Artificial Sequence
<220> FEATURE:
<223> OTHER INFORMATION: CDR-H3 of D3 (Kabat)

<400> SEQUENCE: 78

Asp Arg Gly Ser Tyr Gly Tyr Tyr Tyr Gly Met Asp Val
1 5 10

<210> SEQ ID NO 79
<211> LENGTH: 11
<212> TYPE: PRT
<213> ORGANISM: Artificial Sequence
<220> FEATURE:
<223> OTHER INFORMATION: CDR-L1 of B12 (Kabat)

<400> SEQUENCE: 79

Arg Ala Ser Gln Ser Ile Ser Ser Tyr Leu Asn
1 5 10

<210> SEQ ID NO 80
<211> LENGTH: 7
<212> TYPE: PRT
<213> ORGANISM: Artificial Sequence
<220> FEATURE:
<223> OTHER INFORMATION: CDR-L2 of B12 (Kabat)

<400> SEQUENCE: 80

Ala Ala Ser Ser Leu Gln Ser
1 5

<210> SEQ ID NO 81
<211> LENGTH: 9
<212> TYPE: PRT
<213> ORGANISM: Artificial Sequence
<220> FEATURE:
<223> OTHER INFORMATION: CDR-L3 of B12 (Kabat)

<400> SEQUENCE: 81

Gln Gln Ser Tyr Ser Thr Leu Arg Thr
1 5

<210> SEQ ID NO 82
<211> LENGTH: 5
<212> TYPE: PRT
<213> ORGANISM: Artificial Sequence
<220> FEATURE:
<223> OTHER INFORMATION: CDR-H1 of B12 (Kabat)

<400> SEQUENCE: 82

Gly Tyr Tyr Met His
1 5

<210> SEQ ID NO 83
<211> LENGTH: 17
<212> TYPE: PRT
<213> ORGANISM: Artificial Sequence
<220> FEATURE:
<223> OTHER INFORMATION: CDR-H2 of B12 (Kabat)

<400> SEQUENCE: 83

Trp Ile Asn Pro Asn Ser Gly Gly Thr Asn Tyr Ala Gln Lys Phe Gln
1 5 10 15

Gly

<210> SEQ ID NO 84
<211> LENGTH: 13
<212> TYPE: PRT
<213> ORGANISM: Artificial Sequence
<220> FEATURE:
<223> OTHER INFORMATION: CDR-H3 of B12 (Kabat)

<400> SEQUENCE: 84

Ala Gly Ala Ser Ile Val Gly Ala Thr Ala Leu Asp Tyr
1 5 10

<210> SEQ ID NO 85
<211> LENGTH: 13
<212> TYPE: PRT
<213> ORGANISM: Artificial Sequence
<220> FEATURE:
<223> OTHER INFORMATION: CDR-L1 of E4 (Kabat)

<400> SEQUENCE: 85

Thr Arg Ser Ser Gly Ser Ile Ala Ser Asn Tyr Val Gln
1 5 10

<210> SEQ ID NO 86
<211> LENGTH: 7
<212> TYPE: PRT
<213> ORGANISM: Artificial Sequence
<220> FEATURE:
<223> OTHER INFORMATION: CDR-L2 of E4 (Kabat)

<400> SEQUENCE: 86

Glu Asp Asn Gln Arg Pro Ser
1 5

<210> SEQ ID NO 87
<211> LENGTH: 11
<212> TYPE: PRT
<213> ORGANISM: Artificial Sequence
<220> FEATURE:
<223> OTHER INFORMATION: CDR-L3 of E4 (Kabat)

<400> SEQUENCE: 87

Gln Ser Tyr Asp Thr Gly Asn Arg Asn Tyr Val
1 5 10

<210> SEQ ID NO 88
<211> LENGTH: 5
<212> TYPE: PRT
<213> ORGANISM: Artificial Sequence
<220> FEATURE:
<223> OTHER INFORMATION: CDR-H1 of E4 (Kabat)

<400> SEQUENCE: 88

Ser Tyr Thr Ile Ser
1 5

<210> SEQ ID NO 89
<211> LENGTH: 17
<212> TYPE: PRT

<213> ORGANISM: Artificial Sequence
<220> FEATURE:
<223> OTHER INFORMATION: CDR-H2 of E4 (Kabat)

<400> SEQUENCE: 89

Arg Ile Ile Pro Ile Leu Gly Ile Ala Asn Tyr Ala Gln Lys Phe Gln
1 5 10 15

Gly

<210> SEQ ID NO 90
<211> LENGTH: 12
<212> TYPE: PRT
<213> ORGANISM: Artificial Sequence
<220> FEATURE:
<223> OTHER INFORMATION: CDR-H3 of E4 (Kabat)

<400> SEQUENCE: 90

Gly Pro Ser Leu Asn Tyr Ala Gly Tyr Phe Asp Asn
1 5 10

<210> SEQ ID NO 91
<211> LENGTH: 11
<212> TYPE: PRT
<213> ORGANISM: Artificial Sequence
<220> FEATURE:
<223> OTHER INFORMATION: CDR-L1 of E12 (Kabat)

<400> SEQUENCE: 91

Gln Gly Asp Ser Leu Arg Ser Tyr Tyr Ala Ser
1 5 10

<210> SEQ ID NO 92
<211> LENGTH: 7
<212> TYPE: PRT
<213> ORGANISM: Artificial Sequence
<220> FEATURE:
<223> OTHER INFORMATION: CDR-L2 of E12 (Kabat)

<400> SEQUENCE: 92

Gly Lys Glu Lys Arg Pro Ser
1 5

<210> SEQ ID NO 93
<211> LENGTH: 11
<212> TYPE: PRT
<213> ORGANISM: Artificial Sequence
<220> FEATURE:
<223> OTHER INFORMATION: CDR-L3 of E12 (Kabat)

<400> SEQUENCE: 93

Asn Ser Arg Gly Ser Thr Thr Asp Tyr Met Val
1 5 10

<210> SEQ ID NO 94
<211> LENGTH: 5
<212> TYPE: PRT
<213> ORGANISM: Artificial Sequence
<220> FEATURE:
<223> OTHER INFORMATION: CDR-H1 of E12 (Kabat)

<400> SEQUENCE: 94

Ser Tyr Ala Met His
1 5

<210> SEQ ID NO 95
<211> LENGTH: 17

<212> TYPE: PRT
<213> ORGANISM: Artificial Sequence
<220> FEATURE:
<223> OTHER INFORMATION: CDR-H2 of E12 (Kabat)

<400> SEQUENCE: 95

Val Ile Ser Tyr Asp Gly Ser Asn Lys Tyr Tyr Ala Asp Ser Val Lys
1 5 10 15

Gly

<210> SEQ ID NO 96
<211> LENGTH: 8
<212> TYPE: PRT
<213> ORGANISM: Artificial Sequence
<220> FEATURE:
<223> OTHER INFORMATION: CDR-H3 of E12 (Kabat)

<400> SEQUENCE: 96

Glu Arg Gly Ser Gly Met Asp Val
1 5

<210> SEQ ID NO 97
<211> LENGTH: 11
<212> TYPE: PRT
<213> ORGANISM: Artificial Sequence
<220> FEATURE:
<223> OTHER INFORMATION: CDR-L1 of D1 (Kabat)

<400> SEQUENCE: 97

Lys Ala Ser Gln Asp Ile Asp Asp Asp Met Asn
1 5 10

<210> SEQ ID NO 98
<211> LENGTH: 7
<212> TYPE: PRT
<213> ORGANISM: Artificial Sequence
<220> FEATURE:
<223> OTHER INFORMATION: CDR-L2 of D1 (Kabat)

<400> SEQUENCE: 98

Glu Ala Ser Thr Leu Val Pro
1 5

<210> SEQ ID NO 99
<211> LENGTH: 9
<212> TYPE: PRT
<213> ORGANISM: Artificial Sequence
<220> FEATURE:
<223> OTHER INFORMATION: CDR-L3 of D1 (Kabat)

<400> SEQUENCE: 99

Leu Gln His Asp Lys Phe Pro Tyr Thr
1 5

<210> SEQ ID NO 100
<211> LENGTH: 5
<212> TYPE: PRT
<213> ORGANISM: Artificial Sequence
<220> FEATURE:
<223> OTHER INFORMATION: CDR-H1 of D1 (Kabat)

<400> SEQUENCE: 100

Ser Tyr Gly Ile Ser
1 5

<210> SEQ ID NO 101

<211> LENGTH: 17
<212> TYPE: PRT
<213> ORGANISM: Artificial Sequence
<220> FEATURE:
<223> OTHER INFORMATION: CDR-H2 of D1 (Kabat)

<400> SEQUENCE: 101

Trp Ile Asn Pro Asn Ser Gly Gly Thr Asn Tyr Ala Gln Lys Phe Gln
1 5 10 15

Gly

<210> SEQ ID NO 102
<211> LENGTH: 8
<212> TYPE: PRT
<213> ORGANISM: Artificial Sequence
<220> FEATURE:
<223> OTHER INFORMATION: CDR-H3 of D1 (Kabat)

<400> SEQUENCE: 102

Arg Gly Val Asp Glu Gly Asp Tyr
1 5

<210> SEQ ID NO 103
<211> LENGTH: 13
<212> TYPE: PRT
<213> ORGANISM: Artificial Sequence
<220> FEATURE:
<223> OTHER INFORMATION: CDR-L1 of E6 (Kabat)

<400> SEQUENCE: 103

Thr Gly Ser Ser Gly Asn Ile Ala Ser Asn Tyr Val Gln
1 5 10

<210> SEQ ID NO 104
<211> LENGTH: 7
<212> TYPE: PRT
<213> ORGANISM: Artificial Sequence
<220> FEATURE:
<223> OTHER INFORMATION: CDR-L2 of E6 (Kabat)

<400> SEQUENCE: 104

Arg Asp Asp Gln Arg Pro Ser
1 5

<210> SEQ ID NO 105
<211> LENGTH: 9
<212> TYPE: PRT
<213> ORGANISM: Artificial Sequence
<220> FEATURE:
<223> OTHER INFORMATION: CDR-L3 of E6 (Kabat)

<400> SEQUENCE: 105

Gln Ser Tyr Asp Ser Ser Ser Trp Val
1 5

<210> SEQ ID NO 106
<211> LENGTH: 5
<212> TYPE: PRT
<213> ORGANISM: Artificial Sequence
<220> FEATURE:
<223> OTHER INFORMATION: CDR-H1 of E6 (Kabat)

<400> SEQUENCE: 106

Thr Tyr Asp Ile Thr
1 5

<210> SEQ ID NO 107
<211> LENGTH: 17
<212> TYPE: PRT
<213> ORGANISM: Artificial Sequence
<220> FEATURE:
<223> OTHER INFORMATION: CDR-H2 of E6 (Kabat)

<400> SEQUENCE: 107

Trp Met Asn Pro Asn Ser Gly Asn Ser Arg Ser Ala Gln Lys Phe Gln
1 5 10 15

Gly

<210> SEQ ID NO 108
<211> LENGTH: 15
<212> TYPE: PRT
<213> ORGANISM: Artificial Sequence
<220> FEATURE:
<223> OTHER INFORMATION: CDR-H3 of E6 (Kabat)

<400> SEQUENCE: 108

Gly Asp Tyr Ser Gly Val Val Leu Thr Ala Thr Ala Leu Asp Tyr
1 5 10 15

<210> SEQ ID NO 109
<211> LENGTH: 13
<212> TYPE: PRT
<213> ORGANISM: Artificial Sequence
<220> FEATURE:
<223> OTHER INFORMATION: CDR-L1 of E9 (Kabat)

<400> SEQUENCE: 109

Ser Gly Ser Ser Ser Asn Ile Gly Asn Asn Tyr Val Tyr
1 5 10

<210> SEQ ID NO 110
<211> LENGTH: 7
<212> TYPE: PRT
<213> ORGANISM: Artificial Sequence
<220> FEATURE:
<223> OTHER INFORMATION: CDR-L2 of E9 (Kabat)

<400> SEQUENCE: 110

Arg Asn Asn Gln Arg Pro Ser
1 5

<210> SEQ ID NO 111
<211> LENGTH: 11
<212> TYPE: PRT
<213> ORGANISM: Artificial Sequence
<220> FEATURE:
<223> OTHER INFORMATION: CDR-L3 of E9 (Kabat)

<400> SEQUENCE: 111

Ala Ala Trp Asp Asp Ser Leu Ser Gly Trp Val
1 5 10

<210> SEQ ID NO 112
<211> LENGTH: 5
<212> TYPE: PRT
<213> ORGANISM: Artificial Sequence
<220> FEATURE:
<223> OTHER INFORMATION: CDR-H1 of E9 (Kabat)

<400> SEQUENCE: 112

Ser Tyr Gly Met His
1 5

<210> SEQ ID NO 113
<211> LENGTH: 17
<212> TYPE: PRT
<213> ORGANISM: Artificial Sequence
<220> FEATURE:
<223> OTHER INFORMATION: CDR-H2 of E9 (Kabat)

<400> SEQUENCE: 113

Asn Ile Lys Gln Asp Gly Ser Glu Lys Tyr Tyr Val Asp Ser Val Lys
1 5 10 15

Gly

<210> SEQ ID NO 114
<211> LENGTH: 14
<212> TYPE: PRT
<213> ORGANISM: Artificial Sequence
<220> FEATURE:
<223> OTHER INFORMATION: CDR-H3 of E9 (Kabat)

<400> SEQUENCE: 114

Glu Asp Arg Ile Ala Ala Ala Gly Met Arg Glu Leu Asp Tyr
1 5 10

<210> SEQ ID NO 115
<211> LENGTH: 16
<212> TYPE: PRT
<213> ORGANISM: Artificial Sequence
<220> FEATURE:
<223> OTHER INFORMATION: CDR-L1 of A11 (Kabat)

<400> SEQUENCE: 115

Arg Ser Ser Gln Ser Leu Leu His Ser Asn Gly Tyr Asn Tyr Leu Asp
1 5 10 15

<210> SEQ ID NO 116
<211> LENGTH: 7
<212> TYPE: PRT
<213> ORGANISM: Artificial Sequence
<220> FEATURE:
<223> OTHER INFORMATION: CDR-L2 of A11 (Kabat)

<400> SEQUENCE: 116

Leu Gly Ser Asn Arg Ala Ser
1 5

<210> SEQ ID NO 117
<211> LENGTH: 10
<212> TYPE: PRT
<213> ORGANISM: Artificial Sequence
<220> FEATURE:
<223> OTHER INFORMATION: CDR-L3 of A11 (Kabat)

<400> SEQUENCE: 117

Met Gln Gly Thr His Trp Pro Pro Tyr Thr
1 5 10

<210> SEQ ID NO 118
<211> LENGTH: 5
<212> TYPE: PRT
<213> ORGANISM: Artificial Sequence
<220> FEATURE:
<223> OTHER INFORMATION: CDR-H1 of A11 (Kabat)

<400> SEQUENCE: 118

Ser Tyr Ala Met Thr
1 5

<210> SEQ ID NO 119
<211> LENGTH: 17
<212> TYPE: PRT
<213> ORGANISM: Artificial Sequence
<220> FEATURE:
<223> OTHER INFORMATION: CDR-H2 of A11 (Kabat)

<400> SEQUENCE: 119

Gly Ile Ser Ser Asp Gly Thr Thr Thr Thr Tyr Ala Asp Ser Val Arg
1               5                   10                  15

Gly

<210> SEQ ID NO 120
<211> LENGTH: 11
<212> TYPE: PRT
<213> ORGANISM: Artificial Sequence
<220> FEATURE:
<223> OTHER INFORMATION: CDR-H3 of A11 (Kabat)

<400> SEQUENCE: 120

Asp Gln Leu Leu Gly Trp Asp Ala Leu Asn Val
1               5                   10

<210> SEQ ID NO 121
<211> LENGTH: 6
<212> TYPE: PRT
<213> ORGANISM: Artificial Sequence
<220> FEATURE:
<223> OTHER INFORMATION: CDR-L1 of E3 or E3.1 (IGMT)

<400> SEQUENCE: 121

Ser Leu Arg Asn Phe Tyr
1               5

<210> SEQ ID NO 122
<211> LENGTH: 3
<212> TYPE: PRT
<213> ORGANISM: Artificial Sequence
<220> FEATURE:
<223> OTHER INFORMATION: CDR-L2 of E3 or E3.1 (IGMT)

<400> SEQUENCE: 122

Gly Lys Asn
1

<210> SEQ ID NO 123
<211> LENGTH: 8
<212> TYPE: PRT
<213> ORGANISM: Artificial Sequence
<220> FEATURE:
<223> OTHER INFORMATION: CDR-H1 of E3 or E3.1 (IGMT)

<400> SEQUENCE: 123

Gly Phe Thr Phe Ser Ser Tyr Ala
1               5

<210> SEQ ID NO 124
<211> LENGTH: 8
<212> TYPE: PRT
<213> ORGANISM: Artificial Sequence
<220> FEATURE:
<223> OTHER INFORMATION: CDR-H2 of E3 or E3.1 (IGMT)

<400> SEQUENCE: 124

Ile Ser Gly Ser Gly Gly Ser Thr 1 5

<210> SEQ ID NO 125
<211> LENGTH: 17
<212> TYPE: PRT
<213> ORGANISM: Artificial Sequence
<220> FEATURE:
<223> OTHER INFORMATION: CDR-H3 of E3 or E3.1 (IGMT)

<400> SEQUENCE: 125

Ala Arg Asp Thr Tyr Tyr Tyr Gly Ser Gly Arg Ser Asn Ala Phe Asp
1 5 10 15

Ile

<210> SEQ ID NO 126
<211> LENGTH: 6
<212> TYPE: PRT
<213> ORGANISM: Artificial Sequence
<220> FEATURE:
<223> OTHER INFORMATION: CDR-L1 of B3 (IGMT)

<400> SEQUENCE: 126

Gln Asp Ile Ser Asn Tyr
1 5

<210> SEQ ID NO 127
<211> LENGTH: 3
<212> TYPE: PRT
<213> ORGANISM: Artificial Sequence
<220> FEATURE:
<223> OTHER INFORMATION: CDR-L2 of B3 (IGMT)

<400> SEQUENCE: 127

Asp Ala Ser
1

<210> SEQ ID NO 128
<211> LENGTH: 8
<212> TYPE: PRT
<213> ORGANISM: Artificial Sequence
<220> FEATURE:
<223> OTHER INFORMATION: CDR-H1 of B3 (IGMT)

<400> SEQUENCE: 128

Gly Phe Thr Phe Asp Asp Tyr Ala
1 5

<210> SEQ ID NO 129
<211> LENGTH: 8
<212> TYPE: PRT
<213> ORGANISM: Artificial Sequence
<220> FEATURE:
<223> OTHER INFORMATION: CDR-H2 of B3 (IGMT)

<400> SEQUENCE: 129

Ile Ser Trp Asn Ser Gly Ser Ile
1 5

<210> SEQ ID NO 130
<211> LENGTH: 15
<212> TYPE: PRT
<213> ORGANISM: Artificial Sequence
<220> FEATURE:
<223> OTHER INFORMATION: CDR-H3 of B3 (IGMT)

<400> SEQUENCE: 130

Ala Arg Val Gly Asp Ser Ser Gly Trp Ser Asp Ala Phe Asp Ile
1 5 10 15

<210> SEQ ID NO 131
<211> LENGTH: 6
<212> TYPE: PRT
<213> ORGANISM: Artificial Sequence
<220> FEATURE:
<223> OTHER INFORMATION: CDR-L1 of A10 (IGMT)

<400> SEQUENCE: 131

Gln Ser Val Ser Ser Asn
1 5

<210> SEQ ID NO 132
<211> LENGTH: 3
<212> TYPE: PRT
<213> ORGANISM: Artificial Sequence
<220> FEATURE:
<223> OTHER INFORMATION: CDR-L2 of A10 (IGMT)

<400> SEQUENCE: 132

Gly Ala Ser
1

<210> SEQ ID NO 133
<211> LENGTH: 8
<212> TYPE: PRT
<213> ORGANISM: Artificial Sequence
<220> FEATURE:
<223> OTHER INFORMATION: CDR-H1 of A10 (IGMT)

<400> SEQUENCE: 133

Gly Gly Thr Phe Ser Ser Tyr Ala
1 5

<210> SEQ ID NO 134
<211> LENGTH: 8
<212> TYPE: PRT
<213> ORGANISM: Artificial Sequence
<220> FEATURE:
<223> OTHER INFORMATION: CDR-H2 of A10 (IGMT)

<400> SEQUENCE: 134

Ile Ile Pro Ile Phe Gly Thr Ala
1 5

<210> SEQ ID NO 135
<211> LENGTH: 14
<212> TYPE: PRT
<213> ORGANISM: Artificial Sequence
<220> FEATURE:
<223> OTHER INFORMATION: CDR-H3 of A10 (IGMT)

<400> SEQUENCE: 135

Ala Arg Gly Gly Leu Gly Glu Leu Asp Asn Trp Phe Asp Pro
1 5 10

<210> SEQ ID NO 136
<211> LENGTH: 6
<212> TYPE: PRT
<213> ORGANISM: Artificial Sequence
<220> FEATURE:
<223> OTHER INFORMATION: CDR-L1 of G1 (IGMT)

<400> SEQUENCE: 136

Lys Leu Gly Asp Arg Tyr 1               5

<210> SEQ ID NO 137
<211> LENGTH: 3
<212> TYPE: PRT
<213> ORGANISM: Artificial Sequence
<220> FEATURE:
<223> OTHER INFORMATION: CDR-L2 of G1 (IGMT)

<400> SEQUENCE: 137

Lys Asp Ser
1

<210> SEQ ID NO 138
<211> LENGTH: 8
<212> TYPE: PRT
<213> ORGANISM: Artificial Sequence
<220> FEATURE:
<223> OTHER INFORMATION: CDR-H1 of G1 (IGMT)

<400> SEQUENCE: 138

Gly Gly Thr Phe Ser Ser Tyr Gly
1               5

<210> SEQ ID NO 139
<211> LENGTH: 8
<212> TYPE: PRT
<213> ORGANISM: Artificial Sequence
<220> FEATURE:
<223> OTHER INFORMATION: CDR-H2 of G1 (IGMT)

<400> SEQUENCE: 139

Ile Ser Ala Tyr Asn Gly Asn Thr
1               5

<210> SEQ ID NO 140
<211> LENGTH: 11
<212> TYPE: PRT
<213> ORGANISM: Artificial Sequence
<220> FEATURE:
<223> OTHER INFORMATION: CDR-H3 of G1 (IGMT)

<400> SEQUENCE: 140

Ala Arg Val Gly Val Ala Gly Lys Leu Asp Tyr
1               5                   10

<210> SEQ ID NO 141
<211> LENGTH: 9
<212> TYPE: PRT
<213> ORGANISM: Artificial Sequence
<220> FEATURE:
<223> OTHER INFORMATION: CDR-L1 of G9 (IGMT)

<400> SEQUENCE: 141

Ser Ser Asp Val Gly Gly Tyr Asn Tyr
1               5

<210> SEQ ID NO 142
<211> LENGTH: 3
<212> TYPE: PRT
<213> ORGANISM: Artificial Sequence
<220> FEATURE:
<223> OTHER INFORMATION: CDR-L2 of G9 (IGMT)

<400> SEQUENCE: 142

Asp Val Ser
1

<210> SEQ ID NO 143
<211> LENGTH: 8
<212> TYPE: PRT
<213> ORGANISM: Artificial Sequence
<220> FEATURE:
<223> OTHER INFORMATION: CDR-H1 of G9 (IGMT)

<400> SEQUENCE: 143

Gly Tyr Ser Phe Thr Ser Tyr Trp
1               5

<210> SEQ ID NO 144
<211> LENGTH: 8
<212> TYPE: PRT
<213> ORGANISM: Artificial Sequence
<220> FEATURE:
<223> OTHER INFORMATION: CDR-H2 of G9 (IGMT)

<400> SEQUENCE: 144

Ile Tyr Pro Gly Asp Ser Asp Thr
1               5

<210> SEQ ID NO 145
<211> LENGTH: 13
<212> TYPE: PRT
<213> ORGANISM: Artificial Sequence
<220> FEATURE:
<223> OTHER INFORMATION: CDR-H3 of G9 (IGMT)

<400> SEQUENCE: 145

Ala Ser Gln Tyr Tyr Asp Gly Gly Tyr Tyr Met Asp Val
1               5                   10

<210> SEQ ID NO 146
<211> LENGTH: 6
<212> TYPE: PRT
<213> ORGANISM: Artificial Sequence
<220> FEATURE:
<223> OTHER INFORMATION: CDR-L1 of H2 (IGMT)

<400> SEQUENCE: 146

Ser Leu Arg Asn Tyr Tyr
1               5

<210> SEQ ID NO 147
<211> LENGTH: 3
<212> TYPE: PRT
<213> ORGANISM: Artificial Sequence
<220> FEATURE:
<223> OTHER INFORMATION: CDR-L2 of H2 (IGMT)

<400> SEQUENCE: 147

Gly Asn Asn
1

<210> SEQ ID NO 148
<211> LENGTH: 8
<212> TYPE: PRT
<213> ORGANISM: Artificial Sequence
<220> FEATURE:
<223> OTHER INFORMATION: CDR-H1 of H2 (IGMT)

<400> SEQUENCE: 148

Gly Tyr Thr Phe Thr Ser Tyr Asp
1               5

<210> SEQ ID NO 149
<211> LENGTH: 8
<212> TYPE: PRT
<213> ORGANISM: Artificial Sequence
<220> FEATURE:
<223> OTHER INFORMATION: CDR-H2 of H2 (IGMT)

<400> SEQUENCE: 149

Ile Ser Ala Tyr Asn Gly Asn Thr
1               5

<210> SEQ ID NO 150
<211> LENGTH: 10
<212> TYPE: PRT
<213> ORGANISM: Artificial Sequence
<220> FEATURE:
<223> OTHER INFORMATION: CDR-H3 of H2 (IGMT)

<400> SEQUENCE: 150

Ala Arg Asp Gly Gly Asp Ala Phe Asp Ile
1               5                   10

<210> SEQ ID NO 151
<211> LENGTH: 6
<212> TYPE: PRT
<213> ORGANISM: Artificial Sequence
<220> FEATURE:
<223> OTHER INFORMATION: CDR-L1 of H11 (IGMT)

<400> SEQUENCE: 151

Ser Leu Arg Ser Tyr Tyr
1               5

<210> SEQ ID NO 152
<211> LENGTH: 3
<212> TYPE: PRT
<213> ORGANISM: Artificial Sequence
<220> FEATURE:
<223> OTHER INFORMATION: CDR-L2 of H11 (IGMT)

<400> SEQUENCE: 152

Gly Arg Asn
1

<210> SEQ ID NO 153
<211> LENGTH: 8
<212> TYPE: PRT
<213> ORGANISM: Artificial Sequence
<220> FEATURE:
<223> OTHER INFORMATION: CDR-H1 of H11 (IGMT)

<400> SEQUENCE: 153

Gly Tyr Thr Phe Thr Ser Tyr Tyr
1               5

<210> SEQ ID NO 154
<211> LENGTH: 8
<212> TYPE: PRT
<213> ORGANISM: Artificial Sequence
<220> FEATURE:
<223> OTHER INFORMATION: CDR-H2 of H11 (IGMT)

<400> SEQUENCE: 154

Ile Asn Pro Ser Gly Gly Ser Thr
1               5

<210> SEQ ID NO 155
<211> LENGTH: 10
<212> TYPE: PRT
<213> ORGANISM: Artificial Sequence
<220> FEATURE:
<223> OTHER INFORMATION: CDR-H3 of H11 (IGMT)

<400> SEQUENCE: 155

Ala Arg Asp Ala Gly Ser Ser Ser Asp Tyr
1 5 10

<210> SEQ ID NO 156
<211> LENGTH: 9
<212> TYPE: PRT
<213> ORGANISM: Artificial Sequence
<220> FEATURE:
<223> OTHER INFORMATION: CDR-L1 of F12 (IGMT)

<400> SEQUENCE: 156

Ser Ser Asp Ile Gly Asp Tyr Asp Tyr
1 5

<210> SEQ ID NO 157
<211> LENGTH: 3
<212> TYPE: PRT
<213> ORGANISM: Artificial Sequence
<220> FEATURE:
<223> OTHER INFORMATION: CDR-L2 of F12 (IGMT)

<400> SEQUENCE: 157

Asp Val Ser
1

<210> SEQ ID NO 158
<211> LENGTH: 8
<212> TYPE: PRT
<213> ORGANISM: Artificial Sequence
<220> FEATURE:
<223> OTHER INFORMATION: CDR-H1 of F12 (IGMT)

<400> SEQUENCE: 158

Gly Tyr Ser Phe Thr Ser Tyr Trp
1 5

<210> SEQ ID NO 159
<211> LENGTH: 8
<212> TYPE: PRT
<213> ORGANISM: Artificial Sequence
<220> FEATURE:
<223> OTHER INFORMATION: CDR-H2 of F12 (IGMT)

<400> SEQUENCE: 159

Ile Tyr Pro Gly Asp Ser Asp Thr
1 5

<210> SEQ ID NO 160
<211> LENGTH: 13
<212> TYPE: PRT
<213> ORGANISM: Artificial Sequence
<220> FEATURE:
<223> OTHER INFORMATION: CDR-H3 of F12 (IGMT)

<400> SEQUENCE: 160

Ala Ser Gln Tyr Tyr Asp Gly Gly Tyr Tyr Met Asp Val
1 5 10

<210> SEQ ID NO 161

<211> LENGTH: 6
<212> TYPE: PRT
<213> ORGANISM: Artificial Sequence
<220> FEATURE:
<223> OTHER INFORMATION: CDR-L1 of B9 (IGMT)

<400> SEQUENCE: 161

Gln Ser Ile Ser Arg Tyr
1               5

<210> SEQ ID NO 162
<211> LENGTH: 3
<212> TYPE: PRT
<213> ORGANISM: Artificial Sequence
<220> FEATURE:
<223> OTHER INFORMATION: CDR-L2 of B9 (IGMT)

<400> SEQUENCE: 162

Gly Ala Ser
1

<210> SEQ ID NO 163
<211> LENGTH: 8
<212> TYPE: PRT
<213> ORGANISM: Artificial Sequence
<220> FEATURE:
<223> OTHER INFORMATION: CDR-H1 of B9 (IGMT)

<400> SEQUENCE: 163

Gly Gly Thr Phe Ser Ser Tyr Ala
1               5

<210> SEQ ID NO 164
<211> LENGTH: 8
<212> TYPE: PRT
<213> ORGANISM: Artificial Sequence
<220> FEATURE:
<223> OTHER INFORMATION: CDR-H2 of B9 (IGMT)

<400> SEQUENCE: 164

Ile Ile Pro Ile Phe Gly Thr Ala
1               5

<210> SEQ ID NO 165
<211> LENGTH: 18
<212> TYPE: PRT
<213> ORGANISM: Artificial Sequence
<220> FEATURE:
<223> OTHER INFORMATION: CDR-H3 of B9 (IGMT)

<400> SEQUENCE: 165

Ala Arg Gly Glu Ile Ala Val Ala Gln Asn Trp Asp Tyr Tyr Gly Met
1               5                   10                  15

Asp Val

<210> SEQ ID NO 166
<211> LENGTH: 9
<212> TYPE: PRT
<213> ORGANISM: Artificial Sequence
<220> FEATURE:
<223> OTHER INFORMATION: CDR-L1 of G11 (IGMT)

<400> SEQUENCE: 166

Ser Ser Asp Val Gly Gly Tyr Asn Tyr
1               5

<210> SEQ ID NO 167
<211> LENGTH: 3
<212> TYPE: PRT
<213> ORGANISM: Artificial Sequence
<220> FEATURE:
<223> OTHER INFORMATION: CDR-L2 of G11 (IGMT)

<400> SEQUENCE: 167

Asp Val Ser
1

<210> SEQ ID NO 168
<211> LENGTH: 8
<212> TYPE: PRT
<213> ORGANISM: Artificial Sequence
<220> FEATURE:
<223> OTHER INFORMATION: CDR-H1 of G11 (IGMT)

<400> SEQUENCE: 168

Gly Tyr Ser Phe Thr Ser Tyr Trp
1 5

<210> SEQ ID NO 169
<211> LENGTH: 8
<212> TYPE: PRT
<213> ORGANISM: Artificial Sequence
<220> FEATURE:
<223> OTHER INFORMATION: CDR-H2 of G11 (IGMT)

<400> SEQUENCE: 169

Ile Tyr Pro Gly Asp Ser Asp Thr
1 5

<210> SEQ ID NO 170
<211> LENGTH: 13
<212> TYPE: PRT
<213> ORGANISM: Artificial Sequence
<220> FEATURE:
<223> OTHER INFORMATION: CDR-H3 of G11 (IGMT)

<400> SEQUENCE: 170

Ala Ser Gln Tyr Tyr Asp Gly Gly Tyr Tyr Met Asp Val
1 5 10

<210> SEQ ID NO 171
<211> LENGTH: 6
<212> TYPE: PRT
<213> ORGANISM: Artificial Sequence
<220> FEATURE:
<223> OTHER INFORMATION: CDR-L1 of G6 (IGMT)

<400> SEQUENCE: 171

Ser Leu Arg Arg Tyr Tyr
1 5

<210> SEQ ID NO 172
<211> LENGTH: 3
<212> TYPE: PRT
<213> ORGANISM: Artificial Sequence
<220> FEATURE:
<223> OTHER INFORMATION: CDR-L2 of G6 (IGMT)

<400> SEQUENCE: 172

Gly Gln Asn
1

<210> SEQ ID NO 173

<211> LENGTH: 8
<212> TYPE: PRT
<213> ORGANISM: Artificial Sequence
<220> FEATURE:
<223> OTHER INFORMATION: CDR-H1 of G6 (IGMT)

<400> SEQUENCE: 173

Gly Tyr Thr Phe Thr Ser Tyr Tyr
1 5

<210> SEQ ID NO 174
<211> LENGTH: 8
<212> TYPE: PRT
<213> ORGANISM: Artificial Sequence
<220> FEATURE:
<223> OTHER INFORMATION: CDR-H2 of G6 (IGMT)

<400> SEQUENCE: 174

Ile Ile Pro Ile Phe Gly Thr Ala
1 5

<210> SEQ ID NO 175
<211> LENGTH: 12
<212> TYPE: PRT
<213> ORGANISM: Artificial Sequence
<220> FEATURE:
<223> OTHER INFORMATION: CDR-H3 of G6 (IGMT)

<400> SEQUENCE: 175

Ala Arg Gly Trp Gly Tyr Ser Ser Ser Phe Asp Tyr
1 5 10

<210> SEQ ID NO 176
<211> LENGTH: 8
<212> TYPE: PRT
<213> ORGANISM: Artificial Sequence
<220> FEATURE:
<223> OTHER INFORMATION: CDR-L1 of F11 (IGMT)

<400> SEQUENCE: 176

Ser Ser Asn Ile Gly Thr Asn Thr
1 5

<210> SEQ ID NO 177
<211> LENGTH: 3
<212> TYPE: PRT
<213> ORGANISM: Artificial Sequence
<220> FEATURE:
<223> OTHER INFORMATION: CDR-L2 of F11 (IGMT)

<400> SEQUENCE: 177

Ser Asn Asp
1

<210> SEQ ID NO 178
<211> LENGTH: 8
<212> TYPE: PRT
<213> ORGANISM: Artificial Sequence
<220> FEATURE:
<223> OTHER INFORMATION: CDR-H1 of F11 (IGMT)

<400> SEQUENCE: 178

Gly Phe Thr Phe Ser Ser Tyr Ala
1 5

<210> SEQ ID NO 179
<211> LENGTH: 8

<212> TYPE: PRT
<213> ORGANISM: Artificial Sequence
<220> FEATURE:
<223> OTHER INFORMATION: CDR-H2 of F11 (IGMT)

<400> SEQUENCE: 179

Ile Ser Gly Ser Gly Asp Ser Thr
1 5

<210> SEQ ID NO 180
<211> LENGTH: 12
<212> TYPE: PRT
<213> ORGANISM: Artificial Sequence
<220> FEATURE:
<223> OTHER INFORMATION: CDR-H3 of F11 (IGMT)

<400> SEQUENCE: 180

Ala Arg Glu Trp Glu Leu Gly Asp Ala Phe Asp Ile
1 5 10

<210> SEQ ID NO 181
<211> LENGTH: 6
<212> TYPE: PRT
<213> ORGANISM: Artificial Sequence
<220> FEATURE:
<223> OTHER INFORMATION: CDR-L1 of D3 (IGMT)

<400> SEQUENCE: 181

Gln Ser Ile Ser Ser Tyr
1 5

<210> SEQ ID NO 182
<211> LENGTH: 3
<212> TYPE: PRT
<213> ORGANISM: Artificial Sequence
<220> FEATURE:
<223> OTHER INFORMATION: CDR-L2 of D3 (IGMT)

<400> SEQUENCE: 182

Ala Ala Ser
1

<210> SEQ ID NO 183
<211> LENGTH: 8
<212> TYPE: PRT
<213> ORGANISM: Artificial Sequence
<220> FEATURE:
<223> OTHER INFORMATION: CDR-H1 of D3 (IGMT)

<400> SEQUENCE: 183

Gly Ser Thr Phe Ser Ser Tyr Ala
1 5

<210> SEQ ID NO 184
<211> LENGTH: 8
<212> TYPE: PRT
<213> ORGANISM: Artificial Sequence
<220> FEATURE:
<223> OTHER INFORMATION: CDR-H2 of D3 (IGMT)

<400> SEQUENCE: 184

Ile Ser Gly Ser Gly Gly Ser Thr
1 5

<210> SEQ ID NO 185
<211> LENGTH: 15
<212> TYPE: PRT

<213> ORGANISM: Artificial Sequence
<220> FEATURE:
<223> OTHER INFORMATION: CDR-H3 of D3 (IGMT)

<400> SEQUENCE: 185

Ala Lys Asp Arg Gly Ser Tyr Gly Tyr Tyr Tyr Gly Met Asp Val
1 5 10 15

<210> SEQ ID NO 186
<211> LENGTH: 6
<212> TYPE: PRT
<213> ORGANISM: Artificial Sequence
<220> FEATURE:
<223> OTHER INFORMATION: CDR-L1 of B12 (IGMT)

<400> SEQUENCE: 186

Gln Ser Ile Ser Ser Tyr
1 5

<210> SEQ ID NO 187
<211> LENGTH: 3
<212> TYPE: PRT
<213> ORGANISM: Artificial Sequence
<220> FEATURE:
<223> OTHER INFORMATION: CDR-L2 of B12 (IGMT)

<400> SEQUENCE: 187

Ala Ala Ser
1

<210> SEQ ID NO 188
<211> LENGTH: 8
<212> TYPE: PRT
<213> ORGANISM: Artificial Sequence
<220> FEATURE:
<223> OTHER INFORMATION: CDR-H1 of B12 (IGMT)

<400> SEQUENCE: 188

Gly Tyr Thr Phe Thr Gly Tyr Tyr
1 5

<210> SEQ ID NO 189
<211> LENGTH: 8
<212> TYPE: PRT
<213> ORGANISM: Artificial Sequence
<220> FEATURE:
<223> OTHER INFORMATION: CDR-H2 of B12 (IGMT)

<400> SEQUENCE: 189

Ile Asn Pro Asn Ser Gly Gly Thr
1 5

<210> SEQ ID NO 190
<211> LENGTH: 15
<212> TYPE: PRT
<213> ORGANISM: Artificial Sequence
<220> FEATURE:
<223> OTHER INFORMATION: CDR-H3 of B12 (IGMT)

<400> SEQUENCE: 190

Thr Arg Ala Gly Ala Ser Ile Val Gly Ala Thr Ala Leu Asp Tyr
1 5 10 15

<210> SEQ ID NO 191
<211> LENGTH: 8
<212> TYPE: PRT
<213> ORGANISM: Artificial Sequence
<220> FEATURE:
<223> OTHER INFORMATION: CDR-L1 of E4 (IGMT)

<400> SEQUENCE: 191

Ser Gly Ser Ile Ala Ser Asn Tyr
1 5

<210> SEQ ID NO 192
<211> LENGTH: 3
<212> TYPE: PRT
<213> ORGANISM: Artificial Sequence
<220> FEATURE:
<223> OTHER INFORMATION: CDR-L2 of E4 (IGMT)

<400> SEQUENCE: 192

Glu Asp Asn
1

<210> SEQ ID NO 193
<211> LENGTH: 8
<212> TYPE: PRT
<213> ORGANISM: Artificial Sequence
<220> FEATURE:
<223> OTHER INFORMATION: CDR-H1 of E4 (IGMT)

<400> SEQUENCE: 193

Gly Gly Thr Phe Ser Ser Tyr Thr
1 5

<210> SEQ ID NO 194
<211> LENGTH: 8
<212> TYPE: PRT
<213> ORGANISM: Artificial Sequence
<220> FEATURE:
<223> OTHER INFORMATION: CDR-H2 of E4 (IGMT)

<400> SEQUENCE: 194

Ile Ile Pro Ile Leu Gly Ile Ala
1 5

<210> SEQ ID NO 195
<211> LENGTH: 14
<212> TYPE: PRT
<213> ORGANISM: Artificial Sequence
<220> FEATURE:
<223> OTHER INFORMATION: CDR-H3 of E4 (IGMT)

<400> SEQUENCE: 195

Val Arg Gly Pro Ser Leu Asn Tyr Ala Gly Tyr Phe Asp Asn
1 5 10

<210> SEQ ID NO 196
<211> LENGTH: 6
<212> TYPE: PRT
<213> ORGANISM: Artificial Sequence
<220> FEATURE:
<223> OTHER INFORMATION: CDR-L1 of E12 (IGMT)

<400> SEQUENCE: 196

Ser Leu Arg Ser Tyr Tyr
1 5

<210> SEQ ID NO 197
<211> LENGTH: 3
<212> TYPE: PRT
<213> ORGANISM: Artificial Sequence
<220> FEATURE:

<223> OTHER INFORMATION: CDR-L2 of E12 (IGMT)

<400> SEQUENCE: 197

Gly Lys Glu
1

<210> SEQ ID NO 198
<211> LENGTH: 8
<212> TYPE: PRT
<213> ORGANISM: Artificial Sequence
<220> FEATURE:
<223> OTHER INFORMATION: CDR-H1 of E12 (IGMT)

<400> SEQUENCE: 198

Gly Phe Thr Phe Ser Ser Tyr Ala
1 5

<210> SEQ ID NO 199
<211> LENGTH: 8
<212> TYPE: PRT
<213> ORGANISM: Artificial Sequence
<220> FEATURE:
<223> OTHER INFORMATION: CDR-H2 of E12 (IGMT)

<400> SEQUENCE: 199

Ile Ser Tyr Asp Gly Ser Asn Lys
1 5

<210> SEQ ID NO 200
<211> LENGTH: 10
<212> TYPE: PRT
<213> ORGANISM: Artificial Sequence
<220> FEATURE:
<223> OTHER INFORMATION: CDR-H3 of E12 (IGMT)

<400> SEQUENCE: 200

Ala Arg Glu Arg Gly Ser Gly Met Asp Val
1 5 10

<210> SEQ ID NO 201
<211> LENGTH: 6
<212> TYPE: PRT
<213> ORGANISM: Artificial Sequence
<220> FEATURE:
<223> OTHER INFORMATION: CDR-L1 of D1 (IGMT)

<400> SEQUENCE: 201

Gln Asp Ile Asp Asp Asp
1 5

<210> SEQ ID NO 202
<211> LENGTH: 3
<212> TYPE: PRT
<213> ORGANISM: Artificial Sequence
<220> FEATURE:
<223> OTHER INFORMATION: CDR-L2 of D1 (IGMT)

<400> SEQUENCE: 202

Glu Ala Ser
1

<210> SEQ ID NO 203
<211> LENGTH: 8
<212> TYPE: PRT
<213> ORGANISM: Artificial Sequence
<220> FEATURE:
<223> OTHER INFORMATION: CDR-H1 of D1 (IGMT)

<400> SEQUENCE: 203

Gly Tyr Thr Phe Thr Ser Tyr Gly
1 5

<210> SEQ ID NO 204
<211> LENGTH: 8
<212> TYPE: PRT
<213> ORGANISM: Artificial Sequence
<220> FEATURE:
<223> OTHER INFORMATION: CDR-H2 of D1 (IGMT)

<400> SEQUENCE: 204

Ile Asn Pro Asn Ser Gly Gly Thr
1 5

<210> SEQ ID NO 205
<211> LENGTH: 10
<212> TYPE: PRT
<213> ORGANISM: Artificial Sequence
<220> FEATURE:
<223> OTHER INFORMATION: CDR-H3 of D1 (IGMT)

<400> SEQUENCE: 205

Ala Ser Arg Gly Val Asp Glu Gly Asp Tyr
1 5 10

<210> SEQ ID NO 206
<211> LENGTH: 8
<212> TYPE: PRT
<213> ORGANISM: Artificial Sequence
<220> FEATURE:
<223> OTHER INFORMATION: CDR-L1 of E6 (IGMT)

<400> SEQUENCE: 206

Ser Gly Asn Ile Ala Ser Asn Tyr
1 5

<210> SEQ ID NO 207
<211> LENGTH: 3
<212> TYPE: PRT
<213> ORGANISM: Artificial Sequence
<220> FEATURE:
<223> OTHER INFORMATION: CDR-L2 of E6 (IGMT)

<400> SEQUENCE: 207

Arg Asp Asp
1

<210> SEQ ID NO 208
<211> LENGTH: 8
<212> TYPE: PRT
<213> ORGANISM: Artificial Sequence
<220> FEATURE:
<223> OTHER INFORMATION: CDR-H1 of E6 (IGMT)

<400> SEQUENCE: 208

Gly Tyr Thr Phe Thr Thr Tyr Asp
1 5

<210> SEQ ID NO 209
<211> LENGTH: 8
<212> TYPE: PRT
<213> ORGANISM: Artificial Sequence
<220> FEATURE:
<223> OTHER INFORMATION: CDR-H2 of E6 (IGMT)

<400> SEQUENCE: 209

Met Asn Pro Asn Ser Gly Asn Ser
1 5

<210> SEQ ID NO 210
<211> LENGTH: 17
<212> TYPE: PRT
<213> ORGANISM: Artificial Sequence
<220> FEATURE:
<223> OTHER INFORMATION: CDR-H3 of E6 (IGMT)

<400> SEQUENCE: 210

Ala Thr Gly Asp Tyr Ser Gly Val Val Leu Thr Ala Thr Ala Leu Asp
1 5 10 15

Tyr

<210> SEQ ID NO 211
<211> LENGTH: 8
<212> TYPE: PRT
<213> ORGANISM: Artificial Sequence
<220> FEATURE:
<223> OTHER INFORMATION: CDR-L1 of E9 (IGMT)

<400> SEQUENCE: 211

Ser Ser Asn Ile Gly Asn Asn Tyr
1 5

<210> SEQ ID NO 212
<211> LENGTH: 3
<212> TYPE: PRT
<213> ORGANISM: Artificial Sequence
<220> FEATURE:
<223> OTHER INFORMATION: CDR-L2 of E9 (IGMT)

<400> SEQUENCE: 212

Arg Asn Asn
1

<210> SEQ ID NO 213
<211> LENGTH: 8
<212> TYPE: PRT
<213> ORGANISM: Artificial Sequence
<220> FEATURE:
<223> OTHER INFORMATION: CDR-H1 of E9 (IGMT)

<400> SEQUENCE: 213

Gly Phe Thr Phe Ser Ser Tyr Gly
1 5

<210> SEQ ID NO 214
<211> LENGTH: 8
<212> TYPE: PRT
<213> ORGANISM: Artificial Sequence
<220> FEATURE:
<223> OTHER INFORMATION: CDR-H2 of E9 (IGMT)

<400> SEQUENCE: 214

Ile Lys Gln Asp Gly Ser Glu Lys
1 5

<210> SEQ ID NO 215
<211> LENGTH: 16
<212> TYPE: PRT
<213> ORGANISM: Artificial Sequence
<220> FEATURE:
<223> OTHER INFORMATION: CDR-H3 of E9 (IGMT)

<400> SEQUENCE: 215

Ala Arg Glu Asp Arg Ile Ala Ala Ala Gly Met Arg Glu Leu Asp Tyr
1 5 10 15

<210> SEQ ID NO 216
<211> LENGTH: 11
<212> TYPE: PRT
<213> ORGANISM: Artificial Sequence
<220> FEATURE:
<223> OTHER INFORMATION: CDR-L1 of A11 (IGMT)

<400> SEQUENCE: 216

Gln Ser Leu Leu His Ser Asn Gly Tyr Asn Tyr
1 5 10

<210> SEQ ID NO 217
<211> LENGTH: 3
<212> TYPE: PRT
<213> ORGANISM: Artificial Sequence
<220> FEATURE:
<223> OTHER INFORMATION: CDR-L2 of A11 (IGMT)

<400> SEQUENCE: 217

Leu Gly Ser
1

<210> SEQ ID NO 218
<211> LENGTH: 8
<212> TYPE: PRT
<213> ORGANISM: Artificial Sequence
<220> FEATURE:
<223> OTHER INFORMATION: CDR-H1 of A11 (IGMT)

<400> SEQUENCE: 218

Gly Phe Ser Phe Thr Ser Tyr Ala
1 5

<210> SEQ ID NO 219
<211> LENGTH: 8
<212> TYPE: PRT
<213> ORGANISM: Artificial Sequence
<220> FEATURE:
<223> OTHER INFORMATION: CDR-H2 of A11 (IGMT)

<400> SEQUENCE: 219

Ile Ser Ser Asp Gly Thr Thr Thr
1 5

<210> SEQ ID NO 220
<211> LENGTH: 13
<212> TYPE: PRT
<213> ORGANISM: Artificial Sequence
<220> FEATURE:
<223> OTHER INFORMATION: CDR-H3 of A11 (IGMT)

<400> SEQUENCE: 220

Ala Arg Asp Gln Leu Leu Gly Trp Asp Ala Leu Asn Val
1 5 10

<210> SEQ ID NO 221
<211> LENGTH: 116
<212> TYPE: PRT
<213> ORGANISM: Artificial Sequence
<220> FEATURE:
<223> OTHER INFORMATION: Light chain variable region (E3)

<400> SEQUENCE: 221

```
Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Phe Tyr Ala
            20                  25                  30

Ser Trp Tyr Gln Gln Lys Ser Gly Gln Ala Pro Val Leu Val Met Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Ser His
                85                  90                  95

Leu Thr Gly Val Phe Gly Gly Gly Thr Lys Val Thr Val Leu Gly Gln
            100                 105                 110

Pro Ala Ala Ala
        115
```

<210> SEQ ID NO 222
<211> LENGTH: 124
<212> TYPE: PRT
<213> ORGANISM: Artificial Sequence
<220> FEATURE:
<223> OTHER INFORMATION: Heavy chain variable region (E3 or E3.1)

<400> SEQUENCE: 222

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ile Ser Leu Arg Ala Glu Asp Thr Ala Val Tyr Tyr Cys
                85                  90                  95

Ala Arg Asp Thr Tyr Tyr Tyr Gly Ser Gly Arg Ser Asn Ala Phe Asp
            100                 105                 110

Ile Trp Gly Gln Gly Thr Leu Val Thr Val Ser Ser
        115                 120
```

<210> SEQ ID NO 223
<211> LENGTH: 110
<212> TYPE: PRT
<213> ORGANISM: Artificial Sequence
<220> FEATURE:
<223> OTHER INFORMATION: Light chain variable region (B3)

<400> SEQUENCE: 223

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Phe
85 90 95

Gly Gly Gly Thr Lys Val Asp Ile Lys Arg Thr Ala Ala Ala
100 105 110

<210> SEQ ID NO 224
<211> LENGTH: 122
<212> TYPE: PRT
<213> ORGANISM: Artificial Sequence
<220> FEATURE:
<223> OTHER INFORMATION: Heavy chain variable region (B3)

<400> SEQUENCE: 224

Glu Val Gln Leu Leu Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Gly Asp Ser Ser Gly Trp Ser Asp Ala Phe Asp Ile Trp
100 105 110

Gly Gln Gly Thr Met Val Thr Val Ser Ser
115 120

<210> SEQ ID NO 225
<211> LENGTH: 114
<212> TYPE: PRT
<213> ORGANISM: Artificial Sequence
<220> FEATURE:
<223> OTHER INFORMATION: Light chain variable region (A10)

<400> SEQUENCE: 225

Asp Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Gly Ser Ser Pro Arg
85 90 95

Met Tyr Thr Phe Gly Gln Gly Thr Lys Val Asp Ile Lys Arg Thr Ala
100 105 110

Ala Ala

<210> SEQ ID NO 226
<211> LENGTH: 121
<212> TYPE: PRT
<213> ORGANISM: Artificial Sequence
<220> FEATURE:
<223> OTHER INFORMATION: Heavy chain variable region (A10)

<400> SEQUENCE: 226

Gln Met Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Leu Gly Glu Leu Asp Asn Trp Phe Asp Pro Trp Gly
100 105 110

Gln Gly Thr Leu Val Thr Val Ser Ser
115 120

<210> SEQ ID NO 227
<211> LENGTH: 112
<212> TYPE: PRT
<213> ORGANISM: Artificial Sequence
<220> FEATURE:
<223> OTHER INFORMATION: Light chain variable region (G1)

<400> SEQUENCE: 227

Ser Tyr Glu Leu Thr Gln Pro Pro Ser Leu Ser Val Ser Pro Gly Gln
1 5 10 15

Thr Ala Ser Ile Thr Cys Ser Gly Tyr Lys Leu Gly Asp Arg Tyr Val
20 25 30

Ser Trp Tyr Gln Gln Lys Thr Gly Gln Ser Pro Val Val Val Ile Tyr
35 40 45

Lys Asp Ser Gln Arg Pro Ser Gly Val Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Gly Thr Gly Val
85 90 95

Phe Gly Gly Gly Thr Lys Leu Thr Val Leu Gly Gln Pro Ala Ala Ala
100 105 110

<210> SEQ ID NO 228
<211> LENGTH: 118
<212> TYPE: PRT
<213> ORGANISM: Artificial Sequence
<220> FEATURE:
<223> OTHER INFORMATION: Heavy chain variable region (G1)

<400> SEQUENCE: 228

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr

```
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Glu Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Val Ala Gly Lys Leu Asp Tyr Trp Gly Gln Gly Thr
            100                 105                 110

Leu Val Thr Val Ser Ser
        115


<210> SEQ ID NO 229
<211> LENGTH: 112
<212> TYPE: PRT
<213> ORGANISM: Artificial Sequence
<220> FEATURE:
<223> OTHER INFORMATION: Light chain variable region (B9)

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Ala Tyr Gly Phe Pro Leu
                85                  90                  95

Thr Leu Gly Gly Gly Thr Lys Val Glu Ile Lys Arg Thr Ala Ala Ala
            100                 105                 110


<210> SEQ ID NO 230
<211> LENGTH: 125
<212> TYPE: PRT
<213> ORGANISM: Artificial Sequence
<220> FEATURE:
<223> OTHER INFORMATION: Heavy chain variable region (B9)

<400> SEQUENCE: 230

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gly Glu Ile Ala Val Ala Gln Asn Trp Asp Tyr Tyr Gly Met
            100                 105                 110

Asp Val Trp Gly Gln Gly Thr Leu Val Thr Val Ser Ser
        115                 120                 125


<210> SEQ ID NO 231
<211> LENGTH: 114
<212> TYPE: PRT
<213> ORGANISM: Artificial Sequence
<220> FEATURE:
<223> OTHER INFORMATION: Light chain variable region (H11)

<400> SEQUENCE: 231

Ser Tyr Glu Leu Thr Gln Asp Pro Ala Ala Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Val Val Ile Tyr
        35                  40                  45

Gly Arg Asn Asn Arg Pro Ser Gly Ile Pro Asp Arg Phe Ser Gly Ser
    50                  55                  60

Ser Ser Gly Asp Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Gly Asn His
                85                  90                  95

Tyr Val Phe Gly Thr Gly Thr Lys Leu Thr Val Leu Gly Gln Pro Ala
            100                 105                 110

Ala Ala


<210> SEQ ID NO 232
<211> LENGTH: 117
<212> TYPE: PRT
<213> ORGANISM: Artificial Sequence
<220> FEATURE:
<223> OTHER INFORMATION: Heavy chain variable region (H11)

<400> SEQUENCE: 232

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Ser Ser Ser Asp Tyr Trp Gly Arg Gly Thr Leu
            100                 105                 110

Val Thr Val Ser Ser
        115


<210> SEQ ID NO 233
<211> LENGTH: 118
<212> TYPE: PRT
<213> ORGANISM: Artificial Sequence
<220> FEATURE:
```

<223> OTHER INFORMATION: Light chain variable region (G9)

<400> SEQUENCE: 233

Gln Ser Ala Leu Thr Gln Pro Ala Ser Val Ser Gly Ser Pro Gly Gln
1 5 10 15

Ser Ile Thr Ile Ser Cys Thr Gly Ser Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asp Arg Phe
50 55 60

Ser Gly Ser Lys Ser Gly Asn Met Ala Ser Leu Thr Ile Ser Gly Leu
65 70 75 80

Gln Ala Glu Asp Glu Ala Asp Tyr Tyr Cys Ser Ser Tyr Thr Gly Ser
85 90 95

Ser Thr Leu Asp Val Leu Phe Gly Gly Gly Thr Lys Leu Thr Val Leu
100 105 110

Gly Gln Pro Ala Ala Ala
115

<210> SEQ ID NO 234
<211> LENGTH: 120
<212> TYPE: PRT
<213> ORGANISM: Artificial Sequence
<220> FEATURE:
<223> OTHER INFORMATION: Heavy chain variable region (G9)

<400> SEQUENCE: 234

Gln Val Gln Leu Val Gln Pro Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Ser Gln Tyr Tyr Asp Gly Gly Tyr Tyr Met Asp Val Trp Gly Gln
100 105 110

Gly Thr Leu Val Thr Val Ser Ser
115 120

<210> SEQ ID NO 235
<211> LENGTH: 114
<212> TYPE: PRT
<213> ORGANISM: Artificial Sequence
<220> FEATURE:
<223> OTHER INFORMATION: Light chain variable region (H2)

<400> SEQUENCE: 235

Ser Tyr Glu Leu Thr Gln Asp Pro Ala Val Ser Val Ala Leu Gly Gln
1 5 10 15

Thr Val Arg Ile Thr Cys Gln Gly Asp Ser Leu Arg Asn Tyr Tyr Ala
20 25 30

Ser Trp Tyr Gln Gln Lys Pro Gly Gln Ala Pro Ile Leu Val Ile Ser

```
        35                  40                  45

Gly Asn Asn Lys Arg Pro Ser Gly Ile Pro Asp Arg Phe Ser Gly Ser
    50                  55                  60

Ser Ser Gly Asp Thr Ala Ser Leu Thr Ile Ser Gly Ala Gln Ala Glu
65                  70                  75                  80

Asp Glu Ala Asp Tyr Tyr Cys Asn Ser Leu Asp Ser Thr Tyr Asn His
                85                  90                  95

Pro Ile Phe Gly Gly Gly Thr Lys Val Thr Val Leu Gly Gln Pro Ala
            100                 105                 110

Ala Ala


<210> SEQ ID NO 236
<211> LENGTH: 117
<212> TYPE: PRT
<213> ORGANISM: Artificial Sequence
<220> FEATURE:
<223> OTHER INFORMATION: Heavy chain variable region (H2)

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile His Trp Val Arg Gln Ala Thr Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Gly Asp Ala Phe Asp Ile Trp Gly Gln Gly Thr Leu
            100                 105                 110

Val Thr Val Ser Ser
        115


<210> SEQ ID NO 237
<211> LENGTH: 116
<212> TYPE: PRT
<213> ORGANISM: Artificial Sequence
<220> FEATURE:
<223> OTHER INFORMATION: Light chain variable region (F12)

<400> SEQUENCE: 237

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Ile Gly Asp Tyr
            20                  25                  30

Asp Tyr Val Ser Trp Tyr Gln Gln His Pro Gly Lys Thr Pro Lys Leu
        35                  40                  45

Met Ile Tyr Asp Val Ser Arg Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ala Ser Tyr Thr Ser Ser
                85                  90                  95

Ser Val Val Val Phe Gly Gly Gly Thr Lys Leu Thr Val Leu Gly Gln
```

```
            100                 105                 110

Pro Ala Ala Ala
        115


<210> SEQ ID NO 238
<211> LENGTH: 120
<212> TYPE: PRT
<213> ORGANISM: Artificial Sequence
<220> FEATURE:
<223> OTHER INFORMATION: Heavy chain variable region (F12)

<400> SEQUENCE: 238

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Gln Tyr Tyr Asp Gly Gly Tyr Tyr Met Asp Val Trp Gly Gln
            100                 105                 110

Gly Thr Leu Val Thr Val Ser Ser
        115                 120


<210> SEQ ID NO 239
<211> LENGTH: 117
<212> TYPE: PRT
<213> ORGANISM: Artificial Sequence
<220> FEATURE:
<223> OTHER INFORMATION: Light chain variable region (G11)

<400> SEQUENCE: 239

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Ser Thr Leu Val Val Phe Gly Gly Gly Thr Lys Leu Thr Val Leu Gly
            100                 105                 110

Gln Pro Ala Ala Ala
        115


<210> SEQ ID NO 240
<211> LENGTH: 120
<212> TYPE: PRT
<213> ORGANISM: Artificial Sequence
<220> FEATURE:
```

<223> OTHER INFORMATION: Heavy chain variable region (G11)

<400> SEQUENCE: 240

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Gln Tyr Tyr Asp Gly Gly Tyr Tyr Met Asp Val Trp Gly Gln
            100                 105                 110

Gly Thr Leu Val Thr Val Ser Ser
        115                 120
```

<210> SEQ ID NO 241
<211> LENGTH: 114
<212> TYPE: PRT
<213> ORGANISM: Artificial Sequence
<220> FEATURE:
<223> OTHER INFORMATION: Light chain variable region (G6)

<400> SEQUENCE: 241

```
Ser Tyr Glu Leu Thr Gln Asp Pro Ala Val Ser Val Ala Leu Gly Gln
1               5                   10                  15

Thr Val Thr Ile Thr Cys Gln Gly Asp Ser Leu Arg Arg Tyr Tyr Ala
            20                  25                  30

Thr Trp Tyr Gln Gln Lys Pro Gly Gln Ala Pro Val Leu Val Ile Tyr
        35                  40                  45

Gly Gln Asn Tyr Arg Pro Ser Gly Ile Pro Asp Arg Phe Ser Gly Ser
    50                  55                  60

Asn Ser Gly Thr Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Ala
            100                 105                 110

Ala Ala
```

<210> SEQ ID NO 242
<211> LENGTH: 119
<212> TYPE: PRT
<213> ORGANISM: Artificial Sequence
<220> FEATURE:
<223> OTHER INFORMATION: Heavy chain variable region (G6)

<400> SEQUENCE: 242

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Tyr Ser Ser Ser Phe Asp Tyr Trp Gly Gln Gly
            100                 105                 110

Thr Thr Val Thr Val Ser Ser
        115


<210> SEQ ID NO 243
<211> LENGTH: 116
<212> TYPE: PRT
<213> ORGANISM: Artificial Sequence
<220> FEATURE:
<223> OTHER INFORMATION: Light chain variable region (F11)

<400> SEQUENCE: 243

Gln Ser Val Leu Thr Gln Pro Pro Ser Thr Ser Gly Thr Pro Gly Gln
1               5                   10                  15

Thr Phe Ser Ile Phe Cys Ser Gly Ser Ser Ser Asn Ile Gly Thr Asn
            20                  25                  30

Thr Val Asn Trp Tyr Gln Gln Leu Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Glu Thr Trp Asp Asp Ser Leu
                85                  90                  95

Lys Gly Pro Val Phe Gly Gly Gly Thr Lys Val Thr Val Leu Gly Gln
            100                 105                 110

Pro Ala Ala Ala
        115


<210> SEQ ID NO 244
<211> LENGTH: 119
<212> TYPE: PRT
<213> ORGANISM: Artificial Sequence
<220> FEATURE:
<223> OTHER INFORMATION: Heavy chain variable region (F11)

<400> SEQUENCE: 244

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Thr Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Glu Trp Glu Leu Gly Asp Ala Phe Asp Ile Trp Gly Arg Gly
```

```
            100                 105                 110

Thr Leu Val Thr Val Ser Ser
        115


<210> SEQ ID NO 245
<211> LENGTH: 112
<212> TYPE: PRT
<213> ORGANISM: Artificial Sequence
<220> FEATURE:
<223> OTHER INFORMATION: Light chain variable region (D3)

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Arg Trp
                85                  90                  95

Thr Phe Gly Gln Gly Thr Lys Val Glu Ile Lys Arg Thr Ala Ala Ala
            100                 105                 110


<210> SEQ ID NO 246
<211> LENGTH: 122
<212> TYPE: PRT
<213> ORGANISM: Artificial Sequence
<220> FEATURE:
<223> OTHER INFORMATION: Heavy chain variable region (D3)

<400> SEQUENCE: 246

Glu Val Gln Leu Leu Glu Ser Gly Gly Gly Val Val Gln Pro Gly Arg
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Ser Tyr Gly Tyr Tyr Tyr Gly Met Asp Val Trp
            100                 105                 110

Gly Gln Gly Thr Met Val Thr Val Ser Ser
        115                 120


<210> SEQ ID NO 247
<211> LENGTH: 112
<212> TYPE: PRT
<213> ORGANISM: Artificial Sequence
<220> FEATURE:
<223> OTHER INFORMATION: Light chain variable region (B12)

<400> SEQUENCE: 247
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Arg
                85                  90                  95

Thr Phe Gly Gln Gly Thr Lys Val Glu Ile Lys Arg Thr Ala Ala Ala
            100                 105                 110


<210> SEQ ID NO 248
<211> LENGTH: 122
<212> TYPE: PRT
<213> ORGANISM: Artificial Sequence
<220> FEATURE:
<223> OTHER INFORMATION: Heavy chain variable region (B12)

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Gly Ala Ser Ile Val Gly Ala Thr Ala Leu Asp Tyr Trp
            100                 105                 110

Gly Gln Gly Thr Leu Val Thr Val Ser Ser
        115                 120


<210> SEQ ID NO 249
<211> LENGTH: 118
<212> TYPE: PRT
<213> ORGANISM: Artificial Sequence
<220> FEATURE:
<223> OTHER INFORMATION: Light chain variable region (E4)

<400> SEQUENCE: 249

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
```

```
65                  70                  75                  80

Leu Lys Thr Glu Asp Glu Ala Asp Tyr Tyr Cys Gln Ser Tyr Asp Thr
                85                  90                  95

Gly Asn Arg Asn Tyr Val Phe Gly Thr Gly Thr Gln Leu Thr Val Leu
            100                 105                 110

Gly Gln Pro Ala Ala Ala
        115


<210> SEQ ID NO 250
<211> LENGTH: 121
<212> TYPE: PRT
<213> ORGANISM: Artificial Sequence
<220> FEATURE:
<223> OTHER INFORMATION: Heavy chain variable region (E4)

<400> SEQUENCE: 250

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Met Thr Arg Asp Met Ser Thr Asp Thr Ala Tyr
65                  70                  75                  80

Met Glu Leu Ser Ser Leu Thr Tyr Asp Asp Thr Ala Val Tyr Phe Cys
                85                  90                  95

Val Arg Gly Pro Ser Leu Asn Tyr Ala Gly Tyr Phe Asp Asn Trp Gly
            100                 105                 110

Gln Gly Thr Leu Val Thr Val Ser Ser
        115                 120


<210> SEQ ID NO 251
<211> LENGTH: 114
<212> TYPE: PRT
<213> ORGANISM: Artificial Sequence
<220> FEATURE:
<223> OTHER INFORMATION: Light chain variable region (E12)

<400> SEQUENCE: 251

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Ser Gly Gln Ala Pro Val Leu Val Ile Tyr
        35                  40                  45

Gly Lys Glu Lys Arg Pro Ser Gly Ile Pro Asp Arg Phe Ser Gly Ser
    50                  55                  60

Ser Ser Gly Asn Thr Ala Ser Leu Thr Ile Thr Gly Ala Arg Ala Glu
65                  70                  75                  80

Asp Glu Ala Asp Tyr Tyr Cys Asn Ser Arg Gly Ser Thr Thr Asp Tyr
                85                  90                  95

Met Val Phe Gly Gly Gly Thr Gln Leu Thr Val Leu Gly Gln Pro Ala
            100                 105                 110

Ala Ala
```

<210> SEQ ID NO 252
<211> LENGTH: 117
<212> TYPE: PRT
<213> ORGANISM: Artificial Sequence
<220> FEATURE:
<223> OTHER INFORMATION: Heavy chain variable region (E12)

<400> SEQUENCE: 252

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Gly Met Asp Val Trp Gly Gln Gly Thr Leu
            100                 105                 110

Val Thr Val Ser Ser
        115
```

<210> SEQ ID NO 253
<211> LENGTH: 112
<212> TYPE: PRT
<213> ORGANISM: Artificial Sequence
<220> FEATURE:
<223> OTHER INFORMATION: Light chain variable region (D1)

<400> SEQUENCE: 253

```
Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Ser Ile Ile
        35                  40                  45

Gln Glu Ala Ser Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Lys Phe Pro Tyr
                85                  90                  95

Thr Phe Gly Gln Gly Thr Lys Leu Glu Ile Lys Arg Thr Ala Ala Ala
            100                 105                 110
```

<210> SEQ ID NO 254
<211> LENGTH: 117
<212> TYPE: PRT
<213> ORGANISM: Artificial Sequence
<220> FEATURE:
<223> OTHER INFORMATION: Heavy chain variable region (D1)

<400> SEQUENCE: 254

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Gly Ile Ser Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Arg Gly Val Asp Glu Gly Asp Tyr Trp Gly Gln Gly Thr Met
            100                 105                 110

Val Thr Val Ser Ser
        115
```

<210> SEQ ID NO 255
<211> LENGTH: 116
<212> TYPE: PRT
<213> ORGANISM: Artificial Sequence
<220> FEATURE:
<223> OTHER INFORMATION: Light chain variable region (E6)

<400> SEQUENCE: 255

```
Asn Phe Met Leu Thr Gln Pro His Ser Val Ser Glu Ser Pro Gly Lys
1               5                   10                  15

Thr Val Thr Leu Ser Cys Thr Gly Ser Ser Gly Asn Ile Ala Ser Asn
            20                  25                  30

Tyr Val Gln Trp Tyr Gln His Arg Pro Gly Ser Ala Pro Thr Thr Val
        35                  40                  45

Ile Tyr Arg Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Arg Pro Glu Asp Glu Ala Asp Tyr Tyr Cys Gln Ser Tyr Asp Ser
                85                  90                  95

Ser Ser Trp Val Phe Gly Gly Gly Thr Lys Leu Thr Val Leu Gly Gln
            100                 105                 110

Pro Ala Ala Ala
        115
```

<210> SEQ ID NO 256
<211> LENGTH: 124
<212> TYPE: PRT
<213> ORGANISM: Artificial Sequence
<220> FEATURE:
<223> OTHER INFORMATION: Heavy chain variable region (E6)

<400> SEQUENCE: 256

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Asp Ile Thr Trp Val Arg Gln Ala Pro Gly Gln Gly Leu Glu Trp Met
        35                  40                  45

Gly Trp Met Asn Pro Asn Ser Gly Asn Ser Arg Ser Ala Gln Lys Phe
    50                  55                  60

Gln Gly Arg Val Ser Met Thr Ser Asp Ser Ser Ile Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Thr Gly Asp Tyr Ser Gly Val Val Leu Thr Ala Thr Ala Leu Asp
            100                 105                 110

Tyr Trp Gly Gln Gly Thr Leu Val Thr Val Ser Ser
        115                 120


<210> SEQ ID NO 257
<211> LENGTH: 116
<212> TYPE: PRT
<213> ORGANISM: Artificial Sequence
<220> FEATURE:
<223> OTHER INFORMATION: Light chain variable region (E9)

<400> SEQUENCE: 257

Gln Ser Glu Leu Thr Gln Leu Pro Ser Ala Ser Glu Thr Pro Gly Gln
1               5                   10                  15

Arg Val Thr Ile Ser Cys Ser Gly Ser Ser Ser Asn Ile Gly Asn Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Ala Ala Ala
        115


<210> SEQ ID NO 258
<211> LENGTH: 123
<212> TYPE: PRT
<213> ORGANISM: Artificial Sequence
<220> FEATURE:
<223> OTHER INFORMATION: Heavy chain variable region (E9)

<400> SEQUENCE: 258

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Arg Ile Ala Ala Ala Gly Met Arg Glu Leu Asp Tyr
            100                 105                 110

Trp Gly Gln Gly Thr Leu Val Thr Val Ser Ser
        115                 120


<210> SEQ ID NO 259
<211> LENGTH: 118
```

<212> TYPE: PRT
<213> ORGANISM: Artificial Sequence
<220> FEATURE:
<223> OTHER INFORMATION: Light chain variable region (A11)

<400> SEQUENCE: 259

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Tyr Thr Phe Gly Gln Gly Thr Lys Val Glu Ile
            100                 105                 110

Lys Arg Thr Ala Ala Ala
        115
```

<210> SEQ ID NO 260
<211> LENGTH: 120
<212> TYPE: PRT
<213> ORGANISM: Artificial Sequence
<220> FEATURE:
<223> OTHER INFORMATION: Heavy chain variable region (A11)

<400> SEQUENCE: 260

```
Glu Val Gln Leu Leu Glu Ser Gly Gly Gly Leu Glu Gln Pro Gly Gly
1               5                   10                  15

Phe Leu Arg Leu Ser Cys Ala Ala Ser Gly Phe Ser Phe Thr Ser Tyr
            20                  25                  30

Ala Met Thr Trp Val Arg Gln Ala Pro Gly Lys Gly Leu Glu Trp Val
        35                  40                  45

Ser Gly Ile Ser Ser Asp Gly Thr Thr Thr Thr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Arg Asp Glu Asp Thr Ala Val Tyr Tyr Cys
                85                  90                  95

Ala Arg Asp Gln Leu Leu Gly Trp Asp Ala Leu Asn Val Trp Gly Gln
            100                 105                 110

Gly Thr Met Val Thr Val Ser Ser
        115                 120
```

<210> SEQ ID NO 261
<211> LENGTH: 348
<212> TYPE: DNA
<213> ORGANISM: Artificial Sequence
<220> FEATURE:
<223> OTHER INFORMATION: Light chain variable region (E3) coding gene

<400> SEQUENCE: 261

```
tcctatgagc tgactcagga ccctgctgtg tctgtggcct tgggacagac agtcaggatc     60

acatgccagg gagacagcct cagaaacttt tatgcaagct ggtaccagca gaagtcagga    120
```

caggccccag ttcttgtcat gtatggtaaa aacaaccggc cctcagggat cccagaccga 180
ttctctggct ccacctcagg aaacacagct tccttgacca tcactggggc tcaggcggaa 240
gatgaggctg actattactg taactcccgg gacagcagtg gtagccattt gacgggcgta 300
ttcggcggag ggaccaaggt caccgtccta ggtcagcccg cggccgca 348

<210> SEQ ID NO 262
<211> LENGTH: 372
<212> TYPE: DNA
<213> ORGANISM: Artificial Sequence
<220> FEATURE:
<223> OTHER INFORMATION: Heavy chain variable region (E3 or E3.1) coding gene

<400> SEQUENCE: 262
caggtgcagc tggtggagtc tgggggaggc ttggtacagc ctgggggggtc cctgagactc 60 tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa tacgctgtat 240
ctgcaaatga ttagcctgag agctgaggac acggctgtgt attactgtgc gagagatacg 300
tattactatg gttcggggag aagtaatgct tttgatatat ggggccaggg aaccctggtc 360
accgtctcga gt 372

<210> SEQ ID NO 263
<211> LENGTH: 330
<212> TYPE: DNA
<213> ORGANISM: Artificial Sequence
<220> FEATURE:
<223> OTHER INFORMATION: Light chain variable region (B3) coding gene

<400> SEQUENCE: 263
gacatccaga tgacccagtc tccatcctcc ctgtctgcat ctgtaggaga cagagtcacc 60
atcacttgcc aggcgagtca ggacattagc aactatttga attggtatca gcagaaacca 120
gggaaagccc ctaagctcct gatctacgat gcatccaatt tggaaacagg ggtcccatca 180
aggttcagtg gaagtggatc tgggacagat tttactttca ccatcagcag cctgcagcct 240
gaagatattg caacatatta ctgtcaacag tatgataatc tccctttcgg cggagggacc 300
aaagtggata tcaaacgtac cgcggccgca 330

<210> SEQ ID NO 264
<211> LENGTH: 366
<212> TYPE: DNA
<213> ORGANISM: Artificial Sequence
<220> FEATURE:
<223> OTHER INFORMATION: Heavy chain variable region (B3) coding gene

<400> SEQUENCE: 264
gaggtgcagc tgttggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attagttgga atagtggtag cataggctac 180
gcagactccg tgaagggccg attcaccatc tccagagaca attccaagaa cacgctgtat 240
cttcaaatga acagtctgag agccgaggac acggccgtgt attactgtgc gagagttggg 300
gatagcagtg gctggtccga tgcttttgat atctggggcc aagggacaat ggtcaccgtc 360
tcgagt 366

<210> SEQ ID NO 265
<211> LENGTH: 342
<212> TYPE: DNA
<213> ORGANISM: Artificial Sequence
<220> FEATURE:
<223> OTHER INFORMATION: Light chain variable region (A10) coding gene

<400> SEQUENCE: 265
gatattgtga tgacacagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccaccgg tatcccagcc 180
aggttcagtg gcagtgggtc tgggacagag ttcactctca ccatcagcag cctgcagtct 240
gaagattttg cagtttatta ctgtcagcag tatggtagct cacctcggat gtacactttt 300
ggccagggga ccaaagtgga tatcaaacgt accgcggccg ca 342

<210> SEQ ID NO 266
<211> LENGTH: 363
<212> TYPE: DNA
<213> ORGANISM: Artificial Sequence
<220> FEATURE:
<223> OTHER INFORMATION: Heavy chain variable region (A10) coding gene

<400> SEQUENCE: 266
caaatgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggtggg atcatcccta tctttggtac agcaaactac 180
gcacagaagt tccagggcag agtcacgatt accgcggaca aatccatcag cacagcctac 240
atggagctga gcagcctgag atctgaggac acggccgtgt attactgtgc gagaggcggc 300
ctcggggagt tggacaactg gttcgacccc tggggccagg gaaccctggt caccgtctcg 360
agt 363

<210> SEQ ID NO 267
<211> LENGTH: 336
<212> TYPE: DNA
<213> ORGANISM: Artificial Sequence
<220> FEATURE:
<223> OTHER INFORMATION: Light chain variable region (G1) coding gene

<400> SEQUENCE: 267
tcctatgagc tgactcagcc accctcactg tccgtgtccc caggacagac agccagcatc 60
acctgctcag gatataaact gggagataga tatgtttcct ggtatcagca gaagacaggc 120
cagtcccctg tggtggtcat ctataaagat agccagcggc cctcaggggt ccctgaacga 180
ttctctggct ccaactctgg gaacacagcc actctgacca tcagcgggac ccaggctatg 240
gatgaggctg actattactg tcaggcgtgg gacagcggca ctggggtatt cggcggaggg 300
accaagctga ccgtcctagg tcagcccgcg gccgca 336

<210> SEQ ID NO 268
<211> LENGTH: 354
<212> TYPE: DNA
<213> ORGANISM: Artificial Sequence
<220> FEATURE:
<223> OTHER INFORMATION: Heavy chain variable region (G1) coding gene

<400> SEQUENCE: 268
gaagtgcagc tggtgcagtc tggggctgag gtgaagaagc ctgggtcctc ggtgaaggtc 60

```
tcctgcaagg cttctggagg caccttcagc agctatggta tcagctgggt gcgacaggcc    120

cctggacaag ggcttgagtg gatgggatgg atcagcgctt acaatggtaa cacaaactat    180

gcacaggagc tccagggcag agtcaccatg accacagaca catccacgag cacagcctat    240

atggagctga ggagcctgag atctgacgac acggccgtgt attactgtgc gagagtaggg    300

gtggctggta aacttgacta ctggggccaa ggaaccctgg tcaccgtctc gagt          354


<210> SEQ ID NO 269
<211> LENGTH: 354
<212> TYPE: DNA
<213> ORGANISM: Artificial Sequence
<220> FEATURE:
<223> OTHER INFORMATION: Light chain variable region (G9) coding gene

<400> SEQUENCE: 269

cagtctgcgc tgactcagcc tgcctccgtg tctgggtctc ctggacagtc gatcaccatc     60

tcctgcactg gaagcagcag tgacgttggt ggttataact atgtctcctg gtaccagcaa    120

cacccaggca aagcccccaa actcatgatt tatgatgtca gtaatcggcc ctcaggggtt    180

tctgatcgct tctctggctc caagtctggc aacatggcct ccctgaccat ctctgggctc    240

caggctgagg acgaggctga ttattactgc agctcatata caggaagcag cactctcgac    300

gtgctattcg gcggagggac caagctgacc gtcctaggtc agcccgcggc cgca          354


<210> SEQ ID NO 270
<211> LENGTH: 360
<212> TYPE: DNA
<213> ORGANISM: Artificial Sequence
<220> FEATURE:
<223> OTHER INFORMATION: Heavy chain variable region (G9) coding gene

<400> SEQUENCE: 270

caggtgcagc tggtgcagcc tggagcagag gtgaaaaagc cgggggagtc tctgaagatc     60

tcctgtaagg gttctggata cagctttacc agctactgga tcggctgggt gcgccagatg    120

cccgggaagg gcctggagtg gatggggatc atctatcctg gtgactctga taccagatac    180

agcccgtcct tccaaggcca ggtcaccatc tcagccgaca agtccatcag caccgcctac    240

ctgcagtgga gcagcctgaa ggcctcggac accgccatgt attactgtgc gagtcaatat    300

tacgatgggg gttactacat ggacgtctgg ggccagggaa ccctggtcac cgtctcgagt    360


<210> SEQ ID NO 271
<211> LENGTH: 342
<212> TYPE: DNA
<213> ORGANISM: Artificial Sequence
<220> FEATURE:
<223> OTHER INFORMATION: Light chain variable region (H2) coding gene

<400> SEQUENCE: 271

tcctatgagc tgactcagga ccctgctgtg tcggtggcct tgggacagac agtcaggatc     60

acatgccaag gagacagcct cagaaactat tatgcaagct ggtaccagca gaagccagga    120

caggcccta ttcttgtcat ctctggtaac aacaaacggc cctcggggat cccagaccga    180

ttctctggct ccagctcagg agacacagct tccttgacca tctctggggc tcaggcggaa    240

gatgaggctg actattactg taactcccta gacagcactt ataaccatcc gatattcggc    300

ggagggacca aggtcaccgt cctaggtcag cccgcggccg ca                       342


<210> SEQ ID NO 272
```

<211> LENGTH: 351
<212> TYPE: DNA
<213> ORGANISM: Artificial Sequence
<220> FEATURE:
<223> OTHER INFORMATION: Heavy chain variable region (H2) coding gene

<400> SEQUENCE: 272
caggtccagc ttgtgcagtc tggggctgag gtgaagaagc ctggggcctc agtgaaggtc 60
tcctgcaagg cttctggata caccttcacc agttatgata tccactgggt gcgacaggcc 120
actggacaag ggcttgagtg gatgggatgg atcagcgctt acaatggtaa cacaaactat 180
gcacagaagc tccagggcag agtcaccatg accacagaca catccacgag cacagcctac 240
atggagctga ggagcctgag atctgacgac acggccgtgt attactgtgc gagagatggg 300
ggtgatgctt ttgatatctg gggccaagga accctggtca ccgtctcgag t 351

<210> SEQ ID NO 273
<211> LENGTH: 342
<212> TYPE: DNA
<213> ORGANISM: Artificial Sequence
<220> FEATURE:
<223> OTHER INFORMATION: Light chain variable region (H11) coding gene

<400> SEQUENCE: 273
tcctatgagc tgactcagga ccctgctgcg tctgtggcct tgggacagac agtcaggatc 60
acatgccaag gagacagcct cagaagctat tatgcaagct ggtaccagca gaagccagga 120
caggcccctg tagttgtcat ctatggtaga aacaaccggc cctcagggat cccagaccga 180
ttctctggct ccagctcagg agacacagct tccttgacca tcactggggc tcaggcggaa 240
gatgaggctg actattactg taagtcccgg gacagcagtg gtaaccatta tgtcttcgga 300
actgggacca agctgaccgt cctaggtcag cccgcggccg ca 342

<210> SEQ ID NO 274
<211> LENGTH: 351
<212> TYPE: DNA
<213> ORGANISM: Artificial Sequence
<220> FEATURE:
<223> OTHER INFORMATION: Heavy chain variable region (H11) coding gene

<400> SEQUENCE: 274
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagagatgcc 300
ggcagctcgt ccgattactg gggccgtggc accctggtca ccgtctcgag t 351

<210> SEQ ID NO 275
<211> LENGTH: 348
<212> TYPE: DNA
<213> ORGANISM: Artificial Sequence
<220> FEATURE:
<223> OTHER INFORMATION: Light chain variable region (F12) coding gene

<400> SEQUENCE: 275
cagtctgtgc tgactcagcc tgcctccgtg tctgggtctc ctggacagtc gatcaccatc 60
tcctgcgctg gaaccagcag tgacattggt gattatgact atgtctcctg gtaccaacag 120
cacccaggca agactcccaa actcatgatt tatgatgtca gtaggcggcc ctcaggggtc 180
cctgatcgct tctctggctc caagtctggc aacacggcct ccctgaccat ctctgggctc 240
cagactgagg acgaggctga ttattactgc gcctcatata caagcagcag cgtcgtggtc 300
ttcggcggag ggaccaagct gaccgtccta ggtcagcccg cggccgca 348

<210> SEQ ID NO 276
<211> LENGTH: 360
<212> TYPE: DNA
<213> ORGANISM: Artificial Sequence
<220> FEATURE:
<223> OTHER INFORMATION: Heavy chain variable region (F12) coding gene

<400> SEQUENCE: 276
caggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagtcaatat 300
tacgatgggg gttactacat ggacgtctgg ggccagggca ccctggtcac cgtctcgagt 360

<210> SEQ ID NO 277
<211> LENGTH: 336
<212> TYPE: DNA
<213> ORGANISM: Artificial Sequence
<220> FEATURE:
<223> OTHER INFORMATION: Light chain variable region (B9) coding gene

<400> SEQUENCE: 277
gacatccaga tgacccagtc tccatcctcc ctgtctgcat ctgtaggaga cagagtcacc 60
atcacttgcc gggcaagtca gagcattagc aggtatttaa attggtatca gcagaaacca 120
gggaaagccc ccaagctcct gatctatggt gcatccagtt tgcaaagtgg ggtcccatca 180
aggttcagtg gcagtggatc tgggacagat ttcactctca ccatcagcag tctgcagcct 240
gaagatttcg caacttacca ttgtcaacag gcttacggtt tccccctcac tctcggcgga 300
gggaccaagg tggagatcaa acgtaccgcg gccgca 336

<210> SEQ ID NO 278
<211> LENGTH: 375
<212> TYPE: DNA
<213> ORGANISM: Artificial Sequence
<220> FEATURE:
<223> OTHER INFORMATION: Heavy chain variable region (B9) coding gene

<400> SEQUENCE: 278
caggtgcagc tggtggagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaggggaa 300
atagcagtgg ctcaaaactg ggactactac ggtatggacg tctggggcca gggcaccctg 360
gtcaccgtct cgagt 375

<210> SEQ ID NO 279
<211> LENGTH: 351
<212> TYPE: DNA

<213> ORGANISM: Artificial Sequence
<220> FEATURE:
<223> OTHER INFORMATION: Light chain variable region (G11) coding gene

<400> SEQUENCE: 279
cagtctgcgc tgactcagcc tcgctcagtg tccgggtctc ctggacagtc agtcaccatc 60
tcctgcactg gaaccagcag tgatgttggt ggttataact atgtctcctg gtaccaacag 120
cacccaggca aagcccccaa actcatgatt tatgatgtca gtaagcggcc ctcaggggtc 180
cctgatcgct tctctggctc caagtctggc aacacggcct ccctgacaat ctctgggctc 240
caggctgagg acgaggctga ttattactgc agctcatatt caagcagcag cactctcgtg 300
gttttcggcg gagggaccaa gctgaccgtc ctaggtcagc ccgcggccgc a 351

<210> SEQ ID NO 280
<211> LENGTH: 360
<212> TYPE: DNA
<213> ORGANISM: Artificial Sequence
<220> FEATURE:
<223> OTHER INFORMATION: Heavy chain variable region (G11) coding gene

<400> SEQUENCE: 280
caggtccagc tggtacagtc tggagcagag gtgaaaaagc cgggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagtcaatat 300
tacgatgggg gttactacat ggacgtctgg ggccagggaa ccctggtcac cgtctcgagt 360

<210> SEQ ID NO 281
<211> LENGTH: 342
<212> TYPE: DNA
<213> ORGANISM: Artificial Sequence
<220> FEATURE:
<223> OTHER INFORMATION: Light chain variable region (G6) coding gene

<400> SEQUENCE: 281
tcctatgagc tgactcagga ccctgctgtg tctgtggcct tgggacagac agtcacgatc 60
acatgccaag gagacagcct cagaaggtat tatgcaacct ggtaccagca gaagccagga 120
caggcccctg tccttgtcat ctatggtcaa aactaccggc cctcggggat cccagaccga 180
ttctctggct ccaactcagg aaccacagct tccttgacca tcactggggc tcaggcggaa 240
gatgaggctg actattactg taactcccgg gacagcagtg gtaaccatgt ggtattcggc 300
ggagggacca agctgaccgt cctaggtcag cccgcggccg ca 342

<210> SEQ ID NO 282
<211> LENGTH: 357
<212> TYPE: DNA
<213> ORGANISM: Artificial Sequence
<220> FEATURE:
<223> OTHER INFORMATION: Heavy chain variable region (G6) coding gene

<400> SEQUENCE: 282
gaggtgcagc tggtggagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt actactgtgc gagagggtgg 300
gggtatagca gctcgtttga ctactggggg caagggacca cggtcaccgt ctcgagt 357

<210> SEQ ID NO 283
<211> LENGTH: 348
<212> TYPE: DNA
<213> ORGANISM: Artificial Sequence
<220> FEATURE:
<223> OTHER INFORMATION: Light chain variable region (F11) coding gene

<400> SEQUENCE: 283
cagtctgtgc tgactcagcc accctcaacg tctgggaccc ccgggcagac gttctccatt 60
ttttgttctg gaagcagttc gaacatcgga actaatactg ttaattggta ccagcagctc 120
ccaggaacgg cccccaaact cctcatctat agtaatgatc agcggccctc aggggtccct 180
gaccgattct ctggctccaa gtctggcacc tcagcctccc tggccatcag tgggctccag 240
tctgaggatg aggctgatta ttactgtgaa acatgggatg acagcctgaa aggcccggtg 300
ttcggcgggg ggaccaaggt caccgtccta ggtcagcccg cggccgca 348

<210> SEQ ID NO 284
<211> LENGTH: 357
<212> TYPE: DNA
<213> ORGANISM: Artificial Sequence
<220> FEATURE:
<223> OTHER INFORMATION: Heavy chain variable region (F11) coding gene

<400> SEQUENCE: 284
gaggtgcagc tggtggagtc tgggggaggc ttggtccagc ctggggggtc cctgaaactc 60
tcctgtgcag cgtctggatt cacctttagc agctatgcca tgagctgggt ccgccgggct 120
ccagggaagg ggctggagtg ggtctcaact attagtggta gtggtgatag cacatactac 180
gcagactccg tgaagggccg gttcaccatc tccagagaca attccaagaa cacgctgtat 240
ctgcaaatga acaacctgag agccgaggac acggccgtat attactgtgc gagagaatgg 300
gaactaggcg atgcttttga tatctggggc cgtggcaccc tggtcaccgt ctcgagt 357

<210> SEQ ID NO 285
<211> LENGTH: 336
<212> TYPE: DNA
<213> ORGANISM: Artificial Sequence
<220> FEATURE:
<223> OTHER INFORMATION: Light chain variable region (D3) coding gene

<400> SEQUENCE: 285
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccggtggac gttcggccaa 300
gggaccaagg tggaaatcaa acgtaccgcg gccgca 336

<210> SEQ ID NO 286
<211> LENGTH: 366
<212> TYPE: DNA
<213> ORGANISM: Artificial Sequence
<220> FEATURE:
<223> OTHER INFORMATION: Heavy chain variable region (D3) coding gene

<400> SEQUENCE: 286
gaggtgcagc tgttggagtc tgggggaggc gtggtccagc ctgggaggtc cctgagactc 60
tcctgtgcag cctctggatc cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaagacaga 300
ggcagctatg gttactacta cggtatggac gtctggggcc aagggacaat ggtcaccgtc 360
tcgagt 366

<210> SEQ ID NO 287
<211> LENGTH: 336
<212> TYPE: DNA
<213> ORGANISM: Artificial Sequence
<220> FEATURE:
<223> OTHER INFORMATION: Light chain variable region (B12) coding gene

<400> SEQUENCE: 287
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta ccctccggac gttcggccaa 300
gggaccaagg tggagatcaa acgtaccgcg gccgca 336

<210> SEQ ID NO 288
<211> LENGTH: 366
<212> TYPE: DNA
<213> ORGANISM: Artificial Sequence
<220> FEATURE:
<223> OTHER INFORMATION: Heavy chain variable region (B12) coding gene

<400> SEQUENCE: 288
caggtccagc tggtacagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactac 180
gcacagaagt tccagggcag agtcacgatt accgcggacg aatccacgag cacagcctac 240
atggagctga gcagcctgag atctgaggac acggccgtgt attactgtac gagagccggt 300
gcttctatag tgggagctac cgcgcttgac tactggggcc agggaaccct ggtcaccgtc 360
tcgagt 366

<210> SEQ ID NO 289
<211> LENGTH: 354
<212> TYPE: DNA
<213> ORGANISM: Artificial Sequence
<220> FEATURE:
<223> OTHER INFORMATION: Light chain variable region (E4) coding gene

<400> SEQUENCE: 289
aattttatgc tgactcagcc ccactctgtg tcggagtctc cgggaaagac ggtaaccatc 60
tcctgcaccc gcagcagtgg cagcattgcc agcaactatg tgcagtggta ccagcagcgc 120
ccgggcagtt cccccaccac tgtgatctat gaggataacc aaagaccctc tggggtccct 180
gatcggttct ctggctccat cgacagctcc tccaactctg cctccctcac catctctgga 240
ctgaagactg aggacgaggc tgactactac tgtcagtctt atgataccgg caatcggaat 300
tatgtcttcg gaactgggac ccagctcacc gtcctaggtc agcccgcggc cgca 354

<210> SEQ ID NO 290
<211> LENGTH: 363
<212> TYPE: DNA
<213> ORGANISM: Artificial Sequence
<220> FEATURE:
<223> OTHER INFORMATION: Heavy chain variable region (E4) coding gene

<400> SEQUENCE: 290
caggtgcagc tggtgcaatc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaagg atcatcccta tccttggtat agcaaactac 180
gcacagaagt tccagggcag agtcaccatg accagggaca tgtccacaga cacagcctac 240
atggagttga gcagcctgac atatgatgac acggccgtat atttttgtgt gagaggccct 300
agtcttaatt atgccggcta ttttgacaac tggggccagg gcaccctggt caccgtctcg 360
agt 363

<210> SEQ ID NO 291
<211> LENGTH: 342
<212> TYPE: DNA
<213> ORGANISM: Artificial Sequence
<220> FEATURE:
<223> OTHER INFORMATION: Light chain variable region (E12) coding gene

<400> SEQUENCE: 291
tcctatgagc tgactcagga ccctgctgtg tctgtggcct tgggacagac agtcaggatc 60
acatgccaag gagacagcct cagaagctat tatgcaagct ggtaccagca gaagtcagga 120
caggcccctg tacttgtcat ctatggtaaa gaaaagcgcc cctcagggat cccagaccga 180
ttctctggct ccagctcagg aaacacagct tccttgacca tcactggggc tcgggcggaa 240
gatgaggctg actattactg taactcccgg ggcagcacta ctgactatat ggtgttcggc 300
ggggggaccc agctcaccgt cctaggtcag cccgcggccg ca 342

<210> SEQ ID NO 292
<211> LENGTH: 351
<212> TYPE: DNA
<213> ORGANISM: Artificial Sequence
<220> FEATURE:
<223> OTHER INFORMATION: Heavy chain variable region (E12) coding gene

<400> SEQUENCE: 292
caggtgcagc tggtggagtc cgggggaggc ttagttcagc ctggggggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gagagaacgg 300
ggaagtggta tggacgtctg gggccaagga accctggtca ccgtctcgag t 351

<210> SEQ ID NO 293
<211> LENGTH: 336
<212> TYPE: DNA
<213> ORGANISM: Artificial Sequence
<220> FEATURE:

<223> OTHER INFORMATION: Light chain variable region (D1) coding gene

<400> SEQUENCE: 293
gaaacgacac tcacgcagtc tccagcattc atgtcagcga ctccaggaga caaagtcaac 60
atctcctgca aagccagcca agacattgat gatgatatga actggtacca acagaaacca 120
ggagaagctg ctatttccat tattcaagaa gctagtactc tcgttcctgg aatcccacct 180
cgattcagtg gcagcgggta tggaacagat tttaccctca caattaataa catagaatct 240
gaggatgctg catattactt ctgtctacaa catgataagt tcccgtacac ttttggccag 300
gggaccaagc tggagatcaa acgtaccgcg gccgca 336

<210> SEQ ID NO 294
<211> LENGTH: 351
<212> TYPE: DNA
<213> ORGANISM: Artificial Sequence
<220> FEATURE:
<223> OTHER INFORMATION: Heavy chain variable region (D1) coding gene

<400> SEQUENCE: 294
gaagtgcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagtcggggg 300
gttgatgagg gggactactg gggccaaggg acaatggtca ccgtctcgag t 351

<210> SEQ ID NO 295
<211> LENGTH: 348
<212> TYPE: DNA
<213> ORGANISM: Artificial Sequence
<220> FEATURE:
<223> OTHER INFORMATION: Light chain variable region (E6) coding gene

<400> SEQUENCE: 295
aattttatgc tgactcagcc ccactctgtg tcggagtctc cggggaagac ggttaccctc 60
tcctgcaccg gcagcagcgg caacattgcc agtaactatg tgcagtggta ccagcaccgc 120
ccgggcagtg cccccaccac tgtgatctac cgggatgacc aaagaccctc tggagtccct 180
gatcgcttct ctggctccat cgacagttca tccaactctg cctccctcac gatctctgga 240
ctgaggcctg aggacgaggc tgactattac tgtcagtctt atgatagcag ctcttgggtg 300
ttcggcggag ggaccaagct gaccgtccta ggtcagcccg cggccgca 348

<210> SEQ ID NO 296
<211> LENGTH: 372
<212> TYPE: DNA
<213> ORGANISM: Artificial Sequence
<220> FEATURE:
<223> OTHER INFORMATION: Heavy chain variable region (E6) coding gene

<400> SEQUENCE: 296
caggtccagc ttgtgcagtc tggagcagag gtgaagaagc ctggggcctc agtgaaggtc 60
tcctgcaagg cttctggata caccttcacc acttatgata tcacctgggt gcgacaggcc 120
cctggacaag gccttgagtg gatgggatgg atgaacccga acagtggtaa ctcacgctct 180
gcacagaagt tccagggcag agtcagcatg accagtgact cctccataag cacagcctac 240
atggagctga gcagcctgag atctgaggac acggccgtgt attactgtgc aacaggagac 300
tactcgggtg tggtactaac tgcaacagca cttgactact ggggccaggg aaccctggtc 360
accgtctcga gt 372

<210> SEQ ID NO 297
<211> LENGTH: 348
<212> TYPE: DNA
<213> ORGANISM: Artificial Sequence
<220> FEATURE:
<223> OTHER INFORMATION: Light chain variable region (E9) coding gene

<400> SEQUENCE: 297
cagtctgagc tgactcagct accctcagcg tctgagaccc ccgggcagag ggtcaccatc 60
tcttgttctg gaagcagctc caacatcgga aataattatg tatactggta ccagcaactc 120
cccggaacgg cccccaaact cctcatctat aggaataatc agcggccctc aggggtccct 180
gaccgattct ctggctccaa gtctggcacc tcagcctccc tggccatcag tgggctccgg 240
tccgaggatg aggctgatta ttactgtgca gcatgggatg acagcctgag tggttgggtg 300
ttcggcggag ggaccaagct gaccgtccta ggtcagcccg cggccgca 348

<210> SEQ ID NO 298
<211> LENGTH: 369
<212> TYPE: DNA
<213> ORGANISM: Artificial Sequence
<220> FEATURE:
<223> OTHER INFORMATION: Heavy chain variable region (E9) coding gene

<400> SEQUENCE: 298
caggtgcagc tggtggagtc tgggggaggc ttggtacagc ctgggaggtc cctgagactc 60
tcctgtgcag cgtctggatt caccttcagt agctatggca tgcactgggt ccgccaggct 120
ccagggaagg ggctggagtg ggtggccaac ataaagcaag atggaagtga gaaatactat 180
gtggactctg tgaagggccg attcaccatc tccagagaca acgccaagaa cacgctgtat 240
ctccaaatga acagcctgag agctgaggac acggctgtgt attactgtgc gagagaggac 300
cgtatagcag cagctgggat gcgggagttg gactactggg gccagggcac cctggtcacc 360
gtctcgagt 369

<210> SEQ ID NO 299
<211> LENGTH: 354
<212> TYPE: DNA
<213> ORGANISM: Artificial Sequence
<220> FEATURE:
<223> OTHER INFORMATION: Light chain variable region (A11) coding gene

<400> SEQUENCE: 299
gatattgtga tgacccagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taaccgggcc 180
tccggggtcc ctgacaggtt cagtggcagt ggatcaggca cagattttac actgaaaatc 240
agcagagtgg aggctgagga tgttggggtt tattactgca tgcaaggtac acactggcct 300
ccgtacacct ttggccaggg gaccaaggtg gagatcaaac gtaccgcggc cgca 354

<210> SEQ ID NO 300
<211> LENGTH: 360
<212> TYPE: DNA
<213> ORGANISM: Artificial Sequence
<220> FEATURE:

<223> OTHER INFORMATION: Heavy chain variable region (A11) coding gene

<400> SEQUENCE: 300
gaggtgcagc tgttggagtc tgggggaggc ttggaacagc ctggggggtt cctgagactc 60
tcctgtgcag cctctggatt ctcctttacc agctacgcca tgacctgggt ccgccaggct 120
ccagggaagg ggctggagtg ggtctcaggt attagtagtg atgggaccac tacaacctac 180
gcggactccg tgaggggccg gttcaccatc tccagagaca acgccaagaa cacggtgtat 240
ctccaaatga acagtctgag agacgaggac acggctgtgt attattgtgc aagagatcaa 300
ttgttgggct gggatgctct gaatgtctgg ggccaaggga caatggtcac cgtctcgagt 360

<210> SEQ ID NO 301
<211> LENGTH: 216
<212> TYPE: PRT
<213> ORGANISM: Artificial Sequence
<220> FEATURE:
<223> OTHER INFORMATION: Light chain (E3)

<400> SEQUENCE: 301

Ser Tyr Glu Leu Thr Gln Asp Pro Ala Val Ser Val Ala Leu Gly Gln
1 5 10 15

Thr Val Arg Ile Thr Cys Gln Gly Asp Ser Leu Arg Asn Phe Tyr Ala
20 25 30

Ser Trp Tyr Gln Gln Lys Ser Gly Gln Ala Pro Val Leu Val Met Tyr
35 40 45

Gly Lys Asn Asn Arg Pro Ser Gly Ile Pro Asp Arg Phe Ser Gly Ser
50 55 60

Thr Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Ser His
85 90 95

Leu Thr Gly Val Phe Gly Gly Gly Thr Lys Val Thr Val Leu Gly Gln
100 105 110

Pro Ala Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 302
<211> LENGTH: 451
<212> TYPE: PRT
<213> ORGANISM: Artificial Sequence
<220> FEATURE:
<223> OTHER INFORMATION: Heavy chain (E3 or E3.1)

<400> SEQUENCE: 302

Gln Val Gln Leu Val Glu Ser Gly Gly Gly Leu Val Gln Pro Gly Gly

```
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ile Ser Leu Arg Ala Glu Asp Thr Ala Val Tyr Tyr Cys
                85                  90                  95

Ala Arg Asp Thr Tyr Tyr Tyr Gly Ser Gly Arg Ser Asn Ala Phe Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430
```

His Glu Ala Leu His Asn His Tyr Thr Gln Lys Ser Leu Ser Leu Ser
435 440 445

Leu Gly Lys
450

<210> SEQ ID NO 303
<211> LENGTH: 212
<212> TYPE: PRT
<213> ORGANISM: Artificial Sequence
<220> FEATURE:
<223> OTHER INFORMATION: Light chain (B3)

<400> SEQUENCE: 303

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Phe
85 90 95

Gly Gly Gly Thr Lys Val Asp Ile Lys Arg Thr Ala Ala Ala Pro Ser
100 105 110

Val Phe Ile Phe Pro Pro Ser Asp Glu Gln Leu Lys Ser Gly Thr Ala
115 120 125

Ser Val Val Cys Leu Leu Asn Asn Phe Tyr Pro Arg Glu Ala Lys Val
130 135 140

Gln Trp Lys Val Asp Asn Ala Leu Gln Ser Gly Asn Ser Gln Glu Ser
145 150 155 160

Val Thr Glu Gln Asp Ser Lys Asp Ser Thr Tyr Ser Leu Ser Ser Thr
165 170 175

Leu Thr Leu Ser Lys Ala Asp Tyr Glu Lys His Lys Leu Tyr Ala Cys
180 185 190

Glu Val Thr His Gln Gly Leu Ser Ser Pro Val Thr Lys Ser Phe Asn
195 200 205

Arg Gly Glu Cys
210

<210> SEQ ID NO 304
<211> LENGTH: 449
<212> TYPE: PRT
<213> ORGANISM: Artificial Sequence
<220> FEATURE:
<223> OTHER INFORMATION: Heavy chain (B3)

<400> SEQUENCE: 304

Glu Val Gln Leu Leu Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Asp Ser Ser Gly Trp Ser Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 305
<211> LENGTH: 216

<212> TYPE: PRT
<213> ORGANISM: Artificial Sequence
<220> FEATURE:
<223> OTHER INFORMATION: Light chain (A10)

<400> SEQUENCE: 305

Asp Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Gly Ser Ser Pro Arg
85 90 95

Met Tyr Thr Phe Gly Gln Gly Thr Lys Val Asp Ile Lys Arg Thr Ala
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val Asp Asn Ala Leu Gln Ser Gly Asn
145 150 155 160

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys
180 185 190

Leu Tyr Ala Cys Glu Val Thr His Gln Gly Leu Ser Ser Pro Val Thr
195 200 205

Lys Ser Phe Asn Arg Gly Glu Cys
210 215

<210> SEQ ID NO 306
<211> LENGTH: 448
<212> TYPE: PRT
<213> ORGANISM: Artificial Sequence
<220> FEATURE:
<223> OTHER INFORMATION: Heavy chain (A10)

<400> SEQUENCE: 306

Gln Met Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Leu Gly Glu Leu Asp Asn Trp Phe Asp Pro Trp Gly
100 105 110

```
Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 307
<211> LENGTH: 212
<212> TYPE: PRT
<213> ORGANISM: Artificial Sequence
<220> FEATURE:
<223> OTHER INFORMATION: Light chain (G1)

<400> SEQUENCE: 307

Ser Tyr Glu Leu Thr Gln Pro Pro Ser Leu Ser Val Ser Pro Gly Gln
1               5                   10                  15

Thr Ala Ser Ile Thr Cys Ser Gly Tyr Lys Leu Gly Asp Arg Tyr Val
            20                  25                  30
```

Ser Trp Tyr Gln Gln Lys Thr Gly Gln Ser Pro Val Val Val Ile Tyr
35 40 45

Lys Asp Ser Gln Arg Pro Ser Gly Val Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Gly Thr Gly Val
85 90 95

Phe Gly Gly Gly Thr Lys Leu Thr Val Leu Gly Gln Pro Ala Ala Ala
100 105 110

Pro Ser Val Thr Leu Phe Pro Pro Ser Ser Glu Glu Leu Gln Ala Asn
115 120 125

Lys Ala Thr Leu Val Cys Leu Ile Ser Asp Phe Tyr Pro Gly Ala Val
130 135 140

Thr Val Ala Trp Lys Glu Asp Ser Ser Pro Val Lys Ala Gly Val Glu
145 150 155 160

Thr Thr Thr Pro Ser Lys Gln Ser Asn Asn Lys Tyr Ala Ala Ser Ser
165 170 175

Tyr Leu Ser Leu Thr Pro Glu Gln Trp Lys Ser His Arg Ser Tyr Ser
180 185 190

Cys Gln Val Thr His Glu Gly Ser Thr Val Glu Lys Thr Val Ala Pro
195 200 205

Thr Glu Cys Ser
210

<210> SEQ ID NO 308
<211> LENGTH: 445
<212> TYPE: PRT
<213> ORGANISM: Artificial Sequence
<220> FEATURE:
<223> OTHER INFORMATION: Heavy chain (G1)

<400> SEQUENCE: 308

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Glu Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Val Gly Val Ala Gly Lys Leu Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

```
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 309
<211> LENGTH: 218
<212> TYPE: PRT
<213> ORGANISM: Artificial Sequence
<220> FEATURE:
<223> OTHER INFORMATION: Light chain (G9)

<400> SEQUENCE: 309

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Met Ala Ser Leu Thr Ile Ser Gly Leu
65                  70                  75                  80

Gln Ala Glu Asp Glu Ala Asp Tyr Tyr Cys Ser Ser Tyr Thr Gly Ser
                85                  90                  95
```

```
Ser Thr Leu Asp Val Leu Phe Gly Gly Gly Thr Lys Leu Thr Val Leu
            100                 105                 110

Gly Gln Pro Ala Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215


<210> SEQ ID NO 310
<211> LENGTH: 447
<212> TYPE: PRT
<213> ORGANISM: Artificial Sequence
<220> FEATURE:
<223> OTHER INFORMATION: Heavy chain (G9)

<400> SEQUENCE: 310

Gln Val Gln Leu Val Gln Pro Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Gln Tyr Tyr Asp Gly Gly Tyr Tyr Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 311
<211> LENGTH: 214
<212> TYPE: PRT
<213> ORGANISM: Artificial Sequence
<220> FEATURE:
<223> OTHER INFORMATION: Light chain (H2)

<400> SEQUENCE: 311

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Ile Leu Val Ile Ser
        35                  40                  45

Gly Asn Asn Lys Arg Pro Ser Gly Ile Pro Asp Arg Phe Ser Gly Ser
    50                  55                  60

Ser Ser Gly Asp Thr Ala Ser Leu Thr Ile Ser Gly Ala Gln Ala Glu
65                  70                  75                  80

Asp Glu Ala Asp Tyr Tyr Cys Asn Ser Leu Asp Ser Thr Tyr Asn His
                85                  90                  95

Pro Ile Phe Gly Gly Gly Thr Lys Val Thr Val Leu Gly Gln Pro Ala
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160
```

```
Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 312
<211> LENGTH: 444
<212> TYPE: PRT
<213> ORGANISM: Artificial Sequence
<220> FEATURE:
<223> OTHER INFORMATION: Heavy chain (H2)

<400> SEQUENCE: 312

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile His Trp Val Arg Gln Ala Thr Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Gly Asp Ala Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 313
<211> LENGTH: 214
<212> TYPE: PRT
<213> ORGANISM: Artificial Sequence
<220> FEATURE:
<223> OTHER INFORMATION: Light chain (H11)

<400> SEQUENCE: 313

Ser Tyr Glu Leu Thr Gln Asp Pro Ala Ala Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Val Val Ile Tyr
        35                  40                  45

Gly Arg Asn Asn Arg Pro Ser Gly Ile Pro Asp Arg Phe Ser Gly Ser
    50                  55                  60

Ser Ser Gly Asp Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Gly Asn His
                85                  90                  95

Tyr Val Phe Gly Thr Gly Thr Lys Leu Thr Val Leu Gly Gln Pro Ala
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 314
<211> LENGTH: 444
<212> TYPE: PRT
<213> ORGANISM: Artificial Sequence
<220> FEATURE:
<223> OTHER INFORMATION: Heavy chain (H11)

<400> SEQUENCE: 314

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Ser Ser Ser Asp Tyr Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 315
<211> LENGTH: 216
<212> TYPE: PRT
<213> ORGANISM: Artificial Sequence
<220> FEATURE:
<223> OTHER INFORMATION: Light chain (F12)

<400> SEQUENCE: 315

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Ile Gly Asp Tyr
            20                  25                  30

Asp Tyr Val Ser Trp Tyr Gln Gln His Pro Gly Lys Thr Pro Lys Leu
        35                  40                  45

Met Ile Tyr Asp Val Ser Arg Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ala Ser Tyr Thr Ser Ser
                85                  90                  95

Ser Val Val Val Phe Gly Gly Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 316
<211> LENGTH: 447
<212> TYPE: PRT
<213> ORGANISM: Artificial Sequence
<220> FEATURE:
<223> OTHER INFORMATION: Heavy chain (F12)

<400> SEQUENCE: 316

Gln Val Gln Leu Val Gln Ser Gly Ala Glu Val Lys Lys Pro Gly Glu
```

-continued

```
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Ser Gln Tyr Tyr Asp Gly Gly Tyr Tyr Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430
```

His Asn His Tyr Thr Gln Lys Ser Leu Ser Leu Ser Leu Gly Lys
        435                 440                 445

<210> SEQ ID NO 317
<211> LENGTH: 214
<212> TYPE: PRT
<213> ORGANISM: Artificial Sequence
<220> FEATURE:
<223> OTHER INFORMATION: Light chain (B9)

<400> SEQUENCE: 317

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Ala Tyr Gly Phe Pro Leu
                85                  90                  95

Thr Leu Gly Gly Gly Thr Lys Val Glu Ile Lys Arg Thr Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 318
<211> LENGTH: 452
<212> TYPE: PRT
<213> ORGANISM: Artificial Sequence
<220> FEATURE:
<223> OTHER INFORMATION: Heavy chain (B9)

<400> SEQUENCE: 318

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr

```
65                  70                  75                  80

Met Glu Leu Ser Ser Leu Arg Ser Glu Asp Thr Ala Val Tyr Tyr Cys
                85                  90                  95

Ala Arg Gly Glu Ile Ala Val Ala Gln Asn Trp Asp Tyr Tyr Gly Met
            100                 105                 110

Asp Val Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 319
<211> LENGTH: 217
<212> TYPE: PRT
<213> ORGANISM: Artificial Sequence
<220> FEATURE:
<223> OTHER INFORMATION: Light chain (G11)

<400> SEQUENCE: 319

Gln Ser Ala Leu Thr Gln Pro Arg Ser Val Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Lys Arg Pro Ser Gly Val Pro Asp Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Ser Ser Ser
85 90 95

Ser Thr Leu Val Val Phe Gly Gly Gly Thr Lys Leu Thr Val Leu Gly
100 105 110

Gln Pro Ala Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys
165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

<210> SEQ ID NO 320
<211> LENGTH: 447
<212> TYPE: PRT
<213> ORGANISM: Artificial Sequence
<220> FEATURE:
<223> OTHER INFORMATION: Heavy chain (G11)

<400> SEQUENCE: 320

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Ser Gln Tyr Tyr Asp Gly Gly Tyr Tyr Met Asp Val Trp Gly Gln
100 105 110

Gly Thr Leu Val Thr Val Ser Ser Ala Ser Thr Lys Gly Pro Ser Val

```
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 321
<211> LENGTH: 214
<212> TYPE: PRT
<213> ORGANISM: Artificial Sequence
<220> FEATURE:
<223> OTHER INFORMATION: Light chain (G6)

<400> SEQUENCE: 321

Ser Tyr Glu Leu Thr Gln Asp Pro Ala Val Ser Val Ala Leu Gly Gln
1               5                   10                  15

Thr Val Thr Ile Thr Cys Gln Gly Asp Ser Leu Arg Arg Tyr Tyr Ala
            20                  25                  30

Thr Trp Tyr Gln Gln Lys Pro Gly Gln Ala Pro Val Leu Val Ile Tyr
```

```
        35                  40                  45

Gly Gln Asn Tyr Arg Pro Ser Gly Ile Pro Asp Arg Phe Ser Gly Ser
    50                  55                  60

Asn Ser Gly Thr Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Ala
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 322
<211> LENGTH: 446
<212> TYPE: PRT
<213> ORGANISM: Artificial Sequence
<220> FEATURE:
<223> OTHER INFORMATION: Heavy chain (G6)

<400> SEQUENCE: 322

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Tyr Ser Ser Ser Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 323
<211> LENGTH: 216
<212> TYPE: PRT
<213> ORGANISM: Artificial Sequence
<220> FEATURE:
<223> OTHER INFORMATION: Light chain (F11)

<400> SEQUENCE: 323

Gln Ser Val Leu Thr Gln Pro Pro Ser Thr Ser Gly Thr Pro Gly Gln
1               5                   10                  15

Thr Phe Ser Ile Phe Cys Ser Gly Ser Ser Ser Asn Ile Gly Thr Asn
            20                  25                  30

Thr Val Asn Trp Tyr Gln Gln Leu Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Glu Thr Trp Asp Asp Ser Leu
                85                  90                  95

Lys Gly Pro Val Phe Gly Gly Gly Thr Lys Val Thr Val Leu Gly Gln
```

```
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 324
<211> LENGTH: 446
<212> TYPE: PRT
<213> ORGANISM: Artificial Sequence
<220> FEATURE:
<223> OTHER INFORMATION: Heavy chain (F11)

<400> SEQUENCE: 324

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Thr Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Glu Trp Glu Leu Gly Asp Ala Phe Asp Ile Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
```

```
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 325
<211> LENGTH: 212
<212> TYPE: PRT
<213> ORGANISM: Artificial Sequence
<220> FEATURE:
<223> OTHER INFORMATION: Light chain (D3)

<400> SEQUENCE: 325

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Arg Trp
                85                  90                  95

Thr Phe Gly Gln Gly Thr Lys Val Glu Ile Lys Arg Thr Ala Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
```

```
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210


<210> SEQ ID NO 326
<211> LENGTH: 449
<212> TYPE: PRT
<213> ORGANISM: Artificial Sequence
<220> FEATURE:
<223> OTHER INFORMATION: Heavy chain (D3)

<400> SEQUENCE: 326

Glu Val Gln Leu Leu Glu Ser Gly Gly Gly Val Val Gln Pro Gly Arg
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Ser Tyr Gly Tyr Tyr Tyr Gly Met Asp Val Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
```

```
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 327
<211> LENGTH: 214
<212> TYPE: PRT
<213> ORGANISM: Artificial Sequence
<220> FEATURE:
<223> OTHER INFORMATION: Light chain (B12)

<400> SEQUENCE: 327

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Arg
                85                  90                  95

Thr Phe Gly Gln Gly Thr Lys Val Glu Ile Lys Arg Thr Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 328
<211> LENGTH: 449
<212> TYPE: PRT
<213> ORGANISM: Artificial Sequence
<220> FEATURE:
<223> OTHER INFORMATION: Heavy chain (B12)

<400> SEQUENCE: 328

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Gly Ala Ser Ile Val Gly Ala Thr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365
```

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Arg Leu Thr Val Asp Lys
405 410 415

Ser Arg Trp Gln Glu Gly Asn Val Phe Ser Cys Ser Val Met His Glu
420 425 430

Ala Leu His Asn His Tyr Thr Gln Lys Ser Leu Ser Leu Ser Leu Gly
435 440 445

Lys

<210> SEQ ID NO 329
<211> LENGTH: 218
<212> TYPE: PRT
<213> ORGANISM: Artificial Sequence
<220> FEATURE:
<223> OTHER INFORMATION: Light chain (E4)

<400> SEQUENCE: 329

Asn Phe Met Leu Thr Gln Pro His Ser Val Ser Glu Ser Pro Gly Lys
1 5 10 15

Thr Val Thr Ile Ser Cys Thr Arg Ser Ser Gly Ser Ile Ala Ser Asn
20 25 30

Tyr Val Gln Trp Tyr Gln Gln Arg Pro Gly Ser Ser Pro Thr Thr Val
35 40 45

Ile Tyr Glu Asp Asn Gln Arg Pro Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Thr
85 90 95

Gly Asn Arg Asn Tyr Val Phe Gly Thr Gly Thr Gln Leu Thr Val Leu
100 105 110

Gly Gln Pro Ala Ala Ala Pro Ser Val Thr Leu Phe Pro Pro Ser Ser
115 120 125

Glu Glu Ile Gln Ala Asn Lys Ala Thr Leu Val Cys Leu Ile Ser Asp
130 135 140

Phe Tyr Pro Gly Ala Val Thr Val Ala Trp Lys Ala Asp Ser Ser Pro
145 150 155 160

Val Lys Ala Gly Val Glu Thr Thr Thr Pro Ser Lys Gln Ser Asn Asn
165 170 175

Lys Tyr Ala Ala Ser Ser Tyr Leu Ser Leu Thr Pro Glu Gln Trp Lys
180 185 190

Ser His Arg Ser Tyr Ser Cys Gln Val Thr His Glu Gly Ser Thr Val
195 200 205

Glu Lys Thr Val Ala Pro Thr Glu Cys Ser
210 215

<210> SEQ ID NO 330
<211> LENGTH: 448
<212> TYPE: PRT
<213> ORGANISM: Artificial Sequence
<220> FEATURE:
<223> OTHER INFORMATION: Heavy chain (E4)

<400> SEQUENCE: 330

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Met Thr Arg Asp Met Ser Thr Asp Thr Ala Tyr
65                  70                  75                  80

Met Glu Leu Ser Ser Leu Thr Tyr Asp Asp Thr Ala Val Tyr Phe Cys
                85                  90                  95

Val Arg Gly Pro Ser Leu Asn Tyr Ala Gly Tyr Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

```
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 331
<211> LENGTH: 214
<212> TYPE: PRT
<213> ORGANISM: Artificial Sequence
<220> FEATURE:
<223> OTHER INFORMATION: Light chain (E12)

<400> SEQUENCE: 331

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Ser Gly Gln Ala Pro Val Leu Val Ile Tyr
        35                  40                  45

Gly Lys Glu Lys Arg Pro Ser Gly Ile Pro Asp Arg Phe Ser Gly Ser
    50                  55                  60

Ser Ser Gly Asn Thr Ala Ser Leu Thr Ile Thr Gly Ala Arg Ala Glu
65                  70                  75                  80

Asp Glu Ala Asp Tyr Tyr Cys Asn Ser Arg Gly Ser Thr Thr Asp Tyr
                85                  90                  95

Met Val Phe Gly Gly Gly Thr Gln Leu Thr Val Leu Gly Gln Pro Ala
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 332
<211> LENGTH: 444
<212> TYPE: PRT
<213> ORGANISM: Artificial Sequence
<220> FEATURE:
<223> OTHER INFORMATION: Heavy chain (E12)

<400> SEQUENCE: 332

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Gly Met Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 333
<211> LENGTH: 214
<212> TYPE: PRT
<213> ORGANISM: Artificial Sequence
<220> FEATURE:

<223> OTHER INFORMATION: Light chain (D1)

<400> SEQUENCE: 333

Glu Thr Thr Leu Thr Gln Ser Pro Ala Phe Met Ser Ala Thr Pro Gly
1 5 10 15

Asp Lys Val Asn Ile Ser Cys Lys Ala Ser Gln Asp Ile Asp Asp Asp
20 25 30

Met Asn Trp Tyr Gln Gln Lys Pro Gly Glu Ala Ala Ile Ser Ile Ile
35 40 45

Gln Glu Ala Ser Thr Leu Val Pro Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Lys Phe Pro Tyr
85 90 95

Thr Phe Gly Gln Gly Thr Lys Leu Glu Ile Lys Arg Thr Ala Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Leu Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 334
<211> LENGTH: 444
<212> TYPE: PRT
<213> ORGANISM: Artificial Sequence
<220> FEATURE:
<223> OTHER INFORMATION: Heavy chain (D1)

<400> SEQUENCE: 334

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Ser Arg Gly Val Asp Glu Gly Asp Tyr Trp Gly Gln Gly Thr Met
100 105 110

Val Thr Val Ser Ser Ala Ser Thr Lys Gly Pro Ser Val Phe Pro Leu
115 120 125

```
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 335
<211> LENGTH: 216
<212> TYPE: PRT
<213> ORGANISM: Artificial Sequence
<220> FEATURE:
<223> OTHER INFORMATION: Light chain (E6)

<400> SEQUENCE: 335

```
Asn Phe Met Leu Thr Gln Pro His Ser Val Ser Glu Ser Pro Gly Lys
1               5                   10                  15

Thr Val Thr Leu Ser Cys Thr Gly Ser Ser Gly Asn Ile Ala Ser Asn
            20                  25                  30

Tyr Val Gln Trp Tyr Gln His Arg Pro Gly Ser Ala Pro Thr Thr Val
        35                  40                  45
```

```
Ile Tyr Arg Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Arg Pro Glu Asp Glu Ala Asp Tyr Tyr Cys Gln Ser Tyr Asp Ser
                85                  90                  95

Ser Ser Trp Val Phe Gly Gly Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 336
<211> LENGTH: 451
<212> TYPE: PRT
<213> ORGANISM: Artificial Sequence
<220> FEATURE:
<223> OTHER INFORMATION: Heavy chain (E6)

<400> SEQUENCE: 336

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Asp Ile Thr Trp Val Arg Gln Ala Pro Gly Gln Gly Leu Glu Trp Met
        35                  40                  45

Gly Trp Met Asn Pro Asn Ser Gly Asn Ser Arg Ser Ala Gln Lys Phe
    50                  55                  60

Gln Gly Arg Val Ser Met Thr Ser Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Asp Tyr Ser Gly Val Val Leu Thr Ala Thr Ala Leu Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 337
<211> LENGTH: 216
<212> TYPE: PRT
<213> ORGANISM: Artificial Sequence
<220> FEATURE:
<223> OTHER INFORMATION: Light chain (E9)

<400> SEQUENCE: 337

Gln Ser Glu Leu Thr Gln Leu Pro Ser Ala Ser Glu Thr Pro Gly Gln
1               5                   10                  15

Arg Val Thr Ile Ser Cys Ser Gly Ser Ser Ser Asn Ile Gly Asn Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95
```

```
Ser Gly Trp Val Phe Gly Gly Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 338
<211> LENGTH: 450
<212> TYPE: PRT
<213> ORGANISM: Artificial Sequence
<220> FEATURE:
<223> OTHER INFORMATION: Heavy chain (E9)

<400> SEQUENCE: 338

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Arg Ile Ala Ala Ala Gly Met Arg Glu Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 339
<211> LENGTH: 220
<212> TYPE: PRT
<213> ORGANISM: Artificial Sequence
<220> FEATURE:
<223> OTHER INFORMATION: Light chain (A11)

<400> SEQUENCE: 339

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Tyr Thr Phe Gly Gln Gly Thr Lys Val Glu Ile
            100                 105                 110

Lys Arg Thr Ala Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 340
<211> LENGTH: 447
<212> TYPE: PRT
<213> ORGANISM: Artificial Sequence
<220> FEATURE:
<223> OTHER INFORMATION: Heavy chain (A11)

<400> SEQUENCE: 340

Glu Val Gln Leu Leu Glu Ser Gly Gly Gly Leu Glu Gln Pro Gly Gly
1               5                   10                  15

Phe Leu Arg Leu Ser Cys Ala Ala Ser Gly Phe Ser Phe Thr Ser Tyr
            20                  25                  30

Ala Met Thr Trp Val Arg Gln Ala Pro Gly Lys Gly Leu Glu Trp Val
        35                  40                  45

Ser Gly Ile Ser Ser Asp Gly Thr Thr Thr Thr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Arg Asp Glu Asp Thr Ala Val Tyr Tyr Cys
                85                  90                  95

Ala Arg Asp Gln Leu Leu Gly Trp Asp Ala Leu Asn Val Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 341
<211> LENGTH: 327
<212> TYPE: PRT
<213> ORGANISM: Artificial Sequence
<220> FEATURE:
<223> OTHER INFORMATION: IgG4 Fc

<400> SEQUENCE: 341

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 342
<211> LENGTH: 102
<212> TYPE: PRT
<213> ORGANISM: Artificial Sequence
<220> FEATURE:
<223> OTHER INFORMATION: Kappa constant region

<400> SEQUENCE: 342

Pro Ser Val Phe Ile Phe Pro Pro Ser Asp Glu Gln Leu Lys Ser Gly
1               5                   10                  15

Thr Ala Ser Val Val Cys Leu Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ser Leu Ser
    50                  55                  60

Ser Thr Leu Thr Leu Ser Lys Ala Asp Tyr Glu Lys His Lys Leu Tyr
65                  70                  75                  80

Ala Cys Glu Val Thr His Gln Gly Leu Ser Ser Pro Val Thr Lys Ser
                85                  90                  95

Phe Asn Arg Gly Glu Cys
            100

<210> SEQ ID NO 343
<211> LENGTH: 100
<212> TYPE: PRT
<213> ORGANISM: Artificial Sequence
<220> FEATURE:
<223> OTHER INFORMATION: Lambda constant region

<400> SEQUENCE: 343

Pro Ser Val Thr Leu Phe Pro Pro Ser Ser Glu Glu Leu Gln Ala Asn
1               5                   10                  15

Lys Ala Thr Leu Val Cys Leu Ile Ser Asp Phe Tyr Pro Gly Ala Val
            20                  25                  30

Thr Val Ala Trp Lys Ala Asp Ser Ser Pro Val Lys Ala Gly Val Glu
        35                  40                  45

Thr Thr Thr Pro Ser Lys Gln Ser Asn Asn Lys Tyr Ala Ala Ser Ser
    50                  55                  60

Tyr Leu Ser Leu Thr Pro Glu Gln Trp Lys Ser His Arg Ser Tyr Ser

```
65                  70                  75                  80

Cys Gln Val Thr His Glu Gly Ser Thr Val Glu Lys Thr Val Ala Pro
                85                  90                  95

Thr Glu Cys Ser
            100


<210> SEQ ID NO 344
<211> LENGTH: 106
<212> TYPE: PRT
<213> ORGANISM: Artificial Sequence
<220> FEATURE:
<223> OTHER INFORMATION: Lambda CL.1 constant region

<400> SEQUENCE: 344

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 345
<211> LENGTH: 110
<212> TYPE: PRT
<213> ORGANISM: Artificial Sequence
<220> FEATURE:
<223> OTHER INFORMATION: Light chain variable region (E3.1)

<400> SEQUENCE: 345

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Phe Tyr Ala
            20                  25                  30

Ser Trp Tyr Gln Gln Lys Ser Gly Gln Ala Pro Val Leu Val Met Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Ser His
                85                  90                  95

Leu Thr Gly Val Phe Gly Gly Gly Thr Lys Val Thr Val Leu
            100                 105                 110


<210> SEQ ID NO 346
<211> LENGTH: 330
<212> TYPE: PRT
<213> ORGANISM: Artificial Sequence
<220> FEATURE:
<223> OTHER INFORMATION: Light chain variable region (E3.1) coding gene

<400> SEQUENCE: 346
```

```
Thr Cys Cys Thr Ala Thr Gly Ala Gly Cys Thr Gly Ala Cys Thr Cys
1               5                   10                  15

Ala Gly Gly Ala Cys Cys Cys Thr Gly Cys Thr Gly Thr Gly Thr Cys
            20                  25                  30

Thr Gly Thr Gly Gly Cys Cys Thr Thr Gly Gly Gly Ala Cys Ala Gly
        35                  40                  45

Ala Cys Ala Gly Thr Cys Ala Gly Gly Ala Thr Cys Ala Cys Ala Thr
    50                  55                  60

Gly Cys Cys Ala Gly Gly Gly Ala Gly Ala Cys Ala Gly Cys Cys Thr
65                  70                  75                  80

Cys Ala Gly Ala Ala Ala Cys Thr Thr Thr Thr Ala Thr Gly Cys Ala
                85                  90                  95

Ala Gly Cys Thr Gly Gly Thr Ala Cys Cys Ala Gly Cys Ala Gly Ala
            100                 105                 110

Ala Gly Thr Cys Ala Gly Gly Ala Cys Ala Gly Gly Cys Cys Cys Cys
        115                 120                 125

Ala Gly Thr Thr Cys Thr Thr Gly Thr Cys Ala Thr Gly Thr Ala Thr
    130                 135                 140

Gly Gly Thr Ala Ala Ala Ala Ala Cys Ala Ala Cys Cys Gly Gly Cys
145                 150                 155                 160

Cys Cys Thr Cys Ala Gly Gly Gly Ala Thr Cys Cys Cys Ala Gly Ala
                165                 170                 175

Cys Cys Gly Ala Thr Thr Cys Thr Cys Thr Gly Gly Cys Thr Cys Cys
            180                 185                 190

Ala Cys Cys Thr Cys Ala Gly Gly Ala Ala Ala Cys Ala Cys Ala Gly
        195                 200                 205

Cys Thr Thr Cys Cys Thr Thr Gly Ala Cys Cys Ala Thr Cys Ala Cys
    210                 215                 220

Thr Gly Gly Gly Gly Cys Thr Cys Ala Gly Gly Cys Gly Gly Ala Ala
225                 230                 235                 240

Gly Ala Thr Gly Ala Gly Gly Cys Thr Gly Ala Cys Thr Ala Thr Thr
                245                 250                 255

Ala Cys Thr Gly Thr Ala Ala Cys Thr Cys Cys Cys Gly Gly Gly Ala
            260                 265                 270

Cys Ala Gly Cys Ala Gly Thr Gly Gly Thr Ala Gly Cys Cys Ala Thr
        275                 280                 285

Thr Thr Gly Ala Cys Gly Gly Gly Cys Gly Thr Ala Thr Thr Cys Gly
    290                 295                 300

Gly Cys Gly Gly Ala Gly Gly Gly Ala Cys Cys Ala Ala Gly Gly Thr
305                 310                 315                 320

Cys Ala Cys Cys Gly Thr Cys Cys Thr Ala
                325                 330
```

<210> SEQ ID NO 347
<211> LENGTH: 216
<212> TYPE: PRT
<213> ORGANISM: Artificial Sequence
<220> FEATURE:
<223> OTHER INFORMATION: Light chain (E3.1)

<400> SEQUENCE: 347

```
Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Phe Tyr Ala
            20                  25                  30
```

```
Ser Trp Tyr Gln Gln Lys Ser Gly Gln Ala Pro Val Leu Val Met Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Ser His
                85                  90                  95

Leu Thr Gly Val Phe Gly Gly Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 348
<211> LENGTH: 650
<212> TYPE: PRT
<213> ORGANISM: Artificial Sequence
<220> FEATURE:
<223> OTHER INFORMATION: LILRB1(AAH15731)

<400> SEQUENCE: 348

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175
```

```
Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590
```

```
Ala Glu Glu Asp Arg Gln Met Asp Thr Glu Ala Ala Ala Ser Glu Ala
        595                 600                 605

Pro Gln Asp Val Thr Tyr Ala Gln Leu His Ser Leu Thr Leu Arg Arg
    610                 615                 620

Lys Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650


<210> SEQ ID NO 349
<211> LENGTH: 598
<212> TYPE: PRT
<213> ORGANISM: Artificial Sequence
<220> FEATURE:
<223> OTHER INFORMATION: LILRB2(AAH36827)

<400> SEQUENCE: 349

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala Tyr Asn Leu Ser Ser
    290                 295                 300
```

```
Glu Trp Ser Ala Pro Ser Asp Pro Leu Asp Ile Leu Ile Thr Gly Gln
305                 310                 315                 320

Ile His Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Gly Glu Pro Pro Ala Glu Pro Ser Ile Tyr
            580                 585                 590

Ala Thr Leu Ala Ile His
        595
```

<210> SEQ ID NO 350
<211> LENGTH: 631
<212> TYPE: PRT
<213> ORGANISM: Artificial Sequence
<220> FEATURE:
<223> OTHER INFORMATION: LILRB3(XP_006726377)

<400> SEQUENCE: 350

```
Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Leu Glu Ala Gln Glu Tyr Arg Leu Asp Lys Glu Gly
    50                  55                  60
```

```
Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Gly Gly
                165                 170                 175

Phe Gln Ala Leu Phe Pro Val Gly Pro Val Asn Pro Ser His Arg Trp
            180                 185                 190

Arg Phe Thr Cys Tyr Tyr Tyr Tyr Met Asn Thr Pro Gln Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285

Ser His Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Gly Ser Ser Leu Pro Pro Thr Gly Pro
            420                 425                 430

Pro Ser Thr Pro Gly Leu Gly Arg Tyr Leu Glu Val Leu Ile Gly Val
        435                 440                 445

Ser Val Ala Phe Val Leu Leu Leu Phe Leu Leu Leu Phe Leu Leu Leu
    450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
```

```
                485                 490                 495

Gly Leu Leu Arg Arg Ser Ser Pro Ala Ala Asp Val Gln Glu Glu Asn
            500                 505                 510

Leu Tyr Ala Ala Val Lys Asp Thr Gln Ser Glu Asp Arg Val Glu Leu
        515                 520                 525

Asp Ser Gln Ser Pro His Asp Glu Asp Pro Gln Ala Val Thr Tyr Ala
    530                 535                 540

Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
                565                 570                 575

Asp Arg Gln Met Asp Thr Glu Ala Ala Ala Ser Glu Ala Ser Gln Asp
            580                 585                 590

Val Thr Tyr Ala Gln Leu His Ser Leu Thr Leu Arg Arg Lys Ala Thr
        595                 600                 605

Glu Pro Pro Pro Ser Gln Glu Gly Glu Pro Pro Ala Glu Pro Ser Ile
    610                 615                 620

Tyr Ala Thr Leu Ala Ile His
625                 630


<210> SEQ ID NO 351
<211> LENGTH: 448
<212> TYPE: PRT
<213> ORGANISM: Artificial Sequence
<220> FEATURE:
<223> OTHER INFORMATION: LILRB4(NP_001265355)

<400> SEQUENCE: 351

Met Ile Pro Thr Phe Thr Ala Leu Leu Cys Leu Gly Leu Ser Leu Gly
1               5                   10                  15

Pro Arg Thr His Met Gln Ala Gly Pro Leu Pro Lys Pro Thr Leu Trp
            20                  25                  30

Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
    130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Gly Pro
```

```
    210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
                325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
        355                 360                 365

Arg Arg Glu Met Ala Ser Pro Pro Ser Pro Leu Ser Gly Glu Phe Leu
    370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Arg Leu His
                405                 410                 415

Ser Phe Thr Leu Arg Gln Lys Ala Thr Glu Pro Pro Pro Ser Gln Glu
            420                 425                 430

Gly Ala Ser Pro Ala Glu Pro Ser Val Tyr Ala Thr Leu Ala Ile His
        435                 440                 445


<210> SEQ ID NO 352
<211> LENGTH: 590
<212> TYPE: PRT
<213> ORGANISM: Artificial Sequence
<220> FEATURE:
<223> OTHER INFORMATION: LILRB5(NP_006831)

<400> SEQUENCE: 352

Met Thr Leu Thr Leu Ser Val Leu Ile Cys Leu Gly Leu Ser Val Gly
1               5                   10                  15

Pro Arg Thr Cys Val Gln Ala Gly Thr Leu Pro Lys Pro Thr Leu Trp
            20                  25                  30

Ala Glu Pro Ala Ser Val Ile Ala Arg Gly Lys Pro Val Thr Leu Trp
        35                  40                  45

Cys Gln Gly Pro Leu Glu Thr Glu Glu Tyr Arg Leu Asp Lys Glu Gly
    50                  55                  60

Leu Pro Trp Ala Arg Lys Arg Gln Asn Pro Leu Glu Pro Gly Ala Lys
65                  70                  75                  80

Ala Lys Phe His Ile Pro Ser Thr Val Tyr Asp Ser Ala Gly Arg Tyr
                85                  90                  95

Arg Cys Tyr Tyr Glu Thr Pro Ala Gly Trp Ser Glu Pro Ser Asp Pro
            100                 105                 110

Leu Glu Leu Val Ala Thr Gly Phe Tyr Ala Glu Pro Thr Leu Leu Ala
        115                 120                 125

Leu Pro Ser Pro Val Val Ala Ser Gly Gly Asn Val Thr Leu Gln Cys
```

```
    130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
                165                 170                 175

Gln Ala Leu Phe Pro Val Gly Pro Val Thr Pro Ser Cys Arg Trp Arg
            180                 185                 190

Phe Arg Cys Tyr Tyr Tyr Tyr Arg Lys Asn Pro Gln Val Trp Ser Asn
        195                 200                 205

Pro Ser Asp Leu Leu Glu Ile Leu Val Pro Gly Val Ser Arg Lys Pro
    210                 215                 220

Ser Leu Leu Ile Pro Gln Gly Ser Val Val Ala Arg Gly Gly Ser Leu
225                 230                 235                 240

Thr Leu Gln Cys Arg Ser Asp Val Gly Tyr Asp Ile Phe Val Leu Tyr
                245                 250                 255

Lys Glu Gly Glu His Asp Leu Val Gln Gly Ser Gly Gln Gln Pro Gln
            260                 265                 270

Ala Gly Leu Ser Gln Ala Asn Phe Thr Leu Gly Pro Val Ser Arg Ser
        275                 280                 285

His Gly Gly Gln Tyr Arg Cys Tyr Gly Ala His Asn Leu Ser Pro Arg
    290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                325                 330                 335

Gly Glu Asn Val Thr Leu Leu Cys Gln Ser Trp His Gln Ile Asp Thr
            340                 345                 350

Phe Phe Leu Thr Lys Glu Gly Ala Ala His Pro Pro Leu Cys Leu Lys
        355                 360                 365

Ser Lys Tyr Gln Ser Tyr Arg His Gln Ala Glu Phe Ser Met Ser Pro
    370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                405                 410                 415

Val Ser Gly Pro Ser Gly Asp Pro Ser Leu Ser Pro Thr Gly Ser Thr
            420                 425                 430

Pro Thr Pro Gly Pro Glu Asp Gln Pro Leu Thr Pro Thr Gly Leu Asp
        435                 440                 445

Pro Gln Ser Gly Leu Gly Arg His Leu Gly Val Val Thr Gly Val Ser
    450                 455                 460

Val Ala Phe Val Leu Leu Leu Phe Leu Leu Leu Phe Leu Leu Leu Arg
465                 470                 475                 480

His Arg His Gln Ser Lys His Arg Thr Ser Ala His Phe Tyr Arg Pro
                485                 490                 495

Ala Gly Ala Ala Gly Pro Glu Pro Lys Asp Gln Gly Leu Gln Lys Arg
            500                 505                 510

Ala Ser Pro Val Ala Asp Ile Gln Glu Glu Ile Leu Asn Ala Ala Val
        515                 520                 525

Lys Asp Thr Gln Pro Lys Asp Gly Val Glu Met Asp Ala Arg Ala Ala
    530                 535                 540

Ala Ser Glu Ala Pro Gln Asp Val Thr Tyr Ala Gln Leu His Ser Leu
545                 550                 555                 560
```

```
Thr Leu Arg Arg Glu Ala Thr Glu Pro Pro Pro Ser Gln Glu Arg Glu
                565                 570                 575

Pro Pro Ala Glu Pro Ser Ile Tyr Ala Pro Leu Ala Ile His
            580                 585                 590


<210> SEQ ID NO 353
<211> LENGTH: 489
<212> TYPE: PRT
<213> ORGANISM: Artificial Sequence
<220> FEATURE:
<223> OTHER INFORMATION: LILRA1(NP_006854)

<400> SEQUENCE: 353

Met Thr Pro Ile Val Thr Val Leu Ile Cys Leu Arg Leu Ser Leu Gly
1               5                   10                  15

Pro Arg Thr His Val Gln Ala Gly Thr Leu Pro Lys Pro Thr Leu Trp
            20                  25                  30

Ala Glu Pro Gly Ser Val Ile Thr Gln Gly Ser Pro Val Thr Leu Trp
        35                  40                  45

Cys Gln Gly Ile Leu Glu Thr Gln Glu Tyr Arg Leu Tyr Arg Glu Lys
    50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Gly Glu
225                 230                 235                 240

Ser Leu Thr Leu Gln Cys Val Ser Asp Val Ser Tyr Asp Arg Phe Val
                245                 250                 255

Leu Tyr Lys Glu Gly Glu Arg Asp Phe Leu Gln Leu Pro Gly Pro Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Ser Gly Ala Tyr Asn Leu Ser
    290                 295                 300

Ser Glu Trp Ser Ala Pro Ser Asp Pro Leu Asp Ile Leu Ile Ala Gly
305                 310                 315                 320

Gln Phe Arg Gly Arg Pro Phe Ile Ser Val His Pro Gly Pro Thr Val
                325                 330                 335
```

```
Ala Ser Gly Glu Asn Val Thr Leu Leu Cys Gln Ser Trp Gly Pro Phe
            340                 345                 350

His Thr Phe Leu Leu Thr Lys Ala Gly Ala Ala Asp Ala Pro Leu Arg
        355                 360                 365

Leu Arg Ser Ile His Glu Tyr Pro Lys Tyr Gln Ala Glu Phe Pro Met
    370                 375                 380

Ser Pro Val Thr Ser Ala His Ser Gly Thr Tyr Arg Cys Tyr Gly Ser
385                 390                 395                 400

Leu Ser Ser Asn Pro Tyr Leu Leu Ser His Pro Ser Asp Ser Leu Glu
                405                 410                 415

Leu Met Val Ser Gly Ala Ala Glu Thr Leu Ser Pro Pro Gln Asn Lys
            420                 425                 430

Ser Asp Ser Lys Ala Gly Ala Ala Asn Thr Leu Ser Pro Ser Gln Asn
        435                 440                 445

Lys Thr Ala Ser His Pro Gln Asp Tyr Thr Val Glu Asn Leu Ile Arg
    450                 455                 460

Met Gly Ile Ala Gly Leu Val Leu Val Val Leu Gly Ile Leu Leu Phe
465                 470                 475                 480

Glu Ala Gln His Ser Gln Arg Ser Leu
                485


<210> SEQ ID NO 354
<211> LENGTH: 466
<212> TYPE: PRT
<213> ORGANISM: Artificial Sequence
<220> FEATURE:
<223> OTHER INFORMATION: LILRA2(AAH17412)

<400> SEQUENCE: 354

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Ile Gln Gly Ser Pro Val Thr Leu Arg
        35                  40                  45

Cys Gln Gly Ser Leu Gln Ala Glu Glu Tyr His Leu Tyr Arg Glu Asn
    50                  55                  60

Lys Ser Ala Ser Trp Val Arg Arg Ile Gln Glu Pro Gly Lys Asn Gly
65                  70                  75                  80

Gln Phe Pro Ile Pro Ser Ile Thr Trp Glu His Ala Gly Arg Tyr His
                85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
            180                 185                 190

Tyr Arg Cys Tyr Ala Tyr Asp Ser Asn Ser Pro Tyr Val Trp Ser Leu
        195                 200                 205
```

```
Pro Ser Asp Leu Leu Glu Leu Leu Val Pro Gly Val Ser Lys Lys Pro
    210                 215                 220

Ser Leu Ser Val Gln Pro Gly Pro Met Val Ala Pro Gly Glu Ser Leu
225                 230                 235                 240

Thr Leu Gln Cys Val Ser Asp Val Gly Tyr Asp Arg Phe Val Leu Tyr
                245                 250                 255

Lys Glu Gly Glu Arg Asp Phe Leu Gln Arg Pro Gly Trp Gln Pro Gln
            260                 265                 270

Ala Gly Leu Ser Gln Ala Asn Phe Thr Leu Gly Pro Val Ser Pro Ser
        275                 280                 285

His Gly Gly Gln Tyr Arg Cys Tyr Ser Ala His Asn Leu Ser Ser Glu
    290                 295                 300

Trp Ser Ala Pro Ser Asp Pro Leu Asp Ile Leu Ile Thr Gly Gln Phe
305                 310                 315                 320

Tyr Asp Arg Pro Ser Leu Ser Val Gln Pro Val Pro Thr Val Ala Pro
                325                 330                 335

Gly Lys Asn Val Thr Leu Leu Cys Gln Ser Arg Gly Gln Phe His Thr
            340                 345                 350

Phe Leu Leu Thr Lys Glu Gly Ala Gly His Pro Pro Leu His Leu Arg
        355                 360                 365

Ser Glu His Gln Ala Gln Gln Asn Gln Ala Glu Phe Arg Met Gly Pro
    370                 375                 380

Val Thr Ser Ala His Val Gly Thr Tyr Arg Cys Tyr Ser Ser Leu Ser
385                 390                 395                 400

Ser Asn Pro Tyr Leu Leu Ser Leu Pro Ser Asp Pro Leu Glu Leu Val
                405                 410                 415

Val Ser Ala Ser Leu Gly Gln His Pro Gln Asp Tyr Thr Val Glu Asn
            420                 425                 430

Leu Ile Arg Met Gly Val Ala Gly Leu Val Leu Val Val Leu Gly Ile
        435                 440                 445

Leu Leu Phe Glu Ala Gln His Ser Gln Arg Ser Leu Gln Asp Ala Ala
    450                 455                 460

Gly Arg
465


<210> SEQ ID NO 355
<211> LENGTH: 439
<212> TYPE: PRT
<213> ORGANISM: Artificial Sequence
<220> FEATURE:
<223> OTHER INFORMATION: LILRA3(AAH28208)

<400> SEQUENCE: 355

Met Thr Ser Ile Leu Thr Val Leu Ile Cys Leu Gly Leu Ser Leu Asp
1               5                   10                  15

Pro Arg Thr His Val Gln Ala Gly Pro Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Ser Leu Glu Thr Gln Glu Tyr His Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Leu Ser Ile Thr Trp Glu His Ala Gly Arg Tyr
                85                  90                  95
```

```
Cys Cys Ile Tyr Gly Ser His Thr Val Gly Leu Ser Glu Ser Ser Asp
            100                 105                 110

Pro Leu Glu Leu Val Val Thr Gly Ala Tyr Ser Lys Pro Thr Leu Ser
        115                 120                 125

Ala Leu Pro Ser Pro Val Val Thr Ser Gly Gly Asn Val Thr Ile Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Leu Val Pro Gly Val Ser Lys
    210                 215                 220

Lys Pro Ser Leu Ser Val Gln Pro Gly Pro Val Val Ala Pro Gly Glu
225                 230                 235                 240

Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Thr Cys Ser Gly Ala Tyr Asn Leu Ser
    290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
    370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
                405                 410                 415

Leu Val Val Ser Gly Ala Ala Glu Thr Leu Ser Pro Pro Gln Asn Lys
            420                 425                 430

Ser Asp Ser Lys Ala Gly Glu
        435
```

<210> SEQ ID NO 356
<211> LENGTH: 499
<212> TYPE: PRT
<213> ORGANISM: Artificial Sequence
<220> FEATURE:
<223> OTHER INFORMATION: LILRA4(NP_036408)

<400> SEQUENCE: 356

```
Met Thr Leu Ile Leu Thr Ser Leu Leu Phe Phe Gly Leu Ser Leu Gly
1               5                   10                  15
```

```
Pro Arg Thr Arg Val Gln Ala Glu Asn Leu Pro Lys Pro Ile Leu Trp
            20                  25                  30

Ala Glu Pro Gly Pro Val Ile Thr Trp His Asn Pro Val Thr Ile Trp
        35                  40                  45

Cys Gln Gly Thr Leu Glu Ala Gln Gly Tyr Arg Leu Asp Lys Glu Gly
    50                  55                  60

Asn Ser Met Ser Arg His Ile Leu Lys Thr Leu Glu Ser Glu Asn Lys
65                  70                  75                  80

Val Lys Leu Ser Ile Pro Ser Met Met Trp Glu His Ala Gly Arg Tyr
                85                  90                  95

His Cys Tyr Tyr Gln Ser Pro Ala Gly Trp Ser Glu Pro Ser Asp Pro
            100                 105                 110

Leu Glu Leu Val Val Thr Ala Tyr Ser Arg Pro Thr Leu Ser Ala Leu
        115                 120                 125

Pro Ser Pro Val Val Thr Ser Gly Val Asn Val Thr Leu Arg Cys Ala
    130                 135                 140

Ser Arg Leu Gly Leu Gly Arg Phe Thr Leu Ile Glu Glu Gly Asp His
145                 150                 155                 160

Arg Leu Ser Trp Thr Leu Asn Ser His Gln His Asn His Gly Lys Phe
                165                 170                 175

Gln Ala Leu Phe Pro Met Gly Pro Leu Thr Phe Ser Asn Arg Gly Thr
            180                 185                 190

Phe Arg Cys Tyr Gly Tyr Glu Asn Asn Thr Pro Tyr Val Trp Ser Glu
        195                 200                 205

Pro Ser Asp Pro Leu Gln Leu Leu Val Ser Gly Val Ser Arg Lys Pro
    210                 215                 220

Ser Leu Leu Thr Leu Gln Gly Pro Val Val Thr Pro Gly Glu Asn Leu
225                 230                 235                 240

Thr Leu Gln Cys Gly Ser Asp Val Gly Tyr Ile Arg Tyr Thr Leu Tyr
                245                 250                 255

Lys Glu Gly Ala Asp Gly Leu Pro Gln Arg Pro Gly Arg Gln Pro Gln
            260                 265                 270

Ala Gly Leu Ser Gln Ala Asn Phe Thr Leu Ser Pro Val Ser Arg Ser
        275                 280                 285

Tyr Gly Gly Gln Tyr Arg Cys Tyr Gly Ala His Asn Val Ser Ser Glu
    290                 295                 300

Trp Ser Ala Pro Ser Asp Pro Leu Asp Ile Leu Ile Ala Gly Gln Ile
305                 310                 315                 320

Ser Asp Arg Pro Ser Leu Ser Val Gln Pro Gly Pro Thr Val Thr Ser
                325                 330                 335

Gly Glu Lys Val Thr Leu Leu Cys Gln Ser Trp Asp Pro Met Phe Thr
            340                 345                 350

Phe Leu Leu Thr Lys Glu Gly Ala Ala His Pro Pro Leu Arg Leu Arg
        355                 360                 365

Ser Met Tyr Gly Ala His Lys Tyr Gln Ala Glu Phe Pro Met Ser Pro
    370                 375                 380

Val Thr Ser Ala His Ala Gly Thr Tyr Arg Cys Tyr Gly Ser Arg Ser
385                 390                 395                 400

Ser Asn Pro Tyr Leu Leu Ser His Pro Ser Glu Pro Leu Glu Leu Val
                405                 410                 415

Val Ser Gly Ala Thr Glu Thr Leu Asn Pro Ala Gln Lys Lys Ser Asp
            420                 425                 430
```

```
Ser Lys Thr Ala Pro His Leu Gln Asp Tyr Thr Val Glu Asn Leu Ile
        435                 440                 445

Arg Met Gly Val Ala Gly Leu Val Leu Leu Phe Leu Gly Ile Leu Leu
    450                 455                 460

Phe Glu Ala Gln His Ser Gln Arg Ser Pro Pro Arg Cys Ser Gln Glu
465                 470                 475                 480

Ala Asn Ser Arg Lys Asp Asn Ala Pro Phe Arg Val Val Glu Pro Trp
                485                 490                 495

Glu Gln Ile


<210> SEQ ID NO 357
<211> LENGTH: 299
<212> TYPE: PRT
<213> ORGANISM: Artificial Sequence
<220> FEATURE:
<223> OTHER INFORMATION: LILRA5(NP_067073)

<400> SEQUENCE: 357

Met Ala Pro Trp Ser His Pro Ser Ala Gln Leu Gln Pro Val Gly Gly
1               5                   10                  15

Asp Ala Val Ser Pro Ala Leu Met Val Leu Leu Cys Leu Gly Leu Ser
            20                  25                  30

Leu Gly Pro Arg Thr His Val Gln Ala Gly Asn Leu Ser Lys Ala Thr
        35                  40                  45

Leu Trp Ala Glu Pro Gly Ser Val Ile Ser Arg Gly Asn Ser Val Thr
    50                  55                  60

Ile Arg Cys Gln Gly Thr Leu Glu Ala Gln Glu Tyr Arg Leu Val Lys
65                  70                  75                  80

Glu Gly Ser Pro Glu Pro Trp Asp Thr Gln Asn Pro Leu Glu Pro Lys
                85                  90                  95

Asn Lys Ala Arg Phe Ser Ile Pro Ser Met Thr Glu His His Ala Gly
            100                 105                 110

Arg Tyr Arg Cys Tyr Tyr Tyr Ser Pro Ala Gly Trp Ser Glu Pro Ser
        115                 120                 125

Asp Pro Leu Glu Leu Val Val Thr Gly Phe Tyr Asn Lys Pro Thr Leu
    130                 135                 140

Ser Ala Leu Pro Ser Pro Val Val Thr Ser Gly Glu Asn Val Thr Leu
145                 150                 155                 160

Gln Cys Gly Ser Arg Leu Arg Phe Asp Arg Phe Ile Leu Thr Glu Glu
                165                 170                 175

Gly Asp His Lys Leu Ser Trp Thr Leu Asp Ser Gln Leu Thr Pro Ser
            180                 185                 190

Gly Gln Phe Gln Ala Leu Phe Pro Val Gly Pro Val Thr Pro Ser His
        195                 200                 205

Arg Trp Met Leu Arg Cys Tyr Gly Ser Arg Arg His Ile Leu Gln Val
    210                 215                 220

Trp Ser Glu Pro Ser Asp Leu Leu Glu Ile Pro Val Ser Gly Ala Ala
225                 230                 235                 240

Asp Asn Leu Ser Pro Ser Gln Asn Lys Ser Asp Ser Gly Thr Ala Ser
                245                 250                 255

His Leu Gln Asp Tyr Ala Val Glu Asn Leu Ile Arg Met Gly Met Ala
            260                 265                 270

Gly Leu Ile Leu Val Val Leu Gly Ile Leu Ile Phe Gln Asp Trp His
        275                 280                 285

Ser Gln Arg Ser Pro Gln Ala Ala Ala Gly Arg
```

290 295

<210> SEQ ID NO 358
<211> LENGTH: 481
<212> TYPE: PRT
<213> ORGANISM: Artificial Sequence
<220> FEATURE:
<223> OTHER INFORMATION: LILRA6(NP_001347096)

<400> SEQUENCE: 358

Met Thr Pro Ala Leu Thr Ala Leu Leu Cys Leu Gly Leu Ser Leu Gly
1 5 10 15

Pro Arg Thr Arg Val Gln Ala Gly Pro Phe Pro Lys Pro Thr Leu Trp
20 25 30

Ala Glu Pro Gly Ser Val Ile Ser Trp Gly Ser Pro Val Thr Ile Trp
35 40 45

Cys Gln Gly Ser Leu Glu Ala Gln Glu Tyr Gln Leu Asp Lys Glu Gly
50 55 60

Ser Pro Glu Pro Leu Asp Arg Asn Asn Pro Leu Glu Pro Lys Asn Lys
65 70 75 80

Ala Arg Phe Ser Ile Pro Ser Met Thr Gln His His Ala Gly Arg Tyr
85 90 95

Arg Cys His Tyr Tyr Ser Ser Ala Gly Trp Ser Glu Pro Ser Asp Pro
100 105 110

Leu Glu Leu Val Met Thr Gly Phe Tyr Asn Lys Pro Thr Leu Ser Ala
115 120 125

Leu Pro Ser Pro Val Val Ala Ser Gly Gly Asn Met Thr Leu Arg Cys
130 135 140

Gly Ser Gln Lys Gly Tyr His His Phe Val Leu Met Lys Glu Gly Glu
145 150 155 160

His Gln Leu Pro Arg Thr Leu Asp Ser Gln Gln Leu His Ser Gly Gly
165 170 175

Phe Gln Ala Leu Phe Pro Val Gly Pro Val Thr Pro Ser His Arg Trp
180 185 190

Arg Phe Thr Cys Tyr Tyr Tyr Tyr Thr Asn Thr Pro Arg Val Trp Ser
195 200 205

His Pro Ser Asp Pro Leu Glu Ile Leu Pro Ser Gly Val Ser Arg Lys
210 215 220

Pro Ser Leu Leu Thr Leu Gln Gly Pro Val Leu Ala Pro Gly Gln Ser
225 230 235 240

Leu Thr Leu Gln Cys Gly Ser Asp Val Gly Tyr Asp Arg Phe Val Leu
245 250 255

Tyr Lys Glu Gly Glu Arg Asp Phe Leu Gln Arg Pro Gly Gln Gln Pro
260 265 270

Gln Ala Gly Leu Ser Gln Ala Asn Phe Thr Leu Gly Pro Val Ser Pro
275 280 285

Ser His Gly Gly Gln Tyr Arg Cys Tyr Gly Ala His Asn Leu Ser Ser
290 295 300

Glu Trp Ser Ala Pro Ser Asp Pro Leu Asn Ile Leu Met Ala Gly Gln
305 310 315 320

Ile Tyr Asp Thr Val Ser Leu Ser Ala Gln Pro Gly Pro Thr Val Ala
325 330 335

Ser Gly Glu Asn Val Thr Leu Leu Cys Gln Ser Arg Gly Tyr Phe Asp
340 345 350

Thr Phe Leu Leu Thr Lys Glu Gly Ala Ala His Pro Pro Leu Arg Leu

-continued

```
        355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Gly Ser Ser Leu Pro Pro Thr Gly Pro
            420                 425                 430

Pro Ser Thr Pro Ala Ser His Ala Lys Asp Tyr Thr Val Glu Asn Leu
        435                 440                 445

Ile Arg Met Gly Met Ala Gly Leu Val Leu Val Phe Leu Gly Ile Leu
    450                 455                 460

Leu Phe Glu Ala Gln His Ser Gln Arg Asn Pro Gln Asp Ala Ala Gly
465                 470                 475                 480

Arg


<210> SEQ ID NO 359
<211> LENGTH: 10
<212> TYPE: PRT
<213> ORGANISM: Artificial Sequence
<220> FEATURE:
<223> OTHER INFORMATION: human IgG1 upper hinge

<400> SEQUENCE: 359

Glu Pro Lys Ser Cys Asp Lys Thr His Thr
1               5                   10
```